United States Patent
Luescher et al.

(10) Patent No.: US 12,195,556 B2
(45) Date of Patent: *Jan. 14, 2025

(54) REVERSIBLE PROTEIN MULTIMERS, METHODS FOR THEIR PRODUCTION AND USE

(71) Applicant: Ludwig Institute for Cancer Research Ltd., New York, NY (US)

(72) Inventors: Immanuel F. Luescher, Gollion (CH); Julien Schmidt, Peillonnex (FR); Philippe Guillaume, Les Hopitaux Vieux (FR); Danijel Dojcinovic, Epalinges (CH)

(73) Assignee: Ludwig Institute for Cancer Research Ltd., New York, NY (US)

( * ) Notice: Subject to any disclaimer, the term of this patent is extended or adjusted under 35 U.S.C. 154(b) by 1263 days.

This patent is subject to a terminal disclaimer.

(21) Appl. No.: 16/008,430

(22) Filed: Jun. 14, 2018

(65) Prior Publication Data

US 2018/0346606 A1    Dec. 6, 2018

Related U.S. Application Data

(63) Continuation of application No. 13/877,200, filed as application No. PCT/US2011/054335 on Sep. 30, 2011, now Pat. No. 10,023,657.

(60) Provisional application No. 61/389,092, filed on Oct. 1, 2010.

(51) Int. Cl.
| | |
|---|---|
| A61K 39/385 | (2006.01) |
| A61K 39/00 | (2006.01) |
| C07K 14/74 | (2006.01) |
| C07K 17/00 | (2006.01) |
| C12N 5/0783 | (2010.01) |

(52) U.S. Cl.
CPC .............. *C07K 17/00* (2013.01); *A61K 39/00* (2013.01); *A61K 39/385* (2013.01); *C07K 14/70539* (2013.01); *A61K 2039/605* (2013.01); *A61K 2039/627* (2013.01); *A61K 2039/64* (2013.01)

(58) Field of Classification Search
None
See application file for complete search history.

(56) References Cited

U.S. PATENT DOCUMENTS

| | | | |
|---|---|---|---|
| 8,343,497 B2 | 1/2013 | Shi et al. | |
| 10,023,657 B2 | 7/2018 | Luescher et al. | |
| 2004/0082012 A1 | 4/2004 | Busch et al. | |
| 2010/0226854 A1 | 9/2010 | Scholler et al. | |
| 2013/0289253 A1 | 10/2013 | Luescher et al. | |
| 2015/0329617 A1 | 11/2015 | Winther et al. | |

FOREIGN PATENT DOCUMENTS

| | | | |
|---|---|---|---|
| WO | WO2009039854 A1 | * | 4/2009 |
| WO | WO 2010042876 A1 | * | 4/2010 |

OTHER PUBLICATIONS

HLA Nomenclature (2015) (Year: 2015).*
Liu et al (MHC Complex: Interaction with Peptides. IN: eLS. John Wiley & Sons, Ltd: Chichester, DOI: 10.1002/9780470015902.a0000922.pub2, 2011, pp. 1-12) (Year: 2011).*
Wieczorek et al (Front. Immunol. 2017, vol. 8, article 292: 1-16) (Year: 2017).*
Reche and Reinherz (G. Nicosia et al., Eds. ICARIS 2004, LNCS 3239: 189-1196) (Year: 2004).*
Ali-Khan et al (Curr. Prot. Prot. Sci. 2002, 22.1.1-22.1.19, Suppl. 30, John Wiley & Sons, Inc.) (Year: 2002).*
Woolhouse et al (Phil. Trans. R. Soc. B, 2012, 367: 2864-2871) (Year: 2012).*
Schumacher and Schreiber (Science, 2015, 348: 69-74) (Year: 2015).*
Buonaguro et al (Clin. Vacc. Immunol. 2011, 18(1): 23-34) (Year: 2011).*
Repana et al (Genome Biol. 2019 20: 1-12) (Year: 2019).*
Bornhorst and Falke (Methods. Enzymol. Jul. 2010, 326: 245-254) (Year: 2010).*
Lim et al (Biochem. Biophys. Res. Comm. 2006, 344: 926-930) (Year: 2006).*
Hugues et al (J. Immunol. Methods, 2002, 268: 83-92) (Year: 2002).*
Jonkheijm et al (Angew. Chem. Int. Ed. 2008, 47: 9618-9647) (Year: 2008).*
PCT/US2011/054335, Apr. 13, 2012, *International Search Report and Written Opinion.
Ayyoub et al., Assessment of vaccine-induced CD4 T cell responses to the 119-143 immunodominant region of the tumor-specific antigen NY-ESO-1 using DRB1 *0101 tetramers. Clin Cancer Res. Sep. 15, 2010;16(18):4607-15. doi: 10.1158/1078-0432.CCR-10-1485.
Ayyoub et al., Monitoring of NY-ESO-1 specific CD4+ T cells using molecularly defined MHC class II/His-tag-peptide tetramers. Proc Natl Acad Sci U S A. Apr. 20, 2010;107(16):7437-42. doi: 10.1073/pnas.1001322107.
Cameron et al., Cutting edge: detection of antigen-specific CD4+ T cells by HLA-DR1 oligomers is dependent on the T cell activation state. J Immunol. Jan. 15, 2001;166(2):741-5. Erratum in: J Immunol Feb. 15, 2001;166(4):2887.

(Continued)

*Primary Examiner* — Michael Szperka
*Assistant Examiner* — Marianne Dibrino
(74) *Attorney, Agent, or Firm* — Wolf, Greenfield & Sacks, P.C.

(57) ABSTRACT

Some aspect of this disclosure provide reversible MHC protein multimers, and methods of using such multimers in the detection and/or isolation of specific T-cells or T-cell populations. Because reversible MHC multimers can efficiently be dissociated, the time of MHC binding to T-cell receptors, and, thus, T-cell receptor-mediated T-cell activation can be minimized. The use of reversible MHC multimers as provided herein, accordingly, allows for the detection and isolation of bona fide antigen-specific CD8+ T cells without inducing activation dependent cell death, including rare, therapeutically valuable T-cells expressing T-cell receptors binding tumor antigens with high affinity. Methods for the production and use of reversible multimers are also provided.

18 Claims, 84 Drawing Sheets

Specification includes a Sequence Listing.

(56) References Cited

OTHER PUBLICATIONS

Cao et al., Quantitative evaluation of His-tag purification and immunoprecipitation of tristetraprolin and its mutant proteins from transfected human cells. Biotechnol Prog. Mar.-Apr. 2009;25(2):461-7. doi: 10.1002/btpr.121.

Cebecauer et al., Soluble MHC-peptide complexes induce rapid death of CD8+ CTL. J Immunol. Jun. 1, 2005;174(11):6809-19.

Cecconi et al., Use of MHC class II tetramers to investigate CD4+ T cell responses: problems and solutions. Cytometry A. Nov. 2008;73(11):1010-8. doi: 10.1002/cyto.a.20603.

Danke et al., Autoreactive T cells in healthy individuals. J Immunol. May 15, 2004;172(10):5967-72.

Guillaume et al., Fluorescence-activated cell sorting and cloning of bona fide CD8+ CTL with reversible MHC-peptide and antibody Fab' conjugates. J Immunol. Sep. 15, 2006;177(6):3903-12.

Guillaume et al., Novel soluble HLA-A2/MELAN-A complexes selectively stain a differentiation defective subpopulation of CD8+ T cells in patients with melanoma. Int J Cancer. Aug. 15, 2010;127(4):910-23. doi: 10.1002/ijc.25099.

Guillaume et al., Soluble major histocompatibility complex-peptide octamers with impaired CD8 binding selectively induce Fas-dependent apoptosis. J Biol Chem. Feb. 14, 2003;278(7):4500-9.

Guillaume et al., Soluble MHC-peptide complexes: tools for the monitoring of T cell responses in clinical trials and basic research. Cancer Immun. Sep. 25, 2009;9:7.

Hampl et al., CD4 augments the response of a T cell to agonist but not to antagonist ligands. Immunity. Sep. 1997;7(3):379-85.

Huang et al., Tris-nitrilotriacetic acids of subnanomolar affinity toward hexahistidine tagged molecules. Bioconjug Chem. Aug. 19, 2009;20(8):1667-72. doi: 10.1021/bc900309n.

Jasanoff et al., Structure of a trimeric domain of the MHC class II-associated chaperonin and targeting protein Ii. EMBO J. Dec. 1, 1998;17(23):6812-8.

Luescher et al., Binding of photoreactive lysozyme peptides to murine histocompatibility class II molecules. Proc Natl Acad Sci U S A. Feb. 1988;85(3):871-4.

Rötzschke et al., A pH-sensitive histidine residue as control element for ligand release from HLA-DR molecules. Proc Natl Acad Sci U S A. Dec. 24, 2002;99(26):16946-50.

Wooldridge et al., Tricks with tetramers: how to get the most from multimeric peptide-MHC. Immunology. Feb. 2009;126(2):147-64. doi: 10.1111/j.1365-2567.2008.02848.x. Review. Erratum in: Immunology. Mar. 2009;126(3):447.

Jones, MHC class I and class II structures. Curr Opin Immunol. Feb. 1997;9(1):75-9. doi: 10.1016/s0952-7915(97)80162-8.

Rammensee, Chemistry of peptides associated with MHC class I and class II molecules. Curr Opin Immunol. Feb. 1995;7(1):85-96. doi: 10.1016/0952-7915(95)80033-6.

* cited by examiner

MHC tags under study

BSP: HLA-A*0201.......<u>WEPG</u>SLHHILDAQKMVWNHR (biotin above second H)

His$_6$: HLA-A*0201.......<u>WEPG</u>SHHHHHH

His$_{12}$: HLA-A*0201.......<u>WEPG</u>SHHHHHHHHHHHH

2xHis$_6$: HLA-A*0201.......<u>WEPG</u>SHHHHHHGGGSGGGSGSHHHHHH biotin-maleimide-NTA biotin-maleimide-NTA₂ biotin-maleimide-NTA₄ amino-maleimide-NTA₂ thio-maleimide-NTA₂

Biotin-NTA

SPR binding data

|  | MONO NTA | | | Di-NTA | | |
|---|---|---|---|---|---|---|
|  | $K_{on}$ $M^{-1}sec^{-1}$ $\times 10^4$ | $K_{off}$ $sec^{-1}$ $\times 10^{-3}$ | $K_D$ nM | $K_{on}$ $M^{-1}sec^{-1}$ $\times 10^4$ | $K_{off}$ $sec^{-1}$ $\times 10^{-3}$ | $K_D$ nM |
| HLA-A2-His$_6$ | 0.28 | 11.5 | 4100 | 0.35 | 7.9 | 860 |
| HLA-A2-His$_{12}$ | 1.25 | 2.45 | 196 | 1.46 | 0.59 | 41 |
| HLA-A2-2(His$_6$) | 1.05 | 0.36 | 34 | 1.14 | 0.095 | 12 |

Fig. 4B

Photochemical removal of tags from peptides

| clones | TCR (MFI) PE | CD4 (MFI) FITC | EC50 (nM) |
|---|---|---|---|
| 8 | 35 | 185 | 88 |
| 9 | 25 | 167 | 37 |
| 2 | 22 | 157 | 43 |
| 15 | 33 | 187 | 65 |

Fig. 22E

Preparation of immunopure DR4 - HA$_{306-318}$ monomers using Cy5.5 tagged peptides Preparation of immunopure DR4-HA$_{306-318}$ NTA multimers using the pY-D$_4$ tag Preparation of immunopure DR4-HA$_{306-318}$ NTA multimers using the pY-D$_4$ tag

Effect of peptide tagging on HLA-DR peptide binding

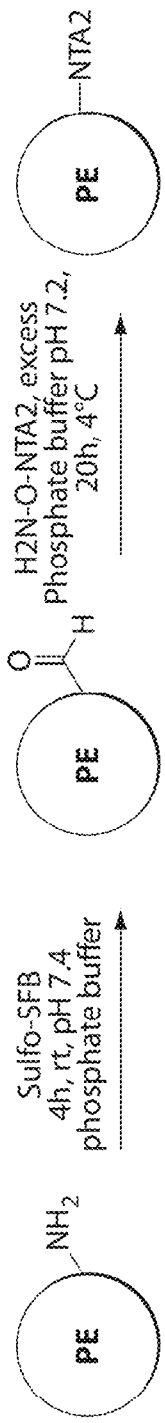
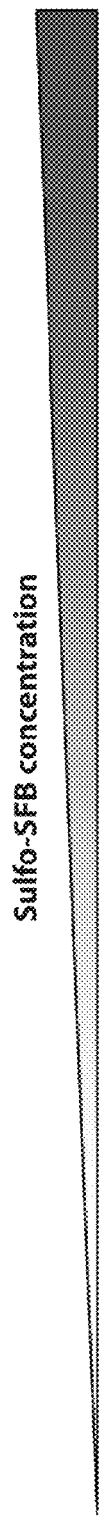
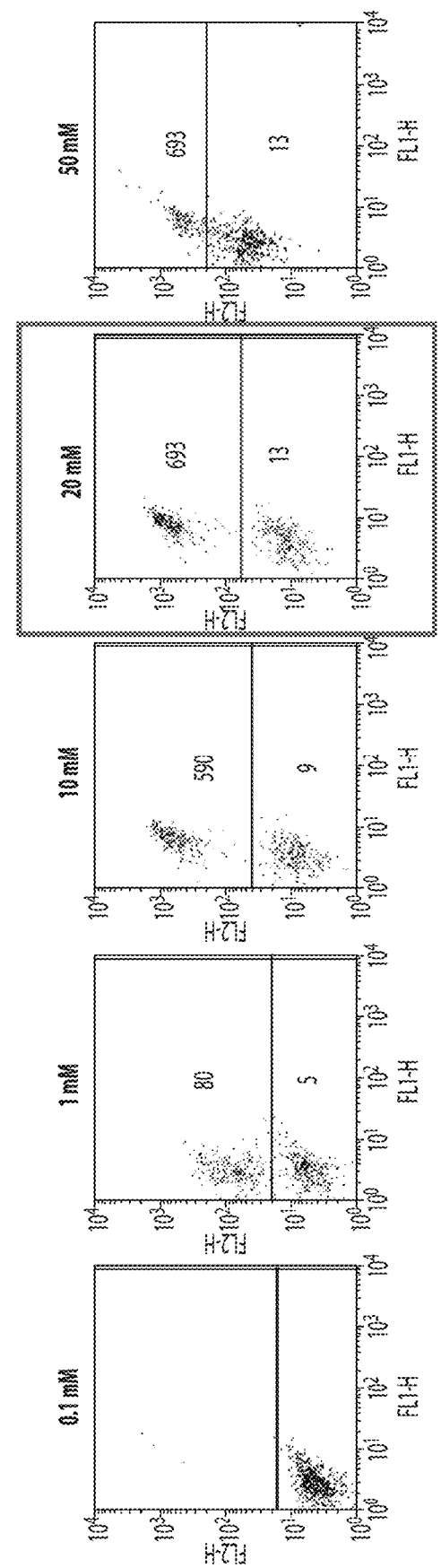
Fig. 29A
Fig. 29B

Fig. 31-2

Name: bioNTA4

Exact Mass = 3322

| Batch | Overall Yields (%) |
|---|---|
| Jun-10 | 61 |
| Feb-11 | 56 |
| Aug-10 | 44 |

| Name | Structure | Batch | Overall Yields (%) |
|---|---|---|---|
| shNTA4 | Exact Mass = 3089 | Sep-10 | 12 |

Fig. 31-4

| Name | Conjugation (peptide to PE) | complex formation | batch to batch reproducibility | storage stability | substitution | CD8 staining 8 nM PBMC (Flu) | CD4 staining 8 nM 37°C clone23-1 |
|---|---|---|---|---|---|---|---|
| BSP conventional | no conjugation | mix biotinylated monomer with SA-PE | very good | 12 months | 4 MHC per SA | 626 | |
| SA-PE-bioNTA2 | mix bioNTA2 with SA-PE (5 fold molar excess) | 4 µg of SA-PE-bioNTA2 with 10 µg 2xHis6 monomer | very good | still good after 3 months | 4 MHC per SA | 575 | |
| SA-PE-bioNTA4 | mix bioNTA4 with SA-PE (5 fold molar excess) | 4 µg of SA-PE-bioNTA4 with 10 µg 2xHis6 monomer | very good | still good after 3 months | 4 MHC per SA | 769 | |

Fig. 32-1

| Name | Conjugation (peptide to PE) | complexe formation | batch to batch reproducibility | storage stability | substitution | CD8 staining 8 nM PBMC (Flu) | CD4 staining 8 nM 37°C clone23-1 |
|---|---|---|---|---|---|---|---|
| PE-shNTA2 | mix shNTA2 with NHS-PEG2-mal derived PE | 0.5 μg of PE-shNTA2 with 10 μg 2xHis6 monomer | medium | N.D | up to 14 peptide per PE | 243 / 5 | |
| PE-shNTA4 | mix shNTA4 with NHS-PEG2-mal derived PE | 0.5 μg of PE-shNTA4 with 10 μg 2xHis6 monomer | medium | N.D | N.D | 133 / 4 | |
| PE-oxNTA2 | mix oxNTA2 with SFB derived PE | 0.5 μg of PE-oxNTA2 with 10 μg 2xHis6 monomer | good | 1 month | up to 20 peptide per PE | 871 | 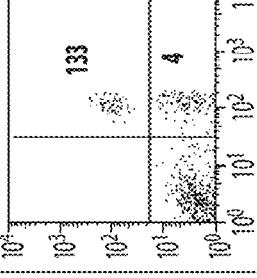 |

Fig. 32-2

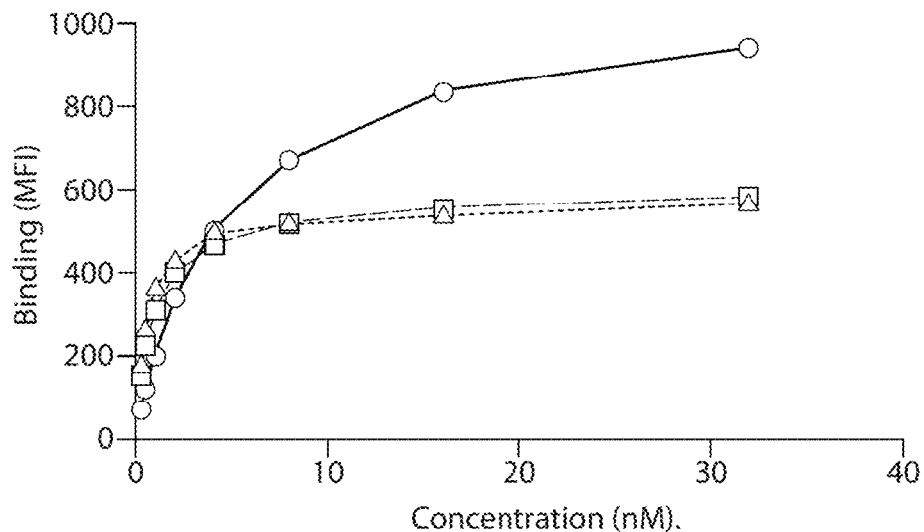
Fig. 33A
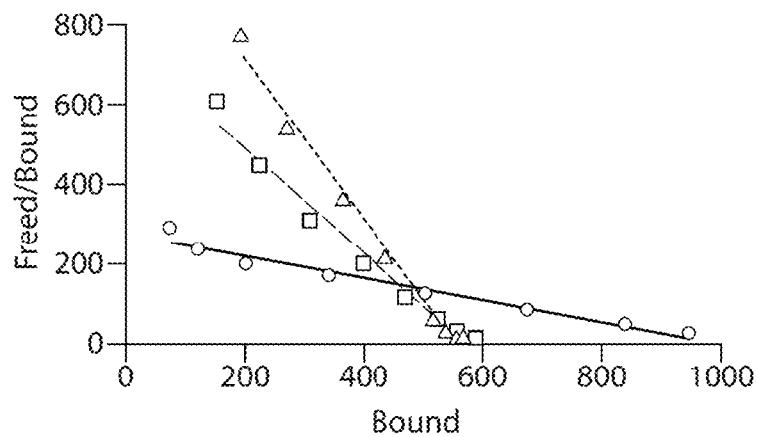
Fig. 33B
| | Bmax | Kd (nM) |
|---|---|---|
| Conventional | 1070 | 4.4 |
| PE-Cys-PEG$_2$-NTA$_2$ | 588.2 | 0.86 |
| PE-HNO-NTA$_2$ | 562.3 | 0.53 |
Fig. 33C

|  | Capacity (µg/ml) | Elution (yield %) | Regeneration* |
|---|---|---|---|
| High Capacity Streptavidin (Pierce) | 120 | 87 | X |
| Monomeric avidin (Pierce) | 52 | 66 | + |
| Streptactin Superflow High Capacity (IBA) | 250 | >90 | +++ |

| sample | flowrate [ml/min] | loading [µg] | flowthrough [µg] | eluate [µg] | recovery [%] |
|---|---|---|---|---|---|
| DTB-Kb OVA | 1 | 250 | 54 | 180 | 72 |
| DTB-Kb OVA | 0.2 | 250 | 45 | 160 | 64 |

Biotin-NTA$_4$

Exact Mass = 3322

```
                       SEQUENCE LISTING

<160> NUMBER OF SEQ ID NOS: 318

<210> SEQ ID NO 1
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 1

Leu His His Ile Leu Asp Ala Gln Lys Met Val Trp Asn His Arg
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 2

Gly Ile Leu Gly Phe Val Phe Thr Leu
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 3

Gly Ile Leu Gly Phe Val Phe Thr Leu
1               5

<210> SEQ ID NO 4
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 4

Gly Gly Gly Ser Gly Gly Gly Ser Gly Ser
1               5                   10

<210> SEQ ID NO 5
<211> LENGTH: 20
<212> TYPE: PRT
<213> ORGANISM: Artificial Sequence
<220> FEATURE:
<223> OTHER INFORMATION: synthetic/recombinant polypeptide

<400> SEQUENCE: 5

Trp Glu Pro Gly Ser Leu His His Ile Leu Asp Ala Gln Lys Met Val
1               5                   10                  15
```

Trp Asn His Arg
            20

<210> SEQ ID NO 6
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 6

Trp Glu Pro Gly Ser His His His His His His
1               5                   10

<210> SEQ ID NO 7
<211> LENGTH: 17
<212> TYPE: PRT
<213> ORGANISM: Artificial Sequence
<220> FEATURE:
<223> OTHER INFORMATION: synthetic/recombinant polypeptide

<400> SEQUENCE: 7

Trp Glu Pro Gly Ser His His His His His His His His His His His
1               5                   10                  15

His

<210> SEQ ID NO 8
<211> LENGTH: 27
<212> TYPE: PRT
<213> ORGANISM: Artificial Sequence
<220> FEATURE:
<223> OTHER INFORMATION: synthetic/recombinant polypeptide

<400> SEQUENCE: 8

Trp Glu Pro Gly Ser His His His His His Gly Gly Gly Ser Gly
1               5                   10                  15

Gly Gly Ser Gly Ser His His His His His His
            20                  25

<210> SEQ ID NO 9
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 9

Gly Gly Gly Ser Gly Gly Gly Ser Gly Ser
1               5                   10

<210> SEQ ID NO 10
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 10

Gly Gly Ser Gly Gly Gly Ser Gly Ser
1               5

<210> SEQ ID NO 11
<211> LENGTH: 10
<212> TYPE: PRT
<213> ORGANISM: Artificial Sequence
<220> FEATURE:

```
<223> OTHER INFORMATION: synthetic/recombinant polypeptide

<400> SEQUENCE: 11

Gly Gly Gly Ser Gly Gly Gly Ser Gly Ser
1               5                   10

<210> SEQ ID NO 12
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 12

Gly Ile Leu Gly Phe Val Phe Thr Leu
1               5

<210> SEQ ID NO 13
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 13

Glu Leu Ala Gly Ile Gly Ile Leu Thr Val
1               5                   10

<210> SEQ ID NO 14
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 14

Gly Leu Cys Thr Leu Val Ala Met Leu
1               5

<210> SEQ ID NO 15
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 15

Asn Leu Val Pro Met Val Ala Thr Val
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 16

Ile Leu Lys Glu Pro Val His Gly Val
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic/recombinant polypeptide
```

```
<400> SEQUENCE: 17

Gly Ile Leu Gly Phe Val Phe Thr Leu
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 18

Gly Leu Tyr Asp Gly Met Glu His Leu
1               5

<210> SEQ ID NO 19
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 19

Glu Leu Ala Gly Ile Gly Ile Leu Thr Val
1               5                   10

<210> SEQ ID NO 20
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 20

Ser Leu Leu Met Trp Ile Thr Gln Cys
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 21

Ser Leu Leu Met Trp Ile Thr Gln Ala
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 22

Tyr Met Asn Gly Thr Met Ser Gln Val
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic/recombinant polypeptide
```

```
<400> SEQUENCE: 23

Cys Thr Glu Leu Lys Leu Ser Asp Tyr
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 24

Glu Val Asp Pro Ile Gly His Leu Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 25

Ser Ser Asp Tyr Val Ile Pro Ile Gly Thr Tyr
1               5                   10

<210> SEQ ID NO 26
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 26

Lys Cys Asp Ile Cys Thr Asp Glu Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 27

Phe Met Asn Lys Phe Ile Tyr Glu Ile
1               5

<210> SEQ ID NO 28
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 28

Gly Leu Ser Pro Asn Leu Asn Arg Phe Leu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 29
```

```
Ser Thr Ala Arg Ile Pro Leu Pro Asn Leu
1               5                   10

<210> SEQ ID NO 30
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 30

Leu Leu Met Trp Glu Ala Val Thr Val
1               5

<210> SEQ ID NO 31
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 31

Leu Leu Thr Glu Lys Ser Arg Trp Ser Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 32

Met Leu Met Ala Gln Glu Ala Leu Ala Phe Leu
1               5                   10

<210> SEQ ID NO 33
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 33

Tyr Leu Ser Gly Ala Asn Leu Asn Leu
1               5

<210> SEQ ID NO 34
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 34

Tyr Leu Ser Gly Ala Asp Leu Asn Leu
1               5

<210> SEQ ID NO 35
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 35
```

-continued

```
Tyr Leu Ser Gly Ala Asn Leu Asp Leu
1               5

<210> SEQ ID NO 36
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 36

Ile Met Ile Gly Val Leu Val Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 37

Gly Val Leu Val Gly Val Ala Leu Ile
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 38

Gly Leu Leu Val Gly Val Ala Leu Ile
1               5

<210> SEQ ID NO 39
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 39

Gly Val Leu Val Gly Val Ala Leu Val
1               5

<210> SEQ ID NO 40
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 40

Gly Leu Leu Val Gly Val Ala Leu Val
1               5

<210> SEQ ID NO 41
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 41

Ser Leu Met Val Ile Leu Glu His Thr
```

```
1               5

<210> SEQ ID NO 42
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 42

Ile Leu Ser Asn Leu Ser Phe Pro Val
1               5

<210> SEQ ID NO 43
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 43

Leu Leu Phe Gly Ser Ile Val Ala Val
1               5

<210> SEQ ID NO 44
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 44

Leu Ile Leu Pro Leu Leu Phe Tyr Leu
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 45

Ala Leu Leu Asn Ile Lys Val Lys Leu
1               5

<210> SEQ ID NO 46
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 46

Ser Val Tyr Asp Phe Phe Val Trp Leu
1               5

<210> SEQ ID NO 47
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 47

Leu Leu Asp Phe Val Arg Phe Met Gly Val
1               5                   10
```

<210> SEQ ID NO 48
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 48

Gly Leu Ala Thr Leu Val Ala Met Leu
1               5

<210> SEQ ID NO 49
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 49

Tyr Met Glu His Asn Asn Val Tyr Thr Val
1               5                   10

<210> SEQ ID NO 50
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 50

Gln Leu Leu Leu Ser Leu Leu Leu Leu
1               5

<210> SEQ ID NO 51
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 51

His Leu Ser Thr Ala Phe Ala Arg Val
1               5

<210> SEQ ID NO 52
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 52

Lys Thr Trp Gly Gln Tyr Trp Gln Val
1               5

<210> SEQ ID NO 53
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 53

Ile Thr Asp Gln Val Pro Phe Ser Val
1               5

```
<210> SEQ ID NO 54
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 54

Ile Met Asp Gln Val Pro Phe Ser Val
1               5

<210> SEQ ID NO 55
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 55

Tyr Leu Glu Pro Gly Pro Val Thr Ala
1               5

<210> SEQ ID NO 56
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 56

Tyr Leu Glu Pro Gly Pro Val Ile Ala
1               5

<210> SEQ ID NO 57
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 57

Leu Leu Asp Gly Thr Ala Thr Leu Arg Leu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 58

Val Leu Tyr Arg Tyr Gly Ser Phe Ser Val
1               5                   10

<210> SEQ ID NO 59
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 59

Val Leu Gly Pro Ile Ser Gly His Val
1               5
```

```
<210> SEQ ID NO 60
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 60

Phe Leu Pro Ser Asp Phe Phe Pro Ser Val
1               5                   10

<210> SEQ ID NO 61
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 61

Lys Ile Phe Gly Ser Leu Ala Phe Leu
1               5

<210> SEQ ID NO 62
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 62

Asp Leu Asn Asn Phe Cys Gln Lys Val
1               5

<210> SEQ ID NO 63
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 63

Met Leu Ala Val Ile Ser Cys Ala Val
1               5

<210> SEQ ID NO 64
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 64

Tyr Met Leu Asp Leu Gln Pro Glu Thr Thr
1               5                   10

<210> SEQ ID NO 65
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 65

Thr Leu Gly Ile Val Cys Pro Ile
1               5

<210> SEQ ID NO 66
```

```
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 66

Cys Val Asn Gly Ser Cys Phe Thr Val
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 67

Cys Val Asn Gly Ser Cys Phe Thr Ile
1               5

<210> SEQ ID NO 68
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 68

Ser Ile Thr Glu Val Glu Cys Phe Leu
1               5

<210> SEQ ID NO 69
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 69

Arg Leu Leu Gln Leu His Ile Thr Met
1               5

<210> SEQ ID NO 70
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 70

Glu Leu Val Arg Arg Ile Leu Ser Arg
1               5

<210> SEQ ID NO 71
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 71

Lys Val Ala Glu Leu Val His Phe Leu
1               5

<210> SEQ ID NO 72
<211> LENGTH: 10
```

```
<212> TYPE: PRT
<213> ORGANISM: Artificial Sequence
<220> FEATURE:
<223> OTHER INFORMATION: synthetic/recombinant polypeptide

<400> SEQUENCE: 72

Ser Leu Gln Leu Val Phe Gly Ile Glu Leu
1               5                   10

<210> SEQ ID NO 73
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 73

Phe Leu Trp Gly Pro Arg Ala Leu Val
1               5

<210> SEQ ID NO 74
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 74

Gly Val Tyr Asp Gly Arg Glu His Thr Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 75

Gly Val Tyr Asp Gly Arg Ile His Thr Val
1               5                   10

<210> SEQ ID NO 76
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 76

Ala Leu Lys Asp Val Glu Glu Arg Val
1               5

<210> SEQ ID NO 77
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 77

Leu Leu Gly Asp Leu Phe Gly Val
1               5

<210> SEQ ID NO 78
<211> LENGTH: 10
<212> TYPE: PRT
```

```
<213> ORGANISM: Artificial Sequence
<220> FEATURE:
<223> OTHER INFORMATION: synthetic/recombinant polypeptide

<400> SEQUENCE: 78

Glu Ala Ala Gly Ile Gly Ile Leu Thr Val
1               5                   10

<210> SEQ ID NO 79
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 79

Ala Ala Ala Gly Ile Gly Ile Leu Thr Val
1               5                   10

<210> SEQ ID NO 80
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 80

Ala Leu Ala Gly Ile Gly Ile Leu Thr Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 81

Val Val Ala Gly Ile Gly Ile Leu Ala Ile
1               5                   10

<210> SEQ ID NO 82
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 82

Leu Ala Gly Ile Gly Ile Leu Thr Val
1               5

<210> SEQ ID NO 83
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 83

Ala Leu Gly Ile Gly Ile Leu Thr Val
1               5

<210> SEQ ID NO 84
<211> LENGTH: 9
<212> TYPE: PRT
<213> ORGANISM: Artificial Sequence
```

```
<220> FEATURE:
<223> OTHER INFORMATION: synthetic/recombinant polypeptide

<400> SEQUENCE: 84

Thr Leu Phe Val Ile Val Pro Val Leu
1               5

<210> SEQ ID NO 85
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 85

Gln Leu Leu Arg Ser Phe Phe Tyr Ile
1               5

<210> SEQ ID NO 86
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 86

Ser Leu Phe Asp Phe Phe Leu His Phe Leu
1               5                   10

<210> SEQ ID NO 87
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 87

Tyr Leu Gln Val Asn Ser Gln Thr Val
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 88

Val Leu Pro Asp Val Phe Ile Arg Cys
1               5

<210> SEQ ID NO 89
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 89

Val Leu Pro Asp Val Phe Ile Arg Cys Val
1               5                   10

<210> SEQ ID NO 90
<211> LENGTH: 9
<212> TYPE: PRT
<213> ORGANISM: Artificial Sequence
<220> FEATURE:
```

```
<223> OTHER INFORMATION: synthetic/recombinant polypeptide

<400> SEQUENCE: 90

Ala Ile Gln Asp Leu Cys Leu Ala Val
1               5

<210> SEQ ID NO 91
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 91

Ala Ile Gln Asp Leu Cys Val Ala Val
1               5

<210> SEQ ID NO 92
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 92

Leu Leu Ser His Gly Ala Val Ile Glu Val
1               5                   10

<210> SEQ ID NO 93
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 93

Ser Leu Ser Lys Ile Leu Asp Thr Val
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 94

Leu Leu Lys Glu Lys Asn Glu Glu Ile
1               5

<210> SEQ ID NO 95
<211> LENGTH: 12
<212> TYPE: PRT
<213> ORGANISM: Artificial Sequence
<220> FEATURE:
<223> OTHER INFORMATION: synthetic/recombinant polypeptide

<400> SEQUENCE: 95

Ser Arg Leu Leu Glu Phe Tyr Leu Ala Met Pro Phe
1               5                   10

<210> SEQ ID NO 96
<211> LENGTH: 9
<212> TYPE: PRT
<213> ORGANISM: Artificial Sequence
<220> FEATURE:
<223> OTHER INFORMATION: synthetic/recombinant polypeptide
```

```
<400> SEQUENCE: 96

Arg Leu Leu Glu Phe Tyr Leu Ala Met
1               5

<210> SEQ ID NO 97
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 97

Ser Leu Ala Gln Asp Ala Pro Pro Leu
1               5

<210> SEQ ID NO 98
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 98

Thr Val Ser Gly Asn Ile Leu Thr Ile
1               5

<210> SEQ ID NO 99
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 99

Ala Leu Leu Met Trp Ile Thr Gln Cys
1               5

<210> SEQ ID NO 100
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 100

Ser Ala Leu Met Trp Ile Thr Gln Cys
1               5

<210> SEQ ID NO 101
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 101

Ser Leu Ala Met Trp Ile Thr Gln Cys
1               5

<210> SEQ ID NO 102
<211> LENGTH: 9
<212> TYPE: PRT
<213> ORGANISM: Artificial Sequence
<220> FEATURE:
<223> OTHER INFORMATION: synthetic/recombinant polypeptide
```

```
<400> SEQUENCE: 102

Ser Leu Leu Ala Trp Ile Thr Gln Cys
1               5

<210> SEQ ID NO 103
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 103

Ser Leu Leu Met Ala Ile Thr Gln Cys
1               5

<210> SEQ ID NO 104
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 104

Ser Leu Leu Met Trp Ala Thr Gln Cys
1               5

<210> SEQ ID NO 105
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 105

Ser Leu Leu Met Trp Ile Ala Gln Cys
1               5

<210> SEQ ID NO 106
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 106

Ser Leu Leu Met Trp Ile Thr Ala Cys
1               5

<210> SEQ ID NO 107
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 107

Ser Leu Leu Met Trp Ile Thr Gln Cys Phe
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 108
```

```
Ser Leu Leu Met Trp Ile Thr Gln Cys Phe Leu
1               5                   10

<210> SEQ ID NO 109
<211> LENGTH: 13
<212> TYPE: PRT
<213> ORGANISM: Artificial Sequence
<220> FEATURE:
<223> OTHER INFORMATION: synthetic/recombinant polypeptide

<400> SEQUENCE: 109

Ser Leu Leu Met Trp Ile Thr Gln Cys Phe Leu Pro Val
1               5                   10

<210> SEQ ID NO 110
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 110

Leu Leu Met Trp Ile Thr Gln Cys Phe
1               5

<210> SEQ ID NO 111
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 111

Leu Leu Met Trp Ile Thr Gln Cys Phe Leu
1               5                   10

<210> SEQ ID NO 112
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 112

Leu Met Trp Ile Thr Gln Cys Phe Leu
1               5

<210> SEQ ID NO 113
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 113

Trp Ile Thr Gln Cys Phe Leu Pro Val
1               5

<210> SEQ ID NO 114
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 114
```

Leu Leu Gly Arg Asn Ser Phe Glu Val
1               5

<210> SEQ ID NO 115
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 115

Leu Ala Gly Ile Gly Ile Leu Ile Val
1               5

<210> SEQ ID NO 116
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 116

Ala Leu Tyr Val Asp Ser Leu Phe Phe Leu
1               5                   10

<210> SEQ ID NO 117
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 117

Val Leu Gln Glu Leu Asn Val Thr Val
1               5

<210> SEQ ID NO 118
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 118

Ile Leu Ser Leu Glu Leu Met Lys Leu
1               5

<210> SEQ ID NO 119
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 119

Lys Val Leu His Trp Asp Pro Glu Thr Val
1               5                   10

<210> SEQ ID NO 120
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 120

Val Leu His Trp Asp Pro Glu Thr Val

```
<210> SEQ ID NO 121
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 121

Lys Ala Ser Glu Lys Ile Phe Tyr Val
1               5

<210> SEQ ID NO 122
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 122

Lys Ala Ser Glu Lys Ile Thr Tyr Val
1               5

<210> SEQ ID NO 123
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 123

Arg Leu Gln Gly Ile Ser Pro Lys Ile
1               5

<210> SEQ ID NO 124
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 124

Ala Leu Gln Gly Ile Ser Pro Lys Ile
1               5

<210> SEQ ID NO 125
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 125

Ala Leu Gln Gly Ala Ser Pro Lys Ile
1               5

<210> SEQ ID NO 126
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 126

Ala Leu Gln Gly Ile Ser Ala Lys Ile
1               5
```

```
<210> SEQ ID NO 127
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 127

Ala Leu Gln Gly Ile Ser Pro Ala Ile
1               5

<210> SEQ ID NO 128
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 128

Lys Ser Ser Glu Lys Ile Val Tyr Val
1               5

<210> SEQ ID NO 129
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 129

Leu Thr Leu Gly Glu Phe Leu Lys Leu
1               5

<210> SEQ ID NO 130
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 130

Leu Met Leu Gly Glu Phe Leu Lys Leu
1               5

<210> SEQ ID NO 131
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 131

Ile Leu Ala Lys Phe Leu His Trp Leu
1               5

<210> SEQ ID NO 132
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 132

Met Leu Leu Ala Val Leu Tyr Cys Leu
1               5
```

```
<210> SEQ ID NO 133
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 133

Tyr Met Asp Gly Thr Met Ser Gln Val
1               5

<210> SEQ ID NO 134
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 134

Leu Leu Phe Ser Phe Ala Gln Ala Val
1               5

<210> SEQ ID NO 135
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 135

Cys Leu Thr Glu Tyr Ile Leu Trp Val
1               5

<210> SEQ ID NO 136
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 136

Arg Met Phe Pro Asn Ala Pro Tyr Leu
1               5

<210> SEQ ID NO 137
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 137

Cys Met Thr Trp Asn Gln Met Asn Leu
1               5

<210> SEQ ID NO 138
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 138

Arg Leu Glu Asp Val Phe Ala Gly Lys
1               5
```

```
<210> SEQ ID NO 139
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 139

Ile Leu Arg Gly Ser Val Ala His Lys
1               5

<210> SEQ ID NO 140
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 140

Gly Ile Leu Gly Phe Val Phe Thr Leu
1               5

<210> SEQ ID NO 141
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 141

Thr Tyr Leu Pro Thr Asn Ala Ser Leu
1               5

<210> SEQ ID NO 142
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 142

Arg Tyr Pro Leu Thr Phe Gly Trp
1               5

<210> SEQ ID NO 143
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 143

Asn Tyr Lys Arg Cys Phe Pro Val Ile
1               5

<210> SEQ ID NO 144
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 144

Leu Leu Met Trp Ile Thr Gln Cys Phe
1               5

<210> SEQ ID NO 145
```

```
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 145

Ile Thr Gln Cys Phe Leu Pro Val Phe
1               5

<210> SEQ ID NO 146
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 146

Leu Tyr Ala Thr Val Ile His Asp Ile
1               5

<210> SEQ ID NO 147
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 147

Val Tyr Ala Glu Thr Lys His Phe Leu
1               5

<210> SEQ ID NO 148
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 148

Ala Phe Leu Pro Trp His Arg Leu Phe
1               5

<210> SEQ ID NO 149
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 149

Cys Met Thr Trp Asn Gln Met Asn Leu
1               5

<210> SEQ ID NO 150
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 150

Arg Trp Pro Ser Cys Gln Lys Lys Phe
1               5

<210> SEQ ID NO 151
<211> LENGTH: 9
```

```
<212> TYPE: PRT
<213> ORGANISM: Artificial Sequence
<220> FEATURE:
<223> OTHER INFORMATION: synthetic/recombinant polypeptide

<400> SEQUENCE: 151

Gly Ile Leu Gly Phe Val Phe Thr Leu
1               5

<210> SEQ ID NO 152
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 152

His Thr Met Glu Val Thr Val Tyr His Arg
1               5                   10

<210> SEQ ID NO 153
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 153

Glu Leu Val His Phe Leu Leu Leu Lys
1               5

<210> SEQ ID NO 154
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 154

Thr Pro Arg Val Thr Gly Gly Gly Ala Met
1               5                   10

<210> SEQ ID NO 155
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 155

Thr Pro Gly Pro Gly Val Arg Tyr Pro Leu
1               5                   10

<210> SEQ ID NO 156
<211> LENGTH: 13
<212> TYPE: PRT
<213> ORGANISM: Artificial Sequence
<220> FEATURE:
<223> OTHER INFORMATION: synthetic/recombinant polypeptide

<400> SEQUENCE: 156

Ala Pro Arg Gly Pro His Gly Gly Ala Ala Ser Gly Leu
1               5                   10

<210> SEQ ID NO 157
<211> LENGTH: 12
<212> TYPE: PRT
```

```
<213> ORGANISM: Artificial Sequence
<220> FEATURE:
<223> OTHER INFORMATION: synthetic/recombinant polypeptide

<400> SEQUENCE: 157

Thr Pro Met Glu Ala Glu Leu Ala Arg Arg Ser Leu
1               5                   10

<210> SEQ ID NO 158
<211> LENGTH: 13
<212> TYPE: PRT
<213> ORGANISM: Artificial Sequence
<220> FEATURE:
<223> OTHER INFORMATION: synthetic/recombinant polypeptide

<400> SEQUENCE: 158

Thr Pro Met Glu Ala Glu Leu Ala Arg Arg Ser Leu Ala
1               5                   10

<210> SEQ ID NO 159
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 159

Gly Ile Leu Gly Phe Val Phe Thr Leu
1               5

<210> SEQ ID NO 160
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 160

Leu Glu Phe Tyr Leu Ala Met Pro Phe
1               5

<210> SEQ ID NO 161
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 161

Ala Val Leu Leu His Glu Glu Ser Met
1               5

<210> SEQ ID NO 162
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 162

Leu Pro His Ser Ser Ser His Trp Leu
1               5

<210> SEQ ID NO 163
<211> LENGTH: 9
<212> TYPE: PRT
<213> ORGANISM: Artificial Sequence
```

```
<220> FEATURE:
<223> OTHER INFORMATION: synthetic/recombinant polypeptide

<400> SEQUENCE: 163

Ile Pro Ser Ile Asn Val His His Tyr
1               5

<210> SEQ ID NO 164
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 164

Asn Pro Asp Ile Val Ile Tyr Gln Tyr
1               5

<210> SEQ ID NO 165
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 165

Glu Ala Ala Gly Ile Gly Ile Leu Thr Val
1               5                   10

<210> SEQ ID NO 166
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 166

Glu Pro Ala Gly Ile Gly Ile Leu Thr Val
1               5                   10

<210> SEQ ID NO 167
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 167

Glu Ala Ala Gly Ile Gly Ile Leu Thr Tyr
1               5                   10

<210> SEQ ID NO 168
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 168

Glu Pro Ala Gly Ile Gly Ile Leu Thr Tyr
1               5                   10

<210> SEQ ID NO 169
<211> LENGTH: 9
<212> TYPE: PRT
<213> ORGANISM: Artificial Sequence
<220> FEATURE:
```

<223> OTHER INFORMATION: synthetic/recombinant polypeptide

<400> SEQUENCE: 169

Leu Ala Met Pro Phe Ala Thr Pro Met
1               5

<210> SEQ ID NO 170
<211> LENGTH: 13
<212> TYPE: PRT
<213> ORGANISM: Artificial Sequence
<220> FEATURE:
<223> OTHER INFORMATION: synthetic/recombinant polypeptide

<400> SEQUENCE: 170

Leu Ala Met Pro Phe Ala Thr Pro Met Glu Ala Glu Leu
1               5                   10

<210> SEQ ID NO 171
<211> LENGTH: 12
<212> TYPE: PRT
<213> ORGANISM: Artificial Sequence
<220> FEATURE:
<223> OTHER INFORMATION: synthetic/recombinant polypeptide

<400> SEQUENCE: 171

Ala Met Pro Phe Ala Thr Pro Met Glu Ala Glu Leu
1               5                   10

<210> SEQ ID NO 172
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 172

Met Pro Phe Ala Thr Pro Met Glu Ala
1               5

<210> SEQ ID NO 173
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 173

Met Pro Phe Ala Thr Pro Met Glu Ala Glu Leu
1               5                   10

<210> SEQ ID NO 174
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 174

Phe Ala Thr Pro Met Glu Ala Glu Leu
1               5

<210> SEQ ID NO 175
<211> LENGTH: 8
<212> TYPE: PRT
<213> ORGANISM: Artificial Sequence
<220> FEATURE:
<223> OTHER INFORMATION: synthetic/recombinant polypeptide

```
<400> SEQUENCE: 175

Leu Pro Val Pro Gly Val Leu Leu
1               5

<210> SEQ ID NO 176
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 176

Leu Pro Ser Ser Ala Asp Val Glu Phe
1               5

<210> SEQ ID NO 177
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 177

Gly Ile Leu Gly Phe Val Phe Thr Leu
1               5

<210> SEQ ID NO 178
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 178

Leu Ala Met Pro Phe Ala Thr Pro Met
1               5

<210> SEQ ID NO 179
<211> LENGTH: 13
<212> TYPE: PRT
<213> ORGANISM: Artificial Sequence
<220> FEATURE:
<223> OTHER INFORMATION: synthetic/recombinant polypeptide

<400> SEQUENCE: 179

Leu Ala Met Pro Phe Ala Thr Pro Met Glu Ala Glu Leu
1               5                   10

<210> SEQ ID NO 180
<211> LENGTH: 12
<212> TYPE: PRT
<213> ORGANISM: Artificial Sequence
<220> FEATURE:
<223> OTHER INFORMATION: synthetic/recombinant polypeptide

<400> SEQUENCE: 180

Ala Met Pro Phe Ala Thr Pro Met Glu Ala Glu Leu
1               5                   10

<210> SEQ ID NO 181
<211> LENGTH: 9
<212> TYPE: PRT
<213> ORGANISM: Artificial Sequence
<220> FEATURE:
<223> OTHER INFORMATION: synthetic/recombinant polypeptide
```

```
<400> SEQUENCE: 181

Met Pro Phe Ala Thr Pro Met Glu Ala
1               5

<210> SEQ ID NO 182
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 182

Met Pro Phe Ala Thr Pro Met Glu Ala Glu Leu
1               5                   10

<210> SEQ ID NO 183
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 183

Gly Ala Val Asp Pro Leu Leu Ala Leu
1               5

<210> SEQ ID NO 184
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 184

Leu Ala Met Pro Phe Ala Thr Pro Met
1               5

<210> SEQ ID NO 185
<211> LENGTH: 13
<212> TYPE: PRT
<213> ORGANISM: Artificial Sequence
<220> FEATURE:
<223> OTHER INFORMATION: synthetic/recombinant polypeptide

<400> SEQUENCE: 185

Leu Ala Met Pro Phe Ala Thr Pro Met Glu Ala Glu Leu
1               5                   10

<210> SEQ ID NO 186
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 186

Phe Ala Thr Pro Met Glu Ala Glu Leu
1               5

<210> SEQ ID NO 187
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 187
```

```
Gly Ile Leu Gly Phe Val Phe Thr Leu
1               5

<210> SEQ ID NO 188
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 188

Gly Val Leu Val Gly Val Ala Leu Ile
1               5

<210> SEQ ID NO 189
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 189

Gly Leu Leu Val Gly Val Ala Leu Ile
1               5

<210> SEQ ID NO 190
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 190

Gly Val Leu Val Gly Val Ala Leu Val
1               5

<210> SEQ ID NO 191
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 191

Gly Leu Leu Val Gly Val Ala Leu Val
1               5

<210> SEQ ID NO 192
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 192

Gly Leu Cys Thr Leu Val Ala Met Leu
1               5

<210> SEQ ID NO 193

<400> SEQUENCE: 193

000

<210> SEQ ID NO 194
<211> LENGTH: 9
```

```
<212> TYPE: PRT
<213> ORGANISM: Artificial Sequence
<220> FEATURE:
<223> OTHER INFORMATION: synthetic/recombinant polypeptide

<400> SEQUENCE: 194

Ile Thr Asp Gln Val Pro Phe Ser Val
1               5

<210> SEQ ID NO 195
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 195

Ile Met Asp Gln Val Pro Phe Ser Val
1               5

<210> SEQ ID NO 196
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 196

Asn Leu Val Pro Met Val Ala Thr Val
1               5

<210> SEQ ID NO 197
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 197

Lys Ile Phe Gly Ser Leu Ala Phe Leu
1               5

<210> SEQ ID NO 198
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 198

Gly Ile Leu Gly Phe Val Phe Thr Leu
1               5

<210> SEQ ID NO 199
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 199

Gly Leu Tyr Asp Gly Met Glu His Leu
1               5

<210> SEQ ID NO 200
<211> LENGTH: 8
<212> TYPE: PRT
```

```
<213> ORGANISM: Artificial Sequence
<220> FEATURE:
<223> OTHER INFORMATION: synthetic/recombinant polypeptide

<400> SEQUENCE: 200

Leu Leu Gly Asp Leu Phe Gly Val
1               5

<210> SEQ ID NO 201
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 201

Glu Ala Ala Gly Ile Gly Ile Leu Thr Val
1               5                   10

<210> SEQ ID NO 202
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 202

Ser Leu Leu Met Trp Ile Thr Gln Cys
1               5

<210> SEQ ID NO 203
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 203

Ser Leu Leu Met Trp Ile Thr Gln Ala
1               5

<210> SEQ ID NO 204
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 204

Leu Leu Gly Arg Asn Ser Phe Glu Val
1               5

<210> SEQ ID NO 205
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 205

Val Leu Gln Glu Leu Asn Val Thr Val
1               5

<210> SEQ ID NO 206
<211> LENGTH: 9
<212> TYPE: PRT
<213> ORGANISM: Artificial Sequence
```

```
<220> FEATURE:
<223> OTHER INFORMATION: synthetic/recombinant polypeptide

<400> SEQUENCE: 206

Ile Leu Ser Leu Glu Leu Met Lys Leu
1               5

<210> SEQ ID NO 207
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 207

Lys Ala Ser Glu Lys Ile Phe Tyr Val
1               5

<210> SEQ ID NO 208
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 208

Lys Ala Ser Glu Lys Ile Thr Tyr Val
1               5

<210> SEQ ID NO 209
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 209

Arg Met Phe Pro Asn Ala Pro Tyr Leu
1               5

<210> SEQ ID NO 210
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 210

Ser Val Tyr Asp Phe Phe Val Trp Leu
1               5

<210> SEQ ID NO 211
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 211

Ser Ile Leu Gln Asp Leu Asn Asn Phe Val
1               5                   10

<210> SEQ ID NO 212
<211> LENGTH: 9
<212> TYPE: PRT
<213> ORGANISM: Artificial Sequence
<220> FEATURE:
```

```
<223> OTHER INFORMATION: synthetic/recombinant polypeptide

<400> SEQUENCE: 212

Gly Ile Leu Gly Phe Val Phe Thr Leu
1               5

<210> SEQ ID NO 213
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 213

Glu Leu Ala Gly Ile Gly Ile Leu Thr Val
1               5                   10

<210> SEQ ID NO 214
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 214

Glu Leu Ala Gly Ile Gly Ile Leu Ile Val
1               5                   10

<210> SEQ ID NO 215
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 215

Ser Leu Leu Met Trp Ile Thr Gln Cys
1               5

<210> SEQ ID NO 216
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 216

Ser Leu Leu Met Trp Ile Thr Gln Cys Phe
1               5                   10

<210> SEQ ID NO 217
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 217

Ser Leu Leu Met Trp Ile Thr Gln Cys Phe Leu
1               5                   10

<210> SEQ ID NO 218
<211> LENGTH: 9
<212> TYPE: PRT
<213> ORGANISM: Artificial Sequence
<220> FEATURE:
<223> OTHER INFORMATION: synthetic/recombinant polypeptide
```

<400> SEQUENCE: 218

Leu Leu Met Trp Ile Thr Gln Cys Phe
1               5

<210> SEQ ID NO 219
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 219

Leu Leu Met Trp Ile Thr Gln Cys Phe Leu
1               5                   10

<210> SEQ ID NO 220
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 220

Leu Met Trp Ile Thr Gln Cys Phe Leu
1               5

<210> SEQ ID NO 221
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 221

Trp Ile Thr Gln Cys Phe Leu Pro Val
1               5

<210> SEQ ID NO 222
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 222

Gly Leu Cys Thr Leu Val Ala Met Leu
1               5

<210> SEQ ID NO 223
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 223

Glu Leu Ala Gly Ile Gly Ile Leu Thr Val
1               5                   10

<210> SEQ ID NO 224
<211> LENGTH: 9
<212> TYPE: PRT
<213> ORGANISM: Artificial Sequence
<220> FEATURE:
<223> OTHER INFORMATION: synthetic/recombinant polypeptide

```
<400> SEQUENCE: 224

Ser Leu Leu Met Trp Ile Thr Gln Ala
1               5

<210> SEQ ID NO 225

<400> SEQUENCE: 225

000

<210> SEQ ID NO 226

<400> SEQUENCE: 226

000

<210> SEQ ID NO 227
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 227

Arg Tyr Leu Glu Asn Gly Lys Glu Thr Leu
1               5                   10

<210> SEQ ID NO 228
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 228

Arg Tyr Leu Lys Asn Gly Lys Glu Thr Leu
1               5                   10

<210> SEQ ID NO 229
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 229

Thr Tyr Leu Pro Thr Asn Ala Ser Leu
1               5

<210> SEQ ID NO 230
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 230

Leu Tyr Gln Asn Val Gly Thr Tyr Val
1               5

<210> SEQ ID NO 231
<211> LENGTH: 9
<212> TYPE: PRT
<213> ORGANISM: Artificial Sequence
<220> FEATURE:
<223> OTHER INFORMATION: synthetic/recombinant polypeptide
```

```
<400> SEQUENCE: 231

Gln Tyr Ile His Ser Ala Asn Val Leu
1               5

<210> SEQ ID NO 232
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 232

Ser Tyr Ile Pro Ser Ala Glu Lys Ile
1               5

<210> SEQ ID NO 233
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 233

Ser Tyr Ile Pro Ser Ala Glu Lys Ile
1               5

<210> SEQ ID NO 234
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 234

Ser Tyr Ile Pro Ser Ala Glu Lys Ile
1               5

<210> SEQ ID NO 235
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 235

Tyr Ile Pro Ser Ala Glu Lys Ile
1               5

<210> SEQ ID NO 236
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 236

Ser Tyr Ile Leu Ser Ala Glu Lys Ile
1               5

<210> SEQ ID NO 237
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 237
```

```
Ser Tyr Ile Ala Ser Ala Glu Lys Ile
1               5
```

<210> SEQ ID NO 238
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 238

```
Asp Thr Leu Val Asn Arg Ile Glu Leu
1               5
```

<210> SEQ ID NO 239
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 239

```
Thr Leu Val Asn Arg Ile Glu Leu
1               5
```

<210> SEQ ID NO 240
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 240

```
Lys Val Pro Arg Asn Gln Asp Trp Leu
1               5
```

<210> SEQ ID NO 241
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 241

```
Arg Ala His Tyr Asn Ile Val Thr Phe
1               5
```

<210> SEQ ID NO 242
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 242

```
Ala Gly Val Asp Asn Arg Glu Cys Ile
1               5
```

<210> SEQ ID NO 243
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 243

```
Ala Ser Asn Glu Asn Met Asp Ala Met
1               5

<210> SEQ ID NO 244
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 244

Ala Ser Asn Glu Asn Met Glu Thr Met
1               5

<210> SEQ ID NO 245
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 245

Ser Ser Leu Glu Asn Phe Arg Ala Tyr Val
1               5                   10

<210> SEQ ID NO 246
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 246

Leu Ser Leu Arg Asn Pro Ile Leu Val
1               5

<210> SEQ ID NO 247
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 247

Lys Ala Val Tyr Asn Phe Ala Thr Cys
1               5

<210> SEQ ID NO 248
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 248

Lys Ala Val Tyr Asn Phe Ala Thr Ala
1               5

<210> SEQ ID NO 249
<211> LENGTH: 11
<212> TYPE: PRT
<213> ORGANISM: Artificial Sequence
<220> FEATURE:
<223> OTHER INFORMATION: synthetic/recombinant polypeptide

<400> SEQUENCE: 249

Ser Gly Val Glu Asn Pro Gly Gly Tyr Cys Leu
```

```
1               5              10
```

<210> SEQ ID NO 250
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 250

```
Phe Gln Pro Gln Asn Gly Gln Phe Ile
1               5
```

<210> SEQ ID NO 251
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 251

```
Lys Cys Ser Arg Asn Arg Gln Tyr Leu
1               5
```

<210> SEQ ID NO 252
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 252

```
Glu Gly Ser Arg Asn Gln Asp Trp Leu
1               5
```

<210> SEQ ID NO 253
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 253

```
Ser Thr His Val Asn His Leu His Cys
1               5
```

<210> SEQ ID NO 254
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 254

```
Arg Leu Leu Glu Phe Tyr Leu Ala Met
1               5
```

<210> SEQ ID NO 255
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 255

```
Arg Arg Leu Gly Arg Thr Leu Leu
1               5
```

<210> SEQ ID NO 256
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 256

Arg Gly Pro Gly Arg Ala Phe Val Thr Ile
1               5                   10

<210> SEQ ID NO 257
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 257

Arg Gly Pro Glu Ser Arg Leu Leu
1               5

<210> SEQ ID NO 258
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 258

Ser Ile Ile Asn Phe Glu Lys Leu
1               5

<210> SEQ ID NO 259
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 259

Ser Val Tyr Asp Phe Phe Val Trp Leu
1               5

<210> SEQ ID NO 260
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 260

Asp Ala Pro Ile Tyr Thr Asn Val
1               5

<210> SEQ ID NO 261
<211> LENGTH: 7
<212> TYPE: PRT
<213> ORGANISM: Artificial Sequence
<220> FEATURE:
<223> OTHER INFORMATION: synthetic/recombinant polypeptide

<400> SEQUENCE: 261

Val Val Tyr Ala Phe Lys Arg
1               5

```
<210> SEQ ID NO 262
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 262

Ser Ser Tyr Arg Arg Pro Val Gly Ile
1               5

<210> SEQ ID NO 263
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 263

Ala Val Tyr Asn Phe Ala Thr Cys
1               5

<210> SEQ ID NO 264
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 264

Tyr Thr Val Lys Tyr Pro Asn Leu
1               5

<210> SEQ ID NO 265
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 265

Arg Cys Gln Ile Phe Ala Asn Ile
1               5

<210> SEQ ID NO 266
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 266

Leu Leu Glu Phe Tyr Leu Ala Met
1               5

<210> SEQ ID NO 267
<211> LENGTH: 8
<212> TYPE: PRT
<213> ORGANISM: Artificial Sequence
<220> FEATURE:
<223> OTHER INFORMATION: synthetic/recombinant polypeptide

<400> SEQUENCE: 267

Val Val Tyr Asp Phe Leu Lys Cys
1               5
```

```
<210> SEQ ID NO 268
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 268

Ser Pro Ser Tyr Val Tyr His Gln Phe
1               5

<210> SEQ ID NO 269
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 269

Ala Met Ala Pro Arg Thr Leu Leu Leu
1               5

<210> SEQ ID NO 270

<400> SEQUENCE: 270

000

<210> SEQ ID NO 271
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 271

Asp Glu Pro Thr Leu Leu Tyr Val Leu Phe Glu Val Phe Asp Val
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 272

Pro Val Ser Lys Met Arg Met Ala Thr Pro Leu Leu Met Gln Ala
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 273

Arg Lys Val Ala Glu Leu Val His Phe Leu Leu Leu Lys Tyr Arg
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: synthetic/recombinant polypeptide
```

```
<400> SEQUENCE: 274

Lys Lys Leu Leu Thr Gln His Phe Val Gln Glu Asn Tyr Leu Glu Tyr
1               5                   10                  15

<210> SEQ ID NO 275
<211> LENGTH: 14
<212> TYPE: PRT
<213> ORGANISM: Artificial Sequence
<220> FEATURE:
<223> OTHER INFORMATION: synthetic/recombinant polypeptide

<400> SEQUENCE: 275

Ser Leu Leu Met Trp Ile Thr Gln Cys Phe Leu Pro Val Phe
1               5                   10

<210> SEQ ID NO 276
<211> LENGTH: 24
<212> TYPE: PRT
<213> ORGANISM: Artificial Sequence
<220> FEATURE:
<223> OTHER INFORMATION: synthetic/recombinant polypeptide

<400> SEQUENCE: 276

Ser Leu Leu Met Trp Ile Thr Gln Cys Phe Leu Pro Val Phe Leu Ala
1               5                   10                  15

Gln Pro Pro Ser Gly Gln Arg Arg
            20

<210> SEQ ID NO 277
<211> LENGTH: 14
<212> TYPE: PRT
<213> ORGANISM: Artificial Sequence
<220> FEATURE:
<223> OTHER INFORMATION: synthetic/recombinant polypeptide

<400> SEQUENCE: 277

Phe Asn Asn Phe Thr Val Ser Phe Trp Leu Arg Val Pro Lys
1               5                   10

<210> SEQ ID NO 278
<211> LENGTH: 20
<212> TYPE: PRT
<213> ORGANISM: Artificial Sequence
<220> FEATURE:
<223> OTHER INFORMATION: synthetic/recombinant polypeptide

<400> SEQUENCE: 278

Gln Ile Leu Asp Gly Glu Asn Cys Thr Leu Ile Asp Ala Leu Leu Gly
1               5                   10                  15

Asp Pro Gln Asp
            20

<210> SEQ ID NO 279
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 279

Gly Arg Ala Met Leu Gly Thr His Thr Met Glu Val Thr Val Tyr
1               5                   10                  15

<210> SEQ ID NO 280
<211> LENGTH: 12
```

```
<212> TYPE: PRT
<213> ORGANISM: Artificial Sequence
<220> FEATURE:
<223> OTHER INFORMATION: synthetic/recombinant polypeptide

<400> SEQUENCE: 280

Glu Glu Ala Ala Gly Ile Gly Ile Leu Thr Val Ile
1               5                   10

<210> SEQ ID NO 281
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 281

Glu Ala Ala Gly Ile Gly Ile Leu Thr Val
1               5                   10

<210> SEQ ID NO 282
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 282

Pro Val Ser Lys Met Arg Met Ala Thr Pro Leu Leu Met Gln Ala
1               5                   10                  15

<210> SEQ ID NO 283
<211> LENGTH: 13
<212> TYPE: PRT
<213> ORGANISM: Artificial Sequence
<220> FEATURE:
<223> OTHER INFORMATION: synthetic/recombinant polypeptide

<400> SEQUENCE: 283

Pro Lys Tyr Val Lys Gln Asn Thr Leu Lys Leu Ala Thr
1               5                   10

<210> SEQ ID NO 284
<211> LENGTH: 16
<212> TYPE: PRT
<213> ORGANISM: Artificial Sequence
<220> FEATURE:
<223> OTHER INFORMATION: synthetic/recombinant polypeptide

<400> SEQUENCE: 284

Ala Cys Tyr Glu Phe Leu Trp Gly Pro Arg Ala Leu Val Glu Thr Ser
1               5                   10                  15

<210> SEQ ID NO 285
<211> LENGTH: 12
<212> TYPE: PRT
<213> ORGANISM: Artificial Sequence
<220> FEATURE:
<223> OTHER INFORMATION: synthetic/recombinant polypeptide

<400> SEQUENCE: 285

Leu Leu Glu Phe Tyr Leu Ala Met Pro Phe Ala Thr
1               5                   10

<210> SEQ ID NO 286
<211> LENGTH: 15
<212> TYPE: PRT
```

```
<213> ORGANISM: Artificial Sequence
<220> FEATURE:
<223> OTHER INFORMATION: synthetic/recombinant polypeptide

<400> SEQUENCE: 286

Leu Lys Glu Phe Thr Val Ser Gly Asn Ile Leu Thr Ile Arg Leu
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 287

Pro Val Ser Lys Met Arg Met Ala Thr Pro Leu Leu Met Gln Ala
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: synthetic/recombinant polypeptide

<400> SEQUENCE: 288

Trp Asn Arg Gln Leu Tyr Pro Glu Trp Thr Glu Ala Gln Arg Leu Asp
1               5                   10                  15

<210> SEQ ID NO 289
<211> LENGTH: 12
<212> TYPE: PRT
<213> ORGANISM: Artificial Sequence
<220> FEATURE:
<223> OTHER INFORMATION: synthetic/recombinant polypeptide

<400> SEQUENCE: 289

Gly Phe Val Phe Thr Leu Thr Val Pro Ser Glu Arg
1               5                   10

<210> SEQ ID NO 290
<211> LENGTH: 24
<212> TYPE: PRT
<213> ORGANISM: Artificial Sequence
<220> FEATURE:
<223> OTHER INFORMATION: synthetic/recombinant polypeptide

<400> SEQUENCE: 290

Phe Trp Arg Gly Glu Asn Gly Arg Lys Thr Arg Ile Ala Tyr Glu Arg
1               5                   10                  15

Met Cys Asn Ile Leu Lys Gly Lys
            20

<210> SEQ ID NO 291
<211> LENGTH: 25
<212> TYPE: PRT
<213> ORGANISM: Artificial Sequence
<220> FEATURE:
<223> OTHER INFORMATION: synthetic/recombinant polypeptide

<400> SEQUENCE: 291

Pro Gly Val Leu Leu Lys Glu Phe Thr Val Ser Gly Asn Ile Leu Thr
1               5                   10                  15

Ile Arg Leu Thr Ala Ala Asp His Arg
            20                  25
```

```
<210> SEQ ID NO 292
<211> LENGTH: 17
<212> TYPE: PRT
<213> ORGANISM: Artificial Sequence
<220> FEATURE:
<223> OTHER INFORMATION: synthetic/recombinant polypeptide

<400> SEQUENCE: 292

Ile Ser Gln Ala Val His Ala Ala His Ala Glu Ile Asn Glu Ala Gly
1               5                   10                  15

Arg

<210> SEQ ID NO 293
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 293

Lys Phe Gly Trp Ser Gly Pro Asp Cys Asn Arg Lys Lys Pro Ala
1               5                   10                  15

<210> SEQ ID NO 294
<211> LENGTH: 20
<212> TYPE: PRT
<213> ORGANISM: Artificial Sequence
<220> FEATURE:
<223> OTHER INFORMATION: synthetic/recombinant polypeptide

<400> SEQUENCE: 294

Gly Leu Asn Gly Pro Asp Ile Tyr Lys Gly Val Tyr Gln Phe Lys Ser
1               5                   10                  15

Val Glu Phe Asp
            20

<210> SEQ ID NO 295
<211> LENGTH: 19
<212> TYPE: PRT
<213> ORGANISM: Artificial Sequence
<220> FEATURE:
<223> OTHER INFORMATION: synthetic/recombinant polypeptide

<400> SEQUENCE: 295

Glu Pro Leu Thr Ser Leu Thr Pro Arg Cys Asn Thr Ala Trp Asn Arg
1               5                   10                  15

Leu Lys Leu

<210> SEQ ID NO 296
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 296

Ala Asp Ile Tyr Thr Phe Pro Leu Glu Asn Ala Pro Ile Gly His
1               5                   10                  15

<210> SEQ ID NO 297
<211> LENGTH: 29
<212> TYPE: DNA
<213> ORGANISM: Artificial Sequence
<220> FEATURE:
```

<223> OTHER INFORMATION: synthetic/recombinant polynucleotide

<400> SEQUENCE: 297
ctttagatct cgaccacgtt tcttggagc                                    29

<210> SEQ ID NO 298
<211> LENGTH: 30
<212> TYPE: DNA
<213> ORGANISM: Artificial Sequence
<220> FEATURE:
<223> OTHER INFORMATION: synthetic/recombinant polynucleotide

<400> SEQUENCE: 298
ctttgaattc cttgctctgt gcagattcag                                   30

<210> SEQ ID NO 299
<211> LENGTH: 15
<212> TYPE: PRT
<213> ORGANISM: Artificial Sequence
<220> FEATURE:
<223> OTHER INFORMATION: synthetic/recombinant polypeptide

<400> SEQUENCE: 299

Gly Leu Asn Asp Ile Phe Glu Ala Gln Lys Ile Glu Trp His Glu
1               5                   10                  15

<210> SEQ ID NO 300
<211> LENGTH: 67
<212> TYPE: DNA
<213> ORGANISM: Artificial Sequence
<220> FEATURE:
<223> OTHER INFORMATION: synthetic/recombinant polynucleotide

<400> SEQUENCE: 300
ctttctggat atctcattcg tgccattcga ttttctgagc ctcgaagatg tcgttcagac    60
cgccacc                                                             67

<210> SEQ ID NO 301
<211> LENGTH: 35
<212> TYPE: PRT
<213> ORGANISM: Artificial Sequence
<220> FEATURE:
<223> OTHER INFORMATION: synthetic/recombinant polypeptide

<400> SEQUENCE: 301

Thr Thr Ala Pro Ser Ala Gln Leu Lys Lys Lys Leu Gln Ala Leu Lys
1               5                   10                  15

Lys Lys Asn Ala Gln Leu Lys Trp Lys Leu Gln Ala Leu Lys Lys Lys
            20                  25                  30

Leu Ala Gln
        35

<210> SEQ ID NO 302
<211> LENGTH: 7
<212> TYPE: PRT
<213> ORGANISM: Artificial Sequence
<220> FEATURE:
<223> OTHER INFORMATION: synthetic/recombinant polypeptide

<400> SEQUENCE: 302

Gly Gly Gly Ser Gly Gly Ser
1               5

<210> SEQ ID NO 303

```
<211> LENGTH: 59
<212> TYPE: DNA
<213> ORGANISM: Artificial Sequence
<220> FEATURE:
<223> OTHER INFORMATION: synthetic/recombinant polynucleotide

<400> SEQUENCE: 303
ctttgatatc tcaatgatgg tgatgatggt ggccggtgcg ctgagccagt tccttttcc      59

<210> SEQ ID NO 304
<211> LENGTH: 88
<212> TYPE: DNA
<213> ORGANISM: Artificial Sequence
<220> FEATURE:
<223> OTHER INFORMATION: synthetic/recombinant polynucleotide

<400> SEQUENCE: 304
ctttgatatc tcagtggtgg tggtggtggt ggctgccgct gccgccgccg ctgccgccgc      60
catgatggtg atgatggtgg ccggtgcg                                        88

<210> SEQ ID NO 305
<211> LENGTH: 35
<212> TYPE: PRT
<213> ORGANISM: Artificial Sequence
<220> FEATURE:
<223> OTHER INFORMATION: synthetic/recombinant polypeptide

<400> SEQUENCE: 305

Thr Thr Ala Pro Ser Ala Gln Leu Glu Lys Glu Leu Gln Ala Leu Glu
1               5                  10                  15

Lys Glu Asn Ala Gln Leu Glu Trp Glu Leu Gln Ala Leu Glu Lys Glu
            20                  25                  30

Leu Ala Gln
        35

<210> SEQ ID NO 306
<211> LENGTH: 10
<212> TYPE: PRT
<213> ORGANISM: Artificial Sequence
<220> FEATURE:
<223> OTHER INFORMATION: synthetic/recombinant polypeptide

<400> SEQUENCE: 306

Ser Gly Ser Gly His His His His His His
1               5                  10

<210> SEQ ID NO 307
<211> LENGTH: 4
<212> TYPE: PRT
<213> ORGANISM: Artificial Sequence
<220> FEATURE:
<223> OTHER INFORMATION: synthetic/recombinant polypeptide

<400> SEQUENCE: 307

Gly Ser Gly Cys
1

<210> SEQ ID NO 308
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 308
```

```
Gly Ile Leu Gly Phe Val Phe Thr Leu
1               5
```

<210> SEQ ID NO 309
<211> LENGTH: 9
<212> TYPE: PRT
<213> ORGANISM: Artificial Sequence
<220> FEATURE:
<223> OTHER INFORMATION: synthetic/recombinant polypeptide

<400> SEQUENCE: 309

```
Gly Ile Leu Gly Phe Val Phe Thr Leu
1               5
```

<210> SEQ ID NO 310
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 310

```
His His His His His His
1               5
```

<210> SEQ ID NO 311
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 311

```
His His His His His His His His His His His His
1               5                   10
```

<210> SEQ ID NO 312
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 312

```
His His His His His His Gly Gly Gly Ser Gly Gly Gly Ser Gly Ser
1               5                   10                  15

His His His His His His
                20
```

<210> SEQ ID NO 313
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Modified by NP-Beta-A-HA306-318

<400> SEQUENCE: 313

```
His His His His His His Gly Ser Gly
1               5
```

<210> SEQ ID NO 314
<211> LENGTH: 4
<212> TYPE: PRT

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by HA306-318
<220> FEATURE:
<221> NAME/KEY: MISC_FEATURE
<222> LOCATION: (4)..(4)
<223> OTHER INFORMATION: Modified by Cy5.5

<400> SEQUENCE: 314

Gly Ser Gly Cys
1

<210> SEQ ID NO 315
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: Modified by NYESO1

<400> SEQUENCE: 315

His His His His His His Ser Gly Ser Gly
1               5                   10

<210> SEQ ID NO 316
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by DTB

<400> SEQUENCE: 316

Ser Gly Ser Gly Pro Lys Tyr Val Lys Gln Asn Thr Leu Lys Leu Ala
1               5                   10                  15

Thr

<210> SEQ ID NO 317
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by HA306-318 NP-Beta-A

<400> SEQUENCE: 317

Gly Ser Gly His His His His His His
1               5

<210> SEQ ID NO 318
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
```

```
<222> LOCATION: (1)..(1)
<223> OTHER INFORMATION: PHOSPHORYLATION
<220> FEATURE:
<221> NAME/KEY: MISC_FEATURE
<222> LOCATION: (8)..(8)
<223> OTHER INFORMATION: Modified by NP-beta-A-HA306-318

<400> SEQUENCE: 318

Tyr Asp Asp Asp Asp Gly Ser Gly
1               5
```

REVERSIBLE PROTEIN MULTIMERS, METHODS FOR THEIR PRODUCTION AND USE

RELATED APPLICATIONS

This application is a continuation under 35 U.S.C. § 120 of U.S. application Ser. No. 13/877,200, filed Jul. 12, 2013, now U.S. Pat. No. 10,023,657, which is a national stage filing under 35 U.S.C. § 371 of international application PCT/US2011/054335, filed Sep. 30, 2011, which was published under PCT Article 21(2) in English, and claims the benefit under 35 U.S.C. § 119(e) of U.S. provisional application Ser. No. 61/389,092, filed on Oct. 1, 2010, the entire disclosures of which are incorporated herein by reference.

REFERENCE TO AN ELECTRONIC SEQUENCE LISTING

The contents of the electronic sequence listing (L046170188US02-SUBSEQ-JRV.txt; Size: 69,908 bytes; and Date of Creation: Jan. 12, 2024) is herein incorporated by reference in its entirety.

BACKGROUND

Fluorescent MHC-peptide multimers, commonly referred to as tetramers are widely used to detect, enumerate, analyze and sort antigen-specific CD8+ T cells (1, 2). Monomeric MHC-peptide complexes are produced by refolding of a MHC heavy and light chain in the presence of a peptide of interest and subsequently are biotinylated at a C-terminally added biotinylation sequence peptide (BSP, LHHILDAQKMVWNHR, SEQ ID NO: 1) the biotin-transferase BirA. Fluorescent conjugates are obtained by reaction of biotinylated MHC-I-peptide monomers with phycoerythrin (PE) or allophycocyanine (APC) labeled streptavidin (2, 3). Although such reagents generally perform well, they have shortcomings: 1) they are heterogeneous in terms of stoichiometry and configuration, which compromises stringent binding analysis (4). 2) The enzymatic biotinylation is tedious, expensive and in the case of unstable MHC-peptide monomers causes degradation during the enzymatic reaction, which is performed at elevated temperatures (5). 3) For some studies antigen-specific CD8+ T cells are isolated by cell sorting (e.g. FACS or MACS). Conventional multimers stably bind to cells and induce strong T cell activation, which can induces death and result in loss of CD8+ T cells, questioning that the surviving cells are representative for the original populations (5-8). To overcome this, reversible multimer have been introduced, which contain low affinity biotin analogues and hence dissociate upon addition of free biotin. With these reagents significantly improved sorting and cloning efficiencies are obtained; however, they are costly and tend to be less stable (5, 8).

SUMMARY

Some aspects of this invention relate to reagents for reversible staining of cells. Some aspects of this invention provide staining reagents that comprise a core structure, referred to herein as a carrier molecule, to which a plurality of monomeric proteins can reversibly bind to form a protein multimer. In some embodiments, the carrier molecule itself is a detectable molecule, for example, a fluorophore. In some embodiments, the proteins that reversibly bind to the carrier molecule are proteins that also specifically bind a molecular target, for example, a specific cellular ligand or receptor, allowing for staining of the molecular target with the protein multimer. Since the bond of the protein and the carrier molecule is reversible, the protein multimer complex can be dissolved, resulting in dissociation of the proteins from the carrier molecule and, thus, in re-monomerization of the bound proteins.

The protein multimers provided by some embodiments described herein are useful, for example, for cell staining and cell isolation procedures. The multimers provided by some embodiments of this invention can be dissolved under non-toxic, physiological conditions, for example, by addition of an agent interfering with the reversible binding of protein and core structure of the multimer. Accordingly, one advantage of the instantly provided protein multimers is that, in contrast to most other staining agents, they do not expose stained cells to the undesirable effects of permanent staining. Dissolution of the multimer structure used for staining live cells avoids undesired biological effects of continued association of cells with a dye or a multimeric protein structure, for example, continued activation of T-cell receptor signaling in MHC-stained T-cells. Staining procedures using the instantly described protein multimers, thus, allow for "minimally invasive" staining of cells, which is a requirement for the isolation of native cells that are sensitive to staining procedures, including, for example, certain T-cell populations.

Some aspects of this invention provide methods and reagents for the generation of peptide-loaded MHC molecules, for example, of peptide-loaded MHC class II molecules. In some embodiments, methods for the efficient production of molecularly defined, homogeneously peptide-loaded MHC class II molecules are provided. In some embodiments, MHC class II molecules are loaded with an antigenic peptide that is conjugated to a tag, for example, a tag allowing for peptide or protein isolation and/or purification by chromatography, for example, by affinity or ion exchange chromatography. In some embodiments, tagged MHC class II binding peptides are provided. In some embodiments, the tag is an acidic tag, for example, a tag comprising a plurality of acidic amino acid residues, or an acidic fluorophore, for example, an acidic cyanine dye. In some embodiments, the tag, for example, the acidic tag, is reversibly conjugated to the antigenic peptide of interest, for example via a cleavable linker. In some embodiments, the cleavable linker is a photocleavable linker. In some embodiments, the cleavable linker comprises a cleavage site for an enzyme, for example, a protease, or a chemical.

Some aspects of the invention, including aspects and embodiments not mentioned in this summary are described in more detail elsewhere in the specification and in the claims.

Some aspects of this invention provide protein multimers that include (a) a multivalent carrier molecule, and (b) a plurality of proteins bound to the carrier molecule. In some embodiments, at least one of the proteins is conjugated to the carrier molecule via a non-covalent bond with a dissociation constant 1 μM>$K_D$≥10 fM. In some embodiments, at least one of the peptides or proteins is conjugated to the carrier molecule via a chelate complex bond.

Some aspects of this invention provide multivalent chelants that comprise a water-soluble carrier molecule and a plurality of chelant moieties conjugated to the carrier molecule.

Some aspects of this invention provide multivalent chelants that comprise a carrier molecule or structure, and a plurality of chelant moieties conjugated to the carrier molecule or structure, wherein the carrier molecule or structure has a diameter of less than 0.1 nm, less than 0.2 nm, less than 0.25 nm, less than 0.3 nm, less than 0.4 nm, less than 0.5 nm, less than 0.6 nm, less than 0.7 nm, less than 0.75 nm, less than 0.8 nm, less than 0.9 nm, less than 1 nm, less than 1.1 nm, less than 1.2 nm, less than 1.3 nm, less than 1.4 nm, less than 1.5 nm, less than 1.6 nm, less than 1.7 nm, less than 1.8 nm, less than 1.9 nm, less than 2 nm, less than 2.5 nm, less than 3 nm, less than 4 nm, less than 5 nm, less than 6 nm, less than 7 nm, less than 8 nm, less than 9 nm, or less than 10 nm. In some embodiments, the diameter of the carrier molecule is less than 20 nm, less than 30 nm, less than 40 nm, less than 50 nm, less than 60 nm, less than 70 nm, less than 80 nm, less than 90 nm, less than 100 nm, less than 200 nm, less than 300 nm, less than 400 nm, less than 500 nm, less than 600 nm, less than 700 nm, less than 800 nm, less than 900 nm, or less than 1 µm.

Some aspects of this invention provide methods for the production of protein multimers that comprise a step of contacting a monomeric chelant moiety-conjugated MHC molecule with a carrier molecule, for example, a water-soluble carrier molecule or a carrier molecule or structure described herein, that is conjugated to a plurality of chelant moieties under conditions suitable for formation of a chelate complex between the chelant moieties conjugated to the MHC molecule and the chelant moieties conjugated to the carrier molecule.

Some aspects of this invention provide methods for the production of MHC molecules that are conjugated to a ligand via a chelate complex bond, comprising a step of contacting an MHC molecule conjugated to a first chelant with a ligand molecule conjugated to a second chelant under conditions suitable for formation of a chelate complex between the first and the second chelant. In some embodiments, the resulting MHC molecule is then contacted with a multivalent binding molecule binding the ligand to produce reversible MHC multimers.

Some aspects of this invention provide methods to generate peptide-loaded MHC molecules that are conjugated to a chelant using MHC binding peptides conjugated to a tag, the methods comprising the steps of providing an MHC molecule bound to an antigenic MHC molecule-binding peptide that is conjugated to a tag via a cleavable linker, removing the tag from the antigenic peptide, and conjugating a chelant moiety to a heavy chain of the MHC molecule.

Some aspects of this invention provide methods for staining, detecting, and isolating cells, the methods comprising a step of contacting a population of cells with a protein multimer as described herein, for example, with a multimer comprising a chelate bond and a detectable label, and performing an assay to detect a cell binding the multimer.

Some aspects of this invention provide method for the isolation of cells that bind a multimer as described herein, the methods comprising the steps of (a) contacting a population of cells with a protein multimer as provided herein, for example, with a multimer comprising a chelate bond and a detectable label, (b) optionally, detecting a cell binding the multimer, and (c) isolating the cell binding the multimer.

Some aspects of this invention provide methods for the manipulation of T-cell populations with protein multimers, the methods comprising a step of contacting a population of cells expressing a T-cell receptor with an MHC multimer as described herein under conditions suitable for the multimer to bind to the T-cell receptor and for a time sufficient for the T-cell receptor/MHC class I molecule interaction to activate a T-cell expressing the T-cell receptor and binding the MHC multimer.

Some aspects of this invention provide cells or cell populations that are contacted with a protein multimer as provided herein, for example, with an MHC multimer.

Some aspects of this invention provide kits comprising peptide-loaded or empty MHC molecules as provided herein.

Some aspects of this invention provide isolated peptide-loaded MHC molecules that comprise an MHC heavy chain, and an antigenic peptide. In some embodiments, the peptide is conjugated to a tag, for example, a tag for ion exchange chromatography.

Some aspects of this invention provide methods for the generation of peptide-loaded MHC molecules, for example, MHC class II molecules, comprising a step of contacting an empty MHC molecule with an antigenic peptide conjugated to a tag under conditions suitable for the antigenic peptide to bind the MHC molecule. In some embodiments, the tag is a tag for ion exchange chromatography and the method, in some embodiments, includes a step of isolating peptide-loaded MHC molecules by performing a chromatography procedure.

Some aspects of this invention provide methods for the generation of MHC class II molecules, empty or peptide-loaded, the method comprising a step of contacting an MHC class II type alpha heavy chain with an MHC class II type beta heavy chain under conditions suitable for the alpha and the beta chain to form a heterodimeric MHC class II molecule. In some embodiments, at least one of the MHC class II heavy chains is conjugated to a tag. In some embodiments, a step of isolating the MHC class II molecule is performed, wherein the isolating comprises a step of chromatography, for example, affinity chromatography.

Some aspects of this invention provide a protein multimer comprising (a) a multivalent carrier molecule, and (b) a plurality of proteins bound to the carrier molecule. In some embodiments, at least one of the plurality of proteins is conjugated to the carrier molecule via a non-covalent bond with a dissociation constant 1 µM>$K_D$≥10 fM. In some embodiments, the dissociation constant is $K_D$≥0.1 pM. In some embodiments, the dissociation constant is $K_D$≥1 pM. In some embodiments, the dissociation constant is $K_D$≥10 pM. In some embodiments, the dissociation constant is $K_D$≥100 pM. In some embodiments, the dissociation constant is $K_D$≥1 nM. In some embodiments, the dissociation constant is $K_D$≥10 nM. In some embodiments, the dissociation constant is $K_D$<100 nM. In some embodiments, the dissociation constant is $K_D$<10 nM. In some embodiments, the dissociation constant is $K_D$<1 nM. In some embodiments, the dissociation constant is $K_D$<100 pM. In some embodiments, the dissociation constant is $K_D$<10 pM. Some aspects of this invention provide a protein multimer comprising (a) a multivalent carrier molecule, and (b) a plurality of proteins bound to the carrier molecule. In some embodiments, at least one of the plurality of proteins is conjugated to the carrier molecule via a chelate complex bond. In some embodiments, the chelate complex bond is a bond with a dissociation constant 5 µM>$K_D$≥1 fM. In some embodiments, the protein is an MHC molecule and the protein multimer is an MHC multimer. In some embodiments, the chelate complex bond comprises a chelant conjugated to the MHC molecule, and a chelant conjugated to the carrier molecule. In some embodiments, the chelant conjugated to the carrier molecule is of a different structure than the chelant conjugated to the MHC molecule. In some embodiments, the MHC molecule comprises an MHC α chain. In some embodiments, the MHC molecule further comprises an MHC α chain or a β2 microglobulin chain. In some embodiments, the MHC molecule is an MHC class I molecule. In some embodiments, the MHC molecule is an MHC class II molecule. In some embodiments, the chelant conjugated to the MHC molecule is C-terminally conjugated to the MHC β chain. In some embodiments, the chelant conjugated to the MHC molecule is C-terminally conjugated to the MHC β chain or the β2 microglobulin chain. In some embodiments, the chelant conjugated to the MHC molecule is a peptide comprising a chelant moiety. In some embodiments, the peptide comprising a chelant moiety is fused to a polypeptide chain comprised by the MHC molecule. In some embodiments, the peptide comprising a chelant moiety comprises a poly-Histidine sequence. In some embodiments, the poly-Histidine sequence comprises 3-24 His residues. In some embodiments, the chelant conjugated to the MHC molecule comprises a His6 (SEQ ID NO: 310) tag, a His12 (SEQ ID NO: 311) tag, or a 2×His6 (SEQ ID NO: 312) tag. In some embodiments, the chelant conjugated to the carrier molecule comprises an NTA moiety. In some embodiments, the NTA moiety is bound to the carrier molecule in mono-NTA configuration. In some embodiments, the NTA moiety is bound to the carrier molecule in poly-NTA configuration. In some embodiments, the NTA moiety is bound to the carrier molecule in di-NTA, or tetra-NTA configuration. In some embodiments, the NTA moiety is bound to a linker. In some embodiments, the linker comprises a maleimide moiety or derivative. In some embodiments, the linker comprises an oxime moiety or derivative. In some embodiments, the linker is between about 9 Å and about 23 Å long. In some embodiments, the linker is covalently bound to the carrier molecule. In some embodiments, the linker is covalently bound to a ligand of a binding molecule, and wherein the binding molecule is covalently bound to the carrier molecule. In some embodiments, the ligand is biotin and the binding molecule is streptavidin. In some embodiments, the chelate complex bond further comprises a divalent cation. In some embodiments, the divalent cation is an Ni2+, Cu2+, Zn2+, Co2+, Cd2+, Sr2+, Mn2+, Fe2+, Mg2+, Ca2+, or Ba2+ ion. In some embodiments, the carrier molecule is a fluorophore, a phycobilin, phycoerythrin or allophycocyanine, a quantum dot (QDOT® (fluorescent particles)), a microsphere (e.g., a fluorescent microsphere (e.g. FLUO-ROSPHERES® type), a magnetic particle, or a nanoparticle. In some embodiments, the MHC molecule is an empty MHC molecule or a peptide-loaded MHC molecule. In some embodiments, the peptide-loaded MHC molecule is chosen from the MHC molecules disclosed in Table 2. In some embodiments, the MHC molecule comprises an HLA-A*0201 heavy chain. In some embodiments, the MHC molecule is loaded with an antigenic peptide. In some embodiments, the MHC molecule is loaded with a peptide comprising the sequence GILGFVFTL (SEQ ID NO: 2). In some embodiments, the multimer is a tetramer. In some embodiments, the antigenic peptide is conjugated to a tag. In some embodiments, the tag is conjugated to the peptide via a cleavable linker. In some embodiments, the linker is a photocleavable linker. In some embodiments, the linker is an NPPA linker. In some embodiments, the linker is a peptide linker that comprises an amino acid sequence that can be cleaved by a protease or by a chemical. In some embodiments, the tag is an acidic peptide tag. In some embodiments, the acidic peptide tag comprises a plurality of acidic amino acid sequences. In some embodiments, the tag is a pY-D4, pY-D5, pY-D6, pY-D7, pY-D8, pY-D9, or pY-D10 tag. In some embodiments, the tag is a pY-E4, pY-E5, pY-E6, pY-E7, pY-E8, pY-E9, or pY-E10 tag. In some embodiments, the tag is a desthiobiotin (DTB) tag.

Some aspects of this invention provide a multivalent chelant comprising a water-soluble carrier molecule, and a plurality of chelant moieties conjugated to the carrier molecule. Some aspects of this invention provide a multivalent chelant comprising a carrier molecule or structure, and a plurality of chelant moieties conjugated to the carrier molecule or structure. In some embodiments, the carrier molecule or structure has a diameter of less than 0.1 nm, less than 0.2 nm, less than 0.25 nm, less than 0.3 nm, less than 0.4 nm, less than 0.5 nm, less than 0.6 nm, less than 0.7 nm, less than 0.75 nm, less than 0.8 nm, less than 0.9 nm, less than mm, less than 1.1 nm, less than 1.2 nm, less than 1.3 nm, less than 1.4 nm, less than 1.5 nm, less than 1.6 nm, less than 1.7 nm, less than 1.8 nm, less than 1.9 nm, less than 2 nm, less than 2.5 nm, less than 3 nm, less than 4 nm, less than 5 nm, less than 6 nm, less than 7 nm, less than 8 nm, less than 9 nm, or less than 10 nm. In some embodiments, the diameter of the carrier molecule is less than 20 nm, less than 30 nm, less than 40 nm, less than 50 nm, less than 60 nm, less than 70 nm, less than 80 nm, less than 90 nm, less than 100 nm, less than 200 nm, less than 300 nm, less than 400 nm, less than 500 nm, less than 600 nm, less than 700 nm, less than 800 nm, less than 900 nm, or less than 1 µm. In some embodiments, the chelant moieties are nitrilotriacetic acid (NTA) moieties. In some embodiments, the NTA moieties are in mono-NTA configuration. In some embodiments, the NTA moieties are in poly-NTA configuration. In some embodiments, the NTA moieties are in di-NTA, or tetra-NTA configuration. In some embodiments, the NTA moieties are bound to a linker. In some embodiments, the linker comprises a maleimide moiety. In some embodiments, the linker comprises an oxime moiety. In some embodiments, the linker is between about 9 Å and about 23 Å long. In some embodiments, the linker is covalently bound to the carrier molecule. In some embodiments, the linker is covalently bound to a ligand of a binding molecule, and wherein the binding molecule is covalently bound to the carrier molecule. In some embodiments, the ligand is biotin and the binding molecule is streptavidin. In some embodiments, the carrier molecule is a fluorophore, a phycobilin, phycoerythrin or allophycocyanine, or a quantum dot (QDOT®). In some embodiments, a plurality of the chelant moieties conjugated to the carrier molecule form chelate complex bonds to a plurality of chelant moiety-conjugated monomeric molecules, thus forming a multimer of the monomeric molecule. In some embodiments, the monomeric molecule is a polyprotein. In some embodiments, the monomeric molecule is a small molecule compound. In some embodiments, the monomeric molecule is a polynucleotide. In some embodiments, the monomeric molecule is a ligand of a receptor. In some embodiments, the receptor is a cell-surface receptor. In some embodiments, the receptor is a T-cell receptor. In some embodiments, the monomeric molecule is an MHC molecule. In some embodiments, the monomeric molecule is an MHC class I molecule. In some embodiments, the MHC molecule comprises an HLA-A*0201 heavy chain. In some embodiments, the MHC molecule is an MHC class II molecule. In some embodiments, the MHC molecule is loaded with an antigenic peptide. In some embodiments, the MHC molecule is loaded with a peptide comprising the sequence GILGFVFTL (SEQ ID NO: 3). In some embodiments, the multivalent chelant is a tetravalent chelant. In some embodiments, the tag is an acidic peptide tag. In some embodiments, the acidic peptide tag comprises a plurality of acidic amino acid sequences. In some embodiments, the tag is a pY-D4, pY-D5, pY-D6, pY-D7, pY-D8, pY-D9, pY-D10, pY-E4, pY-E5, pY-E6, pY-E7, pY-E8, pY-E9, or pY-E10 tag. In some embodiments, the tag is a desthiobiotin (DTB) tag.

Some aspects of this invention provide a method comprising contacting a monomeric chelant moiety-conjugated MHC molecule with a water-soluble carrier molecule conjugated to a plurality of chelant moieties under conditions suitable for formation of a chelate complex between the chelant moieties conjugated to the MHC molecule and the chelant moieties conjugated to the carrier molecule. In some embodiments, the chelant moieties conjugated to the carrier molecule are NTA moieties. In some embodiments, the NTA moieties are in mono-NTA configuration. In some embodiments, the NTA moieties are in poly-NTA configuration. In some embodiments, the NTA moieties are in di-NTA, or tetra-NTA configuration. In some embodiments, the NTA moieties are bound to a linker. In some embodiments, the linker is between about 9 Å and about 23 Å long. In some embodiments, the linker is covalently bound to the carrier molecule. In some embodiments, the linker is covalently bound to a ligand of a binding molecule, and wherein the binding molecule is covalently bound to the carrier molecule. In some embodiments, the ligand is biotin and the binding molecule is streptavidin. In some embodiments, the carrier molecule is a fluorophore. In some embodiments, the carrier molecule is a phycobilin. In some embodiments, the carrier molecule is phycoerythrin or allophycocyanine. In some embodiments, the carrier molecule is a quantum dot (QDOT®). In some embodiments, the carrier molecule is a magnetic particle. In some embodiments, the carrier molecule is a nanoparticle. In some embodiments, the carrier molecule is PE conjugated to streptavidin. In some embodiments, the carrier molecule conjugated to a plurality of chelant moieties is generated by incubating a carrier molecule conjugated to a plurality of binding molecules with an excess of chelant-conjugated ligand under conditions suitable for the ligand to bind the binding molecule. In some embodiments, the molar ratio of carrier:ligand is between 1:2 and 1:10. In some embodiments, the molar ratio of carrier:ligand is 1:5. In some embodiments, the incubating is performed at a temperature between 2-16° C. In some embodiments, the incubating is performed at about 4° C. In some embodiments, the method comprises a step of incubating the carrier molecules contacted with the ligand with NiSO4. In some embodiments, the method comprises a step of contacting the carrier molecule conjugated to a plurality of chelant moieties with a molar excess of the MHC molecule conjugated to a chelant. In some embodiments, the excess is 2-20 fold. In some embodiments, the excess is 10-fold. In some embodiments, the MHC molecule is an MHC class I molecule. In some embodiments, the MHC molecule comprises an HLA-A*0201 heavy chain. In some embodiments, the MHC molecule is an MHC class II molecule. In some embodiments, the MHC molecule is loaded with an antigenic peptide.

Some aspects of this invention provide a method comprising contacting an MHC molecule conjugated to a first chelant with a ligand molecule conjugated to a second chelant under conditions suitable for formation of a chelate complex between the first and the second chelant. In some embodiments, the first chelant comprises a peptide. In some embodiments, the peptide is C-terminally fused to a polypeptide chain comprised by the MHC molecule. In some embodiments, the peptide comprises a poly-Histidine sequence. In some embodiments, the poly-Histidine sequence comprises between 3 and 24 His residues. In some embodiments, the chelant conjugated to the MHC molecule comprises a His6 (SEQ ID NO: 310) tag, a His12 (SEQ ID NO: 311) tag, or a 2×His6 (SEQ ID NO: 312) tag. In some embodiments, the second chelant is NTA. In some embodiments, the NTA is in mono-NTA configuration. In some embodiments, the NTA is in poly-NTA configuration. In some embodiments, the NTA is in di-NTA, or tetra-NTA configuration. In some embodiments, the NTA is bound to a linker. In some embodiments, the linker is covalently bound to the ligand molecule. In some embodiments, the linker is between about 9 Å and about 23 Å long. In some embodiments, the method further comprises contacting the ligand molecule with a multivalent binding molecule under conditions suitable for the ligand to bind the multivalent binding molecule. In some embodiments, the ligand is biotin and the binding molecule is streptavidin. In some embodiments, the binding molecule is conjugated to a carrier molecule. In some embodiments, the carrier molecule is a fluorophore. In some embodiments, the carrier molecule is a phycobilin. In some embodiments, the carrier molecule is phycoerythrin or allophycocyanine. In some embodiments, the carrier molecule is a quantum dot (QDOT®). In some embodiments, the carrier molecule is a magnetic particle. In some embodiments, the carrier molecule is a nanoparticle. In some embodiments, the MHC molecule is an MHC class I molecule. In some embodiments, the MHC molecule comprises an HLA-A*0201 heavy chain. In some embodiments, the MHC molecule is an MHC class II molecule. In some embodiments, the MHC molecule is loaded with an antigenic peptide. In some embodiments, the MHC molecule is loaded with a peptide comprising the sequence GILGFVFTL (SEQ ID NO: 2) or a peptide comprising a sequence provided in Table 2.

Some aspects of this invention provide a method comprising providing an MHC molecule bound to an antigenic MHC molecule-binding peptide that is conjugated to a tag via a cleavable linker, removing the tag from the antigenic peptide, and conjugating a chelant moiety to a heavy chain of the MHC molecule. In some embodiments, the method further comprises contacting a multivalent chelant molecule with the MHC molecule under conditions suitable for the chelant moiety conjugated to the MHC molecule to form a chelate complex bind with a chelant moiety of the multivalent chelant molecule.

Some aspects of this invention provide a method comprising contacting a population of cells with a protein multimer according to any preceding claim, wherein the multimer comprises a chelate bond and a detectable label, and detecting a cell binding the multimer. In some embodiments, the protein multimer is an MHC multimer. In some embodiments, the detectable label is a fluorophore. In some embodiments, detecting is by fluorescent microscopy or cell sorting. In some embodiments, the detectable label is a magnetic particle. In some embodiments, detecting is by isolating the cell binding the multimer. In some embodiments, detecting comprises quantifying a number of cells binding the multimer. In some embodiments, detecting comprises quantifying a number of cells binding the multimer as a ratio to a number of cells of the population of cells that do not bind the multimer. In some embodiments, the method further comprises reversing the binding of the multimer to the cell binding the multimer by contacting the cells binding the multimer with a monomeric chelant moiety competing for the chelate complex bond comprised by the multimer. In some embodiments, the monomeric chelant moiety is an imidazole molecule.

Some aspects of this invention provide a method comprising contacting a population of cells with a protein multimer according to any preceding claim, wherein the multimer comprises a chelate bond and a detectable label; optionally, detecting a cell binding the multimer; and isolating the cell binding the multimer. In some embodiments, the multimer is an MHC multimer. In some embodiments, the method further comprises reversing the binding of the multimer to the cell binding the multimer by contacting the isolated cell binding the multimer with a monomeric chelant moiety competing for the chelate complex bond comprised by the multimer. In some embodiments, the monomeric chelant moiety is an imidazole molecule. In some embodiments, the isolated cell is a T-cell. In some embodiments, the T-cell does not undergo CD8/TCR-mediated activation during the contacting, optionally, during the detection, and during the isolation step. In some embodiments, the isolated T-cell is part of an isolated, native T-cell population.

Some aspects of this invention provide a method comprising, contacting a population of cells expressing a T-cell receptor with an MHC multimer provided herein under conditions suitable for the multimer to bind to the T-cell receptor and for a time sufficient for the T-cell receptor/MHC class I molecule interaction to activate a T-cell expressing the T-cell receptor and binding the MHC multimer. Some aspects of this invention provide a method comprising, contacting a population of cells expressing a T-cell receptor with an MHC multimer provided herein under conditions suitable for the multimer to bind to the T-cell receptor and to render the T-cell non-responsive to a naturally occurring antigen. In some embodiments, the method further comprises contacting the population of T-cells with an agent able to release the chelate complex bond of the MHC multimer after the cells were contacted with the multimer.

Some aspects of this invention provide a cell or cell population comprising a cell contacted with the protein multimer of any preceding claim, wherein the multimer comprises a chelate complex bond. In some embodiments, the multimer is an MHC multimer. In some embodiments, the cell is or has been contacted with an excess of monomeric chelant moieties competing for the chelate complex bond comprised by the multimer.

Some aspects of this invention provide a kit comprising an MHC multimer as provided in any preceding claim. In some embodiments, the MHC multimer is loaded with an antigenic peptide. In some embodiments, the MHC multimer is an empty MHC multimer. In some embodiments, the kit further comprises at least one antigenic peptide that can be loaded onto the empty MHC multimer. In some embodiments, the kit comprises 2, 3, 4, 5, 6, 7, 8, 9, 10, or more than 10 different antigenic peptides. In some embodiments, the antigenic peptides are antigenic peptides of tumor antigens.

Some aspects of this invention provide an isolated peptide-loaded MHC molecule comprising an MHC heavy chain, and an antigenic peptide. In some embodiments, the peptide is conjugated to a tag. In some embodiments, the tag is an affinity tag. In some embodiments, the tag is a desthiobiotin (DTB) tag. In some embodiments, the peptide is conjugated to a tag for ion exchange chromatography. In some embodiments, the MHC molecule is an MHC class II molecule. In some embodiments, the tag is an acidic tag. In some embodiments, the acidic tag is an acidic cyanine dye. In some embodiments, the acidic tag is a peptide tag comprising a plurality of acidic amino acid sequences. In some embodiments, the tag is a pY-D4, pY-D5, pY-D6, pY-D7, pY-D8, pY-D9, or pY-D10 tag. In some embodiments, the tag is a pY-E4, pY-E5, pY-E6, pY-E7, pY-E8, pY-E9, or pY-E10 tag. In some embodiments, the MHC molecule further comprises a heavy chain that is conjugated to a chelant moiety. In some embodiments, the molecule comprises a combination of a heavy chain and an antigenic peptide discloses in Table 2. In some embodiments, the tag is conjugated to the peptide via a cleavable linker. In some embodiments, the linker is a photocleavable linker. In some embodiments, the linker is an NPPA linker. In some embodiments, the linker is a peptide linker that comprises an amino acid sequence that can be cleaved by a protease or by a chemical. In some embodiments, the MHC molecule is comprised in an MHC multimer.

Some aspects of this invention provide a method comprising contacting an empty MHC molecule with an antigenic peptide conjugated to a tag under conditions suitable for the antigenic peptide to bind the MHC molecule. In some embodiments, the MHC molecule is an MHC class II molecule. In some embodiments, the tag conjugated to the MHC class II binding antigenic peptide is an affinity tag that is not a polyhistidine tag. In some embodiments, the tag is a desthiobiotin (DTB) tag. In some embodiments, the tag is an acidic tag. In some embodiments, the acidic tag is an acidic cyanine dye. In some embodiments, the acidic tag is a peptide tag comprising a plurality of acidic amino acid sequences. In some embodiments, the tag is a pY-D4, pY-D5, pY-D6, pY-D7, pY-D8, pY-D9, or pY-D10 tag. In some embodiments, the tag is a pY-E4, pY-E5, pY-E6, pY-E7, pY-E8, pY-E9, or pY-E10 tag. In some embodiments, the tag is conjugated to the peptide via a cleavable linker. In some embodiments, the linker is a photocleavable linker. In some embodiments, the linker is an NPPA linker. In some embodiments, the linker is a peptide linker that comprises an amino acid sequence that can be cleaved by a protease or by a chemical. In some embodiments, the tag is a part of a cleavable linker that remains after cleavage of the linker.

Some aspects of this invention provide a method comprising contacting an MHC class II type alpha heavy chain with an MHC class II type beta heavy chain under conditions suitable for the alpha and the beta chain to form a heterodimeric MHC class II molecule. In some embodiments, at least one of the MHC class II heavy chains is conjugated to a tag, and isolating the MHC class II molecule, wherein the isolating comprises a step of affinity chromatography. In some embodiments, the tag is a protein or peptide tag. In some embodiments, the tag is a poly-His tag. In some embodiments, the His tag comprises 3-12 His residues. In some embodiments, the affinity chromatography is Ni2+-NTA chromatography. In some embodiments, the contacting is performed by expressing both heavy chains in a cell. In some embodiments, the cell is an insect cell. In some embodiments, the MHC class II molecule is "empty" (not loaded with an antigenic, MHC class II binding peptide). In some embodiments, the method further comprises contacting the MHC class II molecule with an MHC class II binding antigenic peptide. In some embodiments, the MHC class II binding antigenic peptide is conjugated to a tag. In some embodiments, the tag is an affinity tag. In some embodiments, the tag conjugated to the MHC class II binding antigenic peptide is an affinity tag that is not a polyhistidine tag. In some embodiments, the tag is a desthiobiotin tag. In some embodiments, the tag is an acidic tag. In some embodiments, the acidic tag is an acidic cyanine dye. In some embodiments, the acidic tag is a peptide tag comprising a plurality of acidic amino acid sequences. In some embodiments, the tag is a pY-D4, pY-D5, pY-D6, pY-D7, pY-D8, pY-D9, or pY-D10 tag. In some embodiments, the tag is a pY-E4, pY-E5, pY-E6, pY-E7, pY-E8, pY-E9, or pY-E10 tag. In some embodiments, the tag is conjugated to the peptide via a cleavable linker. In some embodiments, the tag is a desthiobiotin tag.the linker is a photocleavable linker. In some embodiments, the tag is a desthiobiotin tag.the linker is an NPPA linker. In some embodiments, the tag is a desthiobiotin tag.the linker is a peptide linker that comprises an amino acid sequence that can be cleaved by a protease or by a chemical. In some embodiments, the tag is a desthiobiotin tag.the tag is a part of a cleavable linker that remains after cleavage of the linker.

The subject matter of this application may involve, in some cases, interrelated products, alternative solutions to a particular problem, and/or a plurality of different uses of a single system or article. Other advantages, features, and uses of the invention will become apparent from the following detailed description of non-limiting embodiments of the invention when considered in conjunction with the accompanying drawings.

BRIEF DESCRIPTION OF THE DRAWINGS

FIG. 1A) Structure of a NTA-$Ni^{2+}$-His6 (SEQ ID NO: 310) complex in which $Ni^{2+}$ forms a chelate on one hand with the three carboxyl moieties of NTA and with the imidazole groups of two histidines on the other. FIG. 1B) The conventional biotin-streptavidin PE-MHC class I-peptide multimer. FIG. 1C) NTA multimers in which His tagged MHC-peptide monomers are bound to NTA-PE, obtained by reacting PE streptavidin with biotin-NTA compounds. FIG. 1D) As FIG. 1C), but the NTA moieties are directly conjugated to PE. FIG. 1E) As FIG. 1D) using quantum dots (QDOTs®) instead of PE.

FIG. 2A) Composition of the different C-terminal tags on HLA-A2 including the biotinylation sequence peptide BSP, linear His6 (SEQ ID NO: 310), $His_{12}$ (SEQ ID NO: 311) or two His6 (SEQ ID NO: 312) tags separated by a flexible GGGSGGGSGS (SEQ ID NO:4) spacer. The underlined residues (274-276) mark the C-terminus of the A2 α3 domain. Sequences, from top to bottom, correspond to SEQ ID NOs: 5-8 in FIG. 2A. FIG. 2B) HLA-A2 heavy chains containing the different tags were refolded with β2m in the presence of Flu matrix$_{58-66}$ peptide. The refolding efficiencies expressed as percent with 100% being the one of HLA-A2-BSP.

FIG. 3A) Biotin-mono NTA in which a biotin (circled) is coupled to NTA-lysine via N-(5-(3-maleimido-propionylamino)-1-carboxy-pentyl)iminodiacetyl-cysteine-Na-acetyl-Ns-amino-caproyl. FIG. 3B) biotin-di-NTA in which two NTA lysines were coupled via maleimide to two cysteines spaced by a glycine. FIG. 3C) biotin-tetra-NTA in which two di-NTA moieties are joined via GGGSGGGSGS (SEQ ID NO: 9) spacer. FIG. 3D) Amino-di-NTA, analogous to FIG. 3B) with a free amino group (circled). FIG. 3E) thiol-di-NTA, analogous to FIG. 3D) but with an N-terminal cysteine containing a free thiol (circled). FIG. 3F) Commercially available NTA-biotin (Biotium Inc, Hayward, CA).

FIGS. 4A to 4B. SPR binding studies for the different Ni-NTA linkers and His tags. FIG. 4A) Experimental set up consisting in first loading streptavidin coated sensor chips with biotin-mono-NTA or biotin-di-NTA, followed by saturating with $NiCl_2$ and washing. The changes in resonance units (RU) were measured upon injecting the different A2/Flu complexes over the NTA-$Ni^{2+}$ loaded chips. FIG. 4B) Compilation of the dissociation constants ($K_D$ in nM), binding on-rate constants ($k_{on}$ in $M^{-1} \times sec^{-1} \times 10^4$) and binding off-rates ($k_{off}$ in $sec^{-1} \times 10^{-3}$) recorded at room temperature for the differently His tagged A2/Flu complexes on mono-NTA (FIG. 3A) or di-NTA (FIG. 3B) loaded sensor chips. Sequences correspond to linear His6 (SEQ ID NO: 310), $His_{12}$ (SEQ ID NO: 311) or 2×His$_6$ (SEQ ID NO: 312) tags from top to bottom.

FIG. 5A) Cloned, Flu-specific 81P1 cells were incubated at 20° C. for 30 min with graded concentrations of PE streptavidin A2/Flu$_{58-66}$ multimers containing NTA$_2$×2×His$_6$ (SEQ ID NO: 312) (dark ▲), NTA$_2$×His$_{12}$ (SEQ ID NO: 311) (light ■), NTA×2×His$_6$ (SEQ ID NO: 312) (light ▲); NTA×His$_{12}$ (SEQ ID NO: 311) (dark ■), NTA$_2$×His$_6$ (SEQ ID NO: 310) (light ♦) or NTA×His$_6$ (SEQ ID NO: 310) (dark ♦). For comparison BSP multimers were included (circles). After washing, cell-associated fluorescence was assessed by flow cytometry. FIG. 5B) Alternatively 20° C. binding isotherms were assessed likewise on cloned BCB 70 cells for multimers containing NTA$_2$-biotin (light lines) or NTA$_4$-biotin (dark lines) and A2/Flu$_{58-66}$ complexes with His$_{12}$ (SEQ ID NO: 311) (♦) or 2×His$_6$ (SEQ ID NO: 312) tags (▲).

FIGS. 6A and 6B) Cloned Flu-specific 81P1 cells were incubated at 4° C. for 1 h with multimers (5 nM) containing biotin NTA$_2$ and His$_{12}$ (SEQ ID NO: 311) (FIG. 6A) or 2×His$_6$ (SEQ ID NO: 312) (FIG. 6B) tagged A2/Flu complexes. After washing the cells were incubated at 4° C. in HBSS in the absence (squares) or presence of 50 mM imidazole (triangles), 50 mM imidazole+20 mM EDTA (dashes) or 100 mM imidazole (diamonds) and after the indicated periods of time cell-associated multimers were assessed by flow cytometry. For comparison conventional BSP multimers were included (circles). The inserted numbers indicate the times ($t_{1/2}$) at which half maximal dissociation was observed.

FIG. 8A) Structure of PE, a fluorescent protein of 240,000 Da, has a rigid structure and 24 surface exposed lysines. FIG. 8B) Strategy to couple NTA$_2$-cysteine (FIG. 3E) on PE. In a first step PE was reacted with the maleimide N-hydroxysuccinimidyl ester SM(PEG)$_2$ (succinimidyl-maleido(PEG)$_2$), whereby maleimide groups are conjugated onto PE lysines. In a second step the NTA$_2$ cysteine (FIG. 3E) was added, which by reacting with maleimides on PE forms stable thio-ethers.

FIGS. 15A and 15B) The experiment shown in FIG. 5A was repeated using multimers containing either the short di-NTA-biotin (FIG. 15A)(FIG. 3B) or the long one (FIG. 15B) and A2/Flu₅₈₋₆₆ monomers carrying the 2×His₆ (SEQ ID NO: 312) tag (triangles), His₁₂ (SEQ ID NO: 311) tag (squares) or a His₆ (SEQ ID NO: 310) tag (diamonds). For comparison conventional BSP multimers were included (red circles).

FIGS. 19A and 19B) Cloned BCB 70 cells were incubated at 4° C. for 1 h with 10 nM of A2/Flu₅₈₋₆₆ multimers containing DTB streptavidin PE (FIG. 19A) or NTA₂-PE and 2×His₆ (SEQ ID NO: 312) (FIG. 19B). After washing the cells were incubated at 4° C. (diamonds), 20° C. (squares) or 37° C. (triangles) in FACS buffer supplemented with 2 nM biotin (in FIG. 19A) or 100 mM imidazol (in FIG. 19B). Cell associated fluorescence was determined by flow cytometry after the indicated periods of incubation.

FIG. 21A) To allow photochemical removal of tags from MHC II-restricted peptides, these were added via 2-nitro-phenyl-β-Ala (NPβA); upon UV irradiation this residue is cleft, such that the N-terminal fragment is an amid and the C-terminal one carries a 2-nitroso-phenacetyl-β-acetoyl group. FIG. 21B) HLA-DR4 loaded with H₆-GSG-NPβA-HA₃₀₆₋₃₁₈ peptide (SEQ ID NO: 313) was irradiated at 365+/−40 nm for the indicated periods of time and the % of complexes carrying the His tag was assessed by ELISA using a His tag-specific mAb. FIG. 21C) the same experiment was performed for DR4-HA₃₀₆₋₃₁₈-NPβA-GSG-H₆ (SEQ ID NO: 313) complexes. The inserted numbers ($t_{1/2}$) indicate the time at which half maximal photolysis occurred.

FIGS. 22A to 22E. Comparative staining of HA clones by conventional and immunopure DR4-HA multimers. FIGS. 22A to 22D) The indicated HA₃₀₆₋₃₁₈-specific DR4-restricted Th1 clones were incubated at 37° C. for 2h with the indicated concentrations of the DR4 multimers containing: HA (conventional) (solid circles), H6-GSG-NPβA-HA₃₀₆₋₃₁₈ (SEQ ID NO: 313) (immunopure) (triangles), H6-GSG-NPβA-HA$_{306-318}$ (SEQ ID NO: 313) (immunopure; after UV irradiation) (inverted triangles), HA$_{306-318}$-NPβA-GSG-H$_6$ (SEQ ID NO: 317) (immunopure) (diamonds), HA$_{306-318}$-NPβA-GSG-H$_6$ (SEQ ID NO: 317) (immunopure, after UV irradiation) (two-colored circles). The cells were washed and the cell bound multimers (MFI) assessed by flow cytometry. FIG. 22E) The TCR and CD4 expression of the clones were assessed by flow cytometry and the half maximal IFNγ response (EC50) by ELISA.

FIG. 23A) Empty MHC II molecules are loaded with Cy5.5 tagged peptide and subjected to GFC and anion exchange chromatography. Cy5.5 contains four negative charges, i.e. is strongly negatively charged. FIG. 23B) GFC on a SUPERDEX® (composite matrix of dextran and agarose) S75 column of DR4 after loading with HA$_{306-318}$-GSGC-Cy5.5 (SEQ ID NO: 314) recording of the OD280 (black, protein) and OD675 nm (gray, Cy5.5). FIG. 23C) Assessment of MHC II protein (stippled bars) and Cy5.5 (striped bars) by ELISA using mAb specific for DR4 and Cy5.5, respectively of HA$_{306-318}$-GSGC-Cy5.5 (SEQ ID NO: 314), DR4-HA; DR52b-ESO$_{123-137}$-GSGC-Cy5.5 (SEQ ID NO: 314) and DR52b-ESO$_{123-137}$. FIG. 23D) Anion exchange chromatography on a MONO-Q™ (monodisperse porous polystyrene/divinyl benzene beads) column using the indicated NaCl gradient and recording the OD280 (protein) and OD675 nm (Cy5.5) of the eluant.

FIG. 25A) empty, His tagged DR4 molecules were purified on a Ni$^{2+}$-NTA affinity column, which was eluted with 200 mM imidazol, monitoring the OD280 nm of the eluate. FIG. 25B) The eluted DR4 was subjected to GFC on a SUPERDEX® S200 column again monitoring the OD280 nm of the eluate. FIG. 25C) The collected fractions (gray lines) were analyzed by SDS-PAGE (10% non-reducing) applying a low (2 µg/ml) or high (5 µg/ml) concentration. FIG. 25D) Empty DR4 was loaded with pY-D$_4$-GSG-NPβA-HA$_{306-318}$ (SEQ ID NO: 318) peptide followed by purification by anion exchange chromatography on MONO-Q™ column, which was eluted with the indicated NaCl gradient (upper panel). Fractions (0.5 ml) were collected and their content of DR4 (middle panel) and pY (phospho-tyrosine) (lower panel), respectively, determined by ELSA as shown in the lower two panels.

FIG. 28A) The indicated DR4-restricted, HA-specific T cell clones were pretreated or not with neuraminidase (30 min incubation at 37° C. with 0.03 U/ml of neuraminidase) and incubated with conventional DR4/HA$_{306-318}$ multimers (20 µg/ml) at 37° C. for 2 h. After washing cell-associated multimers (MFI) were assessed by flow cytometry. FIG. 28B) Cloned 10.5 (left panel) or 7.1 (right panel) cells were incubated likewise with the indicated concentrations of conventional DR4/HA$_{306-318}$ multimers and cell associated fluorescence was assessed by flow cytometry.

FIG. 29A to 29B. Staining is a function of PE substitution degree.

FIGS. 33A to 33C. Comparison of conventional, PE-Cys-PEG2-NTA2 and PE-HNO-NTA2 multimers staining.

(FIG. 49A) or room temperature (FIG. 49C) with 10 g/ml of the indicated HA peptide-loaded multimers and analyzed after washing by flow cytometry. Nonspecific background (control) was determined on TT$_{634-653}$ peptide stimulated PBMCs. Specific multimer staining was assessed in cells prepared and stained as in (A) over at different concentrations of multimers (FIG. 49B). For comparison the frequencies of IFNγ$^+$ T cells was assessed by ICS and flow cytometry with (+) or without (−) peptide stimulation (FIG. 49D).

DETAILED DESCRIPTION OF CERTAIN EMBODIMENTS

Figure 1A:
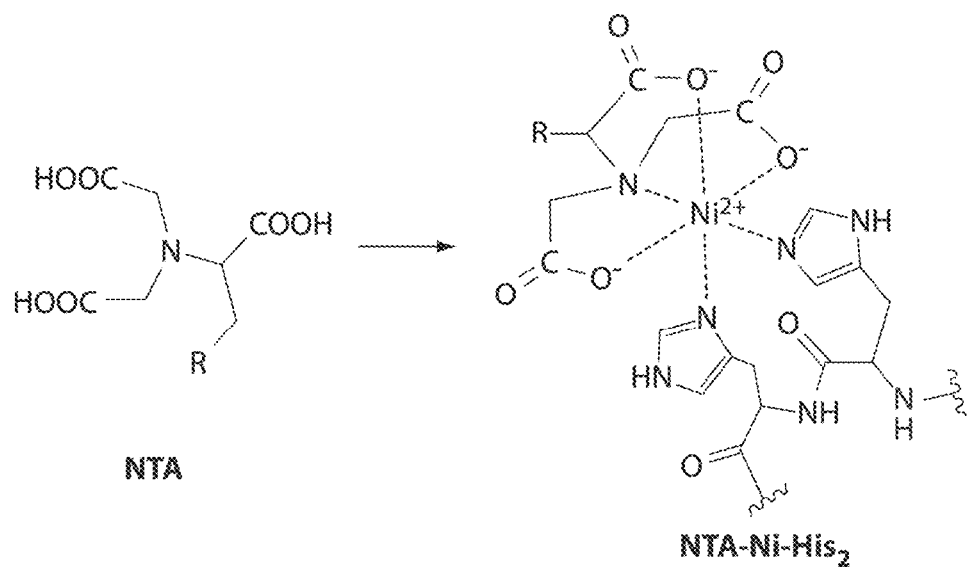
FIGS. 1A to 1E. MHC-peptide complexes under study.
Figure 1B:
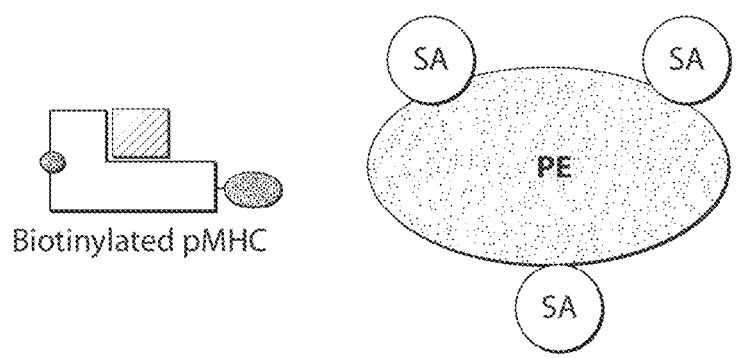

Some aspects of this invention relate to protein multimers in which conjugation of a plurality of monomeric proteins is based on chelate complex bonds between the monomeric proteins and a central carrier molecule. Methods for generation and the use of such protein multimers are also provided herein.

Some aspects of this invention provide "reversible" protein multimers that can be dissociated by releasing the chelate complex bonds between the carrier molecule and the monomeric proteins, for example, by withdrawal of a central ion from the chelate complex bond or by contacting the chelate complex with a free chelant that can displace one of the binding partners forming the chelate complex. This chelate bond release results in re-monomerization of the proteins comprised in the multimer. In some embodiments, multimer assembly and/or re-monomerization are carried out under non-denaturing, physiological, and/or non-toxic conditions, rendering the respective multimers suitable for in vivo, ex vivo, and in vitro applications involving living cells and/or monomeric proteins prone to denaturation.

Some aspects of the invention provide, for the first time, that reversible MHC-peptide multimers can be built on Ni$^{2+}$ NTA-His tag complexes that exhibit equal or superior staining properties as compared to conventional multimers. These novel staining reagents are fully reversible in that they can be rapidly dissociated into monomeric subunits upon addition of imidazol, which allows, for example, sorting of bonafide antigen-specific CD8+ T cells.

Some aspects of this invention provide methods and materials for the preparation of fluorescent MHC protein multimers, in which conjugation is based on chelate complex formation between nitrilotriacetic acid (NTA) and an amino acid sequence comprising a polyhistidine sequence, also referred to as a histidine tag (His tag). In some embodiments, the chelate complexes are formed in the presence of a Ni$^{2+}$ cation. In some embodiments, the His tag comprises 3-12 His residues. In some embodiments, the His tag is a hexahistidine (His$_6$: SEQ ID NO: 310) tag or a 2×His$_6$ (SEQ ID NO: 312) tag, comprising to hexahistidine sequences separated by a short amino acid linker.

Some aspects of this invention are based on the recognition that reversible protein multimers based on chelate complex bonds are stable enough to be useful for various applications, for example, cell or protein staining and isolation procedures, but can be dissociated under physiological, non-toxic conditions, for example, by withdrawing a central ion that is required for the formation of the chelate complex or by contacting them with an agent competing for the chelate complex bond, and thus releasing the bond between carrier molecule and monomeric protein. For example, the reversible Ni$^{2+}$ NTA-His tag interaction-based multimers described herein are "reversible" in that they can be dissociated either by withdrawing the chelant cation (e.g. Ni$^{2+}$ or Co$^{2+}$) or by adding free competing chelant, for example, free imidazol, which displaces the His tag from the chelate complex. Imidazol is commercially available and is commonly used for purification of recombinant proteins on Ni$^{2+}$ NTA affinity chromatography (see e.g. products.invitrogen.com/ivgn/product/K95001?ICID=Search-Product; and QIAExpressionist Handbook, Qiagen Inc., March 2001, available from Qiagen.com; both incorporated herein in their entirety by reference).

For example, the interaction of one Ni$^{2+}$ NTA with a hexahistidine tag (His$_6$: SEQ ID NO: 310) has a dissociation constant (K$_D$) of about 10$^{-6}$-10$^{-7}$M and is sufficiently stable to allow purification of His tagged recombinant proteins from culture supernatants (9, 10). Previous studies have investigated ways to render this interaction more stable. For example, different His tags have been examined and it has been shown that increasing the length of the His tag increases the stability of the complexes (9). In particular it has been demonstrated that linking two His$_6$ (SEQ ID NO: 310) tags via a flexible linker, such as GGGSGGGSGS (SEQ ID NO: 11) provides a high increase in stability (11, 12). Further, linkers have been synthesized that contain two to four NTA groups (13-15). The binding to His tags, in particular longer ones, increases considerably with the number on Ni$^{2+}$ NTA entities. While, in some embodiments, the His tags are expressed tethered, or fused to a recombinant protein, the NTA compounds have to be synthesized, as only mono-NTA (NTA1) derivatives are commercially available. Some aspects of this invention provide optimized configurations of NTA bound to a linker and optimized pairings of specific NTA configurations with specific His-tags to achieve a modulation of chelate complex bond stability over multiple orders of magnitude. Accordingly, reversible multimers, as provided herein, can be customized to fulfill specific requirements of a wide variety of research, diagnostic, and therapeutic applications.

In some embodiments, reversible MHC multimers, for example, reversible MHC class I multimers, are provided. In some embodiments, fluorescently-labeled soluble MHC peptide multimers are provided. In some embodiments, methods for the use of reversible MHC multimers are provided, for example, methods useful to quantitate, isolate and/or characterize antigen-specific T-cells, for example, CD8$^+$ and CD4$^+$ T cells. In some embodiments, methods for the use of MHC multimers are provided that are useful for phenotypic T-cell analysis or for the analysis of T-cell receptor ("TCR") repertoire in a subject.

Conventional MHC multimers are typically prepared by enzymatic biotinylation of monomeric MHC proteins comprising a C-terminal biotinylation sequence peptide (BSP) and subsequent conjugation with streptavidin bound to a fluorescent dye, typically phycoerythrin (PE) or allophycocyanine (APC). Due to the large size of PE and APC, conjugates with streptavidin vary in stoichiometry, accessibility, and orientation of the biotin binding sites, often resulting in variable valency and inhomogeneous populations of MHC multimers. Other types of PE- or APC-based MHC-peptide staining reagents have been described, including Streptamers, desthiobiotin (DTB) multimers, pentamers (Proimmune Inc., FL, USA). Non-phycobilin-based MHC multimers have also been developed, for example Quantum dots loaded with MHC class I-peptide complexes, which allow simultaneous use of multiple MHC class I-peptide specificities in polychrome flow cytometry, Cy5-labeled dimeric, tetrameric and octameric MHC class I-peptide complexes, dextramers (Immudex, Copenhagen, Denmark) and dimeric MHC-peptide-immunoglobulin (Ig) fusion proteins.

While exemplary reversible multimers described herein include reversible MHC protein multimers, it will be apparent to those of skill in the art that the methods and reagents provided herein can be applied to generate reversible multimers of proteins other than MHC proteins. The methods for the generation and use of protein multimers, accordingly, are universally applicable to proteins of different nature, for example, to binding proteins, such as MHC proteins, antibodies, antibody fragments, ligands, adnectins, and receptors or receptor fragments. Exemplary multimers of such binding proteins, namely of peptide-loaded or empty MHC molecules, are provided in the working example section. Further, those of skill in the art will appreciate that virtually any kind of protein can be engineered to form a reversible multimer as provided by aspects of this invention as long as the monomeric protein is amenable to conjugation to a chelant moiety, for example, to addition of a His-tag fusion.

Accordingly, those of skill in the art will appreciate that the methods for the generation of protein multimers described herein can be applied to the generation of additional chelate complex bond-based binding molecules. For example, some embodiments, provide multimers of protein or non-protein binding molecules. The term "binding molecule" as used herein, refers to a molecule that is able to bind a binding partner via non-covalent interaction. Typically, in the context of cells, cell culture, or processing of living cells (e.g. staining, FACS sorting), a binding molecule is able to form a binding interaction with a binding partner that is strong enough to be stable under physiological conditions or under the conditions typically encountered during cell processing. In some embodiments, a binding molecule binds its binding partner with high specificity and/or high affinity. Non-limiting examples of binding molecules are antibodies and antibody fragments (e.g., Fab, F(ab)'2, single chain antibodies, diabodies, etc.), receptors, proteins binding a ligand, aptamers, and adnectins. The term "ligand" is art-recognized and refers to a binding partner of a binding molecule. Ligands can be, for example, proteins, peptides, nucleic acids, small molecules, and carbohydrates. Avidins, for example, streptavidin, are non-limiting examples of binding molecules that can bind a ligand, in this case, for example, biotin.

For example, in some embodiments, reversible antibody fragment, for example, Fab fragment, multimers are provided, in which a plurality of Fab proteins is bound to a central carrier molecule via chalet complex bonds, for example, NTA-His bonds. In some embodiments, the carrier molecule is a fluorescent microsphere, for example, a FLUOROSPHERES® type fluorosphere (see products.invitrogen.com/ivgn/product/F8781?ICID=search-product).

Protein Multimers

Some aspects of this invention provide reversible protein multimers in which a plurality of proteins is conjugated to a central carrier molecule via a non-covalent binding interaction that can be released under physiological conditions, for example, by contacting the multimer with an agent able to displace one of the binding partners from the binding interaction.

The terms "protein," "polypeptide," or "peptide," as used herein, refer to a polymer of at least three amino acid residues linked together by peptide bonds. The terms are interchangeably used herein and refer to proteins, polypeptides, and peptides of any size, structure, or function. Typically, a protein will be at least three amino acids long. In some embodiments, inventive proteins contain only natural amino acids, although in other embodiments non-natural amino acids (e.g., compounds that do not occur in nature but that can be incorporated into a polypeptide chain; see, for example, U.S. Pat. No. 7,045,337, which describes incorporation of non-natural amino acids into proteins) and/or amino acid analogs as are known in the art may alternatively be employed. In some embodiments, one or more of the amino acids in an inventive protein are modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these. In some embodiments, the protein is an MHC molecule.

The term "conjugated," as used herein, refers to an entity, molecule, or moiety that is stably associated with another molecule or moiety via a covalent or non-covalent bond. In some embodiments, the conjugation is via a covalent bond, for example, in the case of a peptide tag conjugated to an MHC protein via fusion of the peptide to a heavy chain of the MHC protein. In other embodiments, the conjugation is via a non-covalent interactions, for example, via hydrogen bonding, van der Waals interactions, hydrophobic interactions, magnetic interactions, or electrostatic interactions.

The term "carrier molecule," as used herein in the context of multimers, refers to a molecule that binds or is conjugated to a plurality of monomeric molecules or entities, or a plurality of binding molecules or moieties that can bind such monomeric molecules or entities. In some embodiments, the carrier molecule is a monomeric molecule, for example, a single molecule of a fluorescent dye. In other embodiments, the carrier molecule is a multimeric molecule, for example, a polymer, or a nanocrystal. For example, in some embodiments, the carrier molecule is a fluorophore, for example, a phycobilin, conjugated to a plurality of binding molecules, for example, streptavidin. The streptavidin molecules, in turn, can bind monomeric molecules, for example, biotin-conjugated MHC monomers. In some embodiments, the carrier molecule is a multivalent chelant molecule. In some embodiments, the carrier molecule is a fluorescent microsphere, for example, a FLUOROSPHERES® type fluorosphere (see products.invitrogen.com/ivgn/product/F8781?ICID=search-product). In some embodiments, the carrier molecule, for example, a fluorophore, is conjugated to a plurality of chelant molecules or moieties, for example, NTA molecules that can form chelate complex bonds with histidine residues in the presence of a divalent cation.

Some aspect of this invention provide optimized chelate complex bond formation between NTA and His chelants by using certain chelant configurations. The term "chelant configuration," as used herein refers to the number and spacing of chelant molecules or moieties in a given structure. For example, if chelant moieties, for example, NTA moieties, are conjugated to a carrier molecule, for example, a multivalent binding molecule or a fluorophore, via a linker, then a configuration in which a single chelant moiety is conjugated to the carrier molecule via a single linker is referred to as mono-configuration (e.g. mono-NTA, or $NTA_1$), a configuration in which two chelant moieties are conjugated to the carrier molecule via a single linker is referred to as di-configuration (e.g. di-NTA, or $NTA_2$), a configuration in which four chelant moieties are conjugated to the carrier molecule via a single linker is referred to as tetra-configuration (e.g. tetra-NTA, or $NTA_4$), and so forth. According to some aspects of this invention, different NTA chelant configurations and linker structures affect chelate complex bond properties, including bond strength and, thus, bond stability and reversibility. Similarly, the number and configuration of Histidine residues in a His tag has been described to affect chelate complex bond properties. In some embodiments, the His tag is a His6 (SEQ ID NO: 310) tag, comprising 6 contiguous His residues, a His12 (SEQ ID NO: 311) tag, comprising 12 contiguous His residues, or a 2×His6 (SEQ ID NO: 312) tag, comprising two sequences of 6 contiguous His residues linked by a short spacer sequence as described in more detail elsewhere herein.

The term "divalent cation" as used herein, refers to an ion that lacks two electrons as compared to the neutral atom. Examples of divalent cations useful in some embodiments of this invention are Ni2+, Cu2+, Zn2+, Co2+, Cd2+, Sr2+, Mn2+, Fe2+, Mg2+, Ca2+, and Ba2+. Other useful divalent cations will be apparent to those of skill in the art and the invention is not limited in this respect.

In some embodiments, the carrier molecule is a monomeric carrier molecule. In some embodiments, the carrier molecule is a multimeric or polymeric carrier molecule. For example, in some embodiments, the carrier molecule is a tetrameric or a hexameric molecule, for example, a fluorophore. In some embodiments, the carrier molecule is a fluorophore, a phycobilin, phycoerythrin or allophycocyanine, a nanocrystal, a quantum dot (QDOT®), a magnetic particle, or a nanoparticle. The terms "quantum dot" and "QDOT®," as used herein, refer to fluorescent inorganic semiconductor nanocrystals in which the excitons are confined in all three spatial dimensions and which are useful as detectable agents in some embodiments of the invention. In some embodiments, the QDOT® comprises CdSe or CdTe. In some embodiments, the QDOT® comprises InP or InGaP. In some embodiments, the QDOT® comprises a core/shell structure, while in other embodiments, the QDOT® is a core-only QDOT®. Exemplary QDOT® and methods for use and production are described in Rech-Genger et al., Quantum dots versus organic dyes as fluorescent labels. Nature Methods 2008 (9):763-775, incorporated herein in its entirety by reference for disclosure of fluorescent QDOT® and organic dyes, and methods of production and use of same).

In some embodiments, the carrier molecule is a water-soluble molecule. The term "water-soluble" is art-recognized and qualifies that an agent can be dissolved in water to a certain degree, or, in other words, that a certain amount of the agent can be dissolved in a certain volume of water. For example, in some embodiments described here, a water-soluble carrier molecule is a carrier molecule that exhibits a solubility in water at 25° C. and 1 ATM of more than 0.1 g/ml, more than 0.2 g/ml, more than 0.25 g/ml, more than 0.3 g/ml, more than 0.4 g/ml, more than 0.5 g/ml, more than 0.6 g/ml, more than 0.7 g/ml, more than 0.8 g/ml, more than 0.9 g/ml, more than 1 g/ml, more than 1.1 g/ml, more than 1.2 g/ml, more than 1.3 g/ml, more than 1.4 g/ml, more than 1.5 g/ml, more than 1.6 g/ml, more than 1.7 g/ml, more than 1.8 g/ml, more than 1.9 g/ml, more than 2 g/ml. more than 2.25 g/ml, more than 2.5 mg/ml, more than 3 g/ml, more than 4 g/ml, more than 5 g/ml, more than 6 g/ml, more than 7 g/ml, more than 8 g/ml, more than 9 g/ml, more than 10 mg/ml, or more than 20 mg/ml.

In some embodiments, the carrier molecule is not water soluble. In some such embodiments, the carrier molecule is highly dispersible in water and/or does not precipitate in aqueous solution under physiological conditions. In some embodiments, the diameter of the carrier molecule is less than 0.1 mm, less than 0.2 nm, less than 0.25 nm, less than 0.3 nm, less than 0.4 nm, less than 0.5 nm, less than 0.6 nm, less than 0.7 nm, less than 0.75 nm, less than 0.8 nm, less than 0.9 nm, less than mm, less than 1.1 nm, less than 1.2 nm, less than 1.3 nm, less than 1.4 nm, less than 1.5 nm, less than 1.6 nm, less than 1.7 nm, less than 1.8 nm, less than 1.9 nm, less than 2 nm, less than 2.5 nm, less than 3 nm, less than 4 nm, less than 5 nm, less than 6 nm, less than 7 nm, less than 8 nm, less than 9 nm, or less than 10 nm. In some embodiments, the diameter of the carrier molecule is less than 20 nm, less than 30 nm, less than 40 nm, less than 50 nm, less than 60 nm, less than 70 nm, less than 80 nm, less than 90 nm, less than 100 nm, less than 200 nm, less than 300 nm, less than 400 nm, less than 500 nm, less than 600 nm, less than 700 nm, less than 800 nm, less than 900 nm, or less than 1 μm.

In some embodiments, the non-covalent interaction is a non-covalent bond with a dissociation constant $K_D$ of 5 μM>$K_D$≥1 fM, for example, of 100 nM>$K_D$≥1 pM, or of 100 nM>$K_D$≥100 fM. The term "dissociation constant," abbreviated as $K_D$ herein, is art-recognized and refers to a specific type of equilibrium constant that measures the propensity of a complex of associated molecules to separate (dissociate) reversibly into the separate molecules. The dissociation constant is the inverse of the association constant. For a general reaction $A_xB_y \leftrightarrow xA+yB$, in which a complex $A_xB_y$ breaks down into xA subunits and yB subunits, the dissociation constant is defined as $$K_d = \frac{[A]^x \times [B]^y}{[A_xB_y]},$$

where [A], [B], and [$A_xB_y$] are the concentrations of A, B, and the complex $A_xB_y$, respectively. In some embodiments, a protein multimer is provided in which at least one of the protein monomers is conjugated to the carrier molecule via a non-covalent bond with a dissociation constant 5 μM>KD>1 nM. In some embodiments, a protein multimer is provided in which at least one of the protein monomers is conjugated to the carrier molecule via a non-covalent bond with a dissociation constant 5 μM>KD≥1 pM. In some embodiments, a protein multimer is provided in which at least one of the protein monomers is conjugated to the carrier molecule via a non-covalent bond with a dissociation constant of less than 2 fM, less than 5 fM, less than 10 fM, less than 20 fM, less than 50 fM, less than 100 fM, less than 250 fM, less than 500 fM, less than 1 pM, less than 2 pM, less than 5 pM, less than 10 pM, less than 20 pM, less than 50 pM, less than 100 pM, less than 250 pM, less than 500 pM, less than 1 nM, less than 5 nM, less than 10 nM, less than 20 nM, less than 50 nM, less than 100 nM, less than 250 nM, less than 500 nM, less than 600 nM, less than 700 nM, less than 800 nM, less than 900 nM, less than 1000 nM, less than 1500 nM, less than 2000 nM, less than 2500 nM, less than 3000 nM, less than 3500 nM, less than 4000 nM, less than 4100 nM, less than 4200 nM, less than 4300 nM, less than 4400 nM, less than 4500 nM, less than 4600 nM, less than 4700 nM, less than 4800 nM, less than 4900 nM, less than 5000 nM, more than 1 fM, more than 5 fM, more than 10 fM, more than 20 fM, more than 25 fM, more than 50 fM, more than 100 fM, more than 200 fM, more than 500 fM, more than 1 pM, more than 1 pM, more than 5 pM, more than 10 pM, more than 20 pM, more than 25 pM, more than 50 pM, more than 100 pM, more than 200 pM, more than 500 pM, more than 1 nM, more than 5 nM, more than 10 nM, more than 20 nM, more than 50 nM, more than 100 nM, more than 200 nM, more than 500 nM, more than 1000 nM, more than 2000 nM, more than 2500 nM, more than 3000 nM, more than 3500 nM, more than 4000 nM, more than 4100 nM, more than 4200 nM, more than 4300 nM, more than 4400 nM, more than 4500 nM, more than 4600 nM, more than 4700 nM, more than 4800 nM, or more than 4900 nM, or any possible combination of any of these values. For example, in some embodiments, a protein multimer is provided in which at least one of the protein monomers is conjugated to the carrier molecule via a non-covalent bond with a dissociation constant of more than 1 pM and less than 10 nM, more than 10 pM and less than 1000 nM, more than 100 pM and less than 500 nM, more than 10 nM and less than 1000 nM, more than 10 nM and less than 100 nM, more than 100 nM and less than 4000 nM, more than 200 nM and less than 3000 nM, more than 500 nM and less than 2000 nM, or more than 500 pM and less than 1000 nM.

In some embodiments, the carrier molecule or the protein, or both, are conjugated to a chelant moiety via a covalently bound linker. The term "linker," as used herein, refers to a chemical structure between two molecules or moieties or between a molecule and a moiety, thus linking the two. In some embodiments, the linker is covalently bound to both linked elements. In some embodiments, the linker is covalently bound to one, but not the other linked element. In some embodiments, the linker is non-covalently bound to one or both elements. For example, in some embodiments, a linker is covalently bound to a carrier molecule and a chelant moiety, while in other embodiments, a linker is covalently bound to a chelant moiety and non-covalently bound to a carrier molecule. In some embodiments, the linker is about 2 Å, about 3 Å, about 4 Å, about 5 Å, about 6 Å, about 7 Å, about 8 Å, about 9 Å, about 10 Å, about 11 Å, about 12 Å, about 13 Å, about 14 Å, about 15 Å, about 16 Å, about 17 Å, about 18 Å, about 19 Å, about 20 Å, about 21 Å, about 22 Å, about 23 Å, about 24 Å, about 25 Å, about 26 Å, about 27 Å, about 28 Å, about 29 Å, about 30 Å, about 35 Å, about 40 Å, about 45 Å, or about 50 Å long. In some embodiments, the linker is longer than about 50 Å.

In some embodiments, NTA moieties are conjugated with a carrier molecule, for example, a PE molecule, using maleimide alkylation chemistry. For example, in some embodiments, PE is first reacted with an NHS-maleimide and the maleimido-PE subsequently with NTA-Cys (SH), resulting in the formation of a stable thio-ether. It is important to note that the maleimido group readily hydrolyzes under certain conditions, which can limit the reproducibility and the degree of conjugation.

In some embodiments, chelate moieties, for example, NTA moieties, are conjugated to a carrier molecule, for example, a PE molecule, with an oxime formation chemistry strategy. Using oxime chemistry has several advantages: i) efficient conjugation in the pH range 5-7; ii) good stability under physiological conditions; and iii) efficient conjugation at low protein concentrations. An exemplary oxime chemistry for attachment of NTA moieties to a carrier is described in the following scheme:

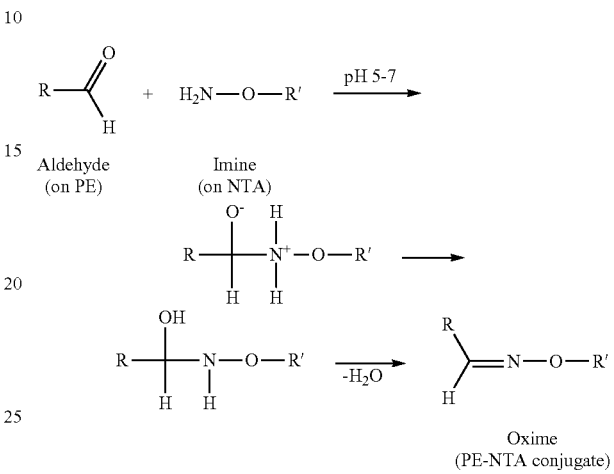

Exemplary Oxime Chemistry Scheme.

The chemistry strategies provided herein, for example, the maleimide and oxime chemistry strategies described, are universally applicable to generate MHC multimers, for example, multimers of MHC class I or class II as described herein. Additional maleimide and oxime chemistry strategies will be apparent to those of skill in the art and it will be appreciated that the disclosure is not limited in this respect.

The use of oxime chemistry, also referred to herein as oxime ligation, has some advantages in the context of the preparation of large bioconjugates, for example, as its formation is compatible with other functional groups often used, namely thiol-maleimide reactions or click chemistry. Oxime formation benefits from the exclusive specificity and reactivity between the aminooxy function and the carbonyl group, since the nitrogen atom behaves as a weak base and as an excellent nucleophile. In general, aldehydes are substantially more reactive than ketones, mainly due to steric effects. The oxime ligation reaction can occur in mild acidic conditions (pH 5) within 1 h but also at physiological conditions (pH 7) in 10 h. The resulting imine bond is covalent and stable under physiological conditions. In some embodiments, aminooxy-containing peptides are obtained by inserting the classical fmoc-Dpr(Aoa)-OH residue at the last stage of solid phase peptide synthesis. Incorporation of this residue is efficient (quantitative yields) and does not require specialized conditions. Final TFA deprotection of the peptide results in a free aminooxy function. The incorporation of the aldehyde moiety on the biomolecule to be derivatized is achieved, in some embodiments, by employing a commercially available sulfo-SFB molecule, that reacts on lysines via succinimidyl ester reaction. One of the advantages of using oxime chemistry over using a thiol-maleimide chemistry strategy is that oxime formation is not subjected to a hydrolysis or degradation reaction. In some embodiments, oxime chemistry strategies lead to better incorporation yields. Another benefit is that the functionalized entities can be prepared and stored for several months before being mixed together.

Oxime chemistry reactions, reagents, and reaction conditions are well known to those of skill in the art. Some reactions, reagents, and reaction conditions are described herein. Additional suitable reactions, reagents, and reaction conditions will be apparent to those of skill in the art and it will be appreciated that this disclosure is not limited in this respect. Suitable reactions, reagents, and reaction conditions are described, for example, in Mathieu Galibert, Olivier Renaudet, Pascal Dumy, and Didier Boturyn. Angew. Chem. Int. Ed. 2011, 50, 1-5; Youhei Sohma and Stephen B. H. Kent. J. AM. CHEM. SOC. 2009, 131, 16313-16318 9 16313; Anouk Dirksen and Philip E. Dawson. Bioconjugate Chem. 2008, 19, 2543-2548; Jenks, W. P. J. Am. Chem. Soc. 1959, 81, 475-481; Rose, K. J. Am. Chem. Soc. 1994, 116, 30-33; Shao, J.; Tam, J. P. J. Am. Chem. Soc. 1995, 117, 3893-3899; Decostaire, I. P.; Lelie'vre, D.; Zhang, H.; Delmas, A. F. Tetrahedron Lett. 2006, 47, 7075-7060; Garanger, E.; Boturyn, D.; Renaudet, O.; Defrancq, E.; Dumy, P. J. Org. Chem. 2006, 71, 2402-2410; and Boturyn, D.; Coll, J. L.; Garanger, E.; Favrot, M. C.; Dumy, P. J. Am. Chem. Soc. 2004, 126, 5730-5739; the entire contents of each of which are incorporated herein by reference.

In some embodiments, a protein multimer is provided in which a plurality of proteins is conjugated to a multivalent carrier molecule and wherein at least one of the proteins is conjugated to the carrier molecule via a chelate complex bond.

The term "chelate complex," as used herein, refers to a chemical structure that comprises two or more separate, non-covalent binding interactions between a polydentate (multiple bonded) molecule or moiety, also referred to as "chelant", and a single central atom, for example, a divalent cation. The term "chelate complex bond," accordingly, refers to a non-covalent bond between two or more chelants that form a chelate complex. In some embodiments, all chelants of a chelate complex are of the same structure. In other embodiments, a chelate complex is formed by chelants of different structures, for example, by a chelant comprising a histidine residue and a chelant comprising an NTA residue. In some embodiments, the central atom is a divalent cation, for example, an $Ni^{+o}$ cation. Chelants, chelant moieties, and suitable central atoms are well known to those of skill in the art and the invention is not limited in this respect.

In some embodiments, a protein multimer is provided in which a plurality of MHC molecules is conjugated to a carrier molecule by a non-covalent bond as described herein, for example, a chelate complex bond or a bond of a $K_D$ value as provided elsewhere herein.

The term "MHC molecule," as used herein, refers to a protein encoded by the major histocompatibility complex, and includes MHC class I and MHC class II molecules. In some embodiments, the MHC molecule is an MHC class I molecule and the MHC multimer is an MHC class I multimer. In some embodiments, the MHC molecule is an MHC class II molecule and the MHC multimer is an MHC class II multimer.

In some embodiments, the MHC molecule is a human MHC molecule. In humans, MHC molecules are also referred to as HLA molecules. In some embodiments, the MHC molecule is an MHC molecule of a non-human mammal, for example, of a mouse, a rat, a rabbit, a non-human primate, a cat, a dog, a goat, a cow, a sheep, a horse, or a pig.

MHC class-I molecules comprise one heavy chain type a that comprises three domains ($\alpha 1$, $\alpha 2$, and $\alpha 3$). In naturally occurring MHC class I molecules. these domains are exposed to the extracellular space, and are linked to the cellular membrane through a transmembrane region. The a chain of MHC class I molecules is associated with a molecule of $\beta 2$ microglobulin, which is not encoded by an MHC gene, but also included within the scope of the term "MHC molecule". MHC class II molecules comprise two heavy chains, one type a and one type $\beta$, each of which comprises two domains: $\alpha 1$ and $\alpha 2$, $\beta 1$ and $\beta 2$, respectively. In naturally occurring MHC class II molecules, these domains are exposed to the extracellular space and are linked to the cellular membrane through a transmembrane region on each of the two chains.

In some embodiments, of this invention, an MHC multimer comprises a genetically engineered MHC molecule. In some embodiments, an MHC molecule as provided herein comprises an extracellular domain of a naturally occurring MHC molecule, or a genetically engineered derivative thereof, but is devoid of all or part of the transmembrane domain or domains. In some embodiments, MHC class II molecules are provided that comprise a leucine zipper in place of the transmembrane domain in order to achieve dimerization of a and $\beta$ chains. Genetically engineered MHC proteins, for example, MHC molecules lacking transmembrane domains, MHC molecules comprising leucine zippers, single chain MHC molecules or MHC molecules fused to an antigenic peptide, are also included in the scope of the term "MHC molecule". In some embodiments, the term "MHC molecule" refers to a complete molecule, for example, an MHC heavy chain type a (genetically engineered or not) that is associated with a molecule of $\beta 2$ microglobulin in the case of an MHC class I molecule, or an MHC heavy chain type $\alpha$ (genetically engineered or not) that is associated with an MHC heavy chain type $\beta$ (genetically engineered or not), for example, via leucine zipper interaction. In some embodiments, the term "MHC molecule" refers to a single component of an MHC molecule, for example, to an MHC heavy chain (e.g. type $\alpha$ or type $\beta$, genetically engineered or not), or to a $\beta 2$ microglobulin. MHC molecules can bind antigenic peptides in a groove formed by the $\alpha 1$ and $\alpha 2$ domains of MHC class I molecules or by the $\alpha 1$ and $\beta 1$ domains of MHC class II molecules. An MHC molecule that has bound an antigenic peptide is referred to herein as a "peptide-loaded" MHC molecule, whereas an MHC molecule that has not bound an antigenic peptide is referred to herein as an "empty" MHC molecule. The term "antigenic peptide," as used herein, refers to a peptide comprising a structure that is recognized by the immune system of a subject. Non-limiting examples of antigenic peptides are a peptide that is recognized by a B or T-cell, e.g. via binding to a T-cell receptor, or a peptide that binds to an antibody or antibody fragment, or a peptide that stimulates an immune response in a subject.

The term "monomeric MHC molecule," "MHC monomer," and "MHC molecule monomer," as used herein, refer to a single MHC molecule, for example, to a single MHC heavy chain, a single MHC heavy chain associated with a 32 microglobulin, or a heterodimer of an MHC type $\alpha$ heavy chain and an MHC type $\beta$ heavy chain. The term "MHC multimer," as used herein, refers to a plurality of MHC molecules associated with each other, for example, via non-covalent interaction with a carrier molecule.

In some embodiments, the term "multimer" excludes dimers, but includes trimers, and multimers of four monomers (tetramers), or of more than four monomers (pentamers, hexamers, septamers, octamers, nonamers, decamers, etc.). In some embodiments, the term "multimer" excludes dimers and trimers, but includes multimers of four and more monomers.

Core Multimer Structure

Some aspects of this invention provide a multivalent chelant, that comprises a plurality of chelant moieties conjugated to a carrier molecule. Such multivalent chelants are useful for the generation of reversible multimers, for example, of reversible protein multimers (e.g. MHC multimers), as described elsewhere herein.

The term "multivalent chelant molecule," as used herein, refers to a carrier molecule comprising or conjugated to a plurality of chelant moieties able to form chelate complex bonds with a plurality of chelant-moiety comprising molecules. For example, a tetravalent chelant molecule is a carrier molecule that is able to form chelate complex bonds to four molecules, for example, four MHC proteins comprising a compatible chelant moiety, thus forming a tetramer of the four molecules held together by chelate complex bonds. A compatible chelant moiety is a chelant moiety able to form a chelate complex bond with the chelant moiety of the carrier molecule. For example, an NTA moiety and a Histidine moiety are compatible chelant moieties, since they can form a chelant complex bond in the presence of a divalent cation. In some embodiments, the multivalent chelant molecule can form a chelate complex bond with 2, 3, 4, 5, 6, 7, 8, 9, 10, 11, 12, 13, 14, 15, 16, 17, 18, 19, 20, 21, 22, 23, 24, 25, 30, 31, 32, 33, 34, 35, 36, 37, 38, 39, 40, 41, 42, 43, 44, 45, 46, 47, 48, 49, 50, 100, or 150 molecules comprising a compatible chelant moiety. In some embodiments, the multivalent chelant molecule can form a chelate complex bond with more than 150 compatible molecules.

In some embodiments, the carrier molecule is a water-soluble molecule as described in more detail elsewhere herein. In some embodiments, the carrier molecule is a non-water soluble molecule as described in more detail elsewhere herein.

In some embodiments, the chelant moieties are tridentate or tetradentate chelant moieties. In some embodiments, the chelant moieties are nitrilotriacetic acid (NTA) moieties. In some embodiments, the chelant moieties are histidine residues, for example, in the form of histidine tags. In some embodiments, the chelate moieties are iminodiacetic acid (IDA) moieties.

In some embodiments, the chelant moieties are covalently bound to the carrier molecule via a linker, for example, via a linker described herein. In some embodiments, each linker is bound to a single chelant moiety (e.g., mono-NTA configuration). In some embodiments, two chelant moieties are bound to a single linker (e.g., di-NTA configuration). In some embodiments, four chelant moieties are bound to a single linker (e.g., tetra-NTA configuration).

Methods for Generation of Protein Multimers

In some embodiments, the invention provides methods for the generation of reversible protein multimers in which a plurality of proteins is conjugated to a carrier molecule via a chelate complex bond. In some such embodiments, the carrier molecule and the protein are conjugated to the respective chelant moieties via covalent bond, for example, via a covalently bound linker. In such embodiments, the only non-covalent bond between carrier molecule and protein monomer is the chelate complex bond. In other embodiments, an additional non-covalent bond is introduced between the carrier molecule and the monomeric protein, for example, a binding molecule/ligand bond, such as a streptavidin/biotin interaction.

Some aspects of this invention provide methods for the generation of protein multimers, for example, of MHC protein multimers. In some embodiments, the method includes a step of contacting a monomeric protein, for example, an MHC molecule, that is conjugated to a chelant moiety with a carrier molecule as provided herein, that is conjugated to a plurality of chelant moieties under conditions suitable for formation of a chelate complex between the chelant moieties conjugated to the MHC molecule and the chelant moieties conjugated to the carrier molecule.

In some embodiments, a method for the generation of protein multimers, for example, MHC protein multimers is provided that includes contacting a protein molecule, for example, an MHC molecule, that is conjugated to a first chelant, for example, a His tag, with a ligand molecule, for example, biotin, conjugated to a second chelant under conditions suitable for formation of a chelate complex between the first and the second chelant. The resulting product is a monomeric protein conjugated to a ligand via a non-covalent chelate complex bond. Such monomers can be assembled to reversible multimers by contacting them with a carrier molecule conjugated to a plurality of ligand-binding molecules or moieties, for example, streptavidin molecules. In some embodiments, a multivalent carrier molecule is generated by contacting a carrier molecule conjugated to a plurality of chelant moieties via non-covalent interaction, for example, via biotin/streptavidin interaction. For example, in some embodiments, a carrier molecule comprising a plurality of streptavidin moieties is contacted with a plurality of biotin molecules that are conjugated to chelant moieties, for example, NTA moieties, via a covalently bound linker as described herein.

In some embodiments, methods for the production of peptide-loaded MHC multimers are provided. While stable, peptide-loaded MHC class I proteins can be obtained by refolding of MHC class I heavy chains with peptides of interest, recombinant MHC class II proteins are more difficult to obtain. In some embodiments, recombinant MHC class II molecules are produced in soluble form by insect expression systems, such as *Drosophila* S2 cells or baculovirus and sf9 cells. With very few exceptions, deletion of the transmembrane (TM) domains of the α and β chains in MHC class II molecules results in the dissociation of the two subunit chains. In some embodiments, chain pairing is re-established by addition of leucine zippers. In some embodiments, empty MHC class II molecules are first isolated and then loaded with an antigenic peptide of interest. Such peptide-loaded MHC class II molecules can then be isolated and used in the production of MHC protein multimers. In some embodiments, for example, in embodiments where the binding interaction between the peptide of interest and an MHC class II molecule is of low strength, peptides can be fused to the N-terminus of the β chain via a flexible linker. Such fusions of MHC class II chains and antigenic peptides, resulting in the production of recombinant, peptide-loaded MHC molecules, are well known to those of skill in the art.

In some embodiments, a chelant moiety, for example, a His tag, is added at the C-terminus of an MHC chain by recombinant addition of a fusion peptide comprising a chelant moiety, for example, in the form of a His tag as described herein. In some embodiments, for example, in some embodiments, in which the peptide-loaded MHC monomer is isolated via a method using a tag attached to the antigenic peptide, a chelant moiety is attached to the isolated, peptide-loaded MHC molecule after isolation. Methods for post-synthesis or post-isolation of chelants to isolated proteins are known to those of skill in the art and exemplary methods are described herein.

While some MHC molecules are instable without a bound antigenic peptide, in some embodiments, the MHC molecule is sufficiently stable without peptide cargo (e.g. HLA DRB1*0101 or DRB1*0401) to allow the production of empty MHC molecules and MHC multimers, e.g., MHC molecules or multimers that are not loaded with an antigenic peptide. In some such embodiments, the MHC monomer is loaded after isolation or purification with the peptide of interest. In some embodiments, the MHC monomer is first incorporated into a reversible MHC multimer as provided herein and subsequently loaded with a peptide of interest. The efficiency of peptide loading strongly depends on its binding strength to the respective MHC molecule. If the binding is below a critical threshold, peptide loading is inefficient and the resulting complexes are of limited stability, both physically and conformationally.

Some embodiments of the invention provide methods for the generation of MHC molecules and multimers that are loaded with an antigenic peptide. In some embodiments, methods and reagents for the production of peptide-loaded MHC class II molecules are provided. The production of peptide-loaded MHC class II molecules is technically difficult, based on the instability of engineered MHC class II heterodimers comprising a and R heavy chains lacking a transmembrane domain, and, in many instances, the low affinity binding interactions between the MHC class II heavy chains and the antigenic peptide. As a result, populations of peptide-loaded MHC class II molecules produced with conventional methods are often heterogeneous in that a significant portion of MHC class II molecules are not or not correctly peptide-loaded. MHC class II multimers produced from such heterogeneous populations of MHC class II molecules often show poor staining performance, great batch-to-batch variability in staining efficiency, and some specific peptide-loaded MHC class II multimers are difficult or impossible to obtain with conventional methods.

Some aspects of this invention provide methods addressing these problems in the production of MHC class II molecules and multimers. For example, some aspects of this invention provide methods and reagents for the generation of peptide-loaded MHC molecule, for example, MHC class II molecules, that include the use of a tag conjugated to the antigenic peptide. In some embodiments MHC molecules that have bound a tagged antigenic peptide are isolated and/or purified by a method that can be carried out under non-denaturing conditions, for example, by certain chromatography methods (e.g., affinity chromatography or ion exchange chromatography). In some embodiments, the tag conjugated to the antigenic peptide can be removed, for example, by cleaving a linker that connects the tag to the antigenic peptide, and methods for tag removal from tagged peptide-loaded MHC molecules, for example, MHC class II molecules, are also provided herein.

In some embodiments, the antigenic peptide of interest is conjugated to a tag. In some embodiment, the tag is a peptide tag, for example, a peptide tag that is N-terminally or C-terminally fused to the antigenic peptide. In some embodiments, the tag is an affinity tag that allows for the isolation of correctly loaded MHC class II molecules by affinity chromatography. Affinity tags are well known to those of skill in the art and examples of peptide tags include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. In some embodiments, the tag is a biotin tag or a biotin variant tag, for example, desthiobiotin (DTB). DTB is a biotin variant that binds about $1 \times 10^6$-fold weaker to streptavidin than biotin. DTB is readily displaced by free biotin, allowing gentle affinity purification based on the reversible DTB-streptavidin conjugation. Conjugation partners similar to streptavidin can also be employed, for example, StreptActin, a mutant of streptavidin. Strep tags, which are peptidic biotin analog, bind also to StreptActin. Desthiobiotin, biotin, streptavidin, StreptActin, strep tags and derivatives of these reagents, as well as methods for the use of these reagents in protein and peptide purification are well known to those of skill in the art. Some methods suitable according to aspects of this invention are described herein, and additional suitable methods will be apparent to those of skill, for example, as described in Howarth M, Chinnapen D J, Gerrow K, Dorrestein P C, Grandy M R, Kelleher N L, El-Husseini A, Ting A Y. A monovalent streptavidin with a single femtomolar biotin binding site. Nat Methods. 2006; 3:267-73; Hirsch J D, Eslamizar L, Filanoski B J, Malekzadeh N, Haugland R P, Beechem J M, Haugland R P. Easily reversible desthiobiotin binding to streptavidin, avidin, and other biotin-binding proteins: uses for protein labeling, detection, and isolation. Anal Biochem. 2002; 308:343-57; Lichty J J, Malecki J L, Agnew H D, Michelson-Horowitz D J, Tan S. Comparison of affinity tags for protein purification. Protein Expr Purif. 2005; 41:98-105; Wu S C, Wong S L. Development of an enzymatic method for site-specific incorporation of desthiobiotin to recombinant proteins in vitro. Anal Biochem. 2004; 331(2):340-8; Maier T, Drapal N, Thanbichler M, Bock A. Strep-tag II affinity purification: an approach to study intermediates of metalloenzyme biosynthesis. Anal Biochem. 1998; 259:68-73; Chen R, Folarin N, Ho V H, McNally D, Darling D, Farzaneh F, Slater N K. Affinity recovery of lentivirus by diaminopelargonic acid mediated desthiobiotin labeling. J Chromatogr B Analyt Technol Biomed Life Sci. 2010; 878:1939-45; Gloeckner C J, Boldt K, Schumacher A, Roepman R, Ueffing M. A novel tandem affinity purification strategy for the efficient isolation and characterisation of native protein complexes. Proteomics. 2007; 7:4228-34; Cass B, Pham P L, Kamen A, Durocher Y. Purification of recombinant proteins from mammalian cell culture using a generic double-affinity chromatography scheme. Protein Expr Purif. 2005 March; 40(1):77-85; Korndörfer I P, Skerra A. Improved affinity of engineered streptavidin for the Strep-tag II peptide is due to a fixed open conformation of the lid-like loop at the binding site. Protein Sci. 2002; 11:883-93; the entire contents of each of which are incorporated herein by reference.

Sequences of peptide tags useful in some embodiments of this invention, for example, the tags described herein, are well known to those of skill in the art, and exemplary tags are described, for example, in Kimple, M. E., and Sondek, J. *Overview of affinity tags for protein purification.* Curr Protoc Protein Sci. 2004 September; Chapter 9:Unit 9.9, incorporated in its entirety herein for disclosure of affinity tags. Those of skill in the art will appreciate that the invention is not limited in this respect.

Some aspects of this invention provide tagged MHC class II binding antigenic peptides and methods of using such peptides. In some embodiments, a tag conjugated to an antigenic peptide is useful for the isolation of the tagged peptide, either alone or when bound to an MHC class II molecule. Methods for isolating tagged peptides are well known to those of skill in the art and include, for example, affinity chromatography and ion exchange chromatography.

In some embodiments, an MHC class II binding peptide is provided or used that is conjugated to a tag. In some embodiments, the tag is an acidic tag. In some embodiments, the acidic tag is an acidic peptide tag, for example, a peptide tag comprising a sequence of 2, 3, 4, 5, 6, 7, 8, 9, 10, 11, 12, 13, 14, 16, 17, 18, 19, 20, or more contiguous acidic amino acid residues. In some embodiments, the acidic amino acid residues glutamic acid (Glu, E) or aspartic acid (Asp, D) residues. In some embodiments, the antigenic peptide is conjugated to an acidic tag that allows for the isolation of correctly loaded MHC class II molecules by anion exchange chromatography. In some embodiments, the tag is a tag comprising a sequence of 2, 3, 4, 5, 6, 7, 8, 9, 10, or more Asp residues, for example, a pY-D4 tag (phosphor-tyrosine followed by four Asp residues), a pY-D5, pY-D6, pY-D7, pY-D8, pY-D9, or pY-D10 tag. In some embodiments, the acidic tag is a tag comprising a sequence of 2, 3, 4, 5, 6, 7, 8, 9, 10, or more Glu residues, for example, a pY-E6 (phosphor-tyrosine followed by six Glu), pY-E7, pY-E8, pY-E9, or a pY-E10 tag. In some embodiments, the acidic tag is an acidic detectable label, for example, an acidic fluorophore. In some embodiments, the acidic fluorophore is a cyanine dye tag, for example, a Cy5 tag, or a Cy5.5 tag. Other acidic tags suitable for peptide or protein isolation and/or purification are well known to those of skill in the art and the invention is not limited in this respect.

In some embodiments, tagged MHC class II binding peptides are provided that are reversibly tagged, e.g., that are tagged with a structure that can be cleaved, resulting in a release of the conjugated tag from the peptide. Methods of using such reversibly tagged peptides are also provided. In some embodiments, the tag is conjugated to the peptide via a cleavable linker. In some embodiments, the linker is a photocleavable linker. In some embodiments, the linker is a 2-nitro-phenyl-β-Ala (NPβA) linker. In some embodiments, the linker is a peptide linker that comprises an amino acid sequence that can be cleaved by a protease or by a chemical. In some embodiments, the tagged peptide is a peptide conjugated to a part of a cleavable linker that remains after cleavage of the linker.

One advantage of a cleavable linker is that after isolation of the peptide-loaded MHC class II molecule with a method relying on the tag, the tag can be removed. Cleavage of a cleavable linker will, in some embodiments, leave part of the linker conjugated to the MHC class II binding peptide. However, some linkers can be designed in a manner that will result in complete removal of the linker from the MHC-class II binding peptide.

Tag removal by linker cleavage is particularly useful in embodiments, where the tag interferes or is suspected to interfere with the binding of the peptide-loaded MHC class II molecule to its target T-cell receptor. Exemplary cleavable linkers are described in more detail elsewhere herein. Additional cleavable linkers are known to those of skill in the art and the invention is not limited in this respect. In some embodiments, the cleavable linker is a photocleavable linker. Photocleavable linkers can be cleaved by irradiation with UV light. Photocleavable linkers are described herein and additional photocleavable linkers are well known in the art. See, for example, Pandori M W, Hobson D A, Olejnik J, Krzymanska-Olejnik E, Rothschild K J, Palmer A A, Phillips T J, Sano T., *Photochemical control of the infectivity of adenoviral vectors using a novel photocleavable biotinylation reagent.* Chem Biol. 2002 May; 9(5):567-73.; Hahner S, Olejnik J, Ludemann H C, Krzymanska-Olejnik E, Hillenkamp F, Rothschild K J. *Matrix-assisted laser desorption/ionization mass spectrometry of DNA using photocleavable biotin.* Biomol Eng. 1999 Dec. 31; 16(1-4):127-33; Olejnik J, Ludemann H C, Krzymanska-Olejnik E, Berkenkamp S, Hillenkamp F, Rothschild K J. *Photocleavable peptide-DNA conjugates: synthesis and applications to DNA analysis using MALDI-MS.* Nucleic Acids Res. 1999 Dec. 1; 27(23):4626-31; Olejnik J, Krzymanska-Olejnik E, Rothschild K J. *Photocleavable aminotag phosphoramidites for 5'-termini DNA/RNA labeling.* Nucleic Acids Res. 1998 Aug. 1; 26(15):3572-6. Olejnik J, Krzymanska-Olejnik E, Rothschild K J. *Photocleavable affinity tags for isolation and detection of biomolecules.* Methods Enzymol. 1998; 291:135-54; Olejnik J, Sonar S, Krzymanska-Olejnik E, Rothschild K J. *Photocleavable biotin derivatives: a versatile approach for the isolation of biomolecules.* Proc Natl Acad Sci USA. 1995 Aug. 1; 92(16):7590-4; all references incorporated herein by reference for disclosure of photocleavable linkers). In some embodiments, a peptide tagged via a cleavable linker is referred to as a reversibly tagged peptide.

In some embodiments, an MHC class II molecule loaded with a reversibly tagged peptide is isolated, for example, by affinity or ion exchange chromatography, and the tag is removed after isolation by cleavage of the linker. In some such embodiments, the MHC class II molecule loaded with a now untagged peptide is then isolated from the cleaved tag, for example, by size fractionation.

In some embodiments, an MHC molecule, for example, an MHC class II molecule conjugated to a chelant moiety is loaded with a tagged peptide. In some embodiments, the peptide tag is an acidic tag, as provided herein, and the chelant moiety is comprised in a peptide tag, for example, a His tag, as provided herein. For example, in some embodiments, an MHC class II molecule is provided that comprises a heavy chain conjugated to a His tag, for example, by C-terminal fusion, and that is loaded with a tagged antigenic peptide, for example, an antigenic peptide conjugated to an acidic tag, for example, a Cy5.5 tag) via a photocleavable linker. In some embodiments, a correctly peptide-loaded MHC class II molecule is isolated by anion exchange chromatography, the tag is cleaved from the antigenic peptide, for example, by UV irradiation, and the peptide-loaded MHC class II molecule thus generated is then assembled into an MHC multimer as described herein.

In some embodiments, an MHC molecule, for example, an MHC molecule loaded with an antigenic peptide is conjugated with a chelant moiety or a peptide tag after production of the MHC molecule or after loading the MHC molecule with the antigenic peptide, or after cleavage of a tag, if present, from a reversibly tagged antigenic peptide bound to the MHC molecule. In some embodiments, such post-production conjugation, for example, to a heavy chain of a peptide-loaded MHC class II molecule, is carried out by site-specific alkylation or a sortase-mediated transpeptidation reaction. In some embodiments, the antigenic peptide is tagged with a His tag, the tag is cleaved after peptide-loading, and a His tag is subsequently appended to a heavy chain of the MHC molecule. Using such "tag exchange" strategies, incompatible tags can be used subsequently, or the same tag can be employed at different positions. Methods for post-synthesis addition of tags to peptides and proteins are well known to those of skill in the art and include, but are not limited to, biotinylation and sortase-mediated protein labeling (for the latter see Popp et al., *Site-Specific Protein Labeling via Sortase-Mediated Transpeptidation* Curr. Protoc. Protein Sci. 56:15.3.1-15.3.9; 2009, incorporated herein by reference in its entirety for disclosure of sortase-mediated transpeptidation reactions).

To give a non-limiting example of an embodiment employing such a tag-exchange strategy: in some embodiments, an MHC class II molecule comprising a sortase target sequence is loaded with a His-tagged MHC class II-binding peptide and peptide-loaded MHC class II molecules are isolated form free peptide and empty MHC class II molecules by affinity chromatography and, optionally, size fractionation. After isolation, the His-tag is cleaved off the MHC class II binding peptide and, optionally, the tag-free MHC class II molecule loaded with the peptide is separated from the cleaved-off tag. In some such embodiments, the heavy chain of the MHC class II molecule is then tagged by performing a sortase-mediated transpeptidation reaction. In some such embodiments, the tag appended to the MHC heavy chain is a peptide tag. In some embodiments, the sortase-appended tag is a His-tag, thus effectively yielding MHC class II molecules in which the His tag was moved from the antigenic peptide to a heavy chain..

In some embodiments that include a charged tag, for example an acidic tag, that is conjugated to an MHC class II binding peptide, a peptide-loaded MHC class II molecule is isolated by ion exchange chromatography. In some embodiments including an acidic tag, anion exchange chromatography is used to isolate the tagged peptide or an MHC class II molecule loaded with the tagged peptide.

Other methods of producing peptide-loaded MHC multimers are known in the art (for example, see Altman et al., Science 274:94 96, 1996; Dunbar et al., Curr. Biol. 8:413 416, 1998; Crawford et al., Immunity 8:675 682, 1998). In all embodiments, non-denaturing conditions are preferred during isolation of empty and peptide-loaded MHC class II molecules.

Some aspects of this invention provide methods and reagents for the generation of "empty" MHC class II molecules. The term "empty" in the context of MHC class II molecules signifies that the MHC molecules are not loaded with an antigenic, MHC class II-binding peptide. Such empty MHC class II molecules are often instable and conventional methods of high-affinity antibody-mediated isolation are typically unsuitable for the preparation of such empty MHC class II molecules because of the denaturing conditions used in such methods.

Some aspects of this invention provide methods that allow gentle purification of fragile "empty" (without nominal peptide cargo) His tagged MHC II molecules by affinity chromatography on Ni2+ nitrilotriacetic acid (NTA) columns. In some embodiments of this invention, methods are provided that allow for the isolation of empty MHC class II molecules that retain the correct folding and dimerization properties. In some embodiments, such methods include a step of tagging a heavy chain comprised in an MHC class II molecule. In some embodiments, the tag is a peptide tag that can be used for isolation of the tagged protein by affinity chromatography or ion exchange chromatography. In some embodiments, the tag is a His tag, for example, a tag that comprises 3-12 Histidine residues. In some embodiments, MHC class II molecules comprising a His-tag labeled heavy chain are isolated by affinity chromatography. In some embodiments, the affinity chromatography uses an Ni2+-NTA resin. Methods for affinity chromatography for the isolation of tagged peptides and proteins are well known to those of skill in the art and it will be appreciated by those of skill that the invention is not limited in this respect.

Empty MHC multimers are useful in that they allow for standardized production of a core reagent that can then be customized for a specific application by loading a specific antigenic peptide of interest onto the multimer.

In some embodiments, a chelant moiety is conjugated to an isolated protein after the protein has been synthesized, for example, post-translationally, or after in situ synthesis, for example, after Fmoc synthesis. In some such embodiments, the chelant moiety is conjugated to the protein, for example, the MHC molecule, for example, to a heavy chain of the MHC molecule by chemical or enzymatic modification. Methods for post-synthesis addition of tags to peptides and proteins are well known to those of skill in the art and include, but are not limited to, biotinylation and sortase-mediated protein labeling (for the latter see Popp et al., *Site-Specific Protein Labeling via Sortase-Mediated Transpeptidation* Curr. Protoc. Protein Sci. 56:15.3.1-15.3.9; 2009, incorporated herein by reference in its entirety for disclosure of sortase-mediated transpeptidation reactions).

Post-isolation addition of a chelant moiety is particularly useful in embodiments, where a chelant moiety would interfere with a synthesis or purification step, for example, in embodiments, where an MHC molecule is loaded with an antigenic peptide that comprises a chelant tag and the tag is used for isolation of peptide-loaded MHC molecules. In some such embodiments, the peptide tag can be cleaved from the antigenic peptide and a chelant tag can be added subsequently to the MHC molecule, for example, to an MHC heavy chain by methods well known to those of skill in the art.

Cell Staining and Detection Methods

Some aspects of this invention provide methods for the staining, detection, and/or isolation of cells using a reversible protein multimer, for example, a reversible MHC multimer, as described herein. In some embodiments, the method comprises contacting a population of cells with a protein multimer, for example, an MHC multimer provided herein. In some embodiments, the multimer comprises a detectable label, for example, a fluorophore, either as the carrier molecule or conjugated to the multimer.

The term "detectable label," as used herein, refers to a molecule or moiety that can be detected, for example, by performing an assay known to those of skill in the art for its detection. A detectable label, accordingly, may be, for example, (i) an isotopic label (e.g., a radioactive or heavy isotope, including, but not limited to, 2H, 3H, 13C, 14C, 15N, 31P, 32P, 35S, 67Ga, 99mTc (Tc-99m), 111In, 123I, 125I, 169Yb, and 186Re), (ii) an affinity label (e.g., an antibody or antibody fragment, an epitope, a ligand or a ligand-binding agent) (iii) and enzymatic label that produce detectable agents when contacted with a substrate (e.g., a horseradish peroxidase or a luciferase); (iii) a dye, (e.g., a colored, luminescent, phosphorescent, or fluorescent molecule, such as a chemical compound or protein). Fluorophores, for example, fluorescent dyes and proteins, are of particular use for embodiments of this invention that involve detection or isolation of living cells. A fluorophore is a molecule or moiety that absorbs light of a specific wavelength and then re-emits light at a different specific wavelength, thus causing the molecule of moiety to be fluorescent. Other detectable labels are known to those of skill in the art and the invention is not limited in this respect. It will be appreciated that a detectable label may be incorporated into any part of the multimeric structure and in any manner that does not interfere with the stability or the function, for example, the binding activity of the multimer.

In some embodiments, the method includes a step of detecting the multimer bound to a cell, for example, to a surface receptor (e.g., a T-cell receptor) of a cell. The method performed to detect the multimer depends, of course, on the nature of the detectable label comprised in the multimer. For example, in some embodiments, where the detectable label is a fluorophore, suitable methods for detection are fluorescence microscopy, cytometry, or FACS.

In some embodiments, the method comprises a step of quantifying the number of detected cells, for example, quantifying the number of T cells expressing a specific TCR in a cell population, for example, in a cell population obtained from a subject. In some embodiments, the quantity of cells, for example, of T-cells expressing a specific TCR, is compared to a reference quantity. In some embodiments, the comparison of the quantity of T-cells expressing a specific TCR in a subject to a reference quantity is used to determine an immune reaction in the subject. In some embodiments, the reference quantity is a quantity measured or expected in a healthy subject or in healthy subjects, or a quantity measured in the subject prior to a clinical intervention, for example, prior to a vaccination, and a quantity in the subject that is higher than the reference is indicative of an immune response in the subject, whereas a quantity in the subject that is lower than the reference is indicative of depletion of a specific T-cell population.

Accordingly, MHC multimers as provided herein are useful, for example, for monitoring immune responses in subjects, either in response to a clinical intervention, for example, a vaccination, or as a result of a disease or condition, for example, a hyperproliferative disease in the subject. In some embodiments, the clinical intervention is a vaccination against a tumor antigen. In some embodiments, the vaccination is a vaccination administered after surgical removal of a tumor expressing the tumor antigen. In some embodiments, the clinical intervention is an intervention aimed to suppress a function of the immune system, for example, by depleting a specific population of T-cells. In some embodiments, the subject is a subject having an autoimmune disease.

In some embodiments, the detection method further comprises a step of releasing the chelate complex bond comprised in the multimer employed, for example, by withdrawing the cation of the complex bond, or by contacting the multimers with an agent able to displace a chelant forming the chelate complex bond.

T Cell Staining Methods

Interactions of T cell antigen receptors (TCRs) with MHC-peptide monomers are characterized by micromolar dissociation constants ($K_D$) and half-lives in the range of seconds. The coordinate binding of CD8 to TCR-associated MHC class I-peptide complexes can considerably strengthen the binding interaction. According to some aspects of this invention, the use of MHC-peptide monomers that are conjugated to reversible multimers substantially increases the overall binding avidity and decreases the dissociation rate to half-lives in the order of hours. Accordingly, the use of MHC multimers as provided herein allows for the efficient staining, detection, and/or isolation of T cells bearing specific TCRs, for example, by fluorescent microscopy, flow cytometry, fluorescence activated cell sorting (FACS), or magnetic-activated cell sorting (MACS).

In some embodiments, MHC multimers and methods are provided that are useful for the staining of CD8$^+$ T-cells. CD8 interacts preferentially with MHC class I molecules. Accordingly, MHC multimers useful for staining of CD8$^+$ T-cells are preferentially MHC class I multimers. CD8 undergoes differentiation- and activation-dependent changes in the glycosylation and sialylation of its β chain, which can profoundly affect cognate and non-cognate MHC class I-peptide binding. Non-cognate CD8 binding to MHC class I-peptide multimers has been reported to increase non-specific multimer binding. Accordingly, in some embodiments, multimers are provided that contain the CD8 binding weakening mutation A245V in the MHC α3 domain. In some embodiments, an MHC class I multimer as provided herein (A245V mutated or not) is used in a staining procedure at a concentration of about 5-30 nM (about 2.5 to 15 µg/ml). At this concentration, non-specific staining is generally low.

Importantly, binding of MHC class I molecules to T-cell receptors can elicit T cell activation events, such as intracellular calcium mobilization, diverse tyrosine phosphorylation and endocytosis of MHC class I-peptide engaged TCR/CD8. For example, MHC class I-peptide complex driven cell activation can induce death of effector cytotoxic T-cells (CTLs) via FasL-dependent apoptosis or severe mitochondrial damage. This can lead to changes in T-cell populations that are contacted with MHC multimers, for example, for cell staining, detection, or isolation, for example, by selective depletion of stained T-cells. In some circumstances, TCR-activation-mediated cell depletion can render isolation of a non-activated T-cell population impossible. Some aspects of this invention provide reversible MHC multimers and methods for their use that avoid this problem by minimizing the time of high-avidity MHC/TCR interaction by re-monomerizing the multimers, thus minimizing undesired TCR activation-mediated effects on stained cells. However, it will be appreciated by those of skill in the art, that the reversible MHC multimers provided herein can also be used in methods that do not include a chelate complex bond release step, thus employing the reversible multimers in the manner conventional multimers would be employed. Accordingly, in some embodiments, methods are provided that exploit MHC multimer TCR activation to deplete specific T-cell populations by MHC-mediated TCR activation. In some such embodiments, reversible MHC multimers as provided herein are used to eradicate antigen-specific CD8+ CTLs.

MHC class II multimer binding to CD4+ T-cells can also lead to T-cell activation and death, for example, of CD4+ effector cells. Accordingly, reversible MHC class II multimers are useful in the staining of CD4+ T-cells and in the isolation of minimally manipulated or activated CD4+ T-cells.

Some aspects of this invention provide reversible MHC multimers and methods for the use of such multimers to analyze the state of activation or differentiation of T-cells, for example, CD8+ and/or CD4+ T-cells. As will be appreciated by those of skill in the art, homogenous populations of MHC multimers of defined structure are preferable over heterogeneous MHC multimer populations. In some embodiments, homogenous populations of MHC multimers, e.g. of dimers, trimers, tetramers, pentamers, hexamers, or decamers, are provided for use in such methods. In some embodiments, the MHC multimers comprise linkers of defined length and flexibility. In some embodiments, the MHC multimers comprise chelant groups in defined configurations, for example, in mono- di- or tetra-chelant configuration. In contrast to heterogeneous multimers, binding studies with defined, homogenous populations of multimers can reveal differentiation- and activation-dependent differences, for example, differentiation- and activation-dependent changes in glycosylation and sialylation of T cell surface molecules involved in antigen recognition of the cells under study which can affect, for example, CD8 participation in MHC class I molecule binding and/or aggregation of TCR and CD8.

It will be apparent to those of skill in the art that the MHC multimers provided herein can be employed alone or in combination with other binding and/or staining agents. For example, in some embodiments, MHC multimers provided herein are used to stain T-cells in combination with staining the cells for an additional antigen, for example, with a staining for intracellular cytokine staining.

In some embodiments, reversible MHC class I-peptide multimers, are provided that comprise a mutation in the 3 domain. In some embodiments, the mutation is a mutation that ablate CD8 binding, e.g. a D227K, T228A in human MHC and D227K, Q226A in mouse MHC molecules. In some embodiments, methods are provided that use such CD8 binding-deficient MHC multimers to stain, detect, and/or isolate CD8-independent T cells, which typically express high affinity TCRs.

For example, in some embodiments, CD8 binding-deficient MHC multimers are provided for the staining, detection, and/or isolation of CD8+ T cells expressing high-affinity TCRs specific for tumor antigens, for example, for MELAN-A/Mart-1, gp100, or tyrosinase. It is known to those of skill in the art that such tumor-antigen specific T-cell tend to express low affinity TCRs and that infrequent CD8+ T cells specific for tumor antigens expressing high affinity TCRs efficiently kill tumor cells. In some embodiments, the use of a reversible MHC class I multimer as provided herein enables efficient identification and isolation of such rare cells with no or only minimal TCR activation, thus allowing for the isolation of native T-cell populations that cannot be isolated with conventional MHC class I multimers.

Further, in some embodiments, CD8 binding-deficient multimers are used to selectively induce FasL (CD95L) expression, resulting in apoptosis of antigen-specific CTLs.

Conditions and protocols for staining, detection, and isolation of cells using multimers are well known to those of skill in the art. In general, methods for the use of conventional MHC multimers are applicable to the reversible MHC multimers as provided herein, modified, where appropriate, to include a step of chelate complex bond release, as described in more detail elsewhere herein.

Staining with reversible MHC multimers can be performed through a wide range of temperatures. In some embodiments, staining is performed at a temperature between 0-37° C.

In some embodiments, MHC multimer staining is performed at 37° C. While staining at 37° C. is rapid, and efficient staining of CD4+ T cells with reversible MHC class II multimers is often observed upon incubations at 37° C. for extended periods of time, reversible MHC class I multimers efficiently effect TCR activation at this temperature.

In some embodiments, staining is performed at 0-4° C. It will be appreciated by those of skill, that MHC multimer binding at low temperatures (e.g., 0-4° C.) tends to be slow, necessitating extended periods of time for staining as compared to staining at higher temperatures. In some embodiments, staining with MHC multimers is performed at ambient temperature, e.g. at 20-30° C., preferably at 22-25° C. In some embodiments, MHC staining is performed in the presence of EDTA (e.g., 5 mM) and/or sodium azide (e.g., 0.02%) to inhibit cell activation. Under these conditions multimer binding is rapid. In some embodiments, staining is performed for about 10 minutes, about 15 minutes, about 20 minutes, about 25 minutes, about 30 minutes, or about 20-45 minutes. In some embodiments, for example, in some embodiments using reversible MHC class II multimers, staining is performed for 30-120 min. Under these conditions, cognate MHC class II complexes binding to TCR (and CD4) are internalized and accumulate over time.

Multimer concentration is an important factor in achieving maximum staining efficiency, and, while exemplary MHC multimer concentrations are provided herein, it will be appreciated by those of skill that it is preferable to test a range of concentrations, for example, in the range of about 5-50 nM (about 2.5-25 µg/ml), or, in the case of low affinity binding, in higher concentration ranges, for example, in the range of about 5-100 nM (about 2.5-50 µg/ml).

In some embodiments in which a cell is contacted with an MHC multimer, for example, with an MHC class II multimer as provided herein, binding of the MHC multimer to the cell is facilitated by desialylation of the cell. Desialylation is a process by which sialyl groups on the cell surface are removed or modified. Methods and reagents for desialylating a cell are described in detail elsewhere herein and additional methods are well known to those of skill in the art. For example, in some embodiments, a cell is contacted with a desialylating agent in order to achieve desialylation. Desialylating agents are, in some embodiments, enzymes, while, in other embodiments, chemicals are used to effect desialylation. Enzymes known to desialylate cell surfaces are, for example, neuraminidases. Methods and conditions suitable for desialylation of cells by contacting them with a neuraminidase are well known to those of skill in the art.

In some embodiments, the cells are pre-treated with neuraminidase under conditions suitable to achieve desialylation of the cells (e.g., treatment with 0.03µ/ml for 30 min at 37° C.).

In some embodiments, staining is increased by inhibiting TCR down modulation with the protein kinase inhibitor dasatinhib. In some embodiments, scarce antigen-specific cells can be enriched by combination of fluorescence-based methods as described herein with a non-fluorescent-based isolation method, for example, with MACS using magnetic beads coated with an antibody against an epitope of the carrier molecule.

Isolation of Cells with Reversible Multimers

In some embodiments, methods for the use of multimers as described herein for isolating specific cells or cell populations are provided. In general, useful multimers for isolation methods comprise a detectable label and the methods include a step of staining the target cell population as described in more detail elsewhere herein. In some embodiments including the isolation of cells, a method of cell separation is employed that allows for the enrichment or the isolation of homogenous populations of cells based on the cells binding the employed multimer, for example, the employed MHC multimer. Such methods are well known in the art and include, for example, FACS and MACS.

In some embodiments, the method of isolating cells with a reversible multimer further includes a step of releasing the chelate bond comprised in the multimer. In some embodiments, this step includes withdrawal of the central ion, for example, the central divalent cation, from the chelate complex. Method for ion withdrawal are well known in the art and include, in some embodiments, washing the cells with a solution that does not contain a significant amount of the divalent cation, or with a solution that comprises an agent that sequesters the divalent cation. In some embodiments, the step of chelate complex bond release includes contacting the chelate complex bond with an agent that displaces a chelant from the chelate complex bond. For example, if the chelate complex bond is formed by an NTA chelant and a histidine residue, the chelate complex bond can be released by contacting it with an imidazole residue, for example, with free imidazole. Imidazole is able to displace a chelant, in this case, the histidine chelant from the complex bond, thus releasing the chelate complex bond of the multimer. The result of this release is the re-monomerization of the proteins comprised in the multimer, for example, of MHC proteins in an MHC multimer.

In some embodiments, re-monomerization of the multimer after staining and/or isolation avoids detrimental effects on the cells and, in embodiments, where the cells are rare and/or sensitive to detrimental effects of staining, allows for efficient isolation of such cells that is cumbersome or impossible with conventional strategies.

Manipulation of T-Cell Populations

In some aspects, this invention provides methods for the manipulation of T-cells using reversible monomers. In some embodiments, the method includes a step of contacting a population of cells expressing a T-cell receptor with an MHC multimer as described herein under conditions suitable for the multimer to bind to the T-cell receptor and for a time sufficient for the T-cell receptor/MHC class I interaction to effect TCR-mediated T-cell activation. In some embodiments, the contacting is performed in vitro. In some embodiments, the contacting is performed ex vivo. In some embodiments, the contacting is performed in vivo. In some embodiments, the cells are contacted with an MHC multimer for a time long enough to activate high-affinity TCR expressing T-cells, but not to activate low affinity TCR expressing T-cells. In some embodiments, the cells are cells from a subject having an autoimmune disease. In some embodiments, the cells are contacted with an MHC multimer that is loaded with an antigenic peptide recognized by T-cells that mediate an autoimmune disease. In some embodiments, the method further comprises measuring the quantity of the T-cells targeted by the MHC multimer, for example, by methods for the identification or detection of T-cells provided herein or otherwise known in the art.

Isolated Cell Populations

Some embodiments of this invention provide isolated cells or cell populations, for example, isolated native, or non-activated T-cell populations obtained by using a reversible multimer or a method as provided herein. In some embodiments, an isolated cell is provided that has been contacted with a reversible multimer provided herein and isolated from a cell population based on the cell binding the multimer, for example, by a method for detection and/or isolation described in more detail elsewhere herein. In some embodiments, the cell is a T-cell. In some embodiments, the T-cell is a native T-cell, or a T-cell that has not undergone TCR-mediated cell activation. In some embodiments, the cell has been contacted with an agent releasing the chelate complex bond of the reversible multimer subsequent to its isolation. In some embodiments, the cell is a T-cell recognizing a tumor antigen. In some embodiments, the cell is a T-cell expressing a TCR that binds a tumor antigen with high affinity. In some embodiments, the cell is a therapeutically valuable cell. In some embodiments, the cell is expanded in vitro after isolation, and used in a therapeutic method. In some embodiments, the therapeutic method includes a step of administering the cell to a subject in need thereof, for example, a subject having a tumor or having an elevated risk of developing a tumor expressing a tumor antigen. In some embodiments, a subject at risk of developing a tumor expressing a tumor antigen is a subject which was diagnosed to have such a tumor and has undergone surgical removal of the tumor.

Further materials, methods, suitable conditions, and useful modifications for the use of reversible MHC multimers as described herein will be apparent to those of skill in the art. Methods for the use of conventional multimers can generally be applied to the use of the inventive multimers provided herein with modifications that do not amount to more than routine experimentation. Examples of such methods are described, for example, in Altman J D, Moss P A, Goulder P J, Barouch D H, McHeyzer-Williams M G, Bell J I, McMichael A J, Davis M M. Phenotypic analysis of antigen-specific T lymphocytes. Science 1996; 274: 94-96.; Bakker A H, Schumacher T N. MHC multimer technology: current status and future prospects. Curr Opin Immunol 2005; 17: 428-433.; Xu X N, Screaton G R. MHC/peptide tetramer-based studies of T cell function. J Immunol Methods 2002; 268: 21-28.; Guillaume P, Baumgaertner P, Neff L, Rufer N, Speiser D E, Luescher I F. Novel soluble HLA-A2/Melan-A complexes selectively stain a differentiation defective subpopulation of CD8+ T cells in melanoma patients. Int J Cancer 2009; in press.; Guillaume P, Legler D F, Boucheron N, Doucey M A, Cerottini J C, Luescher I F. Soluble major histocompatibility complex-peptide octamers with impaired CD8 binding selectively induce Fas-dependent apoptosis. J Biol Chem 2003; 278: 4500-4509.; Neveu B, Echasserieau K, Hill T, Kuus-Reichel K, Houssaint E, Bonneville M, Saulquin X. Impact of CD8-MHC class I interaction in detection and sorting efficiencies of antigen-specific T cells using MHC class I/peptide multimers: contribution of pMHC valency. Int Immunol 2006; 18: 1139-1145.; Knabel M, Franz T J, Schiemann M, Wulf A, Villmow B, Schmidt B, Bernhard H, Wagner H, Busch D H. Reversible MHC multimer staining for functional isolation of T-cell populations and effective adoptive transfer. Nat Med 2002; 8: 631-637.; Guillaume P, Baumgaertner P, Angelov G S, Speiser D, Luescher I F. Fluorescence-activated cell sorting and cloning of bona fide CD8+ CTL with reversible MHC-peptide and antibody Fab' conjugates. J Immunol 2006; 177: 3903-3912.; Yao J, Bechter C, Wiesneth M, Harter G, Gotz M, Germeroth L, Guillaume P, Hasan F, von Harsdorf S, Mertens T, Michel D, Dohner H, Bunjes D, Schmitt M, Schmitt A. Multimer staining of cytomegalovirus phosphoprotein 65-specific T cells for diagnosis and therapeutic purposes: a comparative study. Clin Infect Dis 2008; 46: 96-105.; Chattopadhyay P K, Price D A, Harper T F, Betts M R, Yu J, Gostick E, Perfetto S P, Goepfert P, Koup R A, De Rosa S C, Bruchez M P, Roederer M. Quantum dot semiconductor nanocrystals for immunophenotyping by polychromatic flow cytometry. Nat Med 2006; 12: 972-977.; Cebecauer M, Guillaume P, Hozák P, Mark S, Everett H, Schneider P, Luescher, I F. Soluble MHC-peptide complexes induce rapid death of CD8+ CTL. J Immunol 2005; 174: 6809-6819; Cebecauer M, Guillaume P, Mark S, Michielin O, Boucheron N, Bezard M, Meyer, B H, Segura J M, Vogel H, Luescher I F. CD8+ cytotoxic T lymphocyte activation by soluble major histocompatibility complex-peptide dimers. J Biol Chem 2005; 280: 23820-23828.; Angelov G S, Guillaume P, Cebecauer M, Bosshard G, Dojcinovic D, Baumgaertner P, Luescher I F. Soluble MHC-peptide complexes containing long rigid linkers abolish CTL-mediated cytotoxicity. J Immunol 2006; 176: 3356-3365.; Batard P, Peterson D A, Devêvre E, Guillaume P, Cerottini J C, Rimoldi D, Speiser D E, Winther L, Romero P. Dextramers: new generation of fluorescent MHC class I/peptide multimers for visualization of antigen-specific CD8+ T cells. J Immunol Methods 2006; 310: 136-148.; Fahmy T M, Bieler J G, Schneck J P. Probing T cell membrane organization using dimeric MHC-Ig complexes. J Immunol Methods 2002; 268: 93-106.; van der Merwe P A, Davis S J. Molecular interactions mediating T cell antigen recognition. Annu Rev Immunol 2003; 21: 659-684.; Campanelli R, Palermo B, Garbelli S, Mantovani S, Lucchi P, Necker A, Lantelme E, Giachino C. Human CD8 co-receptor is strictly involved in MHC-peptide tetramer-TCR binding and T cell activation. Int Immunol 2002; 14: 39-44.; Luescher I F, Vivier E, Layer A, Mahiou J, Godeau F, Malissen B, Romero P. CD8 modulation of T-cell antigen receptor-ligand interactions on living cytotoxic T lymphocytes. Nature 1995; 373: 353-356.; Kao C, Daniels M A, Jameson S C. Loss of CD8 and TCR binding to Class I MHC ligands following T cell activation. Int Immunol 2005; 17: 1607-1617.; Comelli E M, Sutton-Smith M, Yan Q, Amado M, Panico M, Gilmartin T, Whisenant T, Lanigan C M, Head S R, Goldberg D, Morris H R, Dell A, Paulson J C. Activation of murine CD4+ and CD8+ T lymphocytes leads to dramatic remodeling of N-linked glycans. J Immunol 2006; 177: 2431-2440.; Wooldridge L, Lissina A, Cole D K, van den Berg H A, Price D A, Sewell A K. Tricks with tetramers: how to get the most from multimeric peptide-MHC. Immunology 2009; 126: 147-164.; Xu X N, Purbhoo M A, Chen N, Mongkolsapaya J, Cox J H, Meier U C, Tafuro S, Dunbar P R, Sewell A K, Hourigan C S, Appay V, Cerundolo V, Burrows S R, McMichael A J, Screaton G R. A novel approach to antigen-specific deletion of CTL with minimal cellular activation using alpha3 domain mutants of MHC class I/peptide complex. Immunity 2001; 14: 591-602.; Demotte N, Stroobant V, Courtoy P J, Van Der Smissen P, Colau D, Luescher I F, Hivroz C, Nicaise J, Squifflet J L, Mourad M, Godelaine D, Boon T, van der Bruggen P. Restoring the association of the T cell receptor with CD8 reverses anergy in human tumor-infiltrating lymphocytes. Immunity 2008; 28: 414-424.; Dimopoulos N, Jackson H M, Ebert L, Guillaume P, Luescher I F, Ritter G, Chen W. Combining MHC tetramer and intracellular cytokine staining for CD8(+) T cells to reveal antigenic epitopes naturally presented on tumor cells. J Immunol Methods 2009; 340: 90-94.; Choi E M, Chen J L, Wooldridge L, Salio M, Lissina A, Lissin N, Hermans I F, Silk J D, Mirza F, Palmowski M J, Dunbar P R, Jakobsen B K, Sewell A K, Cerundolo V. High avidity antigen-specific CTL identified by CD8-independent tetramer staining. J Immunol 2003; 171: 5116-5123.; Pittet M J, Rubio-Godoy V, Bioley G, Guillaume P, Batard P, Speiser D, Luescher I, Cerottini J C, Romero P, Zippelius A. Alpha 3 domain mutants of peptide/MHC class I multimers allow the selective isolation of high avidity tumor-reactive CD8 T cells. J Immunol 2003; 171: 1844-1849.; Wooldridge L, Scriba T J, Milicic A, Laugel B, Gostick E, Price D A, Phillips R E, Sewell A K. Anti-coreceptor antibodies profoundly affect staining with peptide-MHC class I and class II tetramers. Eur J Immunol 2006; 36: 1847-1855.; Scriba T J, Purbhoo M, Day C L, Robinson N, Fidler S, Fox J, Weber J N, Klenerman P, Sewell A K, Phillips R E. Ultrasensitive detection and phenotyping of CD4+ T cells with optimized HLA class II tetramer staining. J Immunol 2005; 175: 6334-6343.; Day C L, Seth N P, Lucas M, Appel H, Gauthier L, Lauer G M, Robbins G K, Szczepiorkowski Z M, Casson D R, Chung R T, Bell S, Harcourt G, Walker B D, Klenerman P, Wucherpfennig K W. Ex vivo analysis of human memory CD4 T cells specific for hepatitis C virus using MHC class II tetramers. J Clin Invest 2003; 112: 831-842.; Mallone R, Nepom G T. MHC Class II tetramers and the pursuit of antigen-specific T cells: define, deviate, delete. Clin Immunol 2004; 110: 232-242.; Reijonen H, Kwok W W. Use of HLA class II tetramers in tracking antigen-specific T cells and mapping T-cell epitopes. Methods 2003; 29: 282-288.; Vollers S S, Stern L J. Class II major histocompatibility complex tetramer staining: progress, problems, and prospects. Immunology 2008; 23: 305-313.; Arnold P Y, La Gruta N L, Miller T, Vignali K M, Adams P S, Woodland D L, Vignali D A. The majority of immunogenic epitopes generate CD4+ T cells that are dependent on MHC class II-bound peptide-flanking residues. J Immunol 2002; 169: 739-749.; Reche P A, Reinherz E L. Definition of MHC supertypes through clustering of MHC peptide-binding repertoires. Methods Mol Biol 2007; 409: 163-173.; Boniface J J, Rabinowitz J D, Wiilfing C, Hampl J, Reich Z, Altman J D, Kantor R M, Beeson C, McConnell H M, Davis M M. Initiation of signal transduction through the T cell receptor requires the multivalent engagement of peptide/MHC ligands. Immunity 1998; 9: 459-466.; Lovitch S B, Unanue E R. Conformational isomers of a peptide-class II major histocompatibility complex. Immunol Rev 2005; 207: 293-313.; Cameron T O, Cochran J R, Yassine-Diab B, Sékaly R P, Stern U. Cutting edge: detection of antigen-specific CD4+ T cells by HLA-DR1 oligomers is dependent on the T cell activation state. J Immunol 2001; 166: 741-745.; Yang J, James E A, Huston L, Danke N A, Liu A W, Kwok W W. Multiplex mapping of CD4 T cell epitopes using class II tetramers. Clin Immunol 2006; 120: 21-32.; Blanchet J S, Valmori D, Dufau I, Ayyoub M, Nguyen C, Guillaume P, Monsarrat B, Cerottini J C, Romero P, Gairin J E. A new generation of Melan-A/MART-1 peptides that fulfill both increased immunogenicity and high resistance to biodegradation: implication for molecular anti-melanoma immunotherapy. J Immunol 2001; 167: 5852-5861.; Schiavetti F, Thonnard J, Colau D, Boon T, Coulie P G. A human endogenous retroviral sequence encoding an antigen recognized on melanoma by cytolytic T lymphocytes. Cancer Res 2002; 62: 5510-5516.; Ali S A, Lynam J, McLean C S, Entwisle C, Loudon P, Rojas J M, McArdle S E, Li G, Mian S, Rees R C. Tumor regression induced by intratumor therapy with a disabled infectious single cycle (DISC) herpes simplex virus (HSV) vector, DISC/HSV/murine granulocyte-macrophage colony-stimulating factor, correlates with antigen-specific adaptive immunity. J Immunol 2002; 168: 3512-3519.; Pardigon N, Darche S, Kelsall B, Bennink J R, Yewdell J W. The T L MHC class Ib molecule has only marginal effects on the activation, survival and trafficking of mouse small intestinal intraepithelial lymphocytes. Int Immunol 2004; 16: 1305-1313.; Guilloux Y, Lucas S, Brichard V G, Van Pel A, Viret C, De Plaen E, Brasseur F, Lethé B, Jotereau F, Boon T. A peptide recognized by human cytolytic T lymphocytes on HLA-A2 melanomas is encoded by an intron sequence of the N-acetylglucosaminyltransferase V gene. J Exp Med 1996; 183: 1173-1183.; Rakoff-Nahoum S, Kuebler P J, Heymann J J, E Sheehy M, M Ortiz G, S Ogg G, Barbour J D, Lenz J, Steinfeld A D, Nixon D F. Detection of T lymphocytes specific for human endogenous retrovirus K (HERV-K) in patients with seminoma. AIDS Res Hum Retroviruses 2006; 22: 52-56.; Liso A, Colau D, Benmaamar R, De Groot A, Martin W, Benedetti R, Specchia G, Martelli M P, Coulie P, Falini B. Nucleophosmin leukaemic mutants contain C-terminus peptides that bind HLA class I molecules. Leukemia 2008; 22: 424-426.; and Matsuki N, Ogasawara K, Takami K, Namba K, Takahashi A, Fukui Y, Sasazuki T, Iwabuchi K, Good R A, Onoé K. Prevention of infection of influenza virus in DQ6 mice, a human model, by a peptide vaccine prepared according to the cassette theory. Vaccine 1999; 17: 1161-1168. All references are incorporated herein in their entirety by reference for disclosure of methods and materials useful for the generation, isolation, and or purification of MHC multimers and for staining, detection, and/or isolation of cells using MHC multimers.

The function and advantage of these and other embodiments of the present invention will be more fully understood from the examples below. The following examples are intended to illustrate the benefits of the present invention, but do not exemplify the full scope of the invention.

EXAMPLES

Example 1

Some aspects of this invention provide a novel type of MHC multimers in which MHC class I-peptide monomers are conjugated to phycobilins (PE or APC) or quantum dots (QDOTs®) via chelate complexes of histidine (His) tags and $Ni^{2+}$-nitrilotriacetic acid (NTA). Hexa ($His_6$: SEQ ID NO: 310), dodeca ($His_{12}$: SEQ ID NO: 311) or tandem hexa (2×$His_6$:SEQ ID NO: 312) histidine tags were fused to HLA-A*0201 (A2) heavy chain and A2-peptide monomers obtained in good yields by refolding. Mono, di and tetra NTA derivatives were synthesized and their interactions with His tagged monomers studied by surface plasmon resonance (SPR) and by CD8+ T cell staining experiments. The results described here indicate that the affinity ($K_D$) increases in the order $His_6$ (SEQ ID NO: 310)>$His_{12}$ (SEQ ID NO: 311)>2×$His_6$ (SEQ ID NO: 312) and mono>di>tetra NTA, respectively, spanning several orders of magnitudes. Staining experiments on influenza-specific CD8+ T cell clones and populations with NTA-His tag A2/Flu$_{58-66}$ multimers indicated that: i) multimers containing 2×$His_6$ (SEQ ID NO: 312) tagged complexes and short di- or tetra NTA moieties were equal or superior compared to conventional multimers; ii) di-NTA or tetra-NTA can be directly coupled to the phycobilin proteins or quantum dot (QDOT®), which circumvents the use of biotin and streptavidin, and renders synthesis simpler and cheaper; iii) these reagents are molecularly better defined than conventional multimers and hence allow better analysis of binding data; iv) NTA-His tag built multimers dissociated rapidly in the presence of 100 mM imidazol ($t_{1/2}$<1 min), which allows sorting of bonafide antigen-specific CD8+ T cells without inducing activation dependent cell death.

Materials and Methods

Abbreviations used herein include: APC: allophycocyanine; β2m: beta-2-microglobulin; BSP: biotinylation sequence peptide; DIEA: di-isopropyl-ethyl-amine; EDIC: 1-ethyl-3-(3-dimethylaminopropyl) carbodiimide; GFC: gel filtration chromatography; Flu: influenza matrix; HOBt: 1-hydroxy-benzo-triazole; NHS: N-hydroxysuccinimide; NTA: nitrilotriacetic acid; PE: phycoerythrin; QDOT®: quantum dot; SPR: surface plasmon resonance; TBTU: O-(benzotriazol-1-yl)-N,N,N',N'-tetramethyluronium tetrafluoroborate.
Chemical Synthesis Protected amino acids and 2-chlorotrityl resin were obtained from Reactolab (Servion, Switzerland), TBTU and HOBt were from Multisynthec (Witten, Germany), maleimide-NTA from Dojindo Laboratories (Kumamoto, Japan). RP-HPLC analyses were performed on Waters HPLC station consisting of two 515 pumps and a Waters 996 photodiode array detector. The purity of all peptides was examined by analytical HPLC on a C18 reverse phase column (UPTISPHERE® (silica based stationary phase) 5 m Cis particles, 250×4.6 mm) and which was eluted with a linear gradient rising from 100% of 0.1% TFA in $H_2O$ to 50% of 0.08% TFA in $CH_3CN$ in 30 min at a flow rate of 1 ml/min. peptides were purified on a semi preparative column (KROMASIL® (C18-octadecyl silane, silica particle) 15 m Cis particles, 250×20 mm) at a flow rate of 3 mL/min, with UV monitoring at 214 nm. The purified peptides were characterized for correct Mr using matrix-assisted laser desorption ionization time-of-flight mass spectrometer (Micromass QTOF Ultima) (Waters Ltd, En Yvelines Cedex, France).

Synthesis of linear peptides—Synthesis of linear peptides was carried out manually in a syringe fitted with a sintered frit using Fmoc/tBu strategy. Coupling reactions were performed using 2 equiv of N-α-Fmoc-protected amino acid relative to the resin loading, activated in situ with 2 equiv of TBTU, 2 equiv of HOBt and 4 equiv of DIEA in DMF (10 mL/g resin) for 1 h. Coupling completion was verified by Kaiser tests. N-α-Fmoc protecting groups were removed by treatment with a piperidine/DMF solution (1:4) (10 mL/g resin) for 5 min. The process was repeated twice, and the completion of deprotection was checked by the UV absorption of the piperidine washing at 299 nm. Peptides were obtained by cleavage of the resin with TFA/$H_2O$/TIPS (92.5/2.5/5) for 3 h and after filtering of the resin precipitated by addition of ether, filtered off, dissolved in water, purified by semi-preparative HPLC and lyophilized.

Coupling of maleimide-NTA to linear peptides—Linear free SH containing peptides were dissolved in phosphate buffer (0.1M, pH 7.2) at a concentration of 0.1 M. Two equivalents of Mal-NTA (relative to SH) were added and the mixture stirred for 1 h under argon. The product was further purified by semi-preparative HPLC and analyzed by Electrospray ionisation on a Micromass QTOF Ultima instrument. Alternatively, in the strategy shown in FIG. 13, the backbone peptide was reacted via in situ carboxyl activation with $N^\alpha,N^\alpha$-Bis[(tert-butyloxycarbonyl)methyl]-L-lysine tert-butyl ester ($H_2N$-NTA(tBu)$_3$), which was synthesized as follow: tert-butyl bromoacetate (1.59 ml, 10.8 mmol) and DIEA (2.30 ml, 13.5 mmol) were added sequentially to a solution of Ns-benzyloxycarbonyl-lysine tert-butyl ester (1.00 g, 2.7 mmol) in DMF (25 ml). The reaction vessel was purged with $N_2$ and then continuously stirred overnight at 55° C. The volatiles were evaporated in vacuo at 60° C. Cyclohexane/ethylacetate (3:1, 15 ml) solution was added to the partially solidified reaction mixture. The resulting slurry was filtered over sintered glass funnel and the precipitate washed three times with the same solvent (3×10 ml). The filtrate was concentrated under reduced pressure and the resulting yellow powder dissolved in methanol (50 ml), the solution purged with $N_2$ followed by addition of 10% Pd/C (20 mg). The reaction mixture was vigorously stirred for 6 hours under H2 atmosphere at room temperature. Pd/C was removed by filtration over celite and the volatiles removed under reduced pressure. The product was purified by silica chromatography with chloroform/methanol (3:1) as the eluent. Yield: 1.03 g (2.4 mmol; 91%). The linear peptide H-K(aminocaproyl-biotin)-PEG-A-E̲*-A-E̲*-OH (*: Fmoc-E-OtBu) was synthesized on an ABI433 peptide synthesizer. Double coupling of each Fmoc-protected amino acid were performed using DIPC and HOBt as coupling reagent. Fmoc was removed by 3×5 min treatment with piperidine 20% in DMF. Each cycle was followed by an acetylation (N-capping) to prevent the synthesis of truncated peptides. Final cleavage was performed in TFA/TIPS/H2O (92.5/5/2.5) for 2 h. The peptide was precipitated with cold ether, dissolved in water and purified by semi-preparative HPLC. Similarly, the synthesis of SH-NTA$_2$ was performed assembling the linear C(Acm)-PEG-C(Trt)-G-C(Trt) on a chlorotrityl resin. After TFA treatment the linear peptide C(Acm)-PEG-C(SH)-G-C(SH) was coupled to maleimide-NTA as described previously. 1 µmol of lyophilized peptide was dissolved in 100 µl of AcOH 20%, the pH was adjusted to 4 with aqueous ammonia. 3 µmol of mercury(II) acetate were added and the mixture stirred for 1 h. 5 µmol of DTT were then added and the mixture stirred for 1 additional hour. The desired product was directly purified by semi-preparative HPLC and analyzed by mass spectrometry.

Surface plasmon resonance experiments—Affinity measurements were performed on a Biacore 3000 instrument equipped with SA coated chips. The eluent buffer (10 mM HEPES, 150 mM NaCl, 50 mM EDTA at pH 7.4) and the dispensor buffer (10 mM HEPES, 150 mM NaCl, 0.005% polysorbate 20, 3 mM EDTA) were filtered and degassed prior to use. Two or five-fold dilutions of His-tagged A2/Flu$_{58-66}$ monomers were freshly prepared in eluent buffer before each experiment. Loading of biotin containing NTA peptides was performed in fresh solution of NTA-biotin peptides dissolved in eluent buffer. A RU (resonance unit) of 100 was used in all experiment. Loading of NTA with Ni$^{2+}$ was performed by injecting NiCl2 solution (500 mM in eluent buffer) and regeneration of the chip with imidazole (500 mM in water) followed by a regeneration solution (10 mM HEPES, 150 mM NaCl, 0.005% polysorbate 20, 350 mM EDTA at pH 7.4). All binding experiments were performed at a flow rate of 100 µl/min, starting with a 1 min injection of NiCl$_2$ solution. Each sample was injected for 5 min followed by 5 min of undisturbed dissociation time. The regeneration procedure consisted of two subsequent 1-min injections of imidazole and regeneration solution.

HLA-A2 Flu 58-66 multimers

Figures 2A, 2B:
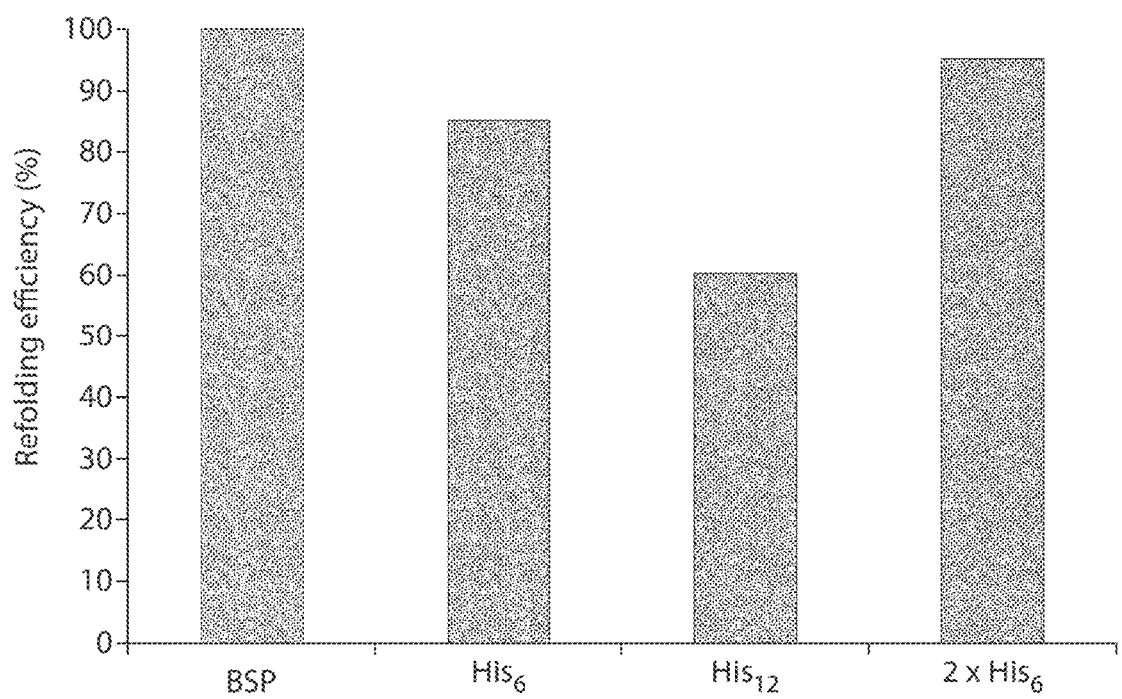
FIGS. 2A to 2B. His tagged HLA-A2 under study and their refolding efficiencies.

HLA-A*0201-peptide complexes—HLA-A*0201 (A2) heavy chains containing the His tags shown in FIG. 2A expressed as inclusion bodies in E. Coli as described previously for the BSP containing heavy chain (3). The different heavy chains were refolded in the presence of hβ2m and the influenza matrix peptide$_{58-66}$ (GILGFVFTL, SEQ ID NO: 12) and purified on a SUPERDEX® S75 column as described (3).

Figure 3A:
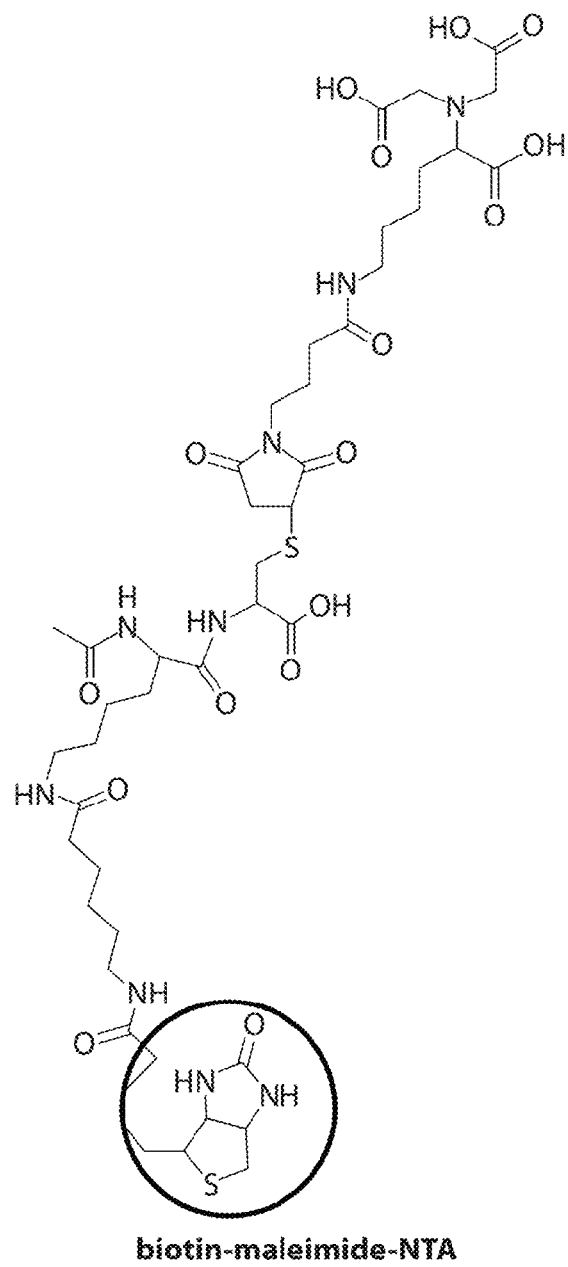
FIGS. 3A to 3F. Structures of the NTA linker under studies.
Figure 3B:
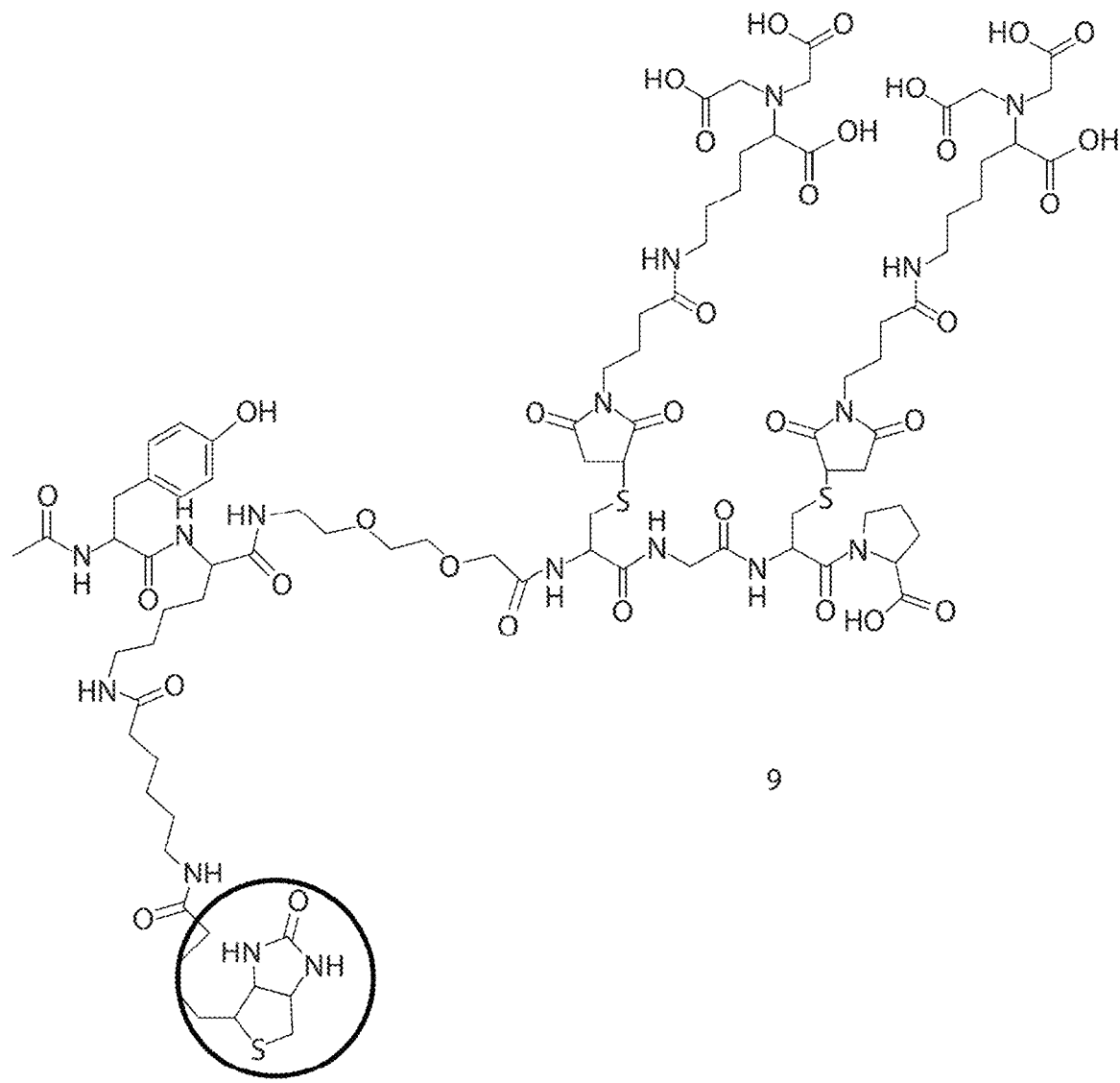
Figure 3C:
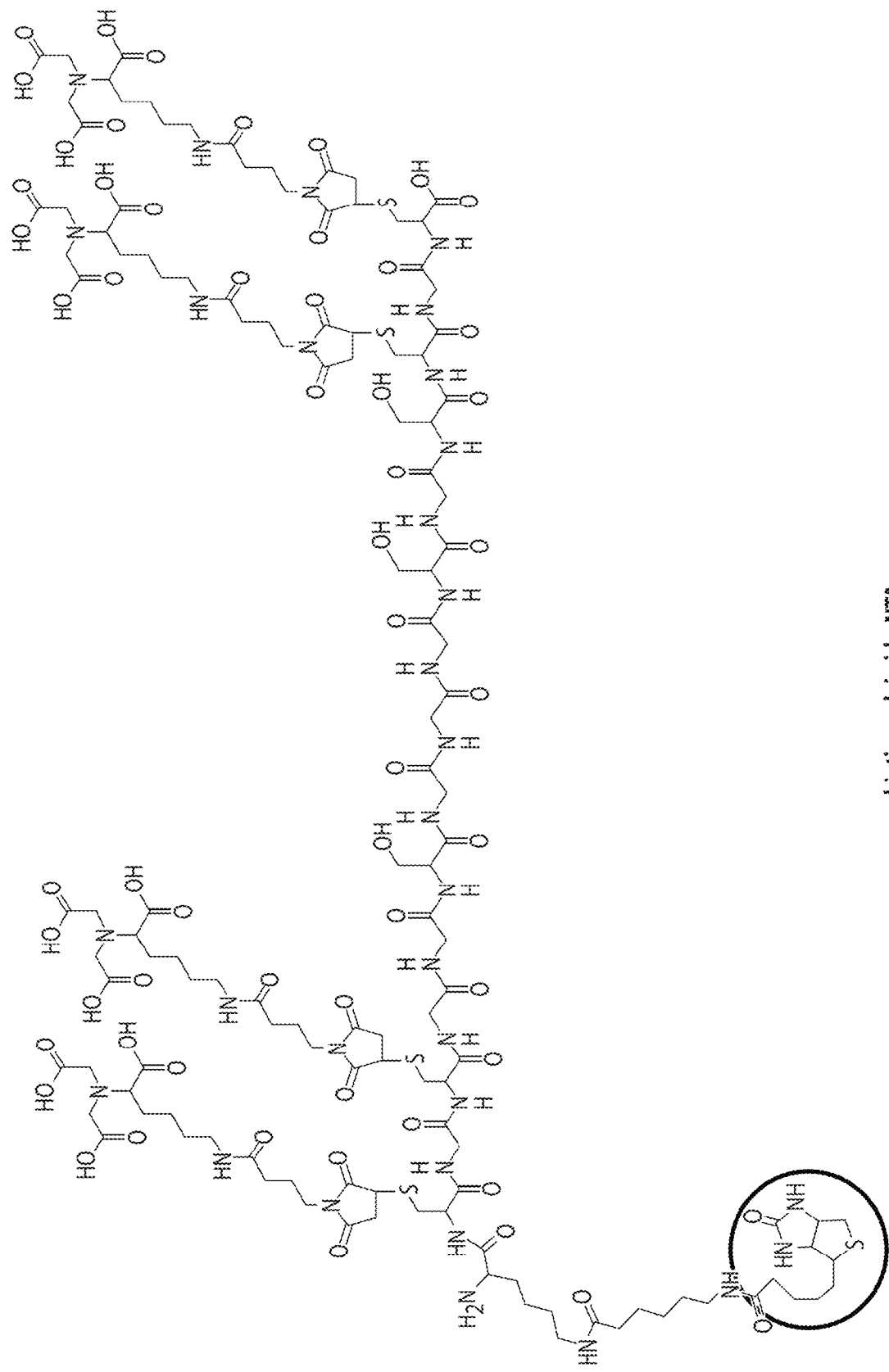
Figure 3D:
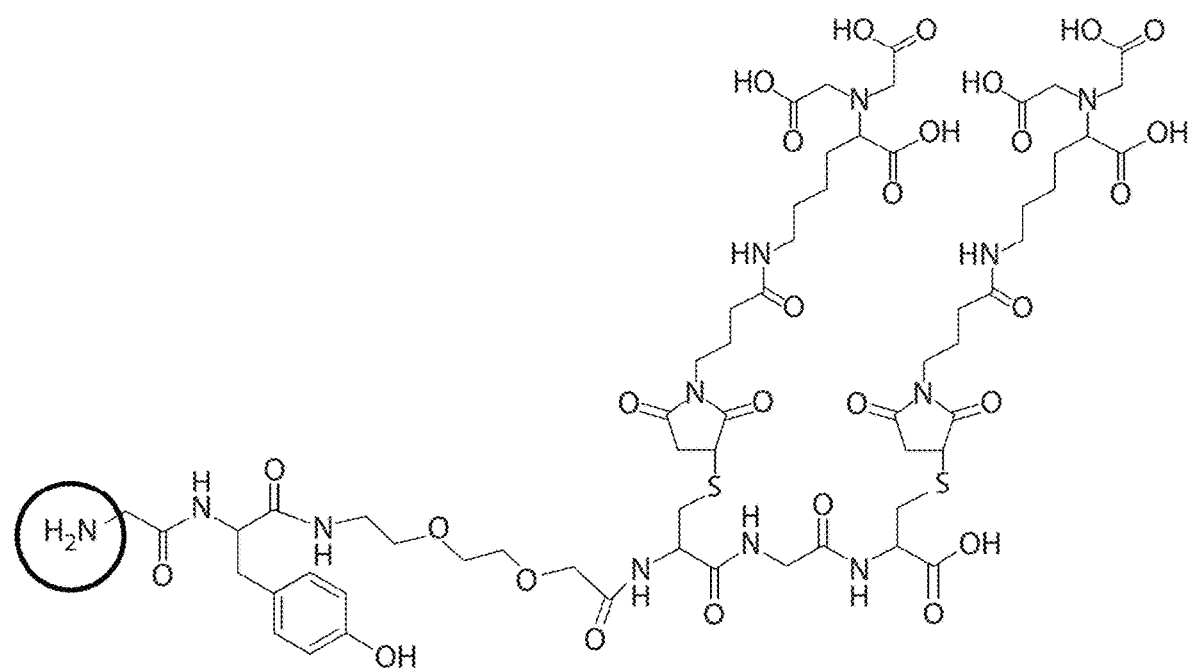
Figure 3E:
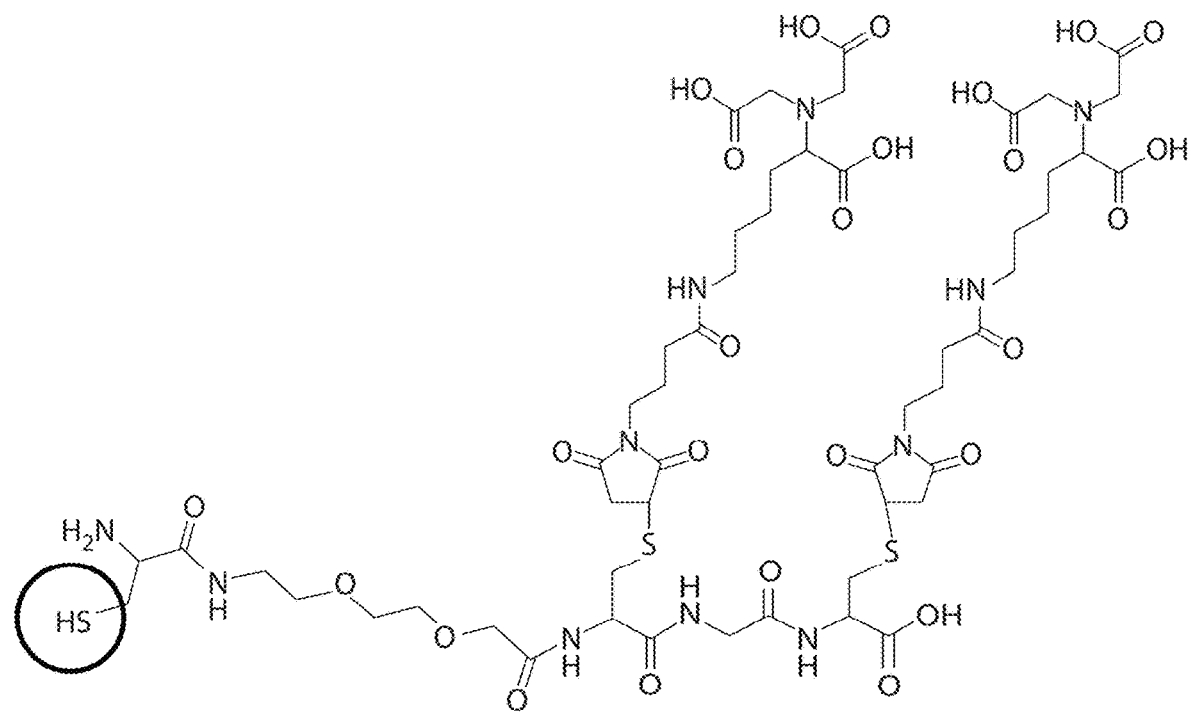

Preparation of A2/Flu 58-66 multimers—Conventional streptavidin PE multimers were prepared as described (3). NTA-streptavidin PE multimers were prepared in two steps. First, streptavidin PE conjugate (INVITROGEN™) was incubated with NTA-biotin peptides (five-fold molar excess) at 4° C. for 1 h followed by incubation for 30 min with NiSO4 (10 mM). Excess of reagents were removed by means of min-spin columns (Zeba™ Spin Desalting Columns (THERMO SCIENTIFIC™). His tagged monomeric A2/Flu complexes were mixed with Ni-NTA-biotin-streptavidin PE conjugate at a ten-fold molar excess and kept at 4° C. until use. NTA$_2$-PE conjugates were prepared by first reacting PE (SIGMA-ALDRICH™) (50 nM) in 0.1 M phosphate buffer, pH 7.2 with 10 mM (or as indicated) SM(PEG)$_2$ (PIERCE™) at room temperature for 2h. Excess reagents were removed by centrifugation through spin columns (supplier). The resulting PE-maleimide conjugates were incubated under argon in 100 mM phosphate buffer, pH 7.0 with 50 mM cysteine-di-NTA at room temperature for 1-2h (FIG. 3E). After incubation for 30 min with NiSO4 (10 mM), excess reagents were removed by centrifugation through spin columns and the concentration of the resulting Ni$^{2+}$NTA$_2$-PE was determined by Bradford.

Cells, Staining Procedures and Flow Cytometry

Cells under study—The HLA-A*0201-restricted, influenza matrix peptide$_{58-66}$-specific CD8+ T cell clones were obtained by limiting dilution cloning from bulk cultures. CD8+ PBMC from healthy donors were prepared by negative selection and were stimulated with Flu$_{58-66}$ peptides as described (4). The clones were re-stimulated in 24-well plates every 15 d in RPMI 1640 medium supplemented with 8% human serum, rIL-2 (150 U/ml) (Hoffmann-la Roche Ltd, Basel, Switzerland) with PHA (1 µg/ml; Sodiag S A, Losone, Switzerland) and 1×10$^6$/ml irradiated allogeneic PBMC (3000 rad) as feeder cells. Bulk cultures were prepared by one or two peptide stimulations of CD8+ T cells obtained from PBMC from a DR4+ healthy donor (IFL).

Multimer binding assays, flow cytometry and analysis. For binding studies CD8+ T cells (5×10$^4$) were incubated for 30-45 min at ambient temperature with graded concentrations of the different A2/Flu$_{58-66}$ complexes in 20 µl of FACS buffer (OptiMEM (INVITROGEN™ AG, Basel, Switzerland) supplemented with 0.5% BSA (SIGMA-ALDRICH™), 15 mM HEPES, 5 mM EDTA, and 5 mM NaN$_3$). In some experiments cells were incubated an additional 20 min at 4° C. with anti-CD8-FITC (IMMUNO TOOLS®). After 30-fold dilution in FACS buffer, cell-associated fluorescence was measured on a LSRII flow cytometer (BD Biosciences). Background binding was determined on a A2/Mealn-A$_{26-35}$ (ELAGIGILTV, SEQ ID NO: 13) clone (EM28-9.24) and was subtracted from the cognate staining. Data were processed using the FLOWJO® software (Tree Star, Inc. Ashland, OR). For dissociation experiments CD8+ T cells were incubated for 45 min at 4° C. with 10 nM of multimers in FACS buffer, diluted 200× fold in FACS buffer and after various periods of incubation at 4° C., cell-associated fluorescence was determined by flow cytometry (0 to 60 min). In some dissociation experiments with NTA multimers FACS buffer was supplemented with imidazol hydrochloride (50 or 100 mM).

Results and Discussion

Figure 1C:
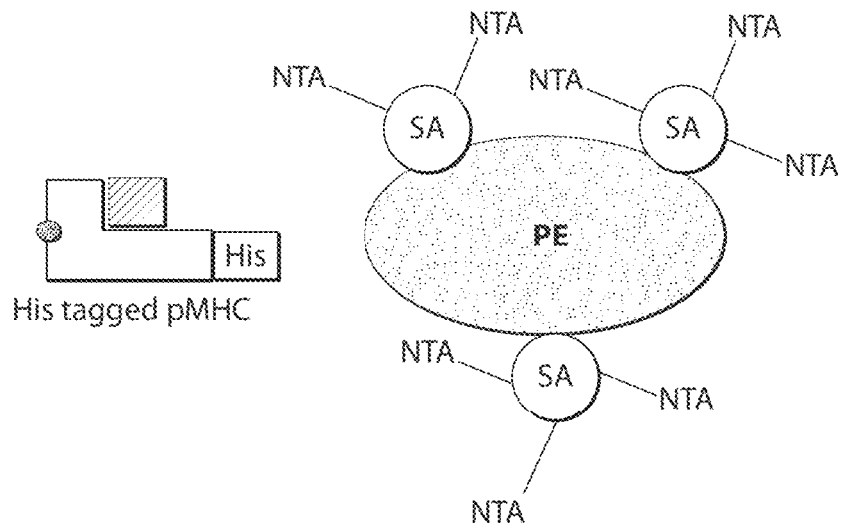
Figure 1D:
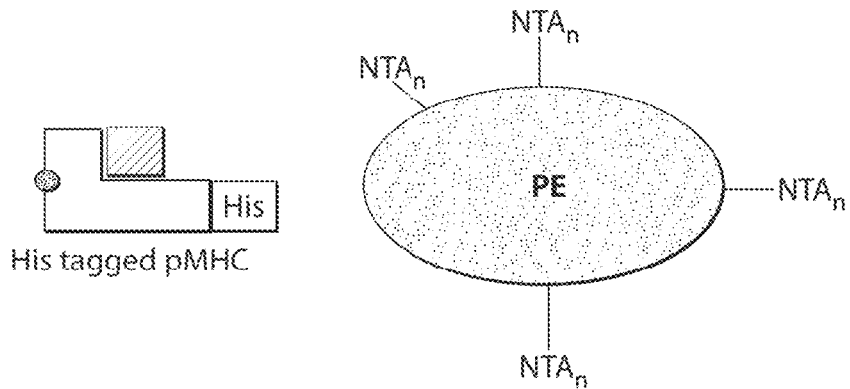
Figure 1E:
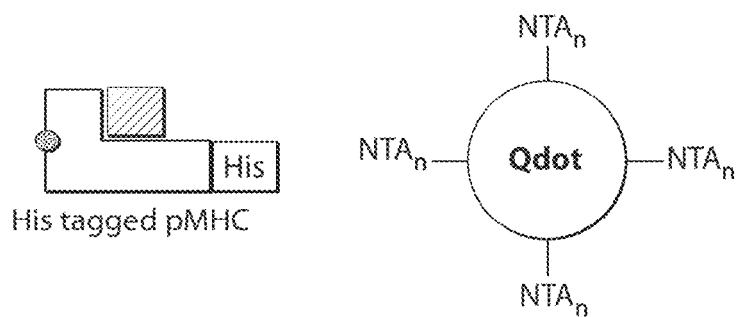

To build sufficiently stable MHC-peptide multimers on Ni$^{2+}$NTA-His tag chelate complexes, we examined the interaction of different His tags and NTA moieties. In the minimal subunit complex one NTA forms a coordinate complex with a Ni$^{2+}$ ion, which in turn can bind two imidazoles, i.e. side chains of histidines (FIG. 1A). Since this subunit complex is not sufficiently stable, we prepared HLA-A*02010/Flu$_{58-66}$ monomers containing C-terminal a hexa-histidine (His$_6$: SEQ ID NO: 310), a dodeca-histidine (His$_{12}$: SEQ ID NO: 311) or double hexa-histidine tag (2×His$_6$: SEQ ID NO: 312) (FIG. 2A). On the other hand we synthesized mono, di- and tetra-NTA compounds, which contained biotin (FIGS. 3A-C). Because the binding of biotin to streptavidin is exceedingly strong (K$_D$~10$^{15}$ M), we used streptavidin either conjugated to PE or immobilized on SPR sensor chips to stably bind the different biotinylated NTA derivatives. Addition of His tagged A2/Flu monomers to PE-streptavidin yielded multimers in which MHC-peptide complexes are conjugated via the NTA-His complexes (FIG. 1C). On the other hand this strategy allowed accurate SPR measurements of the different NTA-His tag interactions (FIG. 3A).

Identification of Suitable His Tags and NTA Linkers

To identify a suitable His tag we prepared A2 heavy chains containing C-terminally added His$_6$ (SEQ ID NO: 310), His$_{12}$ (SEQ ID NO: 311) and 2×His$_6$ (SEQ ID NO: 312) (tandem) His tags (FIG. 2A). These heavy chains were refolded with 02m and Flu matrix$_{58-66}$ peptide following established procedures (3). The refolding efficiency of the 2×His$_6$ (SEQ ID NO: 312) tagged complex was nearly as high (98%) as the one of the BSP complex (FIG. 2B). For the His$_6$ (SEQ ID NO: 310) tagged complex the efficiency was approximately 85% and for the $His_{12}$ (SEQ ID NO: 311) tagged one only 60%. Similar results were obtained when using other peptides (e.g. Melan-A26-35 or NY-ESO-1157-165).

Figure 4A:
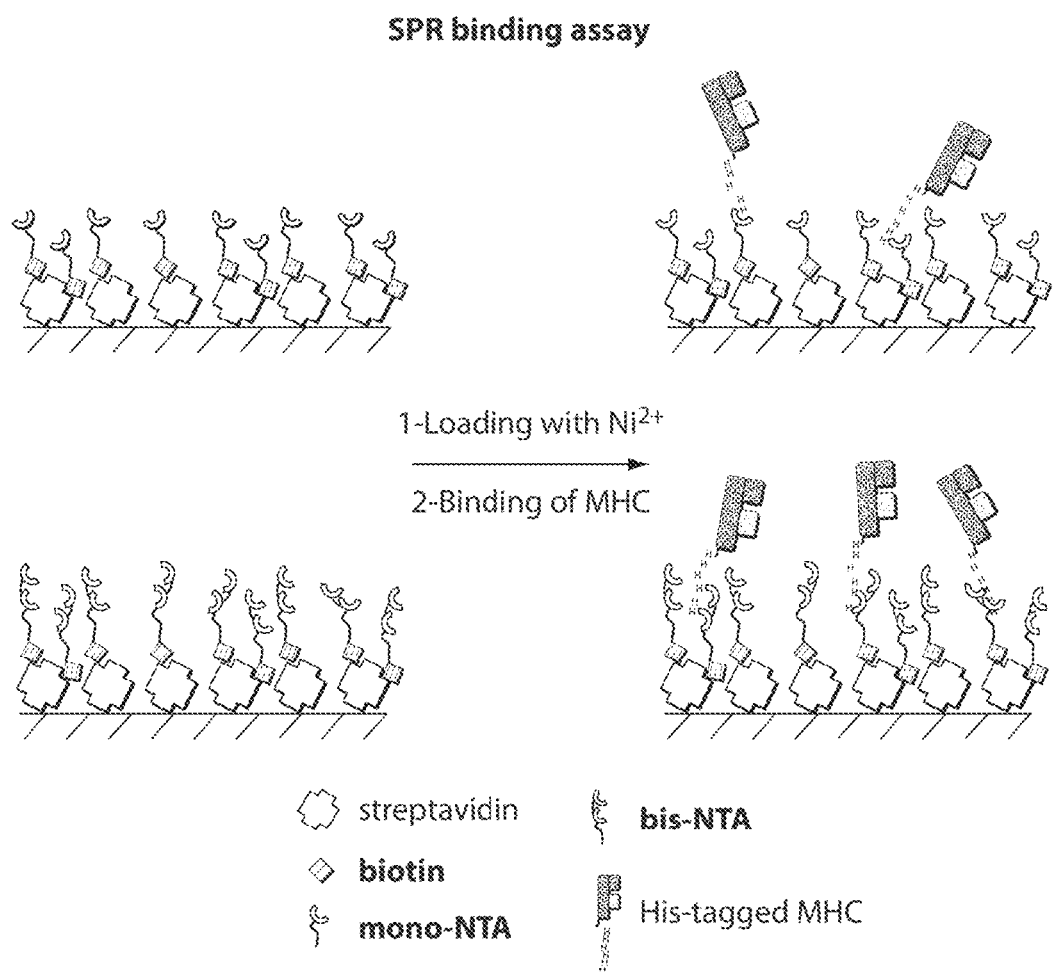

We then synthesized the NTA linker shown in FIGS. 3A-C and examined their binding of the His tagged $A2/Flu_{58-66}$ monomers by SPR. To this end streptavidin coated sensor chips were loaded with the biotinylated NTA compounds and the binding of the monomers measured by the changes in resonance units (RU). On mono-NTA (FIG. 3A) coated chips, the dissociation constant ($K_D$) decreased dramatically from the $His_6$ (SEQ ID NO: 310), to the $His_{12}$ (SEQ ID NO: 311) and $2×His_6$ (SEQ ID NO: 312) tagged complexes (from 4100 to 34 nM) (FIG. 4B). On $NTA_2$ (FIG. 3B) coated chips the $K_D$ values were lower still, reaching 12 nM for the $2×His_6$ (SEQ ID NO: 312)_tagged A2/Flu complex. This increase in affinity was largely accounted for by decreased dissociation rates, i.e. the chelate complexes become increasingly more stable. These findings are consistent with reports showing that the affinity of His tags for $Ni^{2+}$ NTA moieties dramatically increases with their valence and that $NTA_3$ compounds bind $His_6$ (SEQ ID NO: 310) tags with sub-nanomolar $K_D$ (13-15).

Figure 5A:
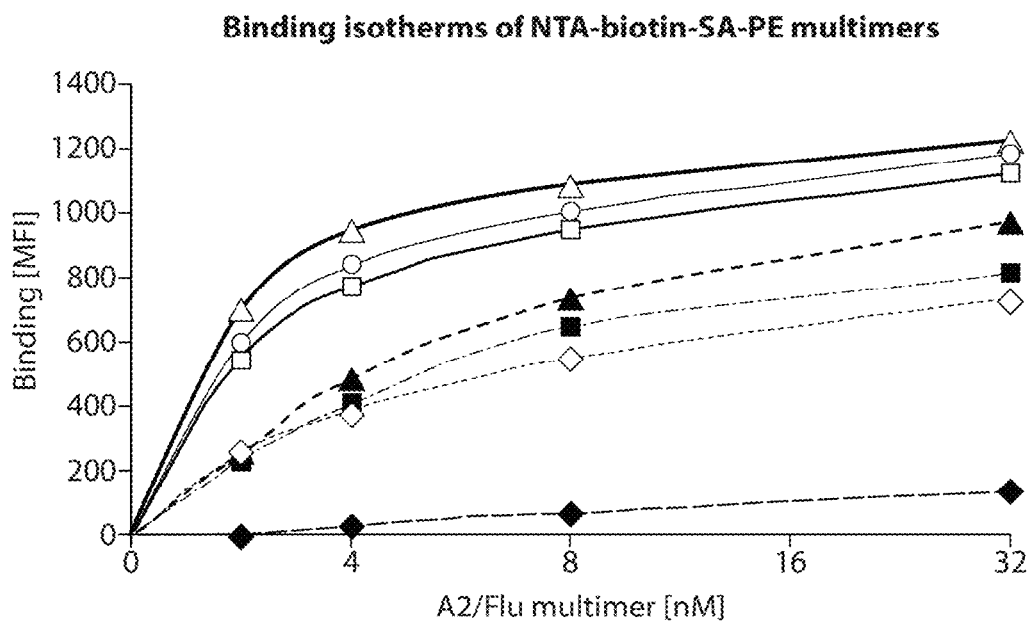
FIGS. 5A to 5B. Bindings isotherms of different NTA-biotin-streptavidin PE A2/Flu$_{58-66}$ multimers.

We next examined staining of the Flu matrix-specific clone 81P1 by $A2/Flu_{58-66}$ multimers containing the same His tags and streptavidin-PE saturated with biotin-$Ni^{2+}NTA$ moieties. The 20° C. binding isotherms of the multimers containing $NTA_2$ were consistently higher than those obtained of mono NTA containing multimers (FIG. 5A). In both cases binding was strongest with multimers containing the $2×His_6$ (SEQ ID NO: 312) tag. Multimers containing this His tag and $NTA_2$ containing exhibited higher binding than conventional multimers. While the binding values for $NTA_2$ complexes with $His_{12}$ (SEQ ID NO: 311) containing complexes was only slightly lower, all other combinations exhibited substantially weaker binding and hence were not further investigated. Similar results were obtained on other Flu clones (data not shown).

Figure 5B:
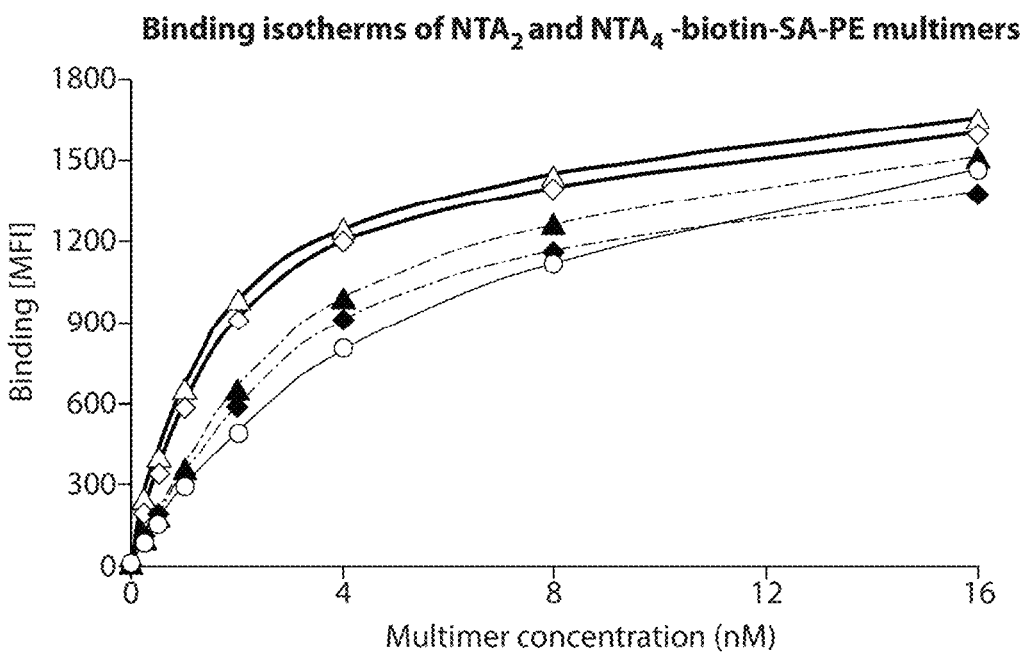

To compare the binding of A2/Flu multimers containing $NTA_4$ and $NTA_2$, we performed similar binding experiments on cloned BCB 70 cells. The 20° C. binding isotherms showed that $NTA_4$ multimers bound more avidly than $NTA_2$ or conventional multimers (FIG. 5B). While in the case of $NTA_4$ the binding of multimers containing the $His_{12}$ (SEQ ID NO: 311) or $2×His_6$ (SEQ ID NO: 312) tag was essentially the same, for the $NTA_2$ multimers those containing the $2×His_6$ (SEQ ID NO: 312) tag exhibited better binding compared to those containing the $His_{12}$ (SEQ ID NO: 311) tag.

Figure 3F:
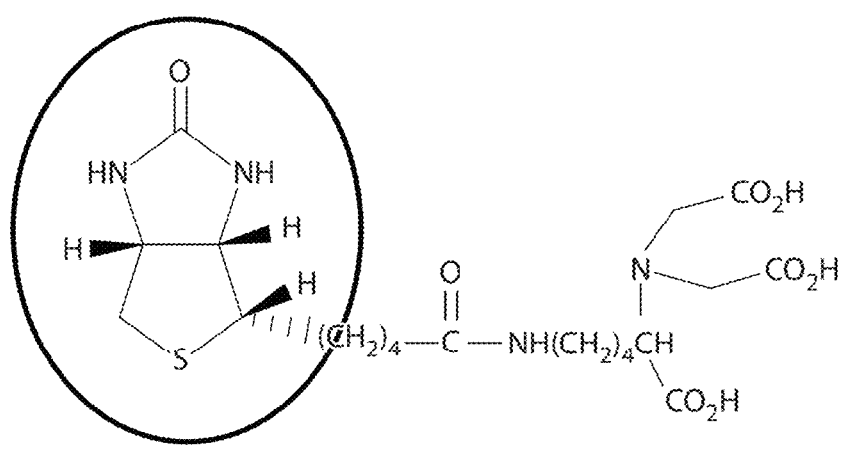
Figures 1, 12:
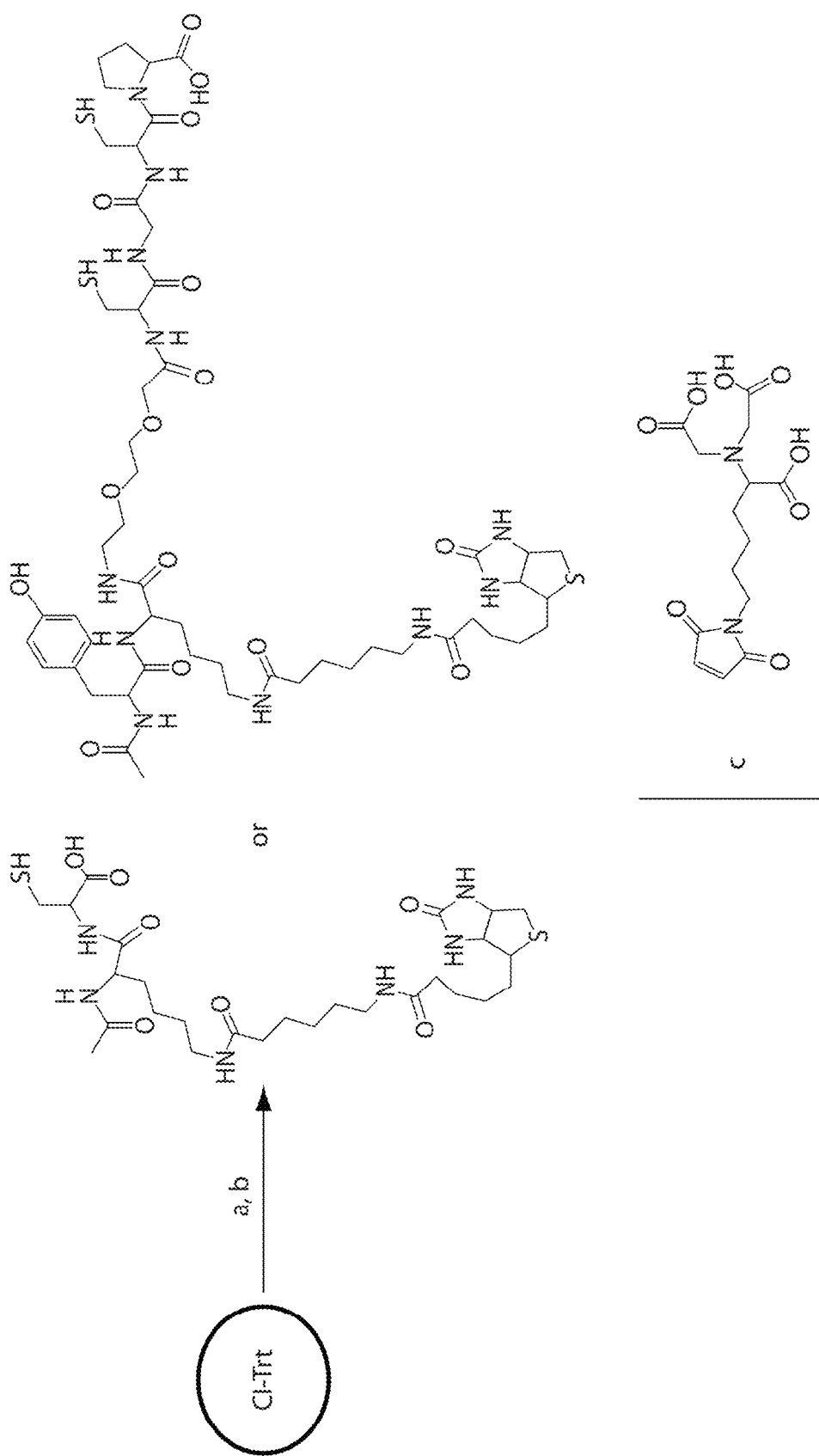
FIG. 12. Synthesis of mono-NTA and di-NTA-biotin. The Compounds shown in FIG. 3A and FIG. 3B were synthesized using: i) solid phase peptide synthesis on chloro-trityl resin; ii) Fmoc for transient protection and ii) coupling with TBTU (2 eq), HOBt (2 eq), DIEA (4 eq) (a) and for deprotection TFA/H2O/TIPS (92.5/2.5/5) (b). The intermediary thiol compounds were reacted with maleimido-NTA-lysine in 100 mM phosphate buffer, pH 7.2 (c). The distance x is about 16 Å and y 23 Å.
Figure 12:
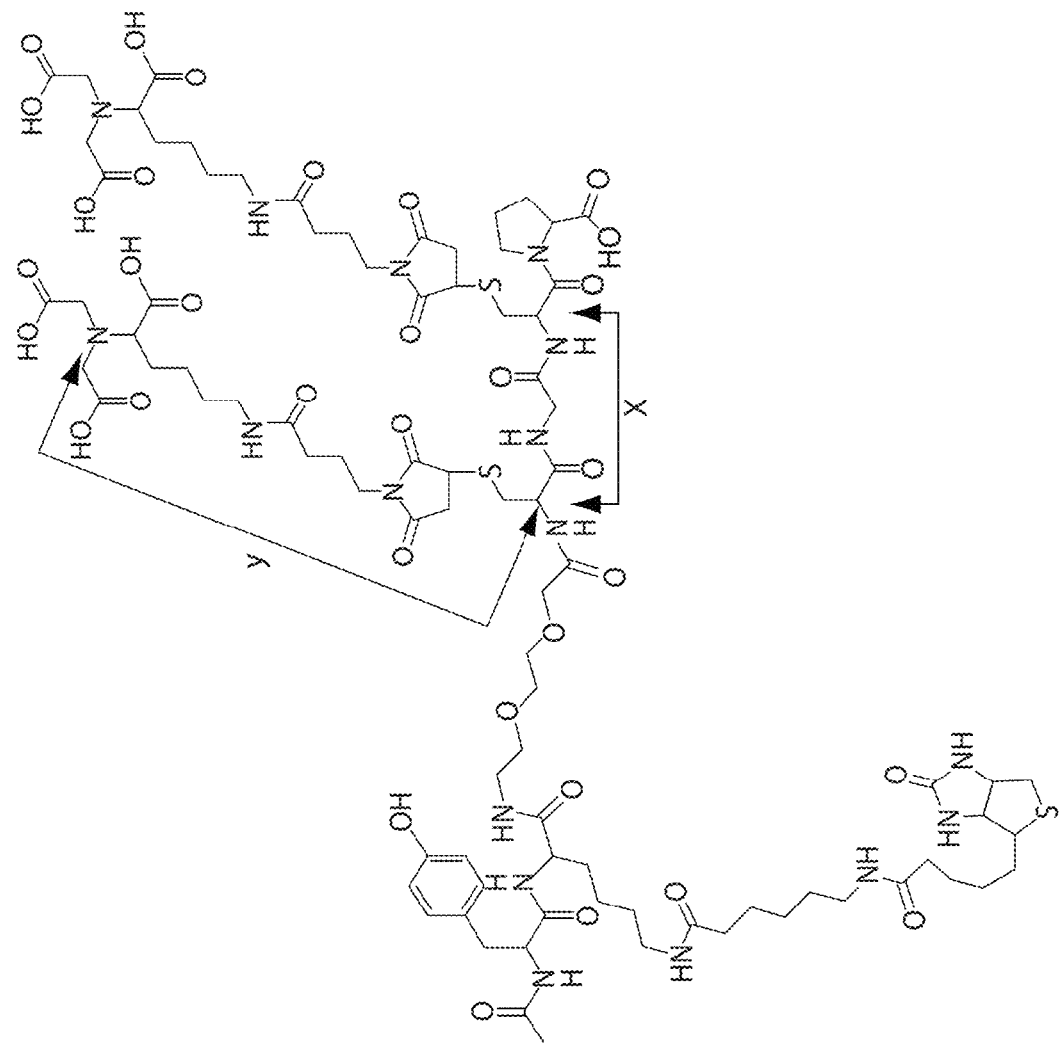
Figure 2:
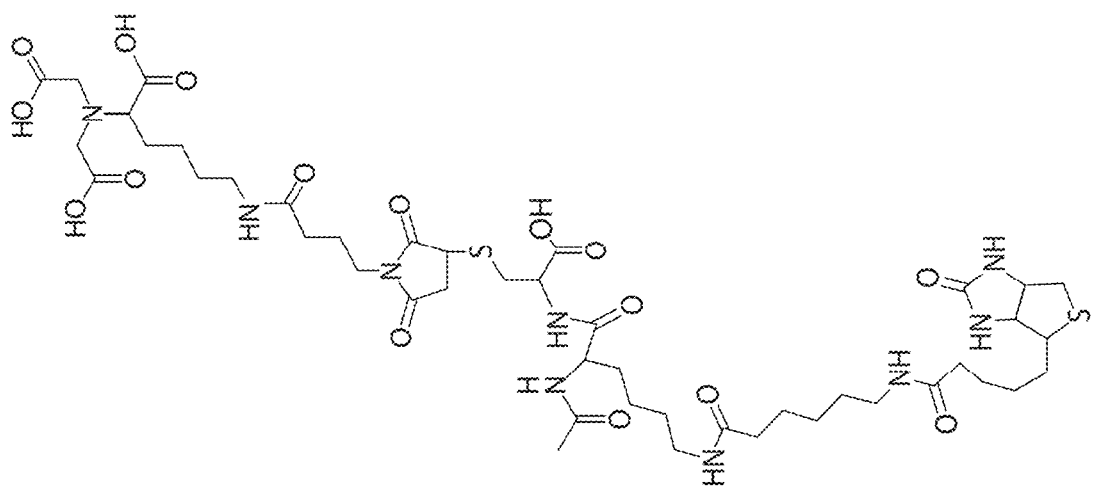
Figure 13:
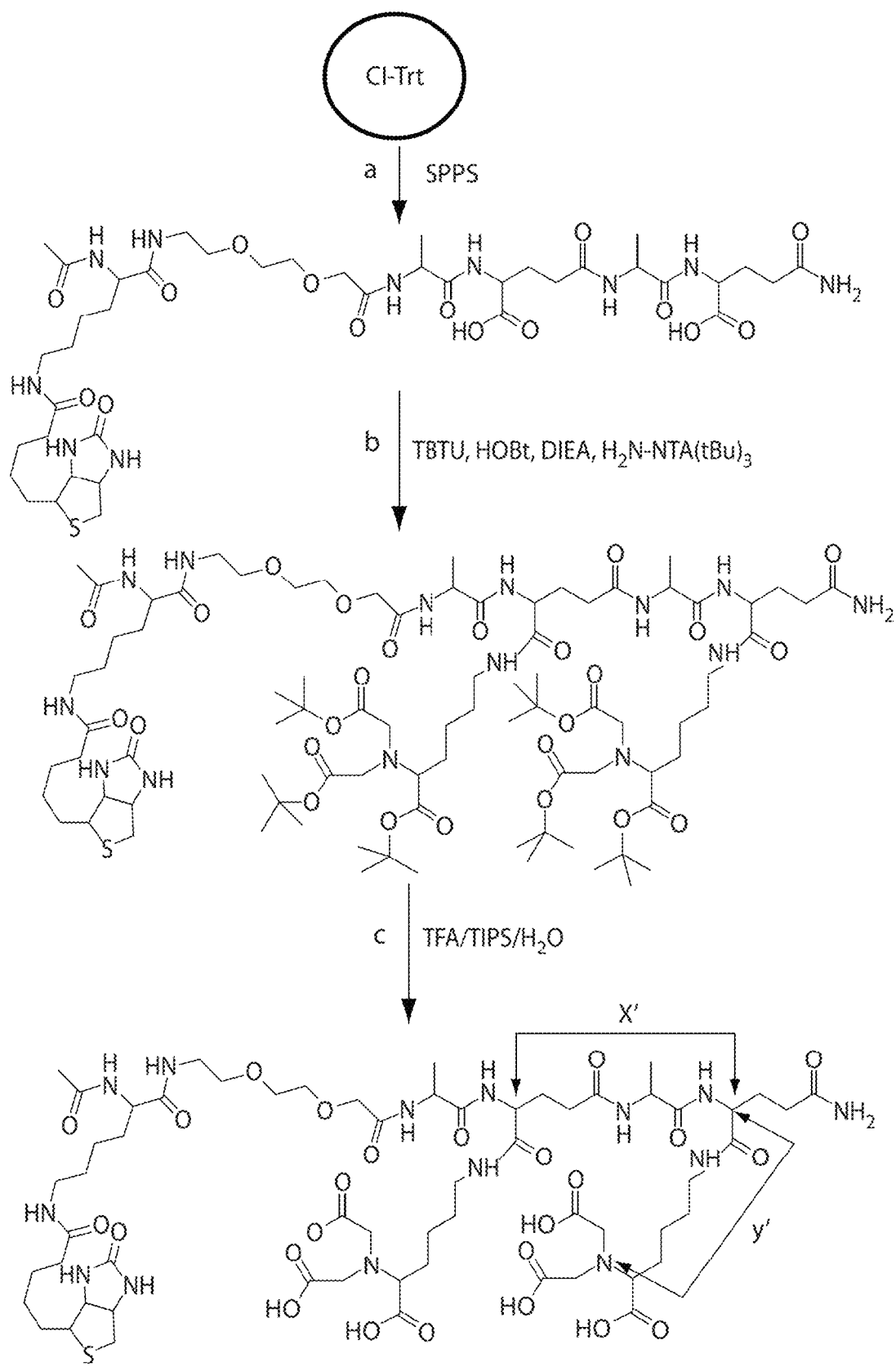
FIG. 13. Synthesis of an alternative di-NTA-biotin. An alternative di-NTA-biotin was synthesized starting on a rink amide chloro-trityl resin to prepare the peptide back bone (a), which was reacted in solution with tri-tert. butyl-NTA lysine (b), followed by complete deprotection (c); in this compound the distance x' is about 19 Å and y' 9 Å.
Figures 1, 14:
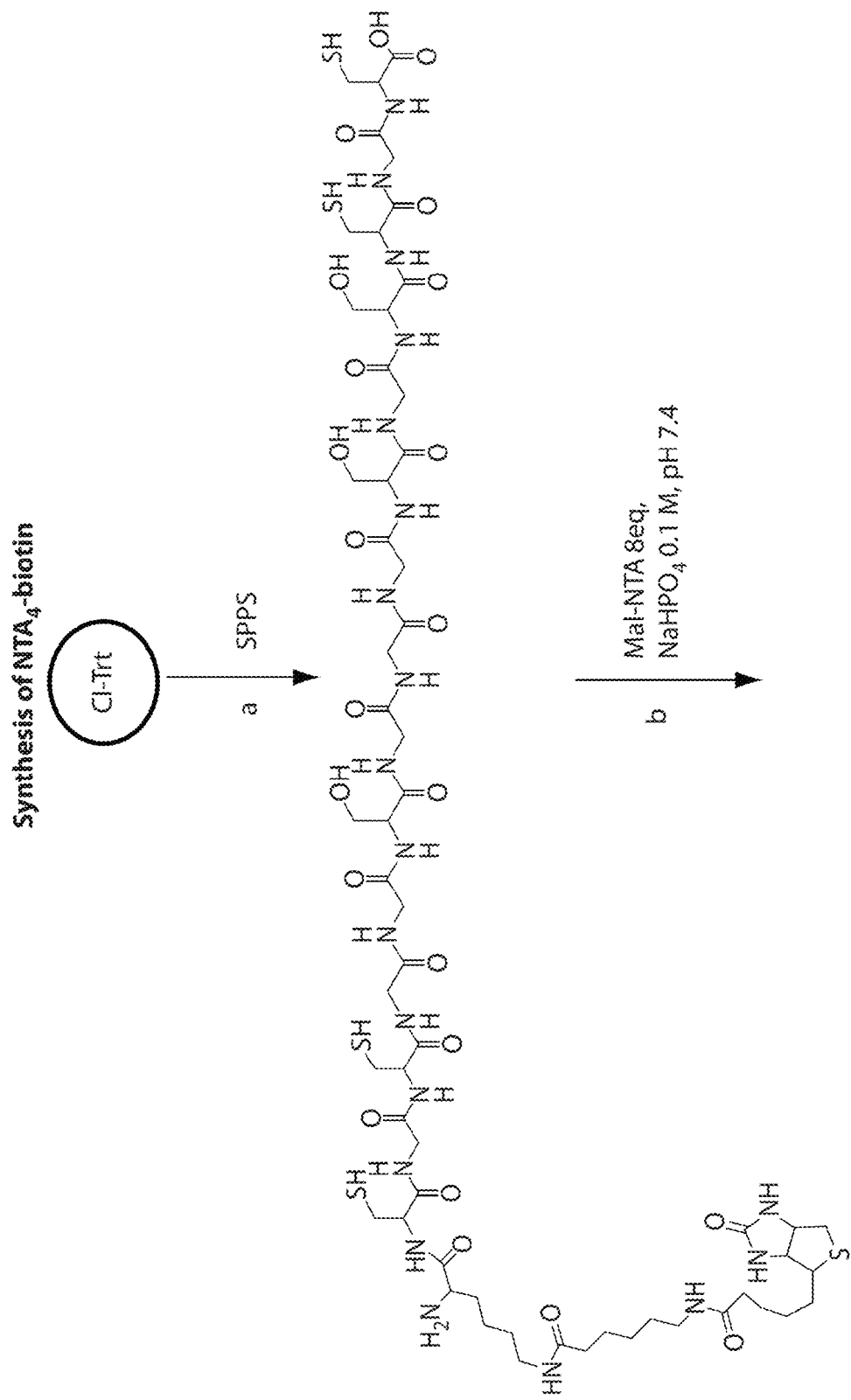
FIG. 14. Synthesis of NTA₄-biotin. In a first step backbone peptide was synthesized by solid phase peptide synthesis on a chloro-trityl resin (a). The deprotected and HPLC purified peptide was reacted in phosphate buffer with 8 equivalents of NTA maleimide (b). The molecules comprises two di-NTA moieties joined by a flexible GGSGGGSGS (SEQ ID NO: 10) linker, which is the same as in the 2×His6 (SEQ ID NO: 312) tag (FIG. 2A).
Figures 2, 14:
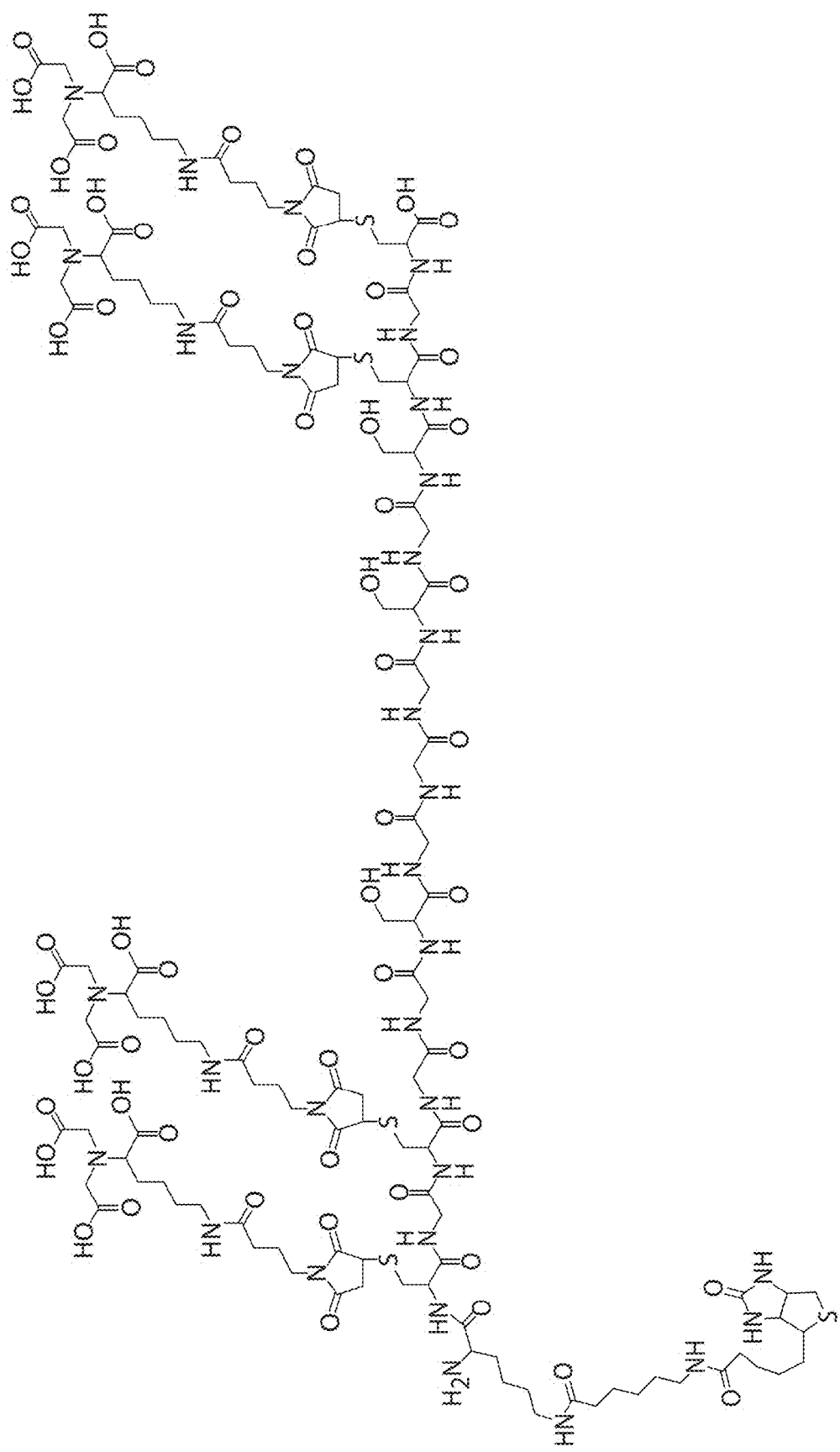
Figure 15A:
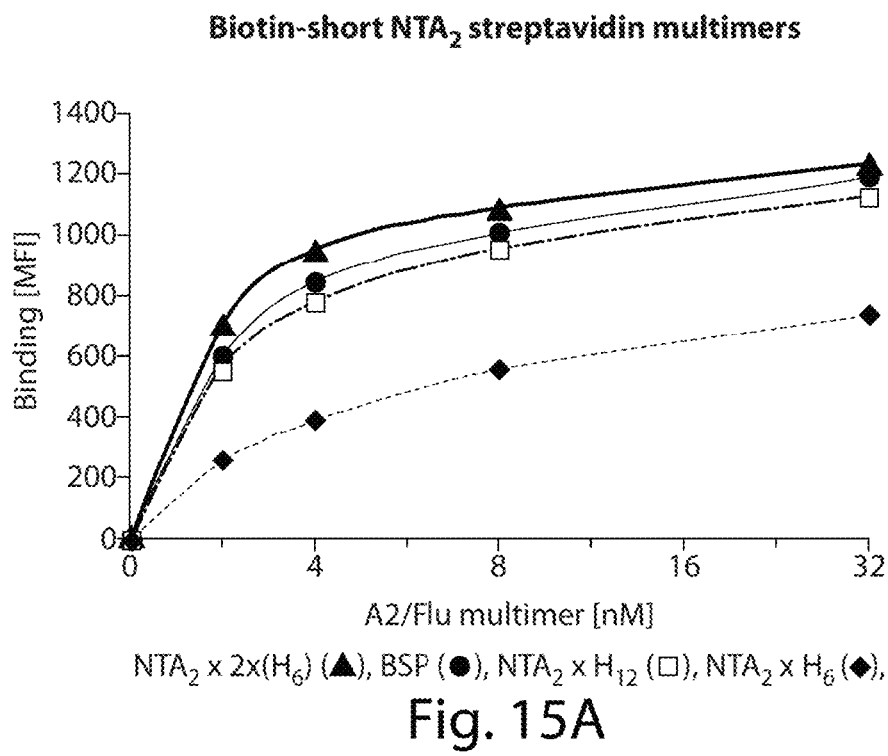
FIGS. 15A to 15B. Multimers containing the short di-NTA linker more avidly stain cloned CD8+ T cells than those containing the long di-NTA linker.
Figure 15B:
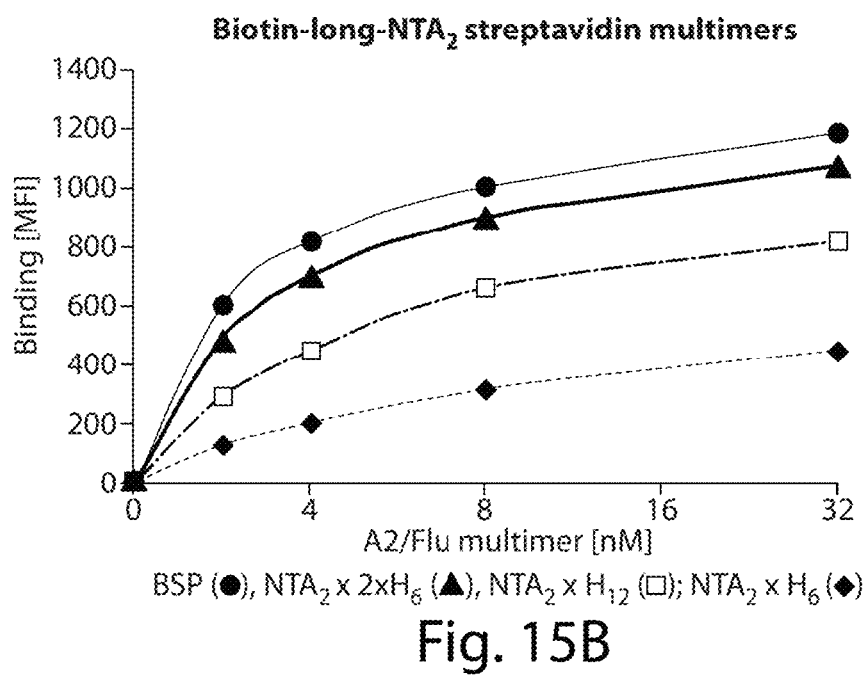

It should be noted that staining results critically depend on the configuration of the NTA molecule. For example, we initially synthesized another biotin-$NTA_2$ compound, in which lysine NTA was coupled via amide bonds to a linear peptide containing two orthogonal carboxyl side chains about 14 Å apart (FIG. 13). Because this is longer (by about 4.4 Å) compared to the other biotin-$NTA_2$ (FIG. 3B, FIG. 12), we refer to this linker as short and the other as long. Binding isotherms on cloned 81P1 cells at 20° C. cells indicated that A2/Flu multimers containing the short performed better than the multimers containing the long $NTA_2$ moiety (FIG. 15). While multimers containing the short $NTA_2$-biotin and $2×His_6$ (SEQ ID NO: 312) tagged A2/Flu complexes exhibited superior binding than conventional multimers (FIG. 15A), all multimers containing the long di-NTA showed inferior binding (FIG. 15B). Moreover, the binding hierarchy of multimers containing the differently tagged A2/Flu complexes and the short, respectively the long $NTA_2$-biotin were remarkably disparate. We also tested multimers containing the commercial NTA-biotin (FIG. 3F) and observed substantially lower binding compared to multimers containing the long NTA-biotin (FIG. 3A) (data not shown).

Taken collectively, these results demonstrate that MHC class I-peptide multimers can be built on NTA-His tag chelate complexes that perform equal or better than conventional BSP multimers. The affinity and stability of $Ni^{2+}NTA$-His tag complexes depends not only on the number of $Ni^{2+}NTA$ entities and histidines, but also on their configuration. This is primarily explained by the number of subunit $Ni^{2+}NTA$-histidine chelate complexes that de facto can be formed (FIG. 1A). Our SPR binding studies indicated that complexes containing $2×His_6$ (SEQ ID NO: 312) tagged A2/Flu complexes have higher affinities (i.e. lower $K_D$ values) and slower dissociation kinetics (i.e. lower $k_{off}$ values (FIG. 4B). This is consistent with previous reports and most likely explained by that two $His_6$ (SEQ ID NO: 310) tags joined by a flexible spacer can interact with more $Ni^{2+}NTA$ entities than the relative rigid $His_{12}$ (SEQ ID NO: 311) tag. Our multimer binding studies on cells are consistent with this, although in the case of $NTA_4$ containing multimer differences were marginal (FIG. 5B). On the other hand our staining results indicate that $Ni^{2+}NTA$ entities form more stable complexes with His tags when they have long flexible side chains, yet short intervening linkers (FIGS. 12-15). Little is known on how binding parameters of NTA-His tag interactions depend on the spatial configuration of the NTA moiety. One study showed that tri-NTA compounds most avidly bind to $His_6$ (SEQ ID NO: 310) tags when they contain minimal spacers (15). To better understand this relationship, we are currently testing additional di and tetra NTA molecules.

Figure 16:
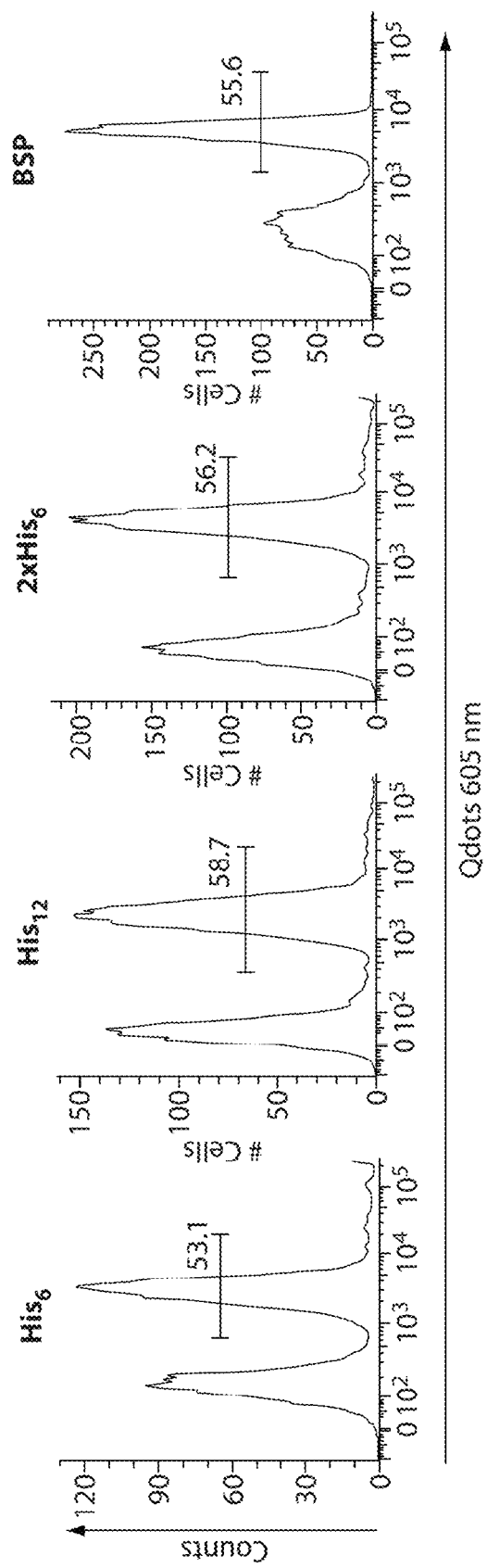
FIG. 16. BCB 70 CTL were incubated likewise with streptavidin coated QDOT® 605 streptavidin conjugate (QDOT®₆₀₅) were loaded with NTA₂-biotin and conjugated with A2/Flu₅₈₋₆₆ monomers containing the indicated tags; after washing the cells were analyzed by flow cytometry. For comparison quantum dots (QDOTs®) loaded with biotinylated monomers were included (BSP). Sequences correspond to linear His₆ (SEQ ID NO: 310), His₁₂ (SEQ ID NO: 311) or 2×His₆ (SEQ ID NO: 312) tags.

We performed staining experiments with multimers containing streptavidin quantum dot (QDOT®) loaded with biotin-$NTA_2$ on 81P1 cells. As shown in FIG. 16 the staining of was similar for all monomers tested, i.e. the nature of the His tag had little effect on the staining. These quantum dots (QDOTs®) are larger than PE, contain more streptavidin on their surface and therefore more $NTA_2$ groups; as discussed below, the density of NTA groups on a surface is another factor determining the stability of complexes with His tagged proteins.

NTA-His Tag Built Multimers are Reversible

Figure 6A:
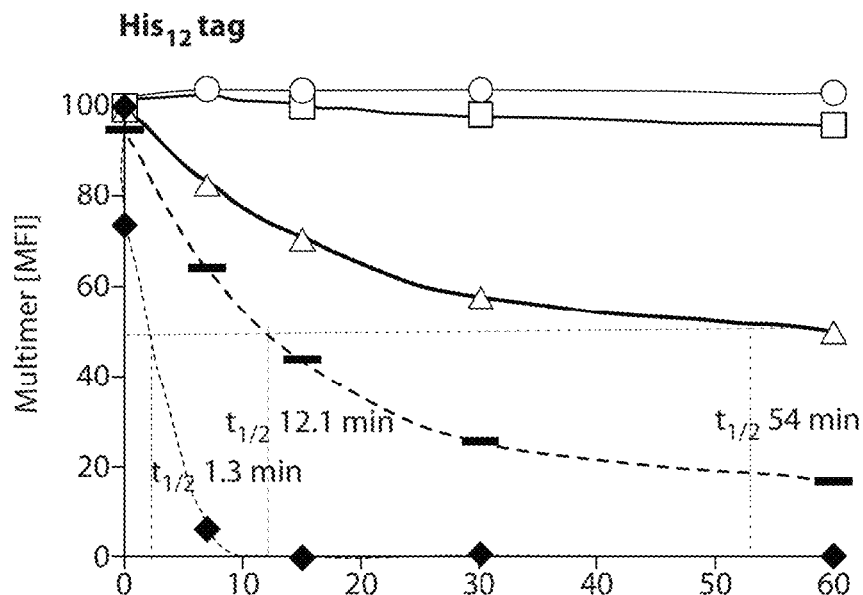
FIGS. 6A to 6B. Dissociation kinetics of different NTA$_2$-biotin-streptavidin A2/Flu$_{58-66}$ multimers.
Figure 6B:
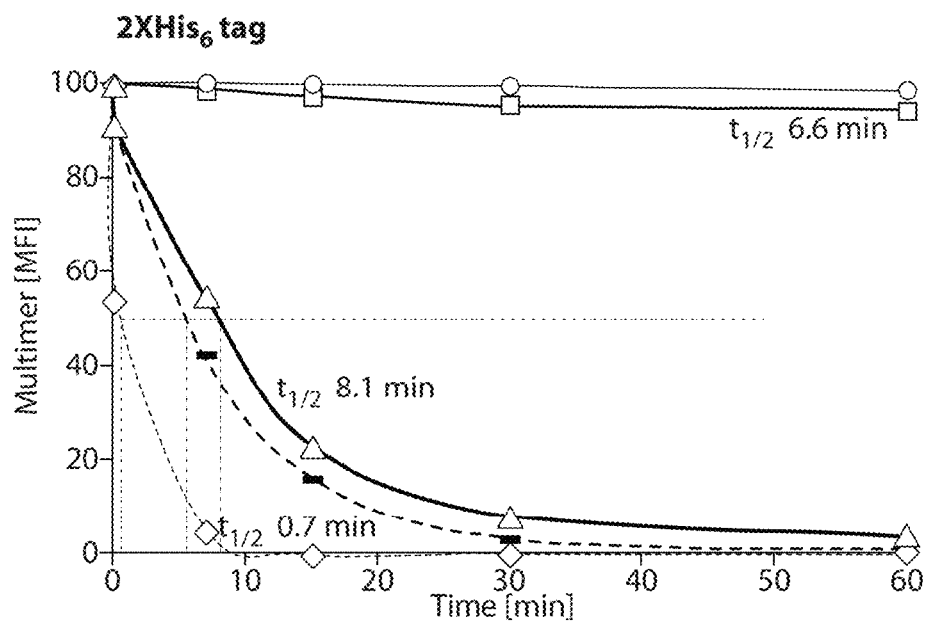

We next assessed the dissociation kinetics of A2/Flu multimers built on $NTA_2$-biotin-PE streptavidin in the presence of different concentrations of imidazol and/or EDTA. Cloned 81P1 cells were stained in the cold with multimers containing $NTA_2$ and $His_{12}$ (SEQ ID NO: 311) or $2×His_6$ (SEQ ID NO: 312) tags, washed and incubated for different periods of time at 4° C. in media containing imidazol. The staining of $2×His_6$ (SEQ ID NO: 312) tag containing multimers decreased more rapidly than the staining of $His_{12}$ (SEQ ID NO: 311) tag containing multimers (FIGS. 6A, B). In the presence of 50 mM imidazole half maximal dissociation was observed after 8.1 and 54 min, respectively. In the presence of 50 mM imdidazol plus 20 mM EDTA the dissociation rate increased and half maximal dissociation was reached after 12.1 and 6.6 min, respectively. In the presence of EDTA alone dissociations were very slow in both cases (data not shown). By contrast, rapid dissociations were observed in the presence of 100 mM imidazole, with half maximal dissociations after 1.3 and 0.7 min, respectively. At higher concentrations of imidazole the dissociation was further accelerated, but in some cases cell viability was affected.

Figure 7:
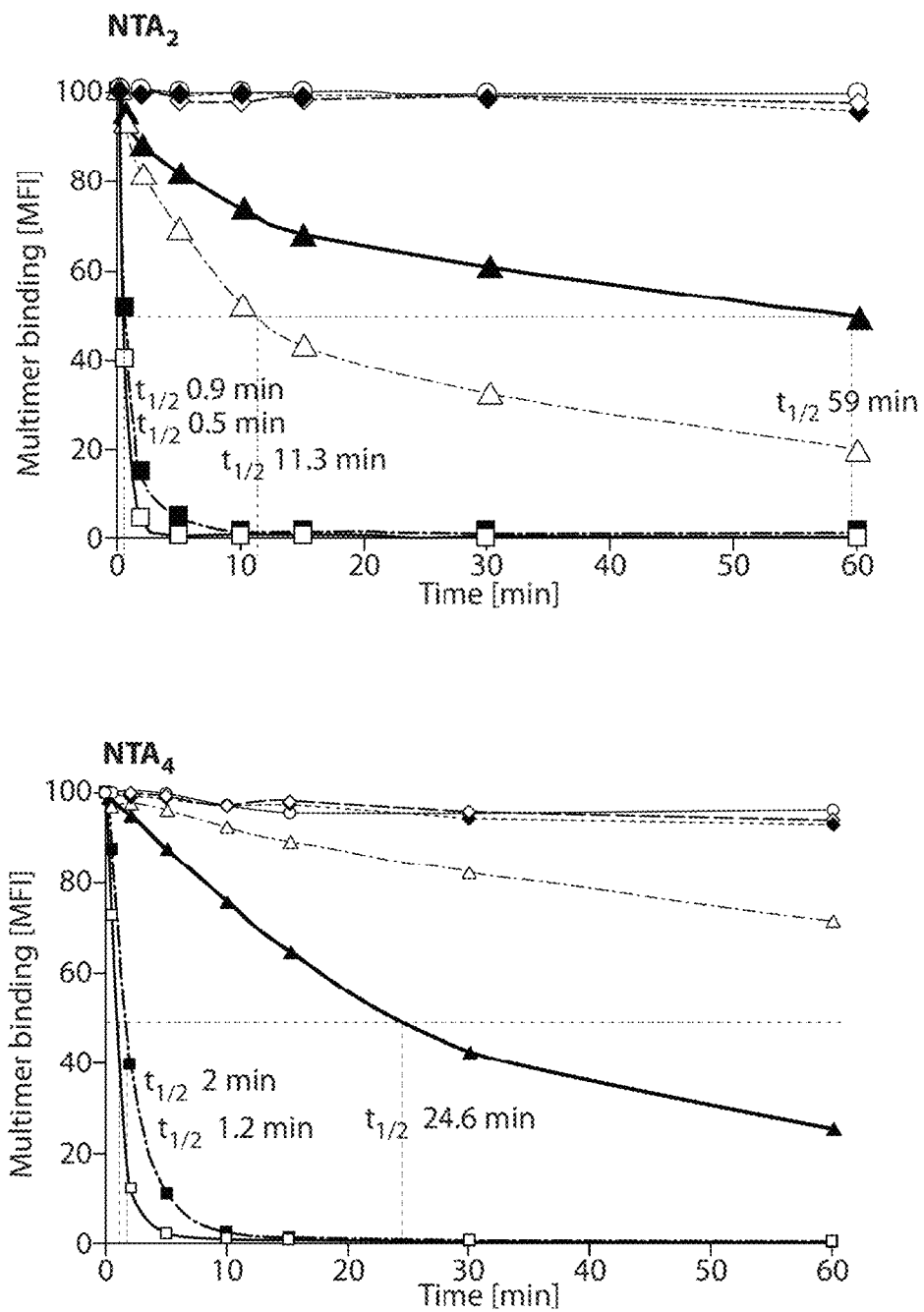
FIG. 7. Dissociation kinetics of NTA$_2$- and NTA$_4$ biotin-streptavidin A2/Flu$_{58-66}$ multimers. Cloned BCB 70 cells were incubated at 4° C. for 1 h with NTA$_2$-biotin-streptavidin PE (top panel) or NTA$_4$-PE A2/Flu multimers (bottom panel) containing the His12 (SEQ ID NO: 311; dark symbols) or 2×His$_6$ tag (SEQ ID NO: 312; light symbols). After washing the cells were incubated at 4° C. in HBSS in the absence (diamonds) or presence of 50 mM imidazole (triangles), or 100 mM imidazole (squares) and after the indicated periods of time cell-associated multimers were assessed by flow cytometry. For comparison conventional BSP multimers were included (circles). The inserted numbers indicate the times ($t_{1/2}$) at which half maximal dissociation was observed.

Analogous dissociation experiments were performed on cloned BCB 70 cells with multimers containing $NTA_2$- and $NTA_4$ biotin-streptavidin A2/Flu$_{58-66}$ multimers. For $NTA_2$ multimers similar results were obtained as in the previous experiment (FIGS. 6A and 7A). The dissociations for $NTA_4$ multimers were slower. In the presence of 50 mM imidazol the half-life for the $His_{12}$ (SEQ ID NO: 311) containing multimer was in the range of hours and for the $2 \times His_6$ (SEQ ID NO: 312) containing one about 25 min (FIG. 7B). However, in the presence of 100 mM imidazol dissociations were much faster, with half-lives of 2 and 1.2 min for the $His_{12}$ (SEQ ID NO: 311) and $2 \times His_6$ (SEQ ID NO: 312) containing multimers, respectively. It is interesting to note that while the physical dissociation of $2 \times His_6$ (SEQ ID NO: 312) tagged molecules from $Ni^{2+}$ NTA was slower compared to $His_{12}$ (SEQ ID NO: 311) tagged molecules (FIG. 4B), the inverse was true when the complexes were dissociated by addition of free imidazol (FIGS. 6, 7).

Preparation, Validation and Application of Biotin Free $NTA_2$-PE MHC Class I-Peptide Multimers.

Figure 8A:
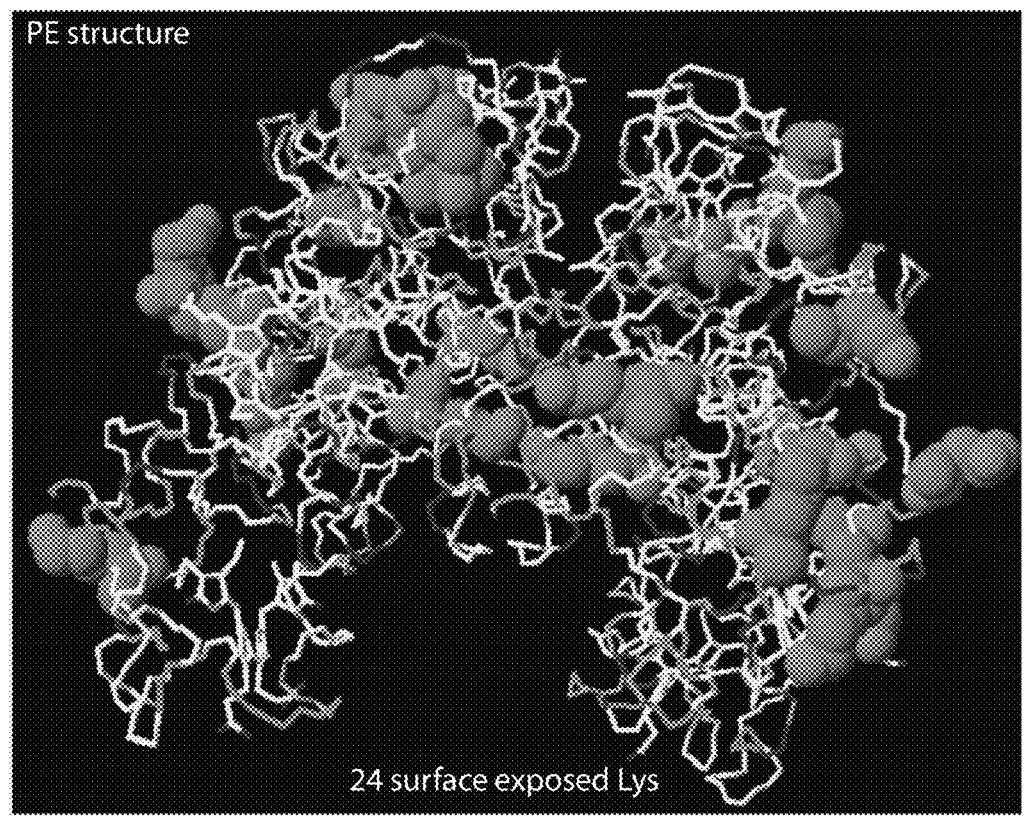
FIGS. 8A to 8B. Preparation of NTA$_2$-PE conjugates.
Figure 8B:
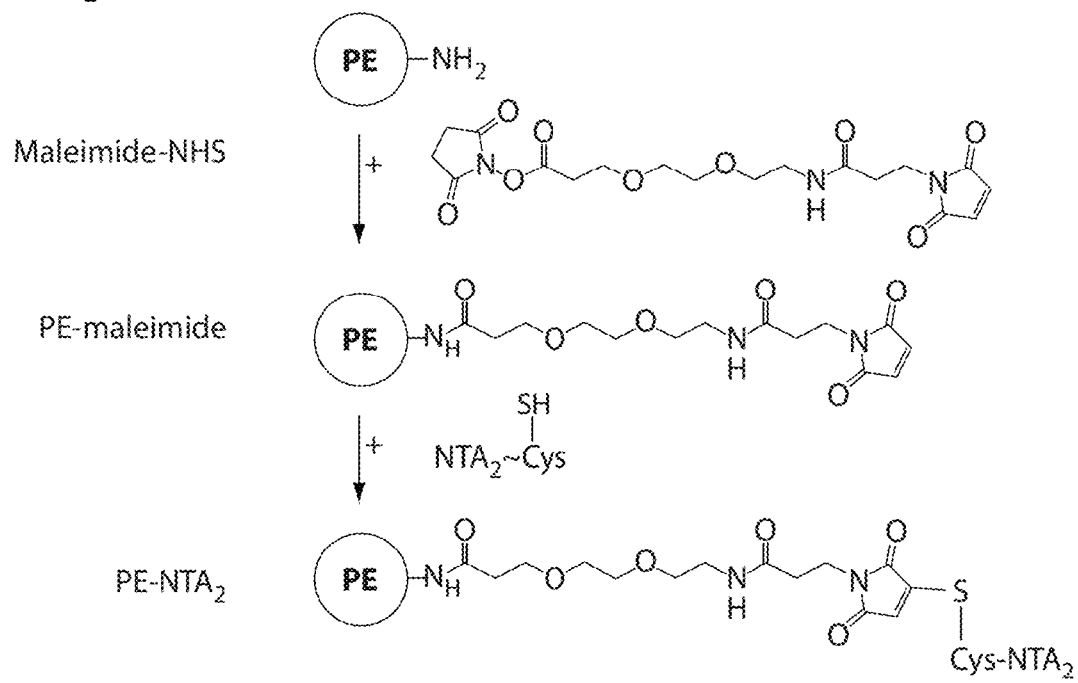

Based on the finding that multimers containing $2 \times His_6$ (SEQ ID NO: 312) tagged MHC class I-peptide monomers and streptavidin-PE saturated with biotinylated short $NTA_2$ were sufficiently stable to efficiently stain CD8+ CTL (FIGS. 1C, 2-5), we coupled $NTA_2$ directly to PE and produced multimers by loading these with $2 \times His_6$ (SEQ ID NO: 312) tagged MHC class I-peptide monomers. To this end PE, which has 24 surface exposed lysine residues, was reacted first with the water soluble maleimide-hydroxy-succinimide ester $SM(PEG)_2$. The resulting maleimide conjugated PE was subsequently reacted with the $NTA_2$-cysteine (see FIG. 3E), yielding stable PE-$NTA_2$ conjugates by thioether formation. (FIG. 8).

Figure 17:
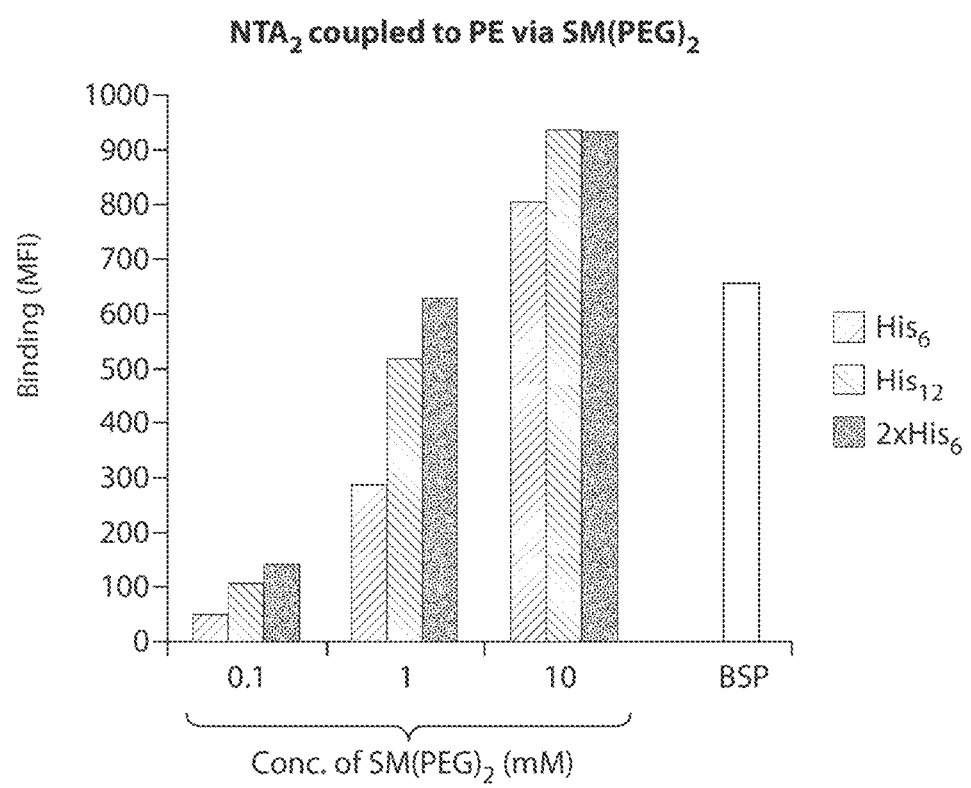
FIG. 17. Impact of the degree of NTA₂ conjugation of PE on NTA₂-PE His tag multimer staining. PE was conjugated with di-NTA as shown in FIG. 8 using a constant concentration of PE (10 nM) and the indicated concentrations of SM(PEG)₂ for 2 h at ambient temperature, followed by alkylation NTA₂-cysteine. The resulting NTA₂-PE conjugates were loaded with A2/Flu₅₈₋₆₆ monomers containing the indicated His tags, the multimers (5 nM) were incubated at 20° C. for 30 min with cloned 81P1 cells. After washing cell-associated multimers were measured by flow cytometry. For comparison conventional BSP multimers were included. Sequences correspond to linear His₆ (SEQ ID NO: 310), His₁₂ (SEQ ID NO: 311) or 2×His₆ (SEQ ID NO: 312) tags.

To find out what degree of conjugation of PE with $NTA_2$ was needed to obtain efficient $NTA_2$-PE multimer staining, we reacted PE with different concentration of $SM(PEG)_2$. The resulting PE maleimide derivatives were exhaustively alkylated with $NTA_2$-cysteine (FIG. 3E) and the resulting $NTA_2$-PE conjugates loaded with A2/Flu monomers carrying different His tags. The efficiency of all $NTA_2$-PE multimers to stain cloned 81P1 CTL increased with the density of $NTA_2$ groups on PE (FIG. 17). While at low degrees of conjugation the multimers containing the $2 \times His_6$ (SEQ ID NO: 312) tag exhibited superior binding, at high degrees the $His_{12}$ (SEQ ID NO: 311) tag containing multimer performed equally well and even the $His_6$ (SEQ ID NO: 310) containing multimer lagged only little behind. This is reminiscent to our experiments with QDOT®$_{605}$ (FIG. 16), but different from the multimer staining with NTA-biotin-streptavidin multimers in which those containing the $2 \times His_6$ (SEQ ID NO: 312) tag performed clearly better than those containing the $His_{12}$ (SEQ ID NO: 311) tag or a simple $His_6$ (SEQ ID NO: 310) tag (FIG. 5A). We argue that at high densities of NTA groups His tags can cooperatively interact with adjacent NTA moieties, whereas at low densities the binding strengths relies primarily on the interactions between individual His tags and NTA moieties.

Figure 9:
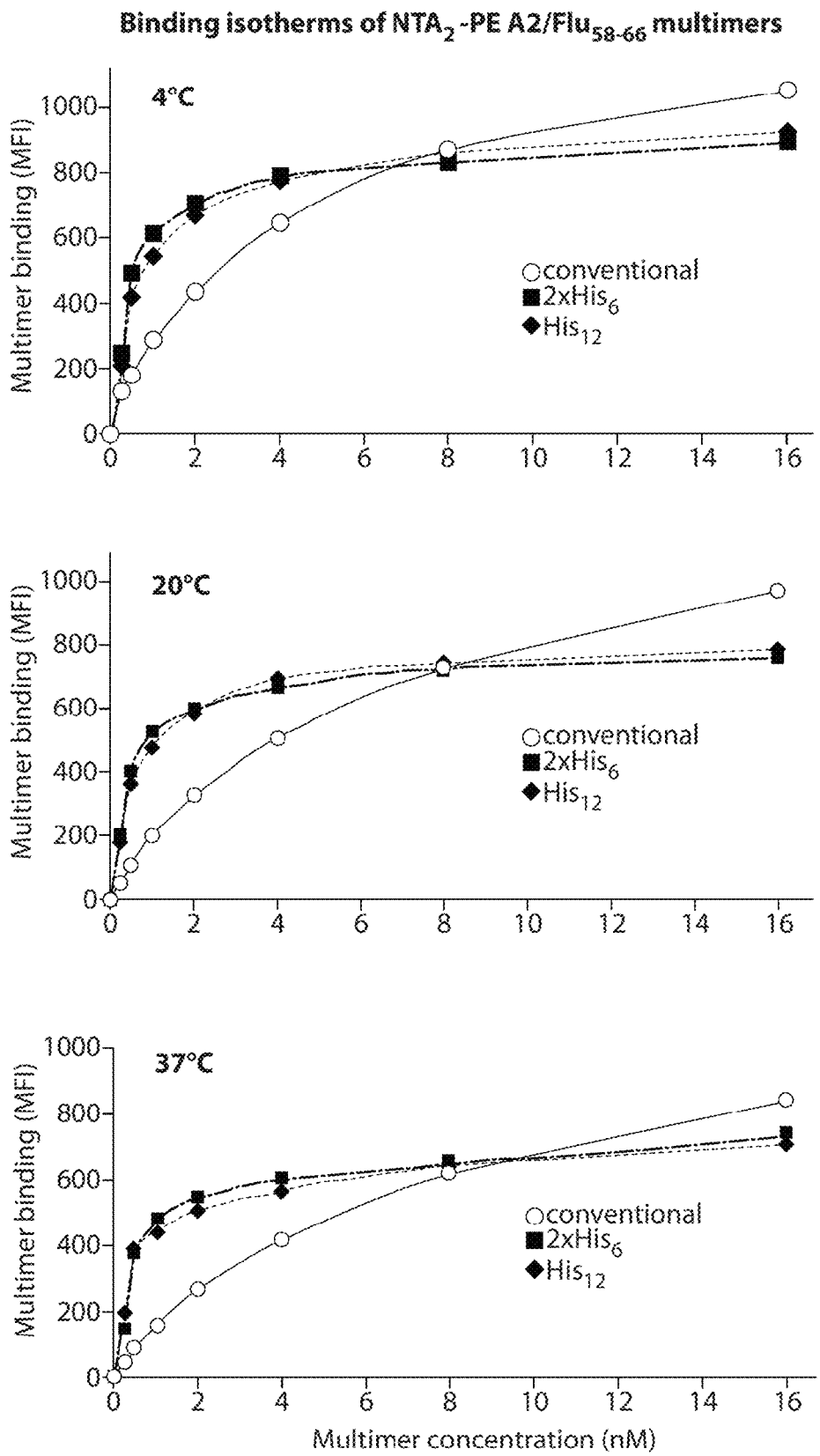
FIG. 9. Binding isotherms of NTA$_2$-PE A2/Flu$_{58-66}$ multimers. Cloned 81P1 cells were incubated for 45 min at the indicated temperatures with graded concentrations of conventional BSP multimers (circles), or with multimers containing NTA$_2$-PE coupled PE and A2/Flu complexes containing the 2×His₆ (SEQ ID NO: 312) tag (squares) or the His₁₂ (SEQ ID NO: 311) tag (diamonds). After washing the cells they were analyzed by flow cytometry.
Figure 18:
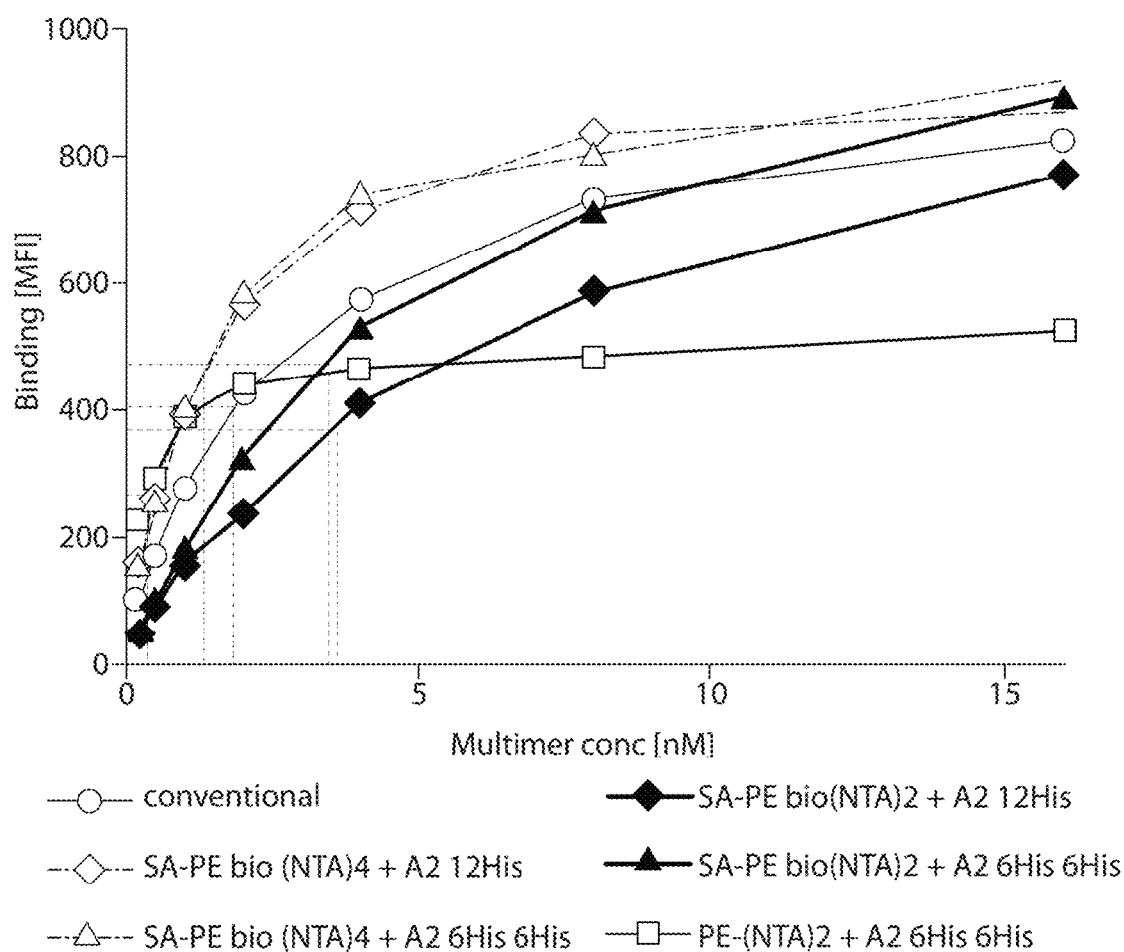
FIG. 18. Binding isotherms of different A2/Flu multimers on a polyclonal Flu-specific CD8+ T cell population. A polyclonal population of Flu-specific CD8+ T cells was incubated at 20° C. for 30 min with A2/Flu multimers containing NTA₄-biotin and 2×His₆ (SEQ ID NO: 312) tag (light triangles, NTA₄-biotin and His₁₂ (SEQ ID NO: 311; light diamonds), NTA₂-biotin and 2×His₆ (SEQ ID NO: 312) tag (dark triangles), NTA₂-biotin and His₁₂ (SEQ ID NO: 311) tag (dark diamonds), NTA₂-PE and 2×His₆ (SEQ ID NO: 312) tag (squares) and conventional BSP multimers (circles). Cell associated fluorescence was measured by flow cytometry.

We next performed binding isotherms on cloned 81P1 cells comparing conventional A2/Flu BSP multimers with multimers containing $NTA_2$-PE and $His_{12}$ (SEQ ID NO: 311) or $2 \times His_6$ (SEQ ID NO: 312) tagged monomers. At all temperatures tested, both $NTA_2$ multimers exhibited a stable binding plateau above 4 nM multimer concentration. By contrast the binding of the BSP multimer increased over the whole concentration range tested (FIG. 9). This is explained by that NTA multimers are molecularly better defined than BSP multimers. While the NTA multimers consist of one PE conjugated with variable numbers of A2/Flu monomers, conventional multimers contain multiple complexes of different sizes and stoichiometries. This heterogeneity stems from the conjugation of PE with streptavidin (2, 3) and therefore the NTA-biotin-streptavidin PE multimers are equally heterogeneous, as reflected by their binding isotherms (FIG. 5, FIG. 18). Importantly, because NTA multimers are better defined, they allow more conclusive binding analysis (e.g. Scatchard analysis) than conventional BSP multimers, i.e. can provide more information on given antigen-specific T cells.

So far all binding experiments were performed on Flu-specific CTL clones. Due to clonal variations such data may not be generally representative. We therefore repeated the binding studies on a population of Flu-specific CD8+ T cells derived from peptide stimulated PBMC of a DR4+ healthy donor. As shown in FIG. 18, the 20° C. binding isotherms on this polyclonal population exhibited essentially the same picture as the one obtained on clones, namely: i) the binding of $NTA_4$ multimer binding was higher than of $NTA_2$ multimer; ii) multimers containing the $2 \times His_6$ (SEQ ID NO: 312) tag bound better than those containing the $His_{12}$ (SEQ ID NO: 311) tag in the case of $NTA_2$, but not $NTA_4$ reagents; iii) the $NTA_2$-PE multimer exhibited clear saturation, whereas all streptavidin-PE containing ones did not; and iv) the $NTA_4$ and $NTA_2$-PE multimers exhibited the highest avidity, i.e. lowest concentrations for half maximal binding.

Figure 10:
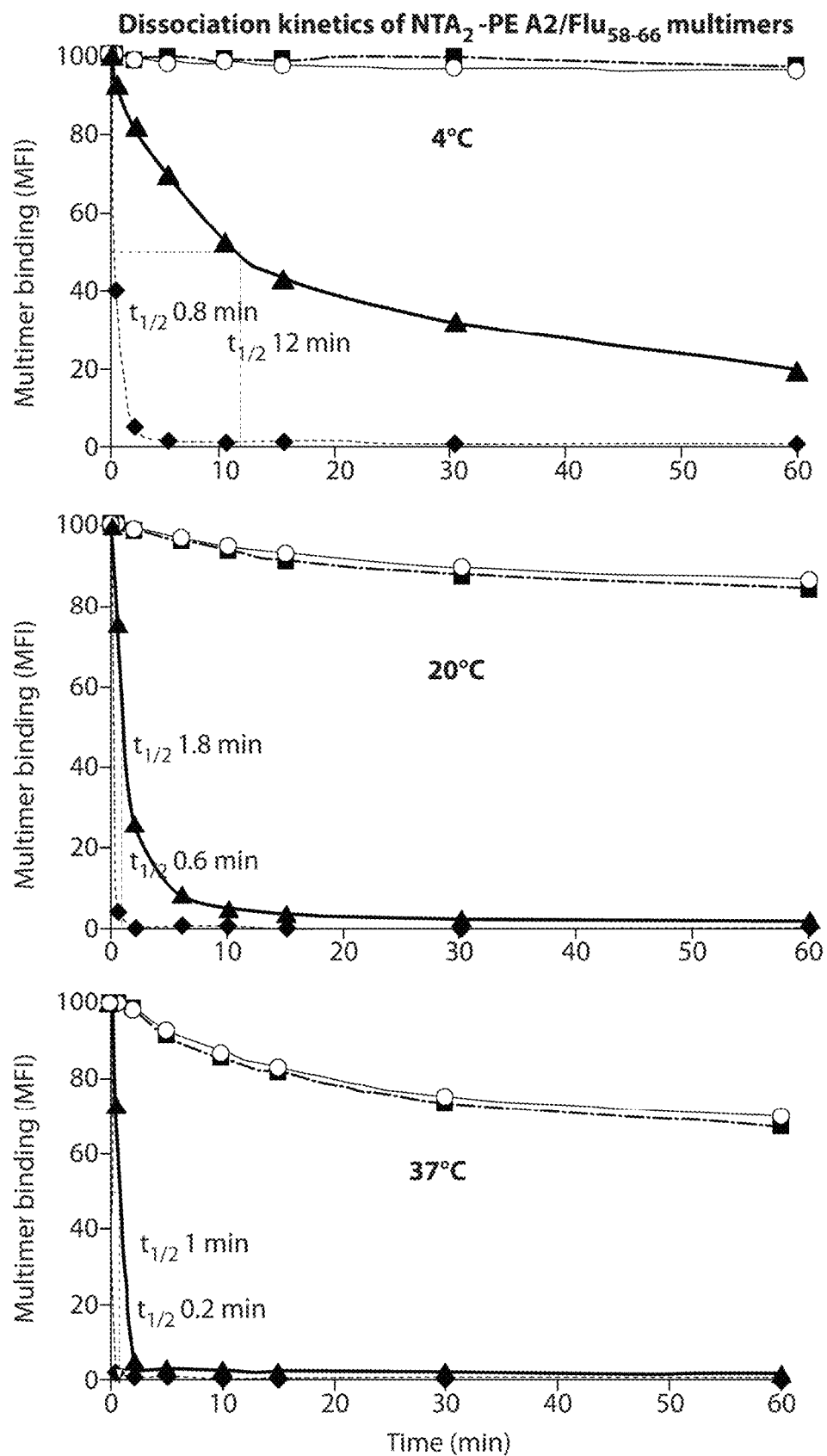
FIG. 10. Dissociation kinetics of NTA₂-PE A2/Flu₅₈₋₆₆ multimers. Cloned BCB 70 cells were incubated for 1 h at 4° C. with conventional BSP multimers (circles) or multimers containing NTA₂-PE conjugated with A2/Flu complexes containing a 2×His₆ (SEQ ID NO: 312) tag. After washing the cells they were incubated at the indicated temperatures in FACS buffer containing or not (squares) 50 mM imidazol (triangles) or 100 mM imidazol (diamonds). After the indicated periods of time the cells were analyzed by flow cytometry.

Finally we performed dissociation kinetics on cloned BCB 70 cells for multimers containing $NTA_2$-PE and $2 \times His_6$ (SEQ ID NO: 312) tagged A2/Flu complexes. In the presence of 50 mM imidazol half maximal dissociation was reached at 4° C. after about 12 min, at 20° C. after 1.8 min and at 37° C. after 1 min (FIG. 10). In the presence of 100 mM imidazol the dissociations were very rapid with half-lives below 1 min; especially at 20° C. and 37° C. the dissociations were too fast to be measured accurately by this flow cytometric analysis.

Reversible MHC Class I-Peptide Complexes Allow Sorting of Antigen-Specific CD8+ T Cells without Inducing Activation Dependent Cell Death.

Figure 19A:
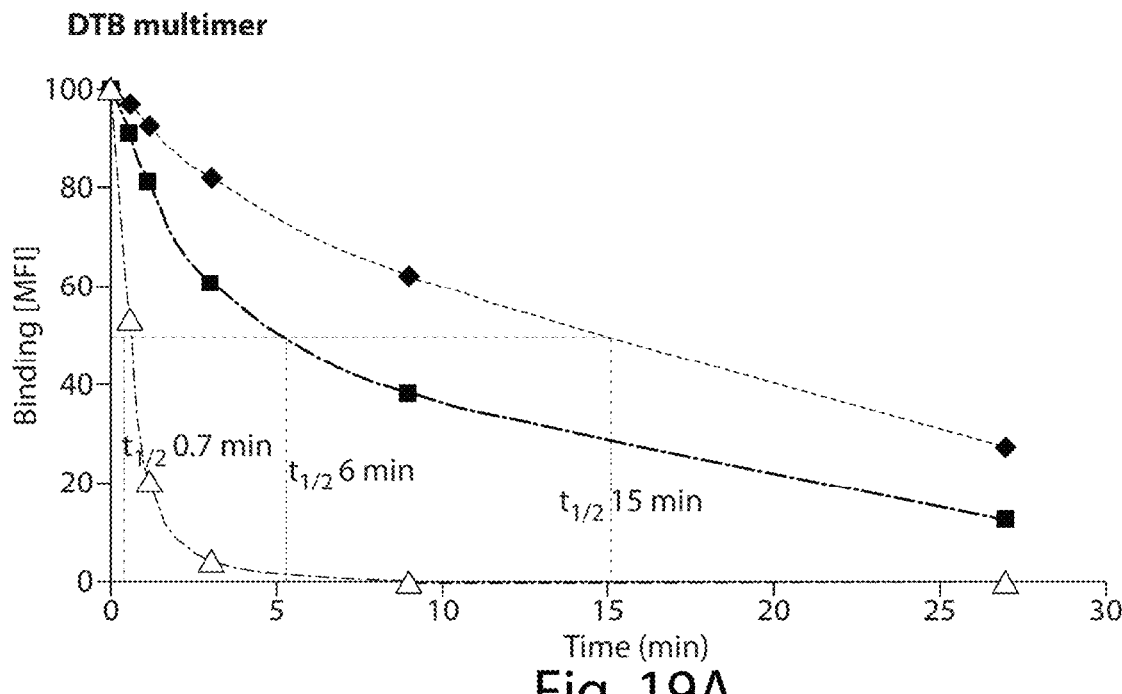
FIGS. 19A to 19B. Dissociation kinetics of A2/Flu₅₈₋₆₆ DTB and NTA₂-PE multimers.
Figure 19B:
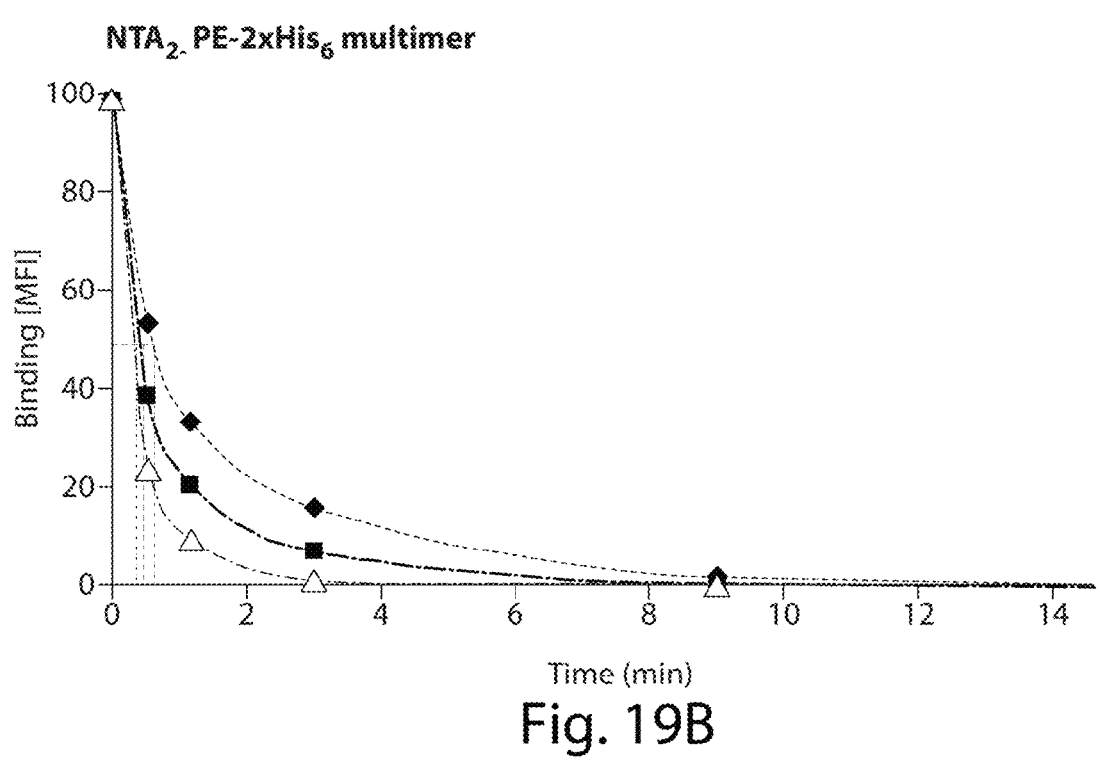

In previous studies we have shown that MHC-I-peptide multimers induce extensive activation-induced death of CD8+ CTL and that this seriously compromises multimer sorting or cloning of antigen-specific CD8+ T cells (5, 6). To circumvent this, we previously made DTB (des-thio-biotin), a low affinity biotin variant, multimers which dissociate in the presence of free biotin (5). We previously demonstrated that antigen-specific CD8+ T cells cloned or sorted with DTB multimers are superior compared to cells sorted/cloned with conventional BSP multimers in terms of cell viability and functionality. To find out whether NTA built multimers would offer the same advantage, we first compared the dissociation kinetics of A2/Flu DTB multimers, with multimers containing $NTA_2$-PE and $2 \times His_6$ (SEQ ID NO: 312) tagged A2/Flu complexes. As shown in FIG. 19 DTB-streptavidin A2/Flu$_{58-66}$ multimers in the presence of 2 mM biotin dissociated considerably slower than $NTA_2$-PE-$2 \times His_6$ (SEQ ID NO: 312) multimers in the presence of 100 mM imidazole. The differences were especially striking at 4° C. and 20° C.

Figure 11:
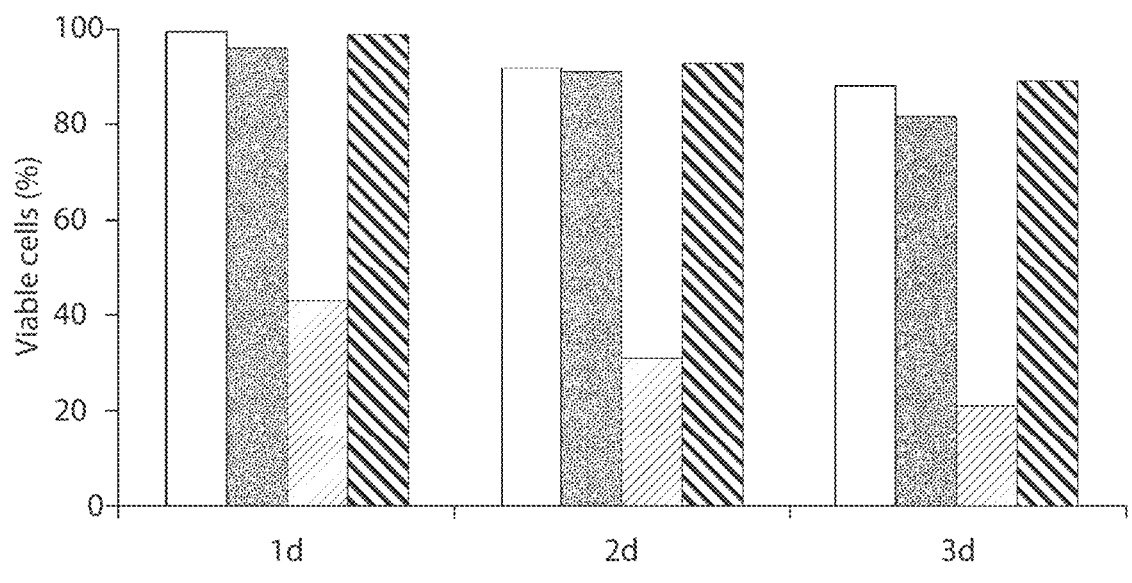
FIG. 11. FACS sorting with reversible NTA₂-PE but not conventional A2/Flu multimers provides high cell viability. Cloned BCB 70 cells were FACS sorted upon staining with the conventional A2/Flu₅₈₋₆₆ BSP (thin striped bars) or NTA₂-PE-2×His₆ (SEQ ID NO: 312) multimers (stippled bars), after 1 wash with 100 mM imidazol the cells were cultured and at the indicated intervals viable cells enumerated by trypan blue exclusion counting. As controls cells were left untreated (white) or washed 1× with 100 mM imidazol (thick striped bars).

To directly examine the usefulness of A2/Flu $NTA_2$-PE $2 \times His_6$ (SEQ ID NO: 312) multimers for FACS sorting, cloned BCB 70 cells were stained with this or conventional BSP multimers. FACS sorted cells were washed once with 100 mM imidazol and viable cells enumerated 1, 2 or 3 d afterwards. As shown in FIG. 11A the percentage of viable cells of $NTA_2$-PE multimer sorted cells was slightly lower compared to untreated cells or cells washed once with cold imidazol. By contrast cells sorted with conventional multimers exhibited only 42% viable cells after id and merely 20% 3d after sorting. Although these experiments need to be extend by including sorting of polyclonal populations and by functional analysis, our results strongly argue that NTA$_2$-PE 2×His$_6$ (SEQ ID NO: 312) multimers are equivalent or superior to reversible DTB multimers; the beneficial effects of this we have described in detail in a previous study (5). The same conjugation strategy can be equally applied to prepare MHC class II multimers or antibody conjugates, i.e. is universally applicable for the preparation of reversible protein conjugates.

In sum, our results demonstrate that MHC class I-peptide multimers can be prepared based on NTA-His tag chelate complexes that perform equally well or better than conventional BSP multimers. Importantly, because NTA complexes rapidly dissociate in the presence of imidazol, they allow isolation of bona fide antigen-specific CD8+ T cells by FACS or MACS, which is considerably advantage to BSP multimers. Because NTA built multimers contain neither biotin nor streptavidin, they are simpler and cheaper to prepare.

REFERENCES

1. Altman J D, Davis M M. MHC-peptide tetramers to visualize antigen-specific T cells. *Curr Protoc Immunol.* 2003; Chapter 17:Unit 17.3.
2. Guillaume P, Dojcinovic D, Luescher I F. Soluble MHC-peptide complexes: tools for the monitoring of T cell responses in clinical trials and basic research. *Cancer Immun.* 2009; 9:7.
3. Guillaume P, Legler D F, Boucheron N, Doucey M A, Cerottini J C, Luescher I F. Soluble major histocompatibility complex-peptide octamers with impaired CD8 binding selectively induce Fas-dependent apoptosis. *J Biol Chem.* 2003; 278:4500-9.
4. Guillaume P, Baumgaertner P, Neff L, Rufer N, Wettstein P, Speiser D E, Luescher I F. 2010. Novel soluble HLA-A2/MELAN-A complexes selectively stain a differentiation defective subpopulation of CD8+ T cells in patients with melanoma. *Int J Cancer* 127:910-23.
5. Guillaume P, Baumgaertner P, Angelov G S, Speiser D, Luescher I F. Fluorescence-activated cell sorting and cloning of bona fide CD8+ CTL with reversible MHC-peptide and antibody Fab' conjugates. *J Immunol.* 2006; 177:3903-3912.
6. Cebecauer M, Guillaume P, Hozák P, Mark S, Everett H, Schneider P, Luescher I F. Soluble MHC-peptide complexes induce rapid death of CD8+ CTL. *J Immunol.* 2005; 174:6809-19.
7. Knabel M, Franz T J, Schiemann M, Wulf A, Villmow B, Schmidt B, Bernhard H, Wagner H, Busch D H. Reversible MHC multimer staining for functional isolation of T-cell populations and effective adoptive transfer. *Nat Med.* 2002; 8:631-7.
8. Neudorfer J, Schmidt B, Huster K M, Anderl F, Schiemann M, Holzapfel G, Schmidt T, Germeroth L, Wagner H, Peschel C, Busch D H, Bernhard H. Reversible HLA multimers (Streptamers) for the isolation of human cytotoxic T lymphocytes functionally active against tumor- and virus-derived antigens. *J Immunol Methods.* 2007; 320:119-131.
9. Knecht S, Ricklin D, Eberle A N, Ernst B. Oligohis-tags: mechanisms of binding to Ni2+-NTA surfaces. *J Mol Recognit.* 2009; 22:270-9.
10. Cao H, Lin R. Quantitative evaluation of His-tag purification and immunoprecipitation of tristetraprolin and its mutant proteins from transfected human cells. *Biotechnol Prog.* 2009; 25:461-7.
11. Khan F, He M, Taussig M J. Double-hexahistidine tag with high-affinity binding for protein immobilization, purification, and detection on ni-nitrilotriacetic acid surfaces. *Anal Chem.* 2006; 78:3072-9.
12. Steinhauer C, Wingren C, Khan F, He M, Taussig M J, Borrebaeck C A. Improved affinity coupling for antibody microarrays: engineering of double-(His)6-tagged single framework recombinant antibody fragments. Proteomics. 2006 6:4227-34.
13. Lata S, Reichel A, Brock R, Tampé R, Piehler J. High-affinity adaptors for switchable recognition of histidine-tagged proteins. *J Am Chem Soc.* 2005; 127:10205-10215.
14. Huang Z, Park J I, Watson D S, Hwang P, Szoka F C Jr. Facile synthesis of multivalent nitrilotriacetic acid (NTA) and NTA conjugates for analytical and drug delivery applications. *Bioconjug Chem.* 2006; 17:1592-600.
15. Huang Z, Hwang P, Watson D S, Cao L, Szoka F C. Tris-Nitrilotriacetic Acids of Subnanomolar Affinity Toward Hexahistidine Tagged Molecules. *Bioconjug Chem.* 2009 Aug. 3.

All references listed are incorporated herein in their entirety by reference.

Example 2

The methods and materials described herein are universally applicable to generate reversible MHC multimers by conjugating a plurality of MHC molecules to a multivalent carrier molecule via a chelate complex bond. While the invention is not limited to specific MHC molecules, Tables 1 and 2 provide exemplary MHC molecules and exemplary antigenic peptides that can be used to produce empty or peptide-loaded reversible MHC molecules using the concepts, methods, and materials provided by aspects of this invention and described in more detail elsewhere herein. Further MHC molecules and antigenic peptides are known in the art and described, for example, in the Tetramer Collection of the Ludwig Institute for Cancer Research (see Guillaume P, Dojcinovic D, Luescher I F. *LICR tetramer collection: Soluble tetrameric MHC/peptide complexes to identify and monitor tumor antigen-specific T cells.* Cancer Immun 2009; URL: cancerimmunity.org/tetramers/; both the publication and the online database are incorporated herein by reference in their entirety for disclosure of useful MHC molecules and antigenic peptides according to aspects of this invention).

TABLE 1

Exemplary MHC class I molecules and antigenic peptides useful for the generation of reversible multimers.

| MHC | Protein | Position | Peptide | SEQ ID NO |
|---|---|---|---|---|
| HLA-A*0201 | EBV BMLF1 | 259-267 | GLCTLVAML | 14 |
| | hCMV pp65 | 495-503 | NLVPMVATV | 15 |
| | HIV RT | 896-904 | ILKEPVHGV | 16 |
| | Influenza M1 | 58-66 | GILGFVFTL | 17 |
| | MAGE-10 | 254-262 | GLYDGMEHL | 18 |
| | MELAN-A / MART-1 | 26-35 | ELAGIGILTV | 19 |

TABLE 1-continued

Exemplary MHC class I molecules and antigenic peptides useful for the generation of reversible multimers.

| MHC | Protein | Position | Peptide | SEQ ID NO |
|---|---|---|---|---|
| | NY-ESO-1 | 157-165 | SLLMWITQC | 20 |
| | | | SLLMWITQA | 21 |
| | Tyrosinase | 369-377 | YMNGTMSQV | 22 |
| HLA-A*0101 | Influenza NP | 44-52 | CTELKLSDY | 23 |
| | MAGE-3 | 168-176 | EVDPIGHLY | 24 |
| | Tyrosinase | 146-156 | SSDYVIPIGTY | 25 |
| | | 243-251 | KCDICTDEY | 26 |
| HLA-A*0201 | AFP | 158-166 | FMNKFIYEI | 27 |
| | | 325-334 | GLSPNLNRFL | 28 |
| | BK polyomavirus VP1 | 90-99 | STARIPLPNL | 29 |
| | | 108-116 | LLMWEAVTV | 30 |
| | B-Raf | 597-606 | LLTEKSRWSV | 31 |
| | CAMEL | 1-11 | MLMAQEALAFL | 32 |
| | CEA | 605-613 | YLSGANLNL | 33 |
| | | | YLSGADLNL | 34 |
| | | | YLSGANLDL | 35 |
| | | 691-699 | IMIGVLVGV | 36 |
| | | 694-702 | GVLVGVALI | 37 |
| | | | GLLVGVALI | 38 |
| | | | GVLVGVALV | 39 |
| | | | GLLVGVALV | 40 |
| | CSPG4 / HMW-MAA | 561-569 | SLMVILEHT | 41 |
| | | 769-777 | ILSNLSFPV | 42 |
| | | 1063-1071 | LLFGSIVAV | 43 |
| | | 2238-2246 | LILPLLFYL | 44 |
| | cytokeratin-18 | 365-373 | ALLNIKVKL | 45 |
| | DCT / TRP-2 | 180-188 | SVYDFFVWL | 46 |
| | EBV NA-6 | 284-293 | LLDFVRFMGV | 47 |
| | EBV BMLF1 | 259-267 | GLATLVAML | 48 |
| | Fibromodulin | 250-259 | YMEHNNVYTV | 49 |
| | G250 / CA-IX | 24-32 | QLLLSLLLL | 50 |
| | | 254-262 | HLSTAFARV | 51 |
| | gp100 / Pmel 17 | 154-162 | KTWGQYWQV | 52 |
| | | 209-217 | ITDQVPFSV | 53 |
| | | | IMDQVPFSV | 54 |
| | | 280-288 | YLEPGPVTA | 55 |
| | | | YLEPGPVTA | 56 |
| | | 457-466 | LLDGTATLRL | 57 |
| | | 476-485 | VLYRYGSFSV | 58 |
| | hCMV pp65 | 14-22 | VLGPISGHV | 59 |
| | hepatitis capsid protein | 18-27 | FLPSDFFPSV | 60 |
| | HER2 / neu | 369-377 | KIFGSLAFL | 61 |
| | HERV | 69-77 | DLNNFCQKV | 62 |
| | HERV-K-Mel | | MLAVISCAV | 63 |
| | HPV16 E7 | 11-20 | YMLDLQPETT | 64 |
| | | 86-93 | TLGIVCPI | 65 |
| | influenza NA | 213-221 | CVNGSCFTV | 66 |
| | | | CVNGSCFTI | 67 |
| | JC polyomavirus VP1 | 36-44 | SITEVECFL | 68 |
| | LAGE-1 | 86-94 | RLLQLHITM | 69 |
| | | 103-111 | ELVRRILSR | 70 |
| | MAGE-3 | 112-120 | KVAELVHFL | 71 |
| | | 157-166 | SLQLVFGIEL | 72 |
| | | 271-279 | FLWGPRALV | 73 |
| | MAGE-4 | 230-239 | GVYDGREHTV | 74 |
| | | | GVYDGRIHTV | 75 |
| | MAGE-C2 | 336-344 | ALKDVEERV | 76 |
| | Mdm2 | 81-88 | LLGDLFGV | 77 |
| | MELAN-A / MART-1 | 26-35 | EAAGIGILTV | 78 |
| | | | AAAGIGILTV | 79 |
| | | | ALAGIGILTV | 80 |
| | | | VVAGIGILAI | 81 |
| | | 27-35 | LAGIGILTV | 82 |
| | | | ALGIGILTV | 83 |
| | MOG | 210-218 | TLFVIVPVL | 84 |
| | mouse TERT | 545-553 | QLLRSFFYI | 85 |
| | | 797-806 | SLFDFFLHFL | 86 |
| | | 981-990 | YLQVNSQTV | 87 |
| | GnT-V | | VLPDVFIRC | 88 |
| | | | VLPDVFIRCV | 89 |
| | NPM-1 | 183-191 | AIQDLCLAV | 90 |
| | | | AIQDLCVAV | 91 |
| | NY-BR-1 | 158-167 | LLSHGAVIEV | 92 |
| | | 960-968 | SLSKILDTV | 93 |
| | | 1365-1373 | LLKEKNEEI | 94 |
| | NY-ESO-1 | 85-96 | SRLLEFYLAMPF | 95 |
| | | 86-94 | RLLEFYLAM | 96 |
| | | 108-116 | SLAQDAPPL | 97 |
| | | 127-135 | TVSGNILTI | 98 |
| | | 157-165 | ALLMWITQC | 99 |
| | | | SALMWITQC | 100 |
| | | | SLAMWITQC | 101 |
| | | | SLLAWITQC | 102 |
| | | | SLLMAITQC | 103 |
| | | | SLLMWATQC | 104 |
| | | | SLLMWIAQC | 105 |
| | | | SLLMWITAC | 106 |
| | | 157-166 | SLLMWITQCF | 107 |
| | | 157-167 | SLLMWITQCFL | 108 |
| | | 157-170 | SLLMWITQCFLPV | 109 |
| | | 158-166 | LLMWITQCF | 110 |
| | | 158-167 | LLMWITQCFL | 111 |
| | | 159-167 | LMWITQCFL | 112 |
| | | 161-169 | WITQCFLPV | 113 |
| | p53 | 264-272 | LLGRNSFEV | 114 |
| | P. aeruginosa probable sulfate transporter | 125-133 | LAGIGILIV | 115 |
| | PRAME | 300-309 | ALYVDSLFFL | 116 |
| | proteinase 3 | 169-177 | VLQELNVTV | 117 |
| | RHAMM | 165-173 | ILSLELMKL | 118 |
| | Rab-38 | 49-58 | KVLHWDPETV | 119 |
| | | 50-58 | VLHWDPETV | 120 |
| | SSX2 | 41-49 | KASEKIFYV | 121 |
| | | | KASEKITYV | 122 |
| | | 103-111 | RLQGISPKI | 123 |
| | | | ALQGISPKI | 124 |
| | | | ALQGASPKI | 125 |
| | | | ALQGISAKI | 126 |
| | | | ALQGISPAI | 127 |
| | SSX4 | 41-49 | KSSEKIVYV | 128 |
| | Surviving | 96-104 | LTLGEFLKL | 129 |
| | | | LMLGEFLKL | 130 |
| | TERT | 540-548 | ILAKFLHWL | 131 |
| | Tyrosinase | 9-Jan | MLLAVLYCL | 132 |
| | | 369-377 | YMDGTMSQV | 133 |
| | Transaldolase | 168-176 | LLFSFAQAV | 134 |
| | vaccinia virus C16/B22 | 60-68 | CLTEYILWV | 135 |
| | WT1 | 126-134 | RMFPNAPYL | 136 |
| | | 235-243 | CMTWNQMNL | 137 |

TABLE 1-continued

Exemplary MHC class I molecules and antigenic peptides useful for the generation of reversible multimers.

| MHC | Protein | Position | Peptide | SEQ ID NO |
|---|---|---|---|---|
| HLA-A*0301 | influenza M1 | 27-35 | RLEDVFAGK | 138 |
|  | influenza NP | 265-273 | ILRGSVAHK | 139 |
| HLA-A*2301 | influenza M1 | 58-66 | GILGFVFTL | 140 |
| HLA-A*2402 | HER2 / neu | 63-71 | TYLPTNASL | 141 |
|  | HIV nef | 135-142 | RYPLTFGW | 142 |
|  | MAGE-4 | 143-151 | NYKRCFPVI | 143 |
|  | NY-ESO-1 | 158-166 | LLMWITQCF | 144 |
|  |  | 162-170 | ITQCFLPVF | 145 |
|  | SAGE | 715-723 | LYATVIHDI | 146 |
|  | TERT | 324-332 | VYAETKHFL | 147 |
|  | Tyrosinase | 206-214 | AFLPWHRLF | 148 |
|  | WT1 | 235-243 | CMTWNQMNL | 149 |
|  |  | 417-425 | RWPSCQKKF | 150 |
| HLA-A*3101 | influenza M1 | 58-66 | GILGFVFTL | 151 |
| HLA-A*6801 | gp100 / Pme1 17 | 182-191 | HTMEVTVYHR | 152 |
|  | MAGE-3 | 115-123 | ELVHFLLLK | 153 |
| HLA-B*0702 | hCMV pp65 | 417-426 | TPRVTGGGAM | 154 |
|  | HIV nef | 129-138 | TPGPGVRYPL | 155 |
|  | NY-ESO-1 | 60-72 | APRGPHGGAASGL | 156 |
|  |  | 98-109 | TPMEAELARRSL | 157 |
|  |  | 98-110 | TPMEAELARRSLA | 158 |
| HLA-B*1302 | influenza M1 | 58-66 | GILGFVFTL | 159 |
| HLA-B*1801 | NY-ESO-1 | 88-96 | LEFYLAMPF | 160 |
| HLA-B*3501 | EBV NA-4 | 488-496 | AVLLHEESM | 161 |
|  | gp100 / Pme1 17 | 630-638 | LPHSSSHWL | 162 |
|  | hCMV pp65 | 123-131 | IPSINVHHY | 163 |
|  | HIV Gag-Pol | 774-782 | NPDIVIYQY | 164 |
|  | MELAN-A / MART-1 | 26-35 | EAAGIGILTV | 165 |
|  |  |  | EPAGIGILTV | 166 |
|  |  |  | EAAGIGILTY | 167 |
|  |  |  | EPAGIGILTY | 168 |
|  | NY-ESO-1 | 92-100 | LAMPFATPM | 169 |
|  |  | 92-104 | LAMPFATPMEAEL | 170 |
|  |  | 93-104 | AMPFATPMEAEL | 171 |
|  |  | 94-102 | MPFATPMEA | 172 |
|  |  | 94-104 | MPFATPMEAEL | 173 |
|  |  | 96-104 | FATPMEAEL | 174 |
|  |  | 116-123 | LPVPGVLL | 175 |
|  | Tyrosinase | 312-320 | LPSSADVEF | 176 |
| HLA-B*3503 | influenza M1 | 58-66 | GILGFVFTL | 177 |
|  | NY-ESO-1 | 92-100 | LAMPFATPM | 178 |
|  |  | 92-104 | LAMPFATPMEAEL | 179 |
|  |  | 93-104 | AMPFATPMEAEL | 180 |
|  |  | 94-102 | MPFATPMEA | 181 |
|  |  | 94-104 | MPFATPMEAEL | 182 |
| HLA-Cw*0304 | importin-α2 / karyopherin | 204-212 | GAVDPLLAL | 183 |
|  | NY-ESO-1 | 92-100 | LAMPFATPM | 184 |
|  |  | 92-104 | LAMPFATPMEAEL | 185 |
|  |  | 96-104 | FATPMEAEL | 186 |
| HLA-Cw*0702 | influenza M1 | 58-66 | GILGFVFTL | 187 |
| HLA-A*0201 | CEA | 694-702 | GVLVGVALI | 188 |
|  |  |  | GLLVGVALI | 189 |
|  |  |  | GVLVGVALV | 190 |
|  |  |  | GLLVGVALV | 191 |
|  | EBV IE63 | 259-267 | GLCTLVAML | 192 |
|  | gp100 / Pme1 17 | 209-217 | ITDQVPFSV | 194 |
|  |  |  | IMDQVPFSV | 195 |
|  | hCMV pp65 | 495-503 | NLVPMVATV | 196 |
|  | HER2 / neu | 369-377 | KIFGSLAFL | 197 |
|  | influenza M1 | 58-66 | GILGFVFTL | 198 |
|  | MAGE-10 | 254-262 | GLYDGMEHL | 199 |
|  | Mdm2 | 81-88 | LLGDLFGV | 200 |
|  | MELAN-A / | 26-35 | EAAGIGILTV | 201 |
|  | NY-ESO-1 | 157-165 | SLLMWITQC | 202 |
|  |  |  | SLLMWITQA | 203 |
|  | p53 | 264-272 | LLGRNSFEV | 204 |
|  | proteinase 3 | 169-177 | VLQELNVTV | 205 |
|  | RHAMM | 165-173 | ILSLELMKL | 206 |
|  | SSX2 | 41-49 | KASEKIFYV | 207 |
|  |  |  | KASEKITYV | 208 |
|  | WT1 | 126-134 | RMFPNAPYL | 209 |
| HLA-A*0201 α1 α2 H-2Kb α3 | DCT / TRP-2 | 180-188 | SVYDFFVWL | 210 |
|  | HERV | 65-74 | SILQDLNNFV | 211 |
|  | influenza M1 | 58-66 | GILGFVFTL | 212 |
|  | MELAN-A / MART-1 | 26-35 | ELAGIGILTV | 213 |
|  |  |  | ELAGIGILIV | 214 |
|  | NY-ESO-1 | 157-165 | SLLMWITQC | 215 |
|  |  | 157-166 | SLLMWITQCF | 216 |
|  |  | 157-167 | SLLMWITQCFL | 217 |
|  |  | 158-166 | LLMWITQCF | 218 |
|  |  | 158-167 | LLMWITQCFL | 219 |
|  |  | 159-167 | LMWITQCFL | 220 |
|  |  | 161-169 | WITQCFLPV | 221 |
| HLA-A*0201 | EBV IE63 | 259-267 | GLCTLVAML | 222 |
|  | MELAN-A / MART-1 | 26-35 | ELAGIGILTV | 223 |
|  | NY-ESO-1 | 157-165 | SLLMWITQA | 224 |
| H-2K$^d$ | HLA-A2 | 194-203 | RYLENGKETL | 227 |
|  | HLA-Cw3 | 194-203 | RYLKNGKETL | 228 |
|  | HER2 / neu | 63-71 | TYLPTNASL | 229 |
|  | influenza HA | 204-212 | LYQNVGTYV | 230 |
|  | mouse ERK2 | 136-144 | QYIHSANVL | 231 |
|  | *P. berghei* CS | 252-260 | SYIPSAEKI | 232 |
|  |  |  | SYIPSAEK(ATTO)I | 233 |
|  |  |  | SYIPSAEK(ABA)I | 234 |
|  |  |  | Dap[Cy5]-YIPSAEK(ABA)I | 235 |
|  |  |  | SYILSAEK(ABA)I | 236 |
|  |  |  | SYIASAEK(ABA)I | 237 |
| H-2D$^b$ | GFP | 117-125 | DTLVNRIEL | 238 |
|  |  | 118-125 | TLVNRIEL | 239 |
|  | Gp100 / Pme1 17 | 25-33 | KVPRNQDWL | 240 |
|  | HPV16 E7 | 49-57 | RAHYNIVTF | 241 |
|  | HPV16 L1 | 165-173 | AGVDNRECI | 242 |
|  | influenza NP (1968) | 366-374 | ASNENMDAM | 243 |
|  | influenza NP (1976) | 366-374 | ASNENMETM | 244 |
|  | influenza PA | 224-233 | SSLENFRAYV | 245 |
|  | influenza PB1 | 62-70 | LSLRNPILV | 246 |
|  | LCMV GPC | 33-41 | KAVYNFATC | 247 |
|  |  |  | KAVYNFATA | 248 |
|  |  | 276-286 | SGVENPGGYCL | 249 |
|  | LCMV NP | 396-404 | FQPQNGQFI | 250 |
|  | mouse HY | 738-746 | KCSRNRQYL | 251 |
|  | mouse gp100 | 25-33 | EGSRNQDWL | 252 |
|  | mouse Spas-1 H8 | 244-252 | STHVNHLHC | 253 |
|  | NY-ESO-1 | 86-94 | RLLEFYLAM | 254 |

TABLE 1-continued

Exemplary MHC class I molecules and antigenic peptides useful for the generation of reversible multimers.

| MHC | Protein | Position | Peptide | SEQ ID NO |
|---|---|---|---|---|
| H-2D$^k$ | MPyV MT | 389-396 | RRLGRTLL | 255 |
| H-2D$^d$ | HIV env | 309-318 | RGPGRAFVTI | 256 |
| | NY-ESO-1 | 81-88 | RGPESRLL | 257 |
| H-2K$^b$ | chicken ovalbumin | 258-265 | SIINFEKL | 258 |
| | DCT / TRP-2 | 180-188 | SVYDFFVWL | 259 |
| | E. coli β-gal | 97-104 | DAPIYTNV | 260 |
| | H4 | 87-93 | VVYAFKR | 261 |
| | influenza PB1 | 703-711 | SSYRRPVGI | 262 |
| | LCMV GPC | 34-41 | AVYNFATC | 263 |
| | LCMV NP | 205-212 | YTVKYPNL | 264 |
| | MHV S | 598-605 | RCQIFANI | 265 |
| | NY-ESO-1 | 87-94 | LLEFYLAM | 266 |
| | SV40 LT | 404-411 | VVYDFLKC | 267 |
| H-2L$^d$ | MLV gp70 AH-1 | 138-147 | SPSYVYHQF | 268 |
| H-2QAI | mouse H2-L / Qdm | 3-11 | AMAPRTLLL | 269 |
| TL T3$^b$ | TL | | | |

TABLE 2

Exemplary MHC class II molecules and antigenic peptides useful for the generation of reversible multimers.

| MHC | Protein | Position | Peptide | SEQ ID NO |
|---|---|---|---|---|
| HLA-DP*0401 | adenovirus hexon | 911-925 | DEPTLLYVLFEVFDV | 271 |
| | CD74 / HLA-DR invariant γ-chain | 103-117 | PVSKMRMATPLLMQA | 272 |
| | MAGE-3 | 111-125 | RKVAELVHFLLLKYR | 273 |
| | | 243-258 | KKLLTQHFVQENYLEY | 274 |
| | NY-ESO-1 | 157-170 | SLLMWITQCFLPVF | 275 |
| | | 157-180 | SLLMWITQCFLPVFLAQPPSGQRR | 276 |
| | tetanus toxin | 947-960 | FNNFTVSFWLRVPK | 277 |
| HLA-DQ*0601 | influenza HA | 57-76 | QILDGENCTLIDALLGDPQD | 278 |
| | gp100 / Pmel 17 | 175-189 | GRAMLGTHTMEVTVY | 279 |
| | MELAN-A / MART-1 | 25-36 | EEAAGIGILTVI | 280 |
| | | 26-35 | EAAGIGILTV | 281 |
| HLA-DR*0101 | CD74 / HLA-DR invariant γ-chain | 103-117 | PVSKMRMATPLLMQA | 282 |
| | influenza HA | 306-318 | PKYVKQNTLKLAT | 283 |
| | MAGE-3 | 267-282 | ACYEFLWGPRALVETS | 284 |
| | NY-ESO-1 | 87-98 | LLEFYLAMPFAT | 285 |
| | | 123-137 | LKEFTVSGNILTIRL | 286 |
| HLA-DR*0401 | CD74 / HLA-DR invariant γ-chain | 103-117 | PVSKMRMATPLLMQA | 287 |
| | gp100 / Pmel 17 | 44-59 | WNRQLYPEWTEAQRLD | 288 |
| | influenza M1 | 61-72 | GFVFTLTVPSER | 289 |
| | influenza NP | 206-229 | FWRGENGRKTRIAYERMCNILKGK | 290 |
| | NY-ESO-1 | 119-143 | PGVLLKEFTVSGNILTIRLTAADHR | 291 |

TABLE 2-continued

Exemplary MHC class II molecules and antigenic peptides useful for the generation of reversible multimers.

| MHC | Protein | Position | Peptide | SEQ ID NO |
|---|---|---|---|---|
| H-2IA$^b$ | chicken ovalbumin | 323-339 | ISQAVHAAHAEINEAGR | 292 |
| | mouse DCT / TRP-2 | 110-124 | KFGWSGPDCNRKKPA | 293 |
| | LCMV Pre-GP-C | 61-80 | GLNGPDIYKGVYQFKSVEFD | 294 |
| | MoMLV env | 120-138 | EPLTSLTPRCNTAWNRLKL | 295 |
| | mouse TRP-1 | 420-434 | ADIYTFPLENAPIGH | 296 |

Additional MHC molecules useful according to aspects of this invention include, but are not limited to MHC molecules comprising a mutant HLA-A*0201 chain, e.g. a chain comprising a D227K, a T228A, a D227K, a T228A, a T233A, and/or A245V mutation. Additional MHC molecules useful according to aspects of this invention further include, but are not limited to HLA-A*1101, HLA-A*3001, HLA-A*3004, HLA-B*0801, HLA-B*2705, HLA-B*5101, HLA-Cw*0303, HLA-Cw*0401, HLA-Cw*0602, HLA-Cw*1402, H-2IAd, and H-2IEd molecules.

In some embodiments, chimeric MHC class I multimers are provided, for example, multimers in which the comprised heavy chains are in part human and in part murine. Further, in some embodiments, peptides comprising modified amino acid residues are provided, for example, ABA, 4-azidobenzoic acid, or Dap, diamino-propionic acid. In some embodiments, peptides are provided that comprise or are conjugated to low molecular weight fluorescent dyes (see, e.g. attotech.com/), for example, for flow cytometry analysis.

Example 3

Universally applicable methods for the preparation of immunopure MHC II-peptide staining reagents are provided herein. A method for isolation of MHC II molecules that have stably bound a peptide of interest conjugated to a tag, which, in some embodiments, can subsequently be removed, for example, by cleavage of a linker connecting the tag to the peptide. Further, a method is provided that allows gentle purification of fragile "empty" (without nominal peptide cargo) His tagged MHC II molecules by affinity chromatography on Ni$^{2+}$ nitrilotriacetic acid (NTA) columns. After isolation of correctly peptide loaded MHC II-peptide complexes these can be directly converted to multimers by reaction with NTA. conjugated phycobilins (e.g. phycoerythrin) or quantum dots (QDOTs®).

Abbreviations used in this example include BSP (biotinylation sequence peptide), DR1 (DRB1*0101); DR4 (DRB1*0401); ESO (NY-ESO-1); GFC (gel filtration chromatography); HA (influenza hemagglutinin); LZ (leucine zipper); NPβA (3-(2-nitrophenyl)-β-alanine); NTA (nitrilotriacetic acid); PE (phycoerythrin); and pY (phospho-tyrosine).

While MHC I-peptide complexes can be obtained by peptide driven refolding in good yields and high purity, soluble recombinant MHC class II proteins cannot and are typically produced by insect expression systems, e.g. Drosophila S2 cells or baculovirus and sf9 cells (1). Deletion of the transmembrane (TM) domains of the α and β chains results in their dissociation, which is re-established by addition of leucine zippers. In some embodiments, for multimer (e.g., "tetramer") formation, a biotinylation sequence peptide (BSP) sequence is added after the leucine zipper (e.g., after the acidic zipper) and enzymatic biotinylation and tetramerization is performed as for MHC I-peptide multimers (1-5). In some embodiments, "empty" (without nominal peptide cargo) MHC II molecules are isolated from culture supernatants by immunoaffinity chromatography and subsequently loaded with a peptide of interest. The efficiency of peptide loading depends on its binding strength to the MHC II molecule; if it is below a threshold, peptide loading is inefficient and the resulting complexes of limited stability. If this strategy is not feasible, peptides can be tethered to the N-terminus of the β chain via a flexible linker (6). This strategy works for some, but not all, complexes. Also, although the peptide is part of the molecule, in the case of weak binding peptides there is no knowing whether or not it is correctly bound in the peptide binding groove.

The staining of antigen-specific CD4+ T cells often is weak and the frequency of stained cells ex vivo very low, usually necessitating prior in vitro peptide stimulation to permit conclusive detection. There are significant differences in multimer staining of CD8+ and CD4+ T cells, such as 1) the staining with MHC II multimers is usually higher at 37° C. than at lower temperatures, which is not the case for MHC I multimers (2, 3, 7); 2) Efficient CD4+ T cell staining requires longer incubation periods, which is explained, at least in part, by accumulation of MHC II multimers by endocytosis; therefore agents that affect cell vitality and cytoskeleton function inhibit CD4+ T cell staining (7, 8). 3) The avidity of MHC II multimer binding is usually lower than the binding of MHC I multimers, mainly because CD8 greatly strengthens MHC-peptide binding to CD8+ T cells, whereas CD4 does not (9, 10). MHC II multimer staining therefore typically requires higher concentrations (up to 100 nM, i.e. about 50 µg/ml) (2-5).

Figure 26:
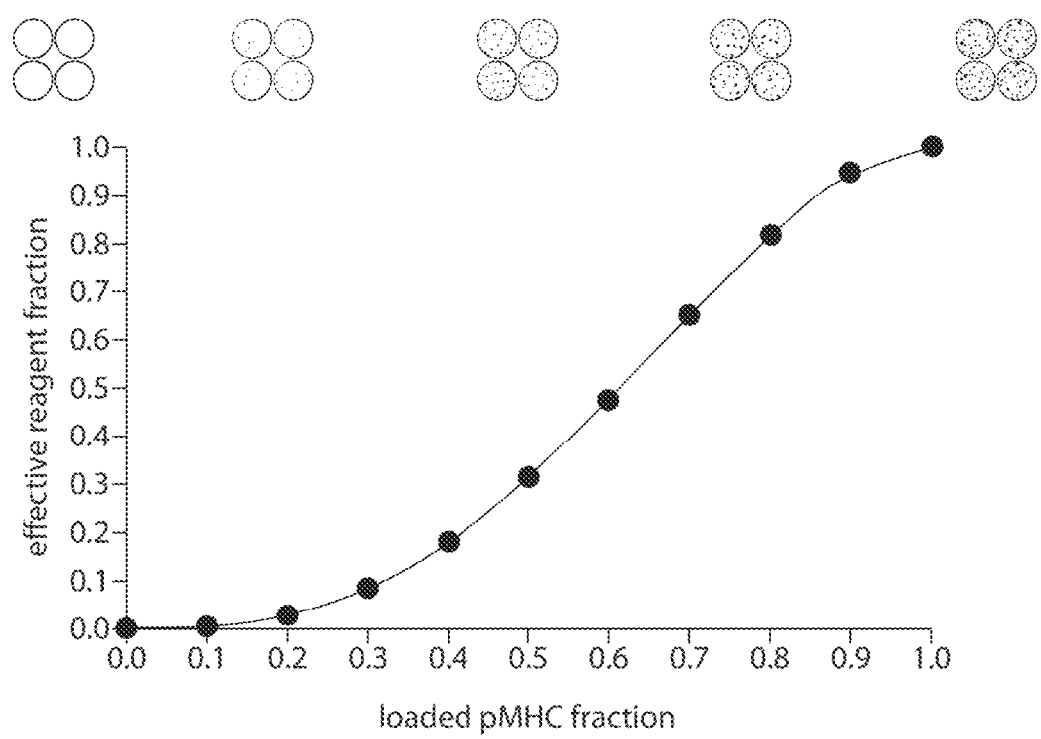
FIG. 26. Impact of peptide loading on tetramer purity. The purity of tetramers decreases rapidly with decreasing peptide loading.

While MHC I-peptide complexes obtained by refolding are highly pure and conformationally uniform, MHC II-peptide complexes obtained by peptide loading of "empty" MHC II proteins or containing tethered-on peptides often are not, which can seriously impair MHC II multimer staining. The commonly used purification of MHC II molecules by immuno-affinity chromatography is not only tedious and expensive, but prone to yield protein denaturation. This decreases the fraction of MHC II molecules that can be loaded with a given peptide and thus the active reagent fraction of multimers prepared with these monomers (FIG. 26). We have previously demonstrated that the quality of MHC II multimers can be dramatically increased when these are produced with molecularly defined monomers, i.e. monomers that contain only the peptide of interest (2, 3). In these studies added a histidine tag ($His_6$: SEQ ID NO: 310) N-terminally of the peptide of interest and after peptide loading isolated correctly loaded complexes by affinity chromatography on $Ni^{2+}$ NTA (nitrilotriacetic acid) columns. While this method is efficient, it has the disadvantage that the peptides are modified with a His tag, which in some cases may affect their binding to MHC molecules and/or their T cell recognition.

Here we report that molecularly defined MHC II-peptide complexes can be isolated by anion exchange chromatography when adding an acidic tag on the peptide of interest. After purification this tag can be removed by means of a photo-cleavable linker. This allowed the use of His tagged MHC II proteins which offered two important advantages: 1) the protein can be purified by gentle affinity purification on $Ni^{2+}$-NTA columns, thereby significantly reducing denaturation of fragile "empty" MHC II molecules. 2) After peptide loading and isolation of immunopure, bona fide (i.e. without peptide tag) MHC II-peptide monomers can be directly converted in multimers. In addition we report that enzymatic de-sialylation of cells increases their MHC II multimer staining by several-fold, which is a simple means to obtain better staining results.

Peptide Synthesis

Protected amino acids and tentagel resin for solid phase peptide synthesis were obtained from Rapp-polymere (Tubingen, Germany and Bachem AG, Bubendorf, Switzerland). The coupling reagents TBTU and HOBt were purchased from Multisynthec (Witten, Germany), Cy5.5-maleimide from GE Healthcare and Fmoc-3-amino-(2-nitrophenyl)-propionic acid from Peptech Corporation (USA). Reverse phase HPLC analyses were performed on a Waters system consisting of two Waters 515 pumps and a Waters 996 photodiode array detector. The purity of all peptides was assessed by analytical HPLC. Analytical HPLC columns (UPTISPHERE® 5 m Cis particles, 250×4.6 mm) was eluted at flow of 1 ml/min, and semi preparative HPLC columns (KROMASIL® 15 m Cis particles, 250×20 mm) at 3 ml/min, with a linear gradient of acetonitril rising in 1 h from 0 to 75% on 0.1% TFA in $H_2O$. The mass of purified peptides was measured by mass spectrometry (MS) on a MALDI-TOF mass spectrometer.

Peptide syntheses were performed using 2 equiv of N-α-Fmoc-protected amino acid relative to the resin loading, activated in situ with 2 equiv of TBTU, 2 equiv of HOBt and 4 equiv of DIEA in DMF (10 ml/g resin) for 1 h. Coupling completion was verified by the Kaiser test. N-α-Fmoc protecting groups were removed by treatment with a piperidine/DMF solution (1:4) (10 ml/g resin) for 5 min. Crude peptides were obtained by treating the resin with a solution of TFA/H2O/TIPS (92.5/2.5/5) for 3 h at ambient temperature. Peptides were precipitated with addition of anhydrous ether, filtered off, dissolved in water, lyophilized and purified by reverse phase HPLC. For the synthesis of Cy5.5 labelled peptides, precursors peptide containing a free thiol were dissolved in DMSO at 10 mM and reacted with one equivalent of Cy5.5-maleimide. After 2h of stirring the mixture was directly subjected to by semi-preparative HPLC.

Photocleavage Under UV Irradiation

Peptides containing the photocleavable amino-acid NPβA in water (50 PM) or MHC II-peptide complexes in PBS (2-20 µM) and irradiated in open 96 well plates with a UV lamp (Vilber Luormat) containing two 15 W mercury fluorescent tubes emitting at 365+/−40 nm at a distance of 10 cm. Samples irradiated for different periods of time were directly analyzed by HPLC and mass spectroscopy.

MHC II-Peptide Complexes

Extracellular coding parts of DR alpha and beta chains were PCR amplified using ctttagatctcgaccacgtttcttggagc (SEQ ID NO: 297) as the 5' primer and ctttgaattccttgctctgtgcagattcag (SEQ ID NO: 298) as the 3' primer from cDNA preparations (Qiagen) of total RNA extracted from human PBMCs, digested with appropriate restriction enzymes and cloned in pMT A BiP/V5/His vector-derived cassette (INVITROGEN™) containing sequences for appropriate leucine zippers and the AviTag (Avidity). The AviTag (GLNDIFEAQKIEWHE, SEQ ID NO: 299) was encoded in an oligo (CTTT CTG GAT ATC TCA TTC GTG CCA TTC GAT TTT CTG AGC CTC GAA GAT GTC GTT CAG ACC GCC ACC, SEQ ID NO: 300) used to extend the basic leucine zipper sequence (TTAPSAQLKKKLQALKK-KNAQLKWKLQALKKKLAQ, SEQ ID NO: 301) separated by a flexible linker (GGGSGGS, SEQ ID NO: 302). Oligos for introduction of a single $His_6$ (CTTTGATATCT-CAATGATGGTGATGATGGTGGCCGGTGCGCT-GAGCCAGTTCCTTTTCC, SEQ ID NO: 303) or a double $His_6$ (CTTTGA-TATCTCAGTGGTGGTGGTGGTGGTGGCTGCC-GCTGCCGCCGCCGCTGCCGCCGCCATGATGGTGAT-GATGGTGGCCGGTGCG, SEQ ID NO: 304) were designed to follow the acidic leucine zipper (TTAP-SAQLEKELQALEKENAQLEWELQALEKELAQ, SEQ ID NO: 305) on the DRα chain separated by a flexible linker mentioned above. All constructs were verified by sequencing.

Soluble "empty" DR1 (DRA, DRB1*0101), DR4 (DRA, DRB1*0401) and DR52b (DRA, DRB3*0202) molecules were produced in Drosophila melanogaster D. Mel-2 cells (a serum-free medium adapted variant of S2 cells) grown in Sf900 II serum-free medium (INVITROGEN™) at room temperature (22-26° C.). Cells were simultaneously transfected with three plasmids (the plasmid for DRA, DRB and pBS-PURO, a plasmid conferring puromycin resistance (a gift from K. Karjalainen, Nanyang Technological University, School of Biological Sciences) using Cellfectin (INVITROGEN™), Singapore). For DR1 and DR4, a population of transfected cells was used, whereas for DR52b high-yielding clones were obtained by limiting dilution. The cells were grown in roller bottles (BD Falcon) rotating at 6 rev/min at room temperature to $5-10*10^6$/ml and protein production was induced by addition of 1 mM $CuSO_4$ for 3-5 days. The yields of purified protein were 2-5 mg per liter of medium.

For immuno-affinity purification a column was used containing Sepharose 4B coupled with L243 (anti-DRalpha) antibody. Soluble "empty" DRs were eluted with 50 mM glycine/HCl buffer pH 11.5 and the eluate was immediately brought to pH 8.0 by addition of 2 M Tris HCl pH 6.8. For peptide loading soluble "empty" molecules were brought to pH 5.5 (DR1 and DR4) or pH 6.0 (DR52b) by addition of 100 mM citric acid and incubated with a peptide of interest (1-5 µM final concentration) for 24 h at 28° C. (DR52b) or 37° C. (DR1, DR4) in the presence of 0.2% octyl 3-D-glucopyranoside (SIGMA-ALDRICH™), protease and phosphatase inhibitor cocktails (Roche). In some cases peptide loaded DR molecules were biotinylated with recombinant BirA biotin transferase (Avidity) according to the supplier's recommendations. Complexes were purified by GFC on a SUPERDEX® S200 column. (GE Healthcare Life Sciences). In the case of MHC II-peptide complexes containing His tagged peptides (e.g. DR4 peptide-NPβA-SGSGHHHHHH, SEQ ID NO: 306), samples were passes through a HisTrap HP column (GE Healthcare Life Sciences), which after washing was eluted with 200 mM imidazole, which subsequently was removed by GFC in PBS on a SUPERDEX® S200 column (GE Healthcare Life Sciences) or by ultrafiltration. In the case of complexes containing Cy5.5 or pY-D4 tagged peptides samples were dialyzed in 5 mM Tris-HCl pH 9.0, 50 mM NaCl and loaded on a Mono Q 5/50 GL column (GE Healthcare Life Sciences), which was eluted with a NaCl gradient rising win 30 min from 0 to 0.5 M NaCl on 20 mM Tris, pH 9.0 at a flow rate of 1 ml and collecting Purified MHC II-peptide complexes were concentrated on an Amicon Ultra-4 filter concentrator, 10,000 MWCO (EMD MILLIPORE™) to 1-2 mg/ml as assessed by the Bradford protein assay (BIO-RAD®). Degree of biotinylation and purity were assessed by the avidin shift assay and was routinely >90%. Briefly, two different amounts of biotinylated concentrated complexes (typically 2 and 5 µg) are mixed or not with 10 µg of avidin (PIERCE™) and run on 12% SDS-PAGE (non-boiling, non-reducing). After staining in GELCODE® (protein gel stain reagent) blue (PIERCE™, gels are scanned and quantified using the IMAGEQUANT® TL software (GE Healthcare Life Sciences).

ELISA Assays

For monitoring of Cy5.5 tagged peptides 10 µl aliquots of fractions were supplemented (10×) with blocking buffer (PBS, 1% BSA, 0.5% Tween 20) and loaded in 1:2 serial dilutions (100 µl/well) in blocking buffer into two wells of 96 well plates (NUNC MAXISORP®), one of which was coated with anti-DR antibody L243, and the other with anti-Cy5.5 antibody (SIGMA-ALDRICH™). After washing bound complexes were revealed with a biotinylated anti-BSP antibody (a gift from Dr. Gennaro DiLibero, Basel University Hospital) and a secondary antibody conjugated with streptavidin-alkaline phosphatase (SIGMA-ALDRICH™). The plates were developed with p-nitrophenyl-phosphate (pNPP; SIGMAFAST™) substrate (SIGMA-ALDRICH™) and absorbance read at 405 nm on an ELISA plate reader. The concentration of $His_6$ (SEQ ID NO: 310) tag was assessed likewise, i.e. biotinylated MHC II-peptide complexes were trapped on streptavidin-coated plates (NUNC MAXISORP®) and His tag detected by means of Ni-NTA alkaline phosphatase (His-Detector, KPL).

Peptide Competition Assay

For each test peptide eight wells of a 96-well plate (NUNC MAXISORP®) were filled with 50 ul a citrate saline buffer (50 mM citrate, 200 mM NaCl, pH 5.5) containing 1 µg recombinant empty DR1 protein (1 µg), 0.2% octyl-glucoside, complete protease inhibitors (Roche) and 0.2 µM biotin-$HA_{306-318}$ peptide. Competitor peptides were added to final concentrations of 1000, 300, 100, 10, 3, 1, 0.3 and 0.1 µM. After overnight incubation at 37° C. the samples were diluted 4-fold with PBS supplemented with 0.1% BSA and 0.05% Tween 20 and 100 µl applied into 96 well plates previously coated with L243 antibody (2 µg/ml); after 1 h of incubation at room temperature the plates were washed, incubated with streptavidin-alkaline phosphatase (SIGMA-ALDRICH™) (1:10,000); after 1 h the plates were washed and developed with pNPP SIGMAFAST™ substrate (SIGMA-ALDRICH™) and absorbance read at 405 nm.

Cells Under Study

DR4-restricted, $HA_{306-318}$-specific CD4+ T cell clones were obtained by limiting dilution cloning of a DR4 $HA_{306-318}$ multimer-sorted population of a CD4+ T cell line generated from PBMC of a healthy donor (HD137) that was propagated by stimulation with 2 M $HA_{306-318}$ peptide and 7-irradiated CD4⁻ PBMC in RPMI-1640, 10% human serum AB, supplemented with 100 U/ml of hIL-2. The clones were propagated by phyto-hemagglutinin (PHA) (Oxoid) stimulations every 2-3 weeks. DR1-restricted, ESO-specific CD4+ T cell lines were derived and maintained as described previously (3). ESO-specific CD4+ cells from A2/DR1 mice were obtained as follows: groups of mice (n=4-5) were immunized by injections (s.c. at the base of the tail) of 50 µl of emulsion containing the indicated peptides (50 µg of peptide emulsified in 50 µl PBS and 50 µl complete Freund's adjuvant (DIFCO); 7-8 days later the draining lymph nodes were removed and homogenized by passing through a cell strainer (BD Falcon) to obtain single cell suspensions for further analysis.

Tetramers and Staining

Biotinylated DR-peptide complexes were multimerized by mixing with small aliquots of streptavidin-PE (INVITROGEN™) up to the calculated 4:1 stoichiometric equivalent. Cells were stained in 50 µl of FACS buffer (PBS, 0.5% BSA, 2 mM EDTA, 0.05% sodium azide) for 1 hour at 37° C. In the case of neuraminidase treatment, cells were incubated with 0.03 U/ml of neuraminidase from *V. cholerae* (Roche) in complete medium and washed twice prior to tetramer staining. In some experiments fluorescent antibodies (e.g. anti-CD4) were added after multimer staining and incubated at 0-4° C. for 15 min. After 2 washes the cells were suspended in 300 µl buffer and analyzed by flow cytometry on a FACSCalibur (BD). Propidium iodide (INVITROGEN™) was added just before acquisition for exclusion of dead cells. Human cells were fixed in 2% formaldehyde (POLYSCIENCES™) in FACS buffer analysis. Data analysis was performed with FLOWJO® 7.6 software (TreeStar).

Preparation and Evaluation of Immunopure Biotin-Streptavidin Multimers

Figure 20:
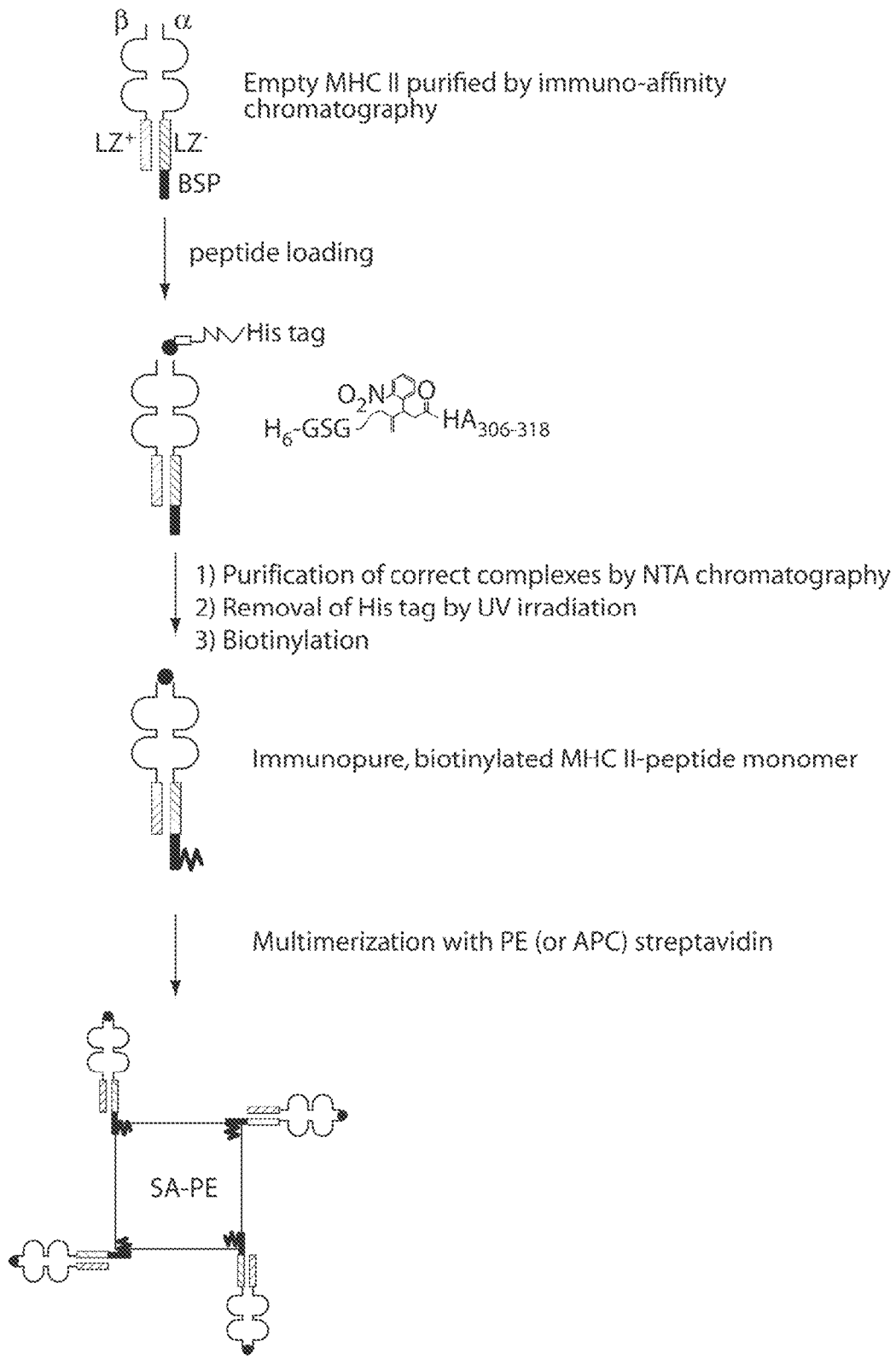
FIG. 20. Preparation of immunopure biotin-streptavidin multimers. Empty soluble MHC II molecules containing C-terminal leucine zippers are purified from supernatants by immuno-affinity chromatography and loaded with a peptide conjugated with His₆ (SEQ ID NO: 310) tag via a photocleavable linker. The complexes containing this peptide are isolated by affinity chromatography on a Ni²⁺-NTA, thereafter the tag is removed by photolysis. The resulting immunopure MHC II peptide monomers are enzymatically biotinylated and multimerized with PE streptavidin. H₆-GSG-NPβA-HA₃₀₆₋₃₁₈ corresponds to SEQ ID NO: 313).
Figure 21A:
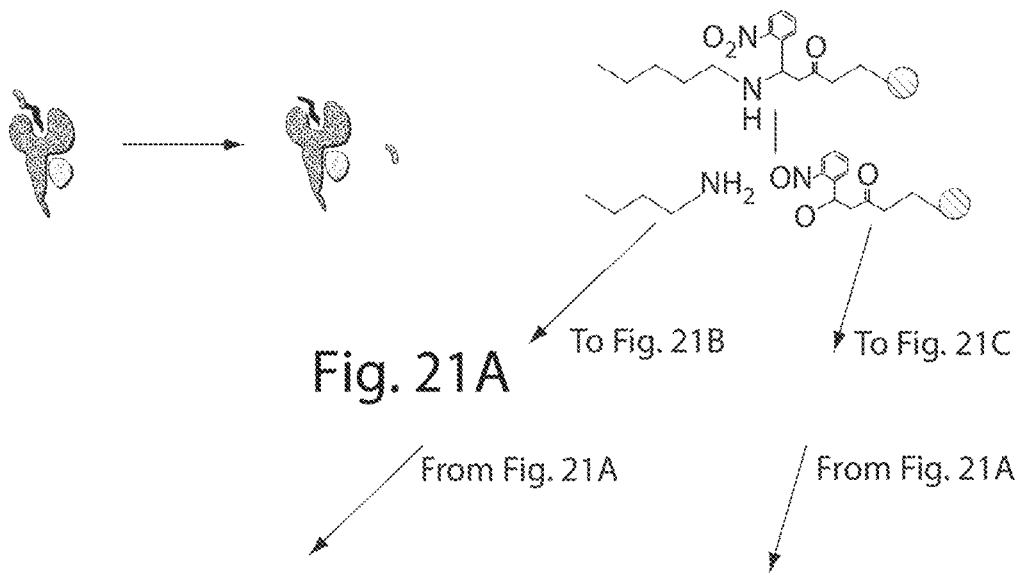
FIGS. 21A to 21C. Photochemical removal of tags from MHC II binding peptides.
Figure 21B:
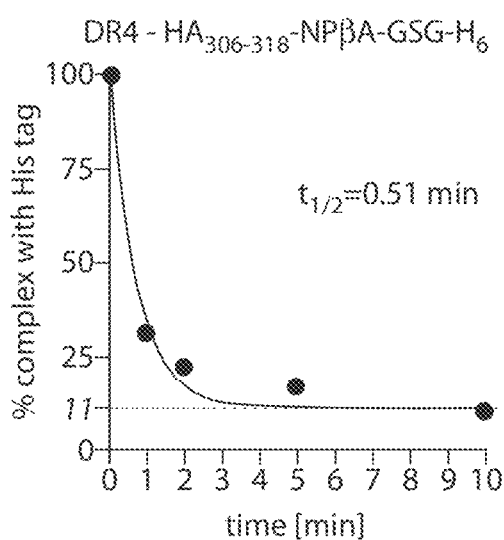
Figure 21C:
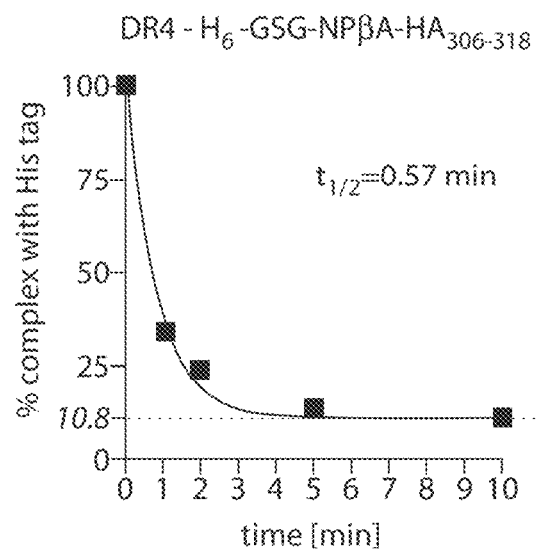
Figure 22A:
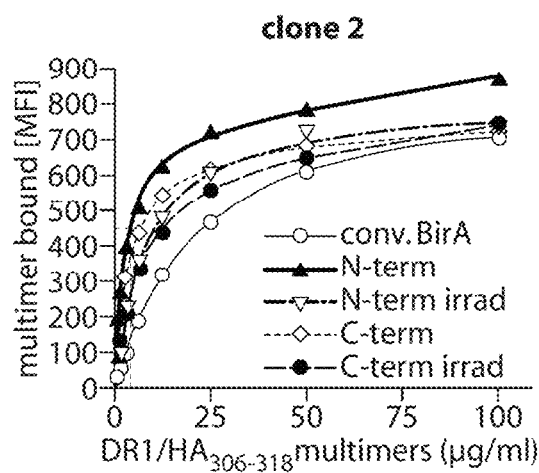
Figure 22B:
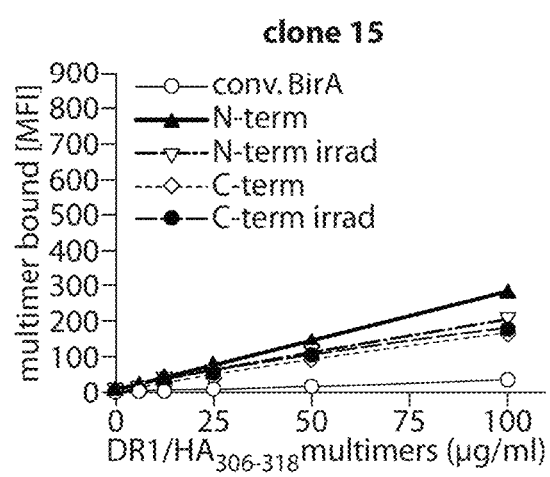
Figure 22C:
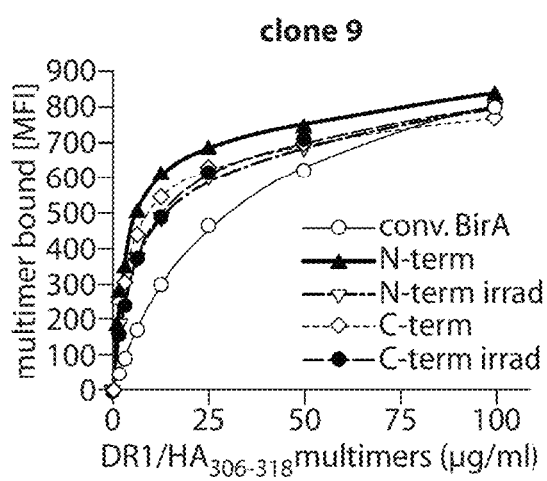
Figure 22D:
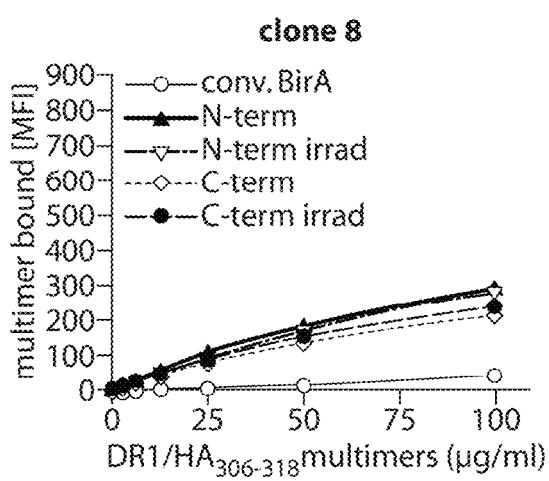

In order to produce immunopure MHC II-peptide complexes, we used a $His_6$ (SEQ ID NO: 310) tag linked via a short flexible GSG linker ($H_6$-GSG-, SEQ ID NO: 313) to the N-terminus of the peptide of interest, which allowed isolation of pure complexes by affinity chromatography on $Nia'^0$ NTA columns (2, 3). Although in these studies the added $His_6$ (SEQ ID NO: 310) tag had only modest effects on T cell recognition and/or MHC binding, this may not be the case in other applications. In order to avoid this, we introduced 3-(2-nitrophenyl)-β-alanine (NPβA) between the $H_6$-GSG (SEQ ID NO: 313) moiety and the peptide of interest (FIG. 20). This tag (H6-GSG-NpβA, SEQ ID NO: 313) can be added N- or C-terminally to the peptide of interest (FIG. 21). Upon UV irradiation at 365 nm the NPβA residue is cleft, resulting in the removal of the His tag after its use for affinity purification of MHC II-peptide complexes (FIG. 21A). NPβA has been used for the preparation of conditional MHC I-peptide ligands and its usefulness is well documented (11, 12). As shown for immunopure DR4/$HA_{306-318}$ complexes carrying the His tag either N-terminally ($His_6$-GSG-NPβA-$HA_{306-318}$, SEQ ID NO: 313 or C-terminally ($HA_{306-318}$ NPβA-GSG-$H_6$, SEQ ID NO: 317) the tag is cleft rapidly upon UV irradiation at 365+/−40 nm, with 50% cleavage achieved after 0.51 and 0.57 min, respectively (FIGS. 21B, C). It should be noted that this cleavage is only about 90% complete; higher cleavage yields can be achieved by using two NPβA groups (12).

When the His tag is added C-terminally at the peptide, it emerges after photo-cleavage as an amide, i.e. its C-terminal carboxyl group is an amide (FIG. 21A). Conversely when the tag is added N-terminally the peptide carries after photolysis an N-terminal 2-nitroso-phenacetyl-β-acetoyl moiety (FIG. 21A). To compare the staining of immunopure DR4-HA tetramer prepared by using either the N- or C-terminal His tag with and without photo-cleavage, we performed 37° C. binding isotherms on four DR4-restricted, HA-specific Th1 clones. On all four clones the binding of immunopure multimers was considerably more avid as compared to the conventional DR4/HA multimer (FIGS. 22A-D). The differences were particularly striking on the low affinity clones 15 and 8. The multimer containing the N-terminally tagged HA peptide ($His_6$-GSG-NPβA-$HA_{306-318}$, SEQ ID NO: 313) exhibited the most efficient binding on all clones tested. After photolytic removal of the His tag the staining efficiency decreased on clone 2, less on clones 9 and 15, but remained unchanged on clone 8. Conversely, multimers containing the C-terminally tagged HA peptide ($HA_{306-318}$-NPβA-GSG-$H_6$, SEQ ID NO: 317) exhibited modestly increased (clone 2) or the same binding (clones 8, 9, 15) compared to the multimers in which the tag was removed by photolysis. Importantly, after UV irradiation mediated removal of the tag both multimers (i.e. those carrying $His_6$-GSG-NPβA-$HA_{306-318}$ (SEQ ID NO: 313) and $HA_{306-318}$ NPβA-GSG-$H_6$, SEQ ID NO: 317) stained all four clones very similar, arguing that the small modifications of the peptide by the photo-cleavage little affect multimer staining (FIGS. 21A, 22A-D).

Figure 27A:
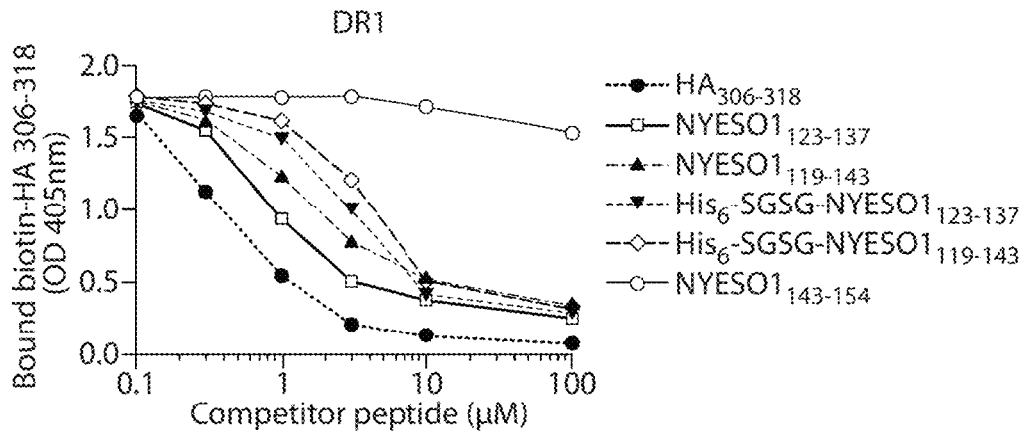
FIG. 27A to 27C. Effect of His tags on peptide binding to DR1, DR4 and DR52b. The binding of the indicated NY-ESO-1 peptides carrying a N-terminal His$_6$ (SEQ ID NO: 310) tag or not to DR1 (FIG. 27A), DR4 (FIG. 27B) and DR52b (FIG. 27C) was determined in a competition as described in Materials and Methods. The His$_6$-SGSG-NYESO1 sequences correspond to SEQ ID NO: 315.
Figure 27B:
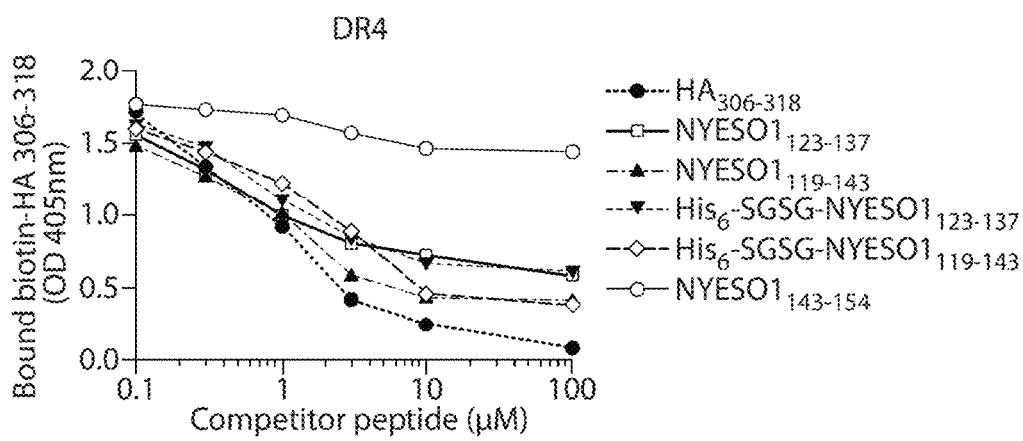
Figure 27C:
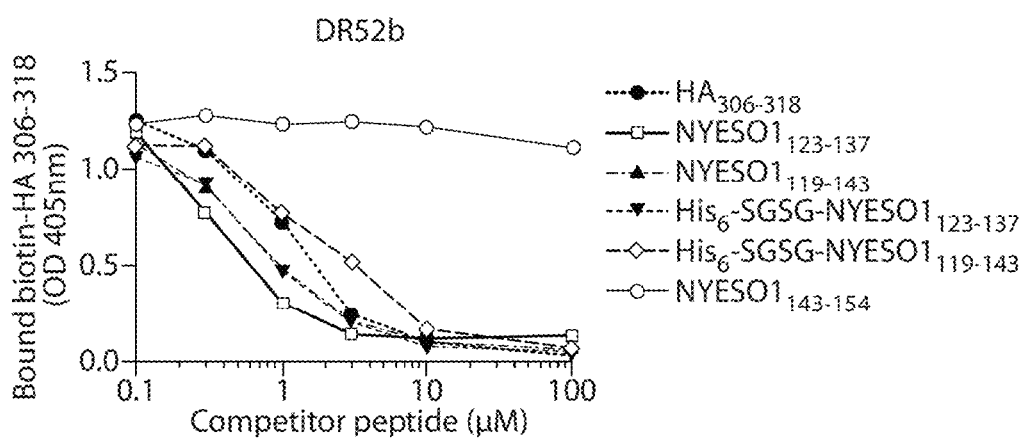

Taken collectively these results demonstrate that purification of correctly loaded MHC II-peptide monomers very significantly increases multimer binding. As we have shown previously this is critical for the detection of antigen-specific CD4+ T cells directly ex vivo (2, 3). Moreover, our results indicate that the presence of an N-terminal $His_6$ (SEQ ID NO: 310) tag can artificially increase multimer staining (FIG. 22). This is explained, at least in part, by increased peptide binding to the restricting MHC II molecule (FIG. 27 and refs. 2, 3). This we observed for the N-terminally, but not (or barely) for the C-terminally His tagged peptide (FIG. 22). This observation is consistent with reports showing that adding tags N-terminal to MJC II binding peptides such as invariant chain derived KEY tags (13, 14) or photoreactive groups (15) can considerably increase their binding. In newly synthesized MHC II molecules the peptide binding site is occupied by the CLIP sequence of the invariant chain (Ii), which on its way to the plasma membrane "clings" to invariant regions, mainly of the β2 domain, situated in front of the N-terminal portion of the peptide binding groove (16). One might argue that thus increased peptide binding could be a means to increase multimer staining. This, however, is risky as this engagement of this invariant region on MHC II proteins may provoke extended conformational changes, which may alter the fidelity of the multimer staining (17). We therefore strongly advocate the use of photo-cleavable tags, which can be removed after purification of correctly loaded MHC II-peptide monomers.

Preparation of Immunopure DR4-$HA_{306-318}$ Monomers Using Cy5.5 Tagged Peptides.

Figure 23A:
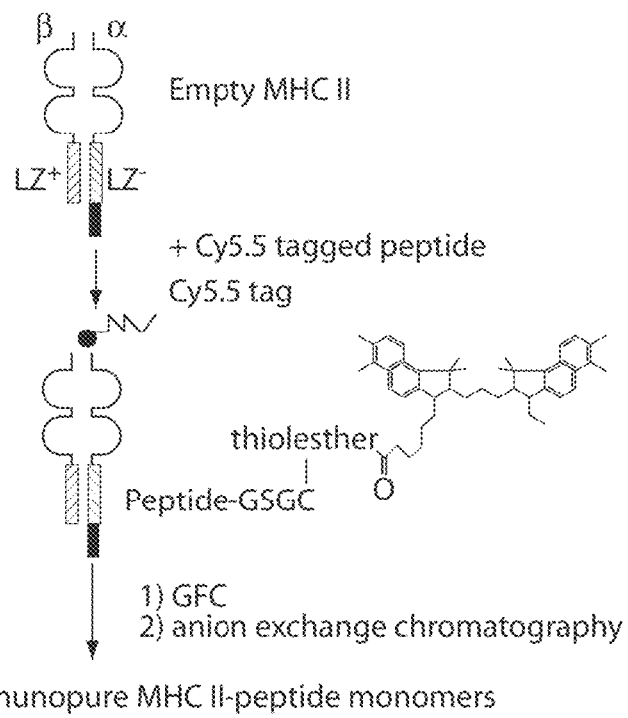
FIGS. 23A to 23D. Preparation of immunopure DR4-HA$_{306-318}$ monomers using Cy5.5. tagged peptides.
Figure 23B:
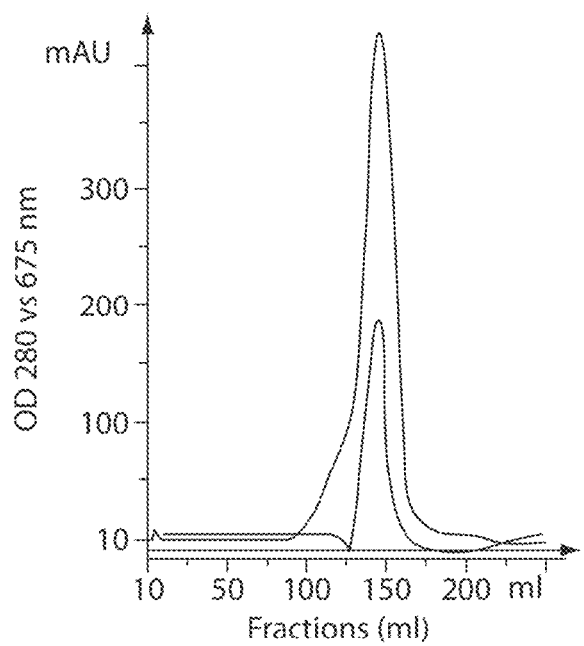

A major shortcoming of conventional MHC II multimer synthesis is that one does not know what fraction of the MHC II molecules have bound the peptide of interest. This fraction can be highly variable, depending on the MHC II molecule, its purification and on the peptide and loading procedures. Because the effective multimer fraction decreases with the fraction of correctly peptide loaded monomers (FIG. 26) a frequent, probably the most frequent failure of poor or undetectable MHC II multimer staining is inadequate peptide loading. In order to able to directly monitor MHC II peptide loading, we used Cy5.5 as tag for labelling antigenic peptides. Cy5.5 (and Cy5) is a blue fluorescent low molecular dye that can be coupled to peptides via amides or thioethers (FIG. 23A, gelifesciences.com). To establish a proof a principle, we loaded DR4 with Cy5.5 labelled $HA_{306-318}$ peptide ($HA_{306-318}$-GSGC-Cy5.5, SEQ ID NO: 307) and analyzed the reaction mixture by GCF on SUPERDEX® S200 column recording the OD of the eluent at 675 nm (Cy5.5) and 280 nm (protein) (FIG. 23B). From the integrated peak surfaces and the molar extinction coefficients, the ratio of Cy5.5 (i.e. peptide) and protein (i.e. DR4) was calculated to be 0.42, i.e. 42% of the input DR4 molecules had bound the blue peptide. Analogous experiments were performed with DR52b and Cy5.5 labelled NY-ESO-1 peptide$_{123-137}$, in which case peptide loading was remarkably poor (<10%) and no significant staining was observed with the corresponding multimers (data not shown and ref. 2).

Figure 23C:
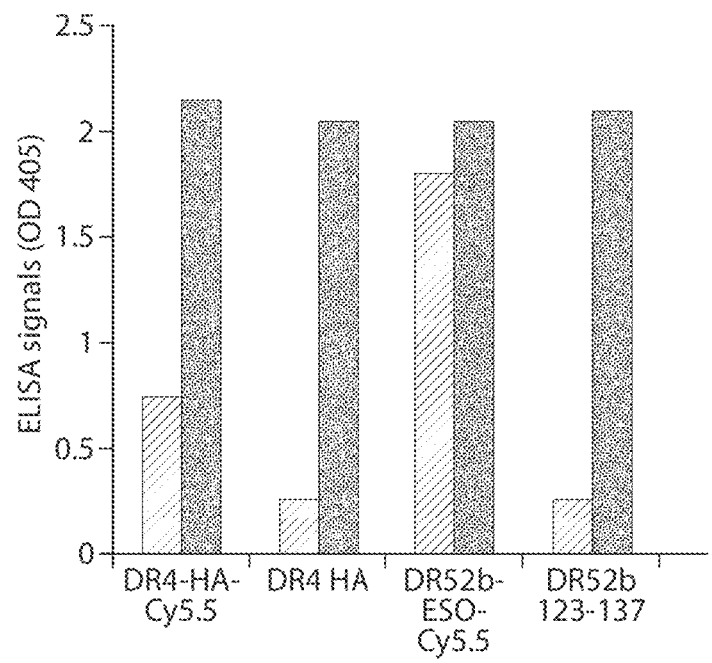
Figure 23D:
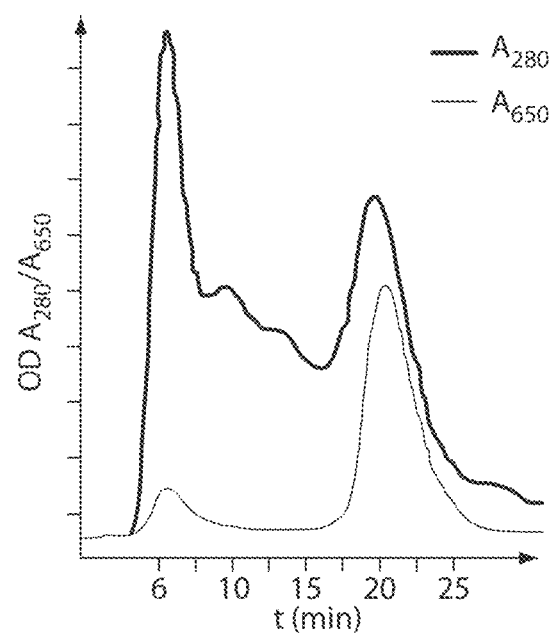

As for $His_6$ (SEQ ID NO: 310) tagged peptides, the content of Cy5.5 (or Cy5) labelled peptide in MC II-peptide complexes can also be detected by ELISA, using Cy dye specific antibodies (FIG. 23C). Moreover and importantly Cy5.5 contains four negatively charged sulfonyl groups (S03-), i.e. is strongly acidic. This allows quantitative separation of the Cy5.5-peptide loaded DR4 molecules from other DR4 molecules by anion exchange chromatography (FIG. 23D). Although this method allows direct assessment of peptide loading efficiency and isolation of immunopure MHC II-peptide complexes, it has disadvantages, such as i) the synthesis of Cy5.5 labelled peptides is expensive and tedious and ii) the removal of Cy5.5 by photolysis by means of a NPβA linker is not feasible due to quenching.

Preparation of Immunopure MHC II-Peptide NTA Multimers Using the pY-D4-Tag

Figure 24:
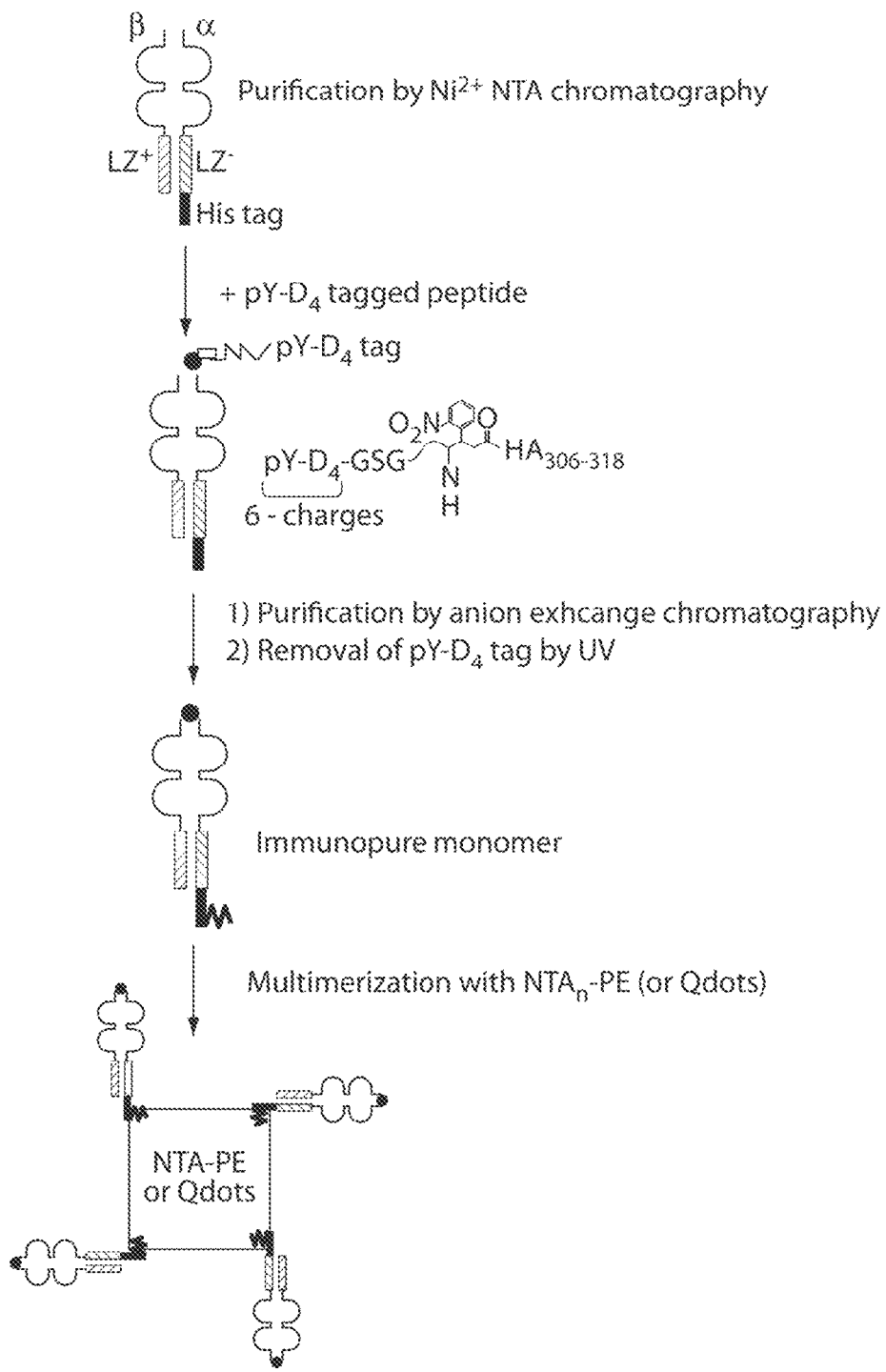
FIG. 24. Preparation of immunopure MHC II-peptide NTA multimers using the pY-D4-tag. Empty MHC II molecules containing a C-terminal His tag at the acidic leucine zipper are purified by affinity chromatography on NTA columns and loaded with given peptides (e.g. HA$_{306-318}$) containing the strongly negatively charged phospho-tyrosine-Asp$_4$ (pY-D$_4$) tag. The peptide loading is monitored by ELISA using anti-pY mAb. Immunopure monomers are obtained by anion exchange chromatography, from which the pY-D4 tag is removed by UV irradiation and NTA multimers upon reaction with NTA-PE or NTA quantum dots (QDOTs®). The sequence corresponds to a 2×His$_6$ (SEQ ID NO: 312) tag.

Isolation of "empty" MHC II molecules from culture supernatants by immuno-affinity chromatography is not only costly and often inefficient, but is a major cause for extensive protein denaturation. In order to obtain efficient MHC protein recovery, high affinity antibodies are used, which for elution require the use of extreme pH (e.g. 11.5) at which empty MHC II molecules start to denature. To circumvent this we added at the DRA chain C-terminal of the leucine zipper a His tag, which allows gently and universal purification of empty MHC II molecules by affinity chromatography on commercially available $Ni^{2+}$ NTA columns (FIG. 24). This necessitated the use of another tag to be used for the purification of correctly peptide loaded MHC II-peptide complexes. Encouraged by the finding that a negatively charged tag allows purification of correctly loaded MHC complexes, we searched for a related strategy, namely for a negatively charged tag that can be readily synthesized and then be removed by photolysis. As new tag we used phospho-tyrosine-Asp4 (pY-D4), which can be detected by anti-pY antibodies in ELISA and having six negative charges is expected to allow separation of loaded MHC II molecules by anion exchange chromatography (FIG. 24). Moreover and importantly, after peptide loading, purification of correctly peptide loaded complexes and removal of the pY-D4 tag by photolysis, the His tag can be used again to directly form fluorescent staining reagents by reaction with $NTA_n$-PE or $NTA_n$-QDOTs® (as described for MHC I-peptide complexes in the first technical report).

Figure 25A:
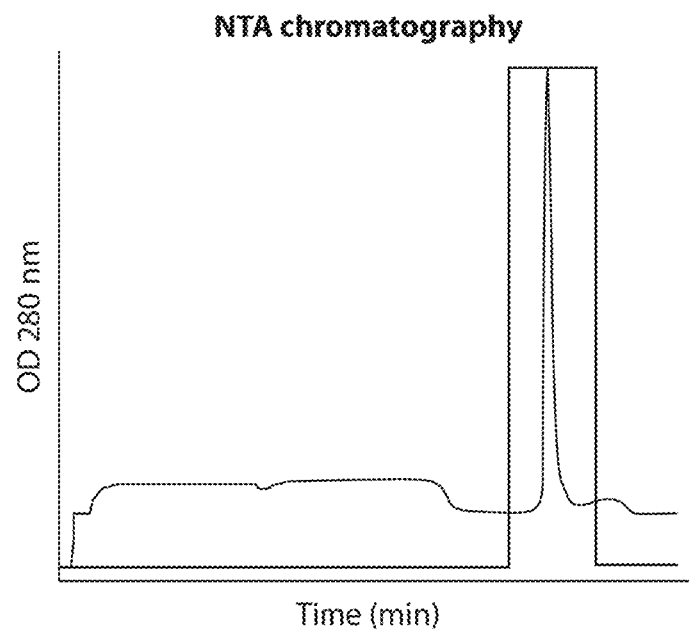
FIGS. 25A to 25D. Preparation and testing of immunopure DR4/HA$_{306-318}$ NTA multimers.
Figure 25B:
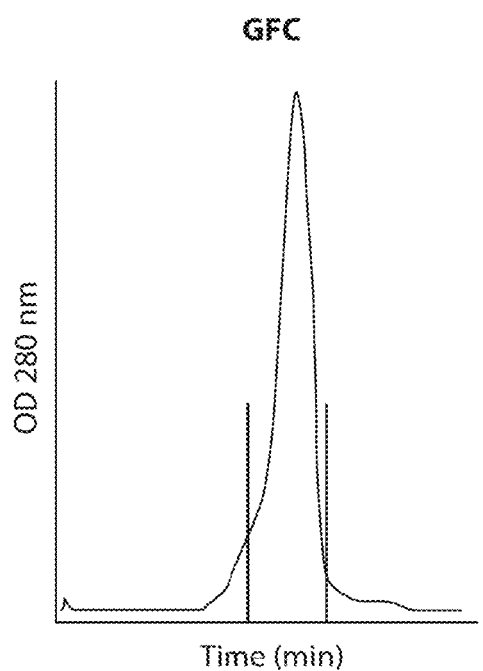
Figure 25C:
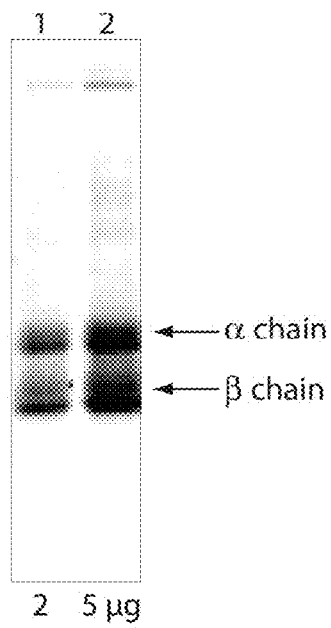
Figure 25D:
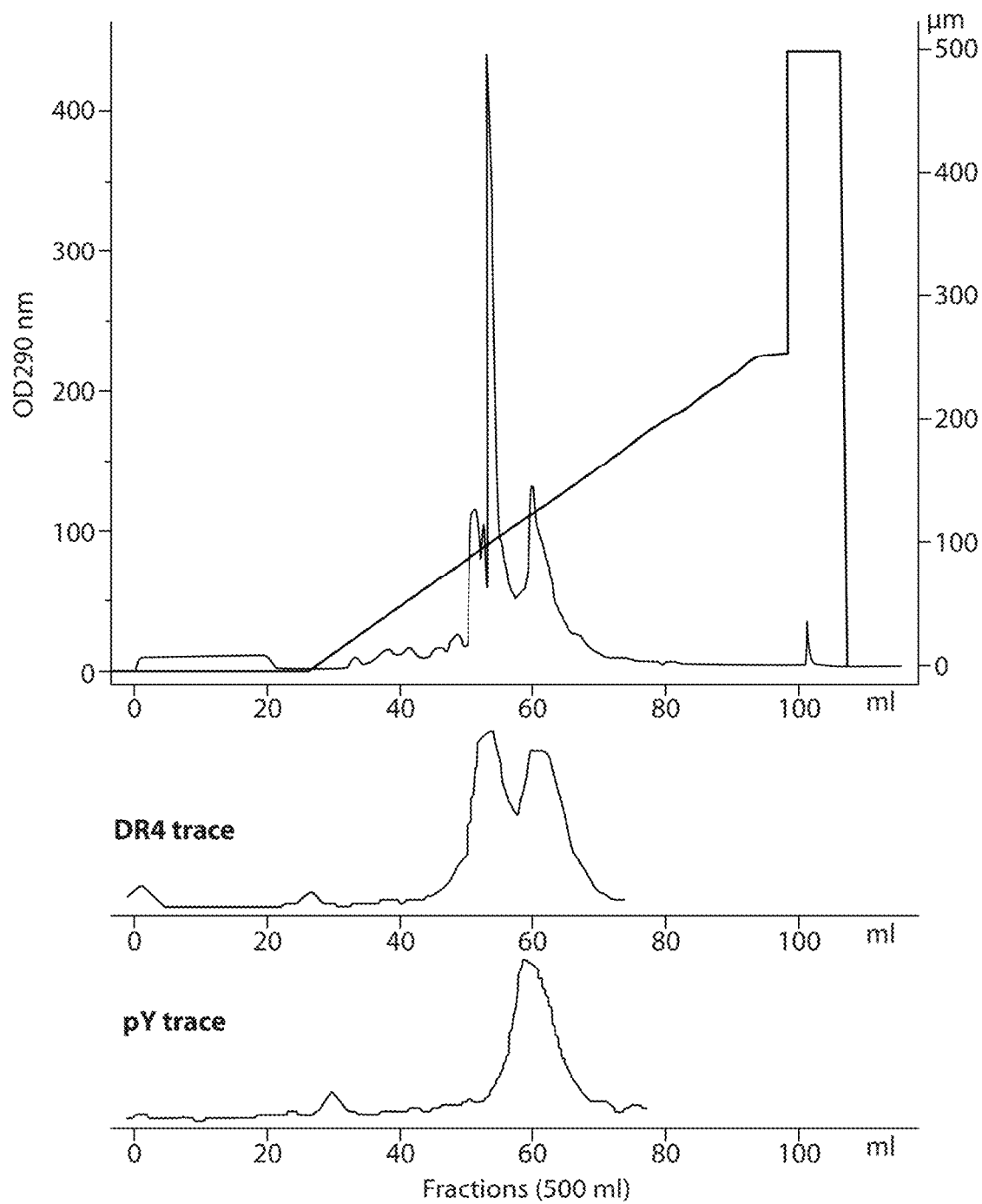

To validate the feasibility of this strategy, we passed a supernatant from S2 cells secreting soluble $His_6$ (SEQ ID NO: 310) tagged DR4 over a $Ni^{2+}$-NTA column. After washing the column, it was eluted with 200 mM imidazole, whereby DR4 eluted in a sharp peak, which according to GFC on a SUPERDEX® S200 column and SDS-PAGE was pure (FIGS. 25A-C). This material was then loaded with pY-D4-GSG-NPβA-$HA_{306-318}$ (SEQ ID NO: 318) peptide and subjected to anion exchange chromatography on MONO-Q™ column, which was eluted with the indicated NaCl gradient and on the OD of the eluate was monitored at 280 nm and the content of DR4 and pY, respectively, of the fractions determined by ELISA (FIG. 25D). This analysis showed that DR4 containing the acidic pY-D4-GSG-NPβA-$HA_{306-318}$ (SEQ ID NO: 318) peptide eluted after DR4 molecules carrying no or different peptides, similarly as observed for the Cy5.5 tagged HA peptide (FIG. 23D). Because phospho-tyrosine a priori is susceptible to enzymatic de-phosphorylation (although with complete phosphates inhibitors, e.g. from Roche, this can be prevented) we also tested para-sulfate-tyrosine (e.g. $Y(SO_4)$-$D_4$) as tag, but observed lesser shifts of the acidic peptide containing DR4 complexes (data not shown). In order to further to extend and optimize the separation of correctly loaded MHC II-peptide complexes we have evaluated variations in the conditions of the anion exchange chromatography (e.g. different buffers and NaCl gradients) as well other acidic tags (pY-$E_{4-8}$) as well as other MHC II molecules (e.g. DR1 and DR52b) and other peptides (e.g. NY-ESO-$1_{123-137}$). From these experiments it is apparent that correctly loaded MHC II peptide complexes can be separated from other MHC II molecules by anion exchange chromatography; however for general usage the best suitable acidic tags and chromatography conditions may differ somewhat from those described here.

Figure 28A:
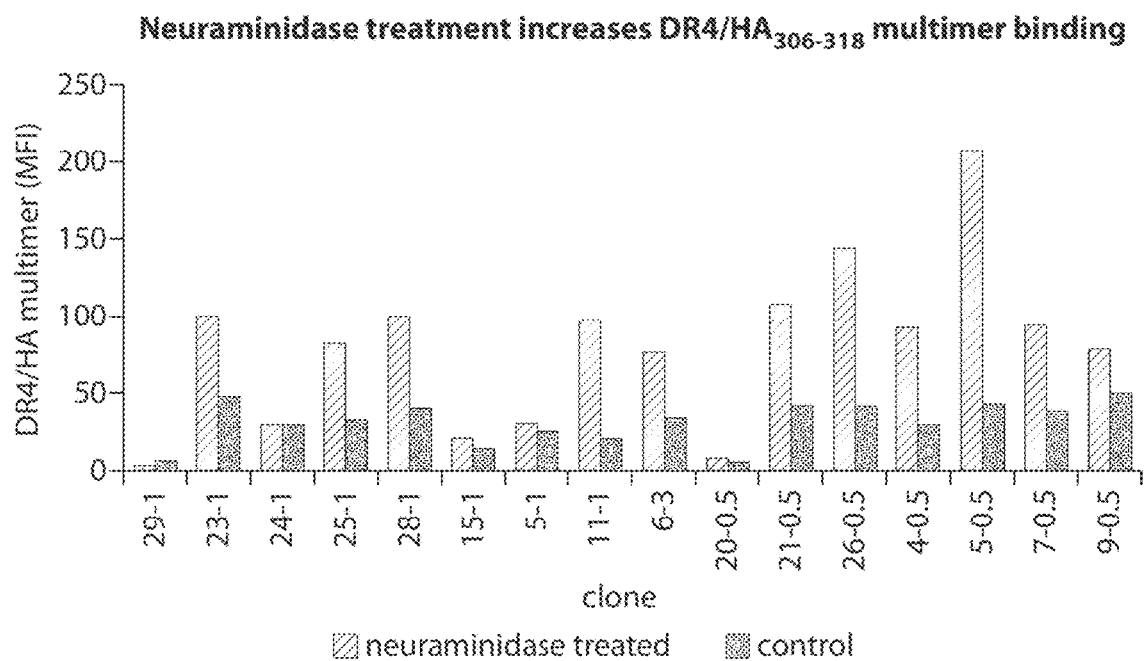
FIGS. 28A to 28B. Neuraminidase treatment increases DR4/HA$_{306-318}$ multimer binding.
Figure 28B:
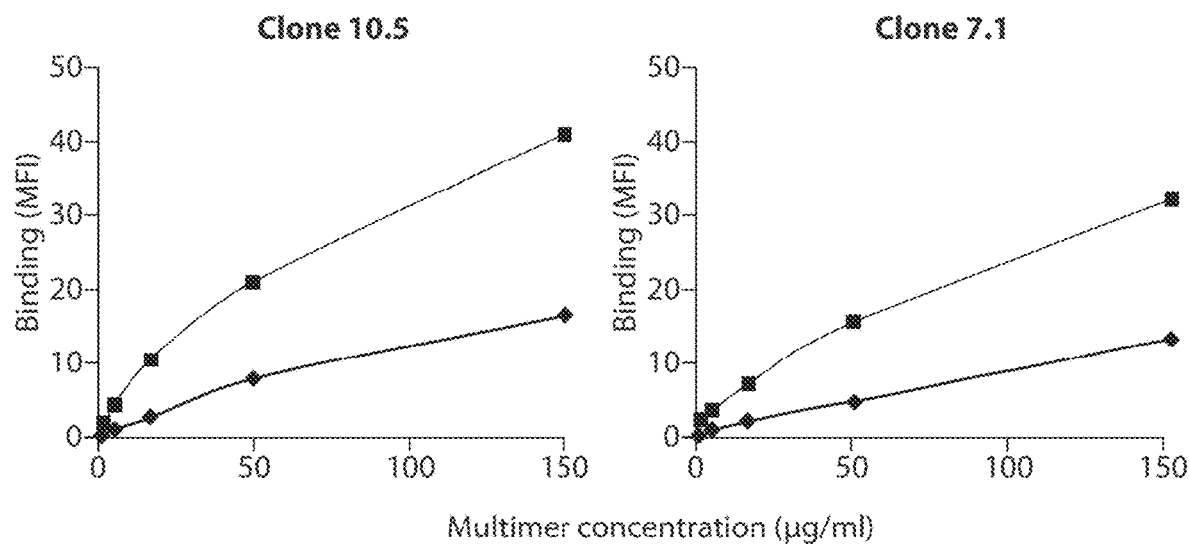

Over a dozen of different reagents were investigated for their ability to increase MHC II multimer staining. It was determined that brief pre-treatment of the cells with neuraminidase increases multimer binding by 2-5-fold. This was observed on a range of DR4-restricted, HA-specific CD4+ T cell clones (FIG. 28) and on populations of HA peptide stimulated PBMC from healthy donors. Because MHC II multimer staining tends to be weak, this observation suggests pre-treatment of the cells with neuraminidase, an enzyme that removes sialic acid residues on cellular surface proteins (18) increases MHC class II multimer staining efficiency.

REFERENCES

1. Guillaume P, Dojcinovic D, Luescher I F. Soluble MHC-peptide complexes: tools for the monitoring of T cell responses in clinical trials and basic research. *Cancer Immun.* 2009; 9:7.
2. Ayyoub M, Dojcinovic D, Pignon P, Raimbaud I, Schmidt J, Luescher I, Valmori D. Monitoring of N Y-ESO-1 specific CD4+ T cells using molecularly defined MHC class II/His-tag-peptide tetramers. *Proc Natl Acad Sci USA.* 2010; 107:7437-42.
3. Maha Ayyoub, Pascale Pignon, Danijel Dojcinovic, Isabelle Raimbaud, Lloyd J. Old, Immanuel Luescher and Danila Valmori 2010. Assessment of vaccine-induced CD4 T cell responses to the 119-143 immunodominant region of the tumor-specific antigen N Y-ESO-1 using DRB1*0101 tetramers. *Clin. Cancer Res.* accepted.
4. Danke N A, Koelle D M, Yee C, Beheray S, Kwok W W. Autoreactive T cells in healthy individuals. *J Immunol.* 2004; 172:5967-72.
5. Cecconi V, Moro M, Del Mare S, Dellabona P, Casorati G. Use of MHC class II tetramers to investigate CD4+ T cell responses: problems and solutions. *Cytometry A.* 2008; 73:1010-8.
6. Cunliffe S L, Wyer J R, Sutton J K, Lucas M, Harcourt G, Klenerman P, McMichael A J, Kelleher A D. Optimization of peptide linker length in production of MHC class II/peptide tetrameric complexes increases yield and stability, and allows identification of antigen-specific CD4+ T cells in peripheral blood mononuclear cells. *Eur J Immunol.* 2002; 32:3366-75.
7. Cameron T O, Cochran J R, Yassine-Diab B, Sékaly R P, Stern L J. Cutting edge: detection of antigen-specific CD4+ T cells by HLA-DR1 oligomers is dependent on the T cell activation state. *J Immunol.* 2001: 166:741-5.
8. Wooldridge L, Lissina A, Cole D K, van den Berg H A, Price D A, Sewell A K. Tricks with tetramers: how to get the most from multimeric peptide-MHC. *Immunology* 2009; 126:147-64.

9. Luescher I F, Vivier E, Layer A, Mahiou J, Godeau F, Malissen B, Romero P. CD8 modulation of T-cell antigen receptor-ligand interactions on living cytotoxic T lymphocytes. *Nature* 1995; 373:353-6.
10. Hampl J, Chien Y H, Davis M M. CD4 augments the response of a T cell to agonist but not to antagonist ligands. *Immunity* 1997; 7:379-85.
11. Toebes M, Coccoris M, Bins A, Rodenko B, Gomez R, Nieuwkoop N J, van de Kasteele W, Rimmelzwaan G F, Haanen J B, Ovaa H, Schumacher T N. Design and use of conditional MHC class I ligands. *Nat Med.* 2006; 12:246-51.
12. Celie P H, Toebes M, Rodenko B, Ovaa H, Perrakis A, Schumacher T N. U V-induced ligand exchange in MHC class I protein crystals. *J Am Chem Soc.* 2009; 131:12298-304.
13. Kallinteris N L, Lu X, Blackwell C E, von Hofe E, Humphreys R E, Xu M. Ii-Key/MHC class II epitope hybrids: a strategy that enhances MHC class II epitope loading to create more potent peptide vaccines. *Expert Opin Biol Ther.* 2006 6:1311-21.
14. Kallinteris N L, Lu X, Wu S, Hu H, Li Y, Gulfo J V, Humphreys R E, Xu M. Ii-Key/MHC class II epitope hybrid peptide vaccines for HIV. *Vaccine.* 2003 21:4128-32.
15. Luescher I F, Allen P M, Unanue E R. Binding of photoreactive lysozyme peptides to murine histocompatibility class II molecules. *Proc Natl Acad Sci USA.* 1988 85:871-4.
16. Jasanoff A, Wagner G, Wiley D C. Structure of a trimeric domain of the MHC class II-associated chaperonin and targeting protein Ii. *EMBO J.* 1998; 17:6812-8.
17. Rötzschke O, Lau J M, Hofstätter M, Falk K, Strominger J L. A pH-sensitive histidine residue as control element for ligand release from HLA-DR molecules. *Proc Natl Acad Sci USA.* 2002; 99:16946-50.
18. Chen X, Varki A. Advances in the biology and chemistry of sialic acids. *ACS Chem Biol.* 2010; 5:163-76.

The entire contents of all of the references (including literature references, issued patents, published patent applications, and co-pending patent applications) cited throughout this application are hereby expressly incorporated by reference for the purposes or subject matter referenced herein. In case of a conflict between a reference incorporated herein and the instant disclosure, the teaching of the instant disclosure shall control.

Example 4

PE-NTA-A2/peptide multimers—a new type of staining reagent based on oxime ligation. To generate PE-NTA multimers, 1 nmol Phycoerythrine (PE) was first reacted in phosphate buffer, pH 7.4, with 20 mM of sulfo-SFB (sulfo-succinimidyl-formylbenzoate) for 4 h at room temperature. The resulting activated-PE was subsequently dialyzed in 2 L PBS over 2 days and then coupled in phosphate buffer (pH 7.2) with a large excess of $H_2N$—O—$NTA_2$ or $H_2N$—O—$NTA_4$ aminooxy-containing peptide. After overnight reaction at 4° C., bioconjugates were loaded with $Ni^{2+}$ and dialyzed in 2 L PBS over 2 days. PE-NO-$NTA_2$ or PE-NO-$NTA_4$ obtained were conjugated with A2/peptide-2×$His_6$ (SEQ ID NO: 312) complexes to generate biotin SA free PE-$NTA_2$ or PE-$NTA_4$ multimers.

Staining is a Function of PE Substitution Degree.

The staining characteristics of the multimers generated via oxime chemistry were investigated. FIG. 29A illustrates a scheme of PE activation with sulfo-SFB and conjugation with $H_2N$—O-$NTA_2$ via oxime ligation. FIG. 29B: PE (1 nM) was activated with the indicated concentrations of sulfo-SFB and conjugated with an excess of NTA peptide. 0.5 μg of PE-NO-$NTA_2$ were mixed with 5 μg of A2/Flu58-66-2×His6 (SEQ ID NO: 312) monomers. Flu matrix 58-66-specific BC74cells were stained with 8 nM of the different conjugates at room temperature for 30 min and analyzed by flow cytometry. SFB: succinimidyl-p-formylbenzoate.

Figure 30A:
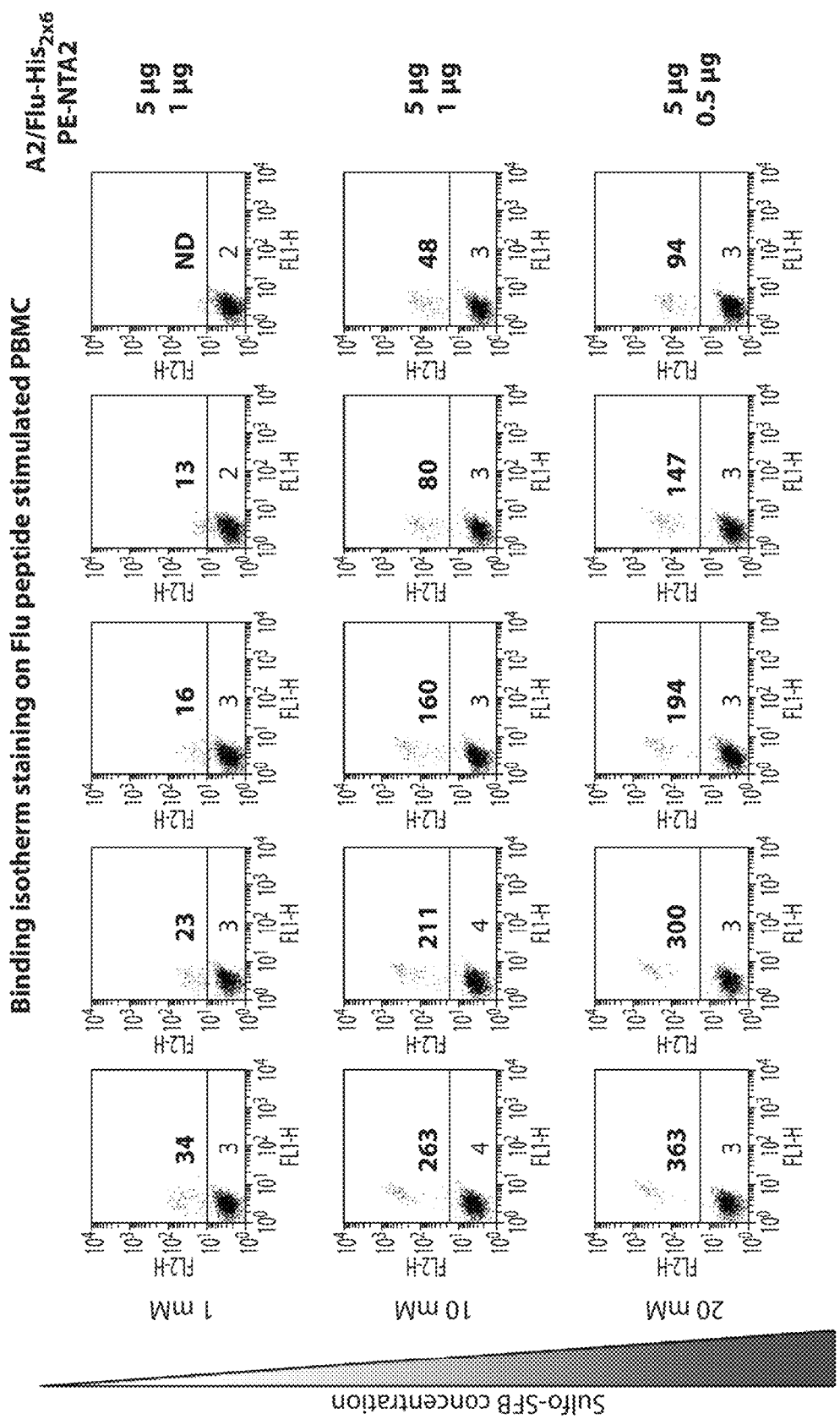
FIGS. 30A to 30B. Staining isotherms on Flu stimulated PBMC with different multimers at different concentrations. The x-axis provides the multimer concentration (in nM). The sequence in FIG. 30A corresponds to a 2×His$_6$ (SEQ ID NO: 312) tag.
Figure 30B:
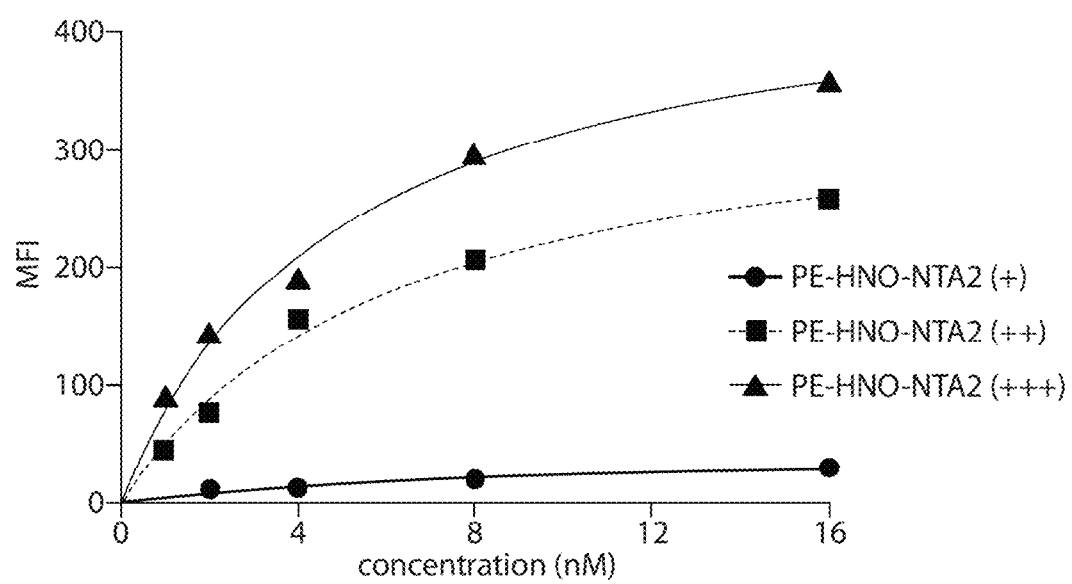

FIG. 30 shows staining isotherms on Flu stimulated PBMC. FIG. 30A: PE activated with 1, 10 or 20 mM sulfo-SFB was coupled to $NTA_2$ peptide via oxime ligation and subsequently mixed with A2/Flu-2×His6 (SEQ ID NO: 312) A2/Flu58-66 monomers. Flu matrix peptide stimulated PBMC were stained with different concentrations of the conjugates and analyzed by flow cytometry. The numbers indicate MFI of specific (above the bar in each graph) and non-specific (below the bar) staining. The right hand numbers indicate the input amounts of monomers (upper number) and PE-NTA2 (lower number). FIG. 30B: Data plotted using GraphPad Prism software.

Figures 1, 31:
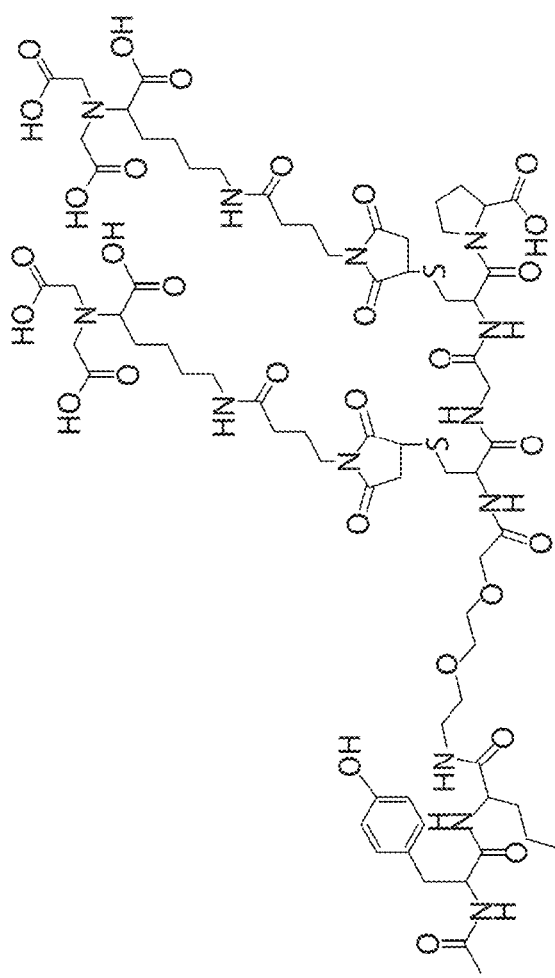
FIG. 31. Exemplary NTA linkers.
Figures 3, 31:
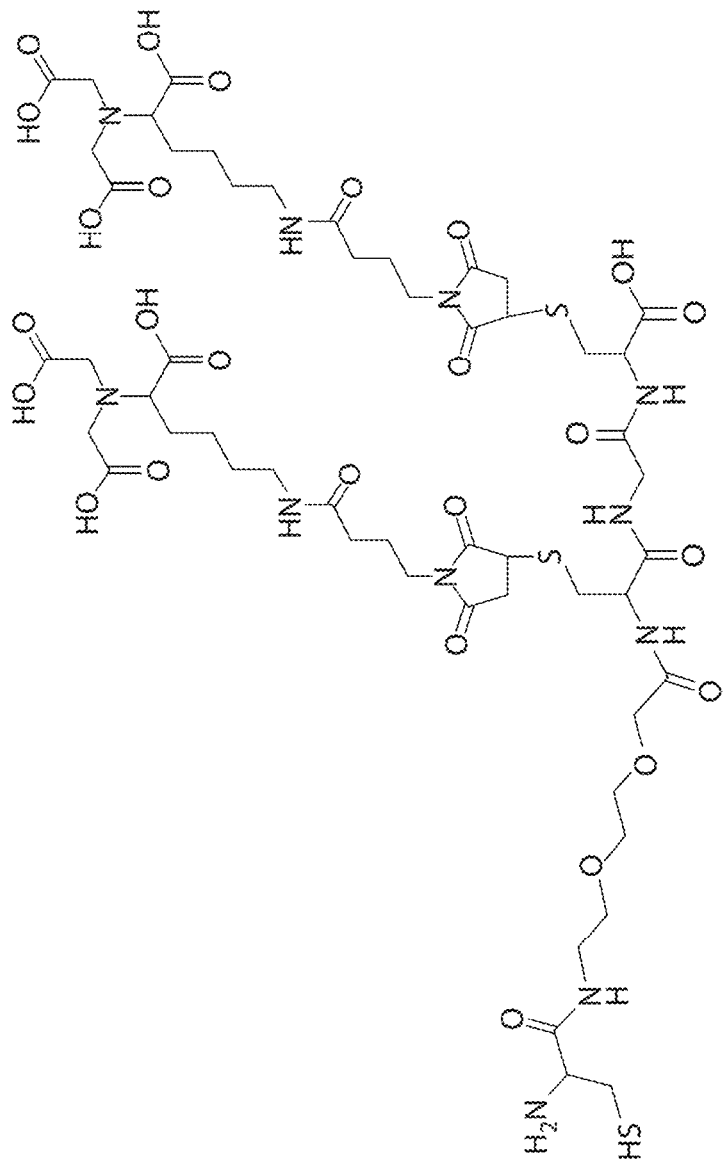
Figures 5, 31:
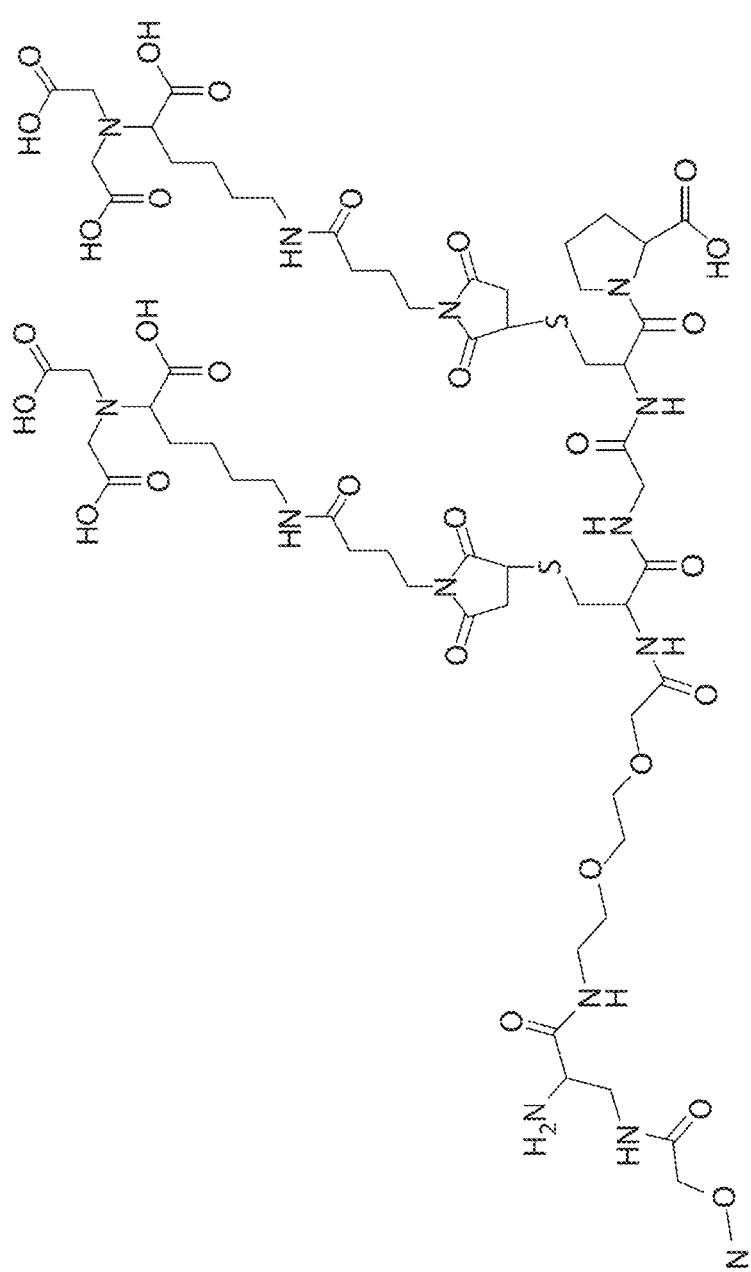
Figures 6, 31:
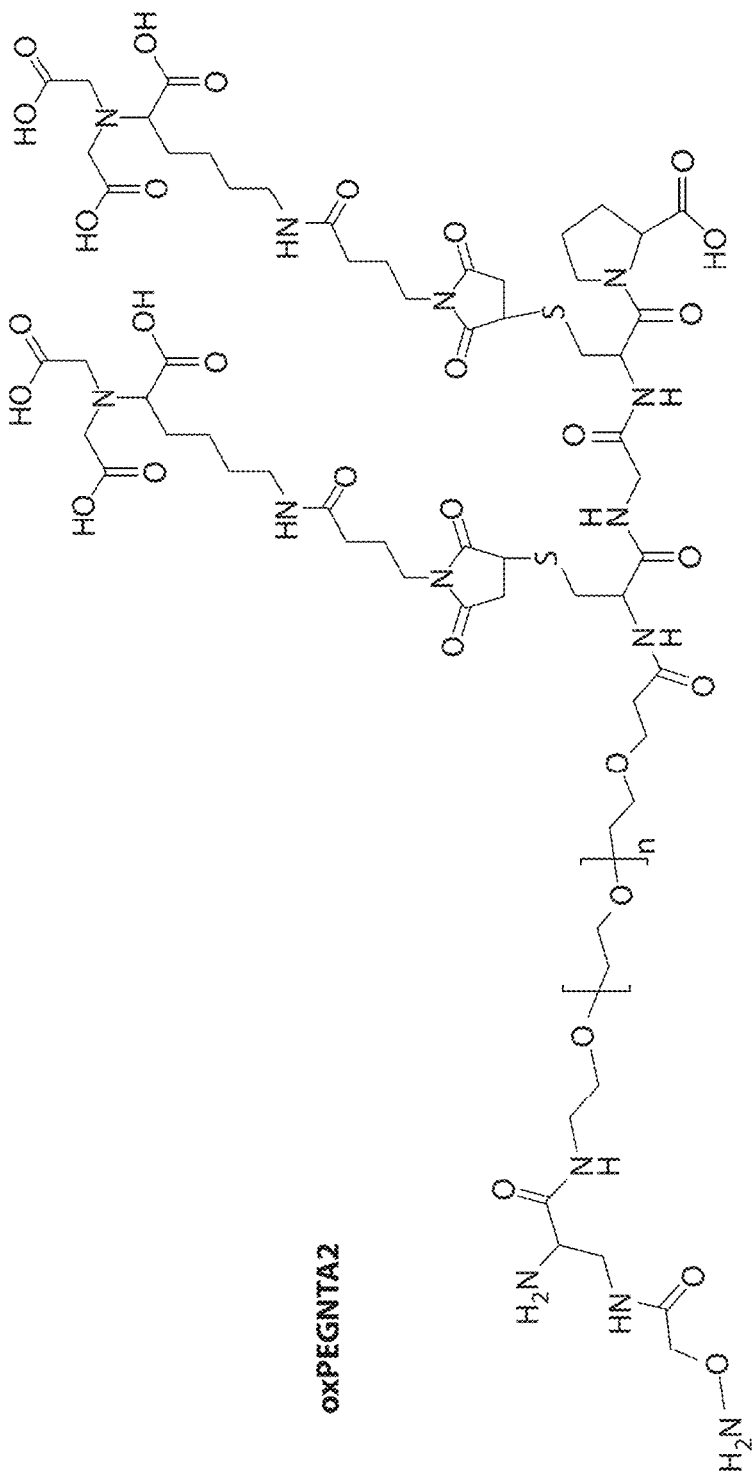
Figures 7, 31:
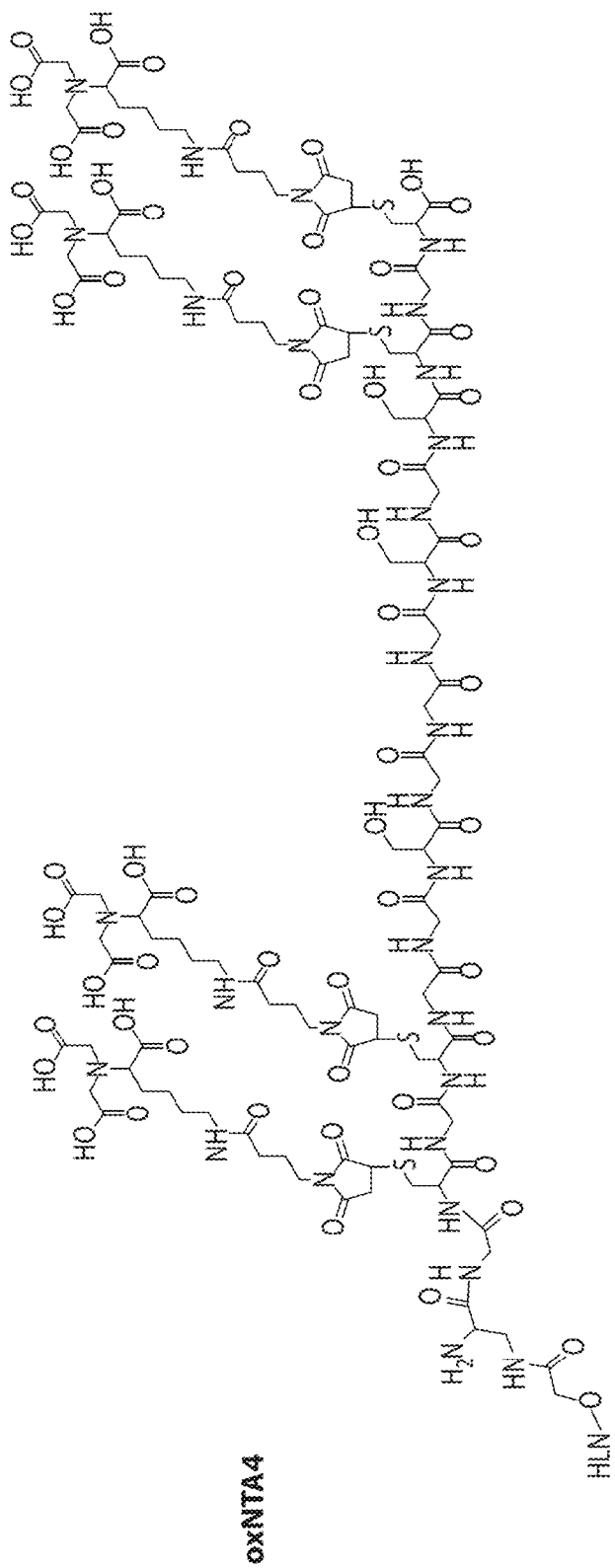

FIG. 31 shows exemplary NTA linkers that were synthesized and tested. The bioNTA4 and oxNTA2 linkers were determined to be of particular interest for the generation of MHC I and MHC II multimers and were used for further testing as described below. The $bioNTA_2$ and $bioNTA_4$ compounds contain biotin-NTA2 or 4, all others contain N terminal Cys(SH)-$PEG_2$ on $NTA_2$ or $NTA_4$ to be used for conjugation with maleimido-PE. The non-biotin compounds contain N-terminal imines and $NTA_2$ linked via a $PEG_2$ Spacer, a $PEG_4$ spacer, or a dipeptide linker (bottom).

Figures 3, 32:
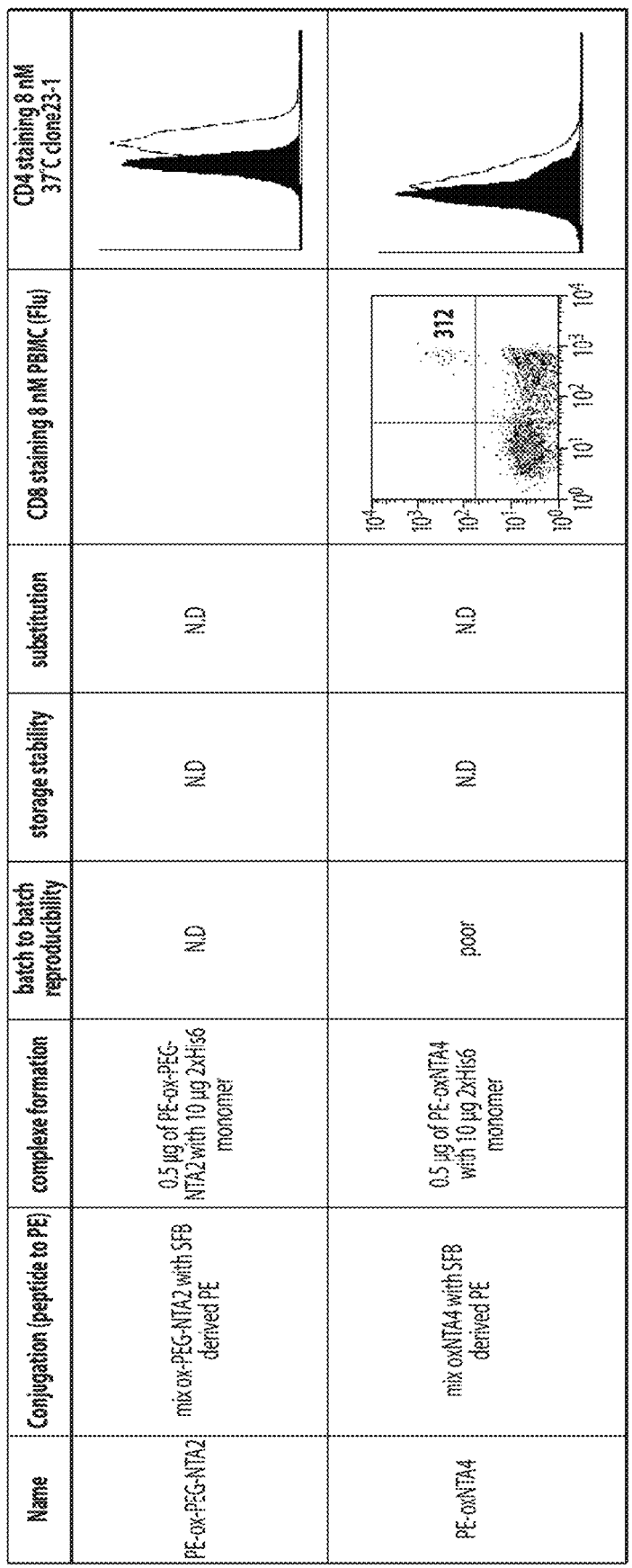
FIG. 32. Staining performance of PE conjugates comprising A2/Flu$_{58-66}$ monomers, or DR4/Flu HA$_{306-318}$ monomers. The sequence corresponds to a 2×His$_6$ (SEQ ID NO: 312) tag.

PE conjugates with these linkers were obtained and the performance of these conjugates was tested. The conjugates comprised either A2/Flu58-66 monomers, which were tested in staining of Flu peptide stimulated PBMC, or comprised DR4/Flu HA306-318 monomers, which were tested in staining of Flu-Specific CD4+ T cells (FIG. 32). From these initial tests, the biotin-NTA4 and SA-PE multimers appear to perform similar to conventional BSP multimers, but result in better stainings of both $CD8^+$ and $CD4^+$ T cells. In addition, the multimers described herein are fully reversible, as explained in more detail elsewhere herein, which allows sorting of antigen-specific T cells without causing activation dependent T cell death. The data presented here indicates that the PEG2-NTA2-comprising PE-NTAmers coupled to PE via oxime bond formation exhibit an improved staining performance as compared to multimers obtained by conjugation via maleimides. This may in par be due to an increased degree of conjugation associated with the use of oxime-chemistry.

Comparison of Conventional, PE-Cys-PEG2-NTA2 and PE-HNO-NTA2 Multimers Staining.

FIG. 33A shows the results of an experiment in which cloned, Flu matrix 58-66-specific $CD8^+$ 81P1 cells were incubated at 20° C. for 30 min with graded concentration of conventional multimers (circles), PE-Cys-$PEG_2$-$NTA_2$ NTAmers (squares), or PE-HNO-$NTA_2$ NTAmers (triangles). Cell-associated PE fluorescence was then assessed by flow cytometry. The binding data of FIG. 33A were subjected to Scatchard analysis (FIG. 33 B), and $K_D$ and $B_{max}$ were calculated from the results of the Scatchard Analysis (FIG. 33C).

Reducing of Background Staining by Milk Supplements.

Figures 1, 34:
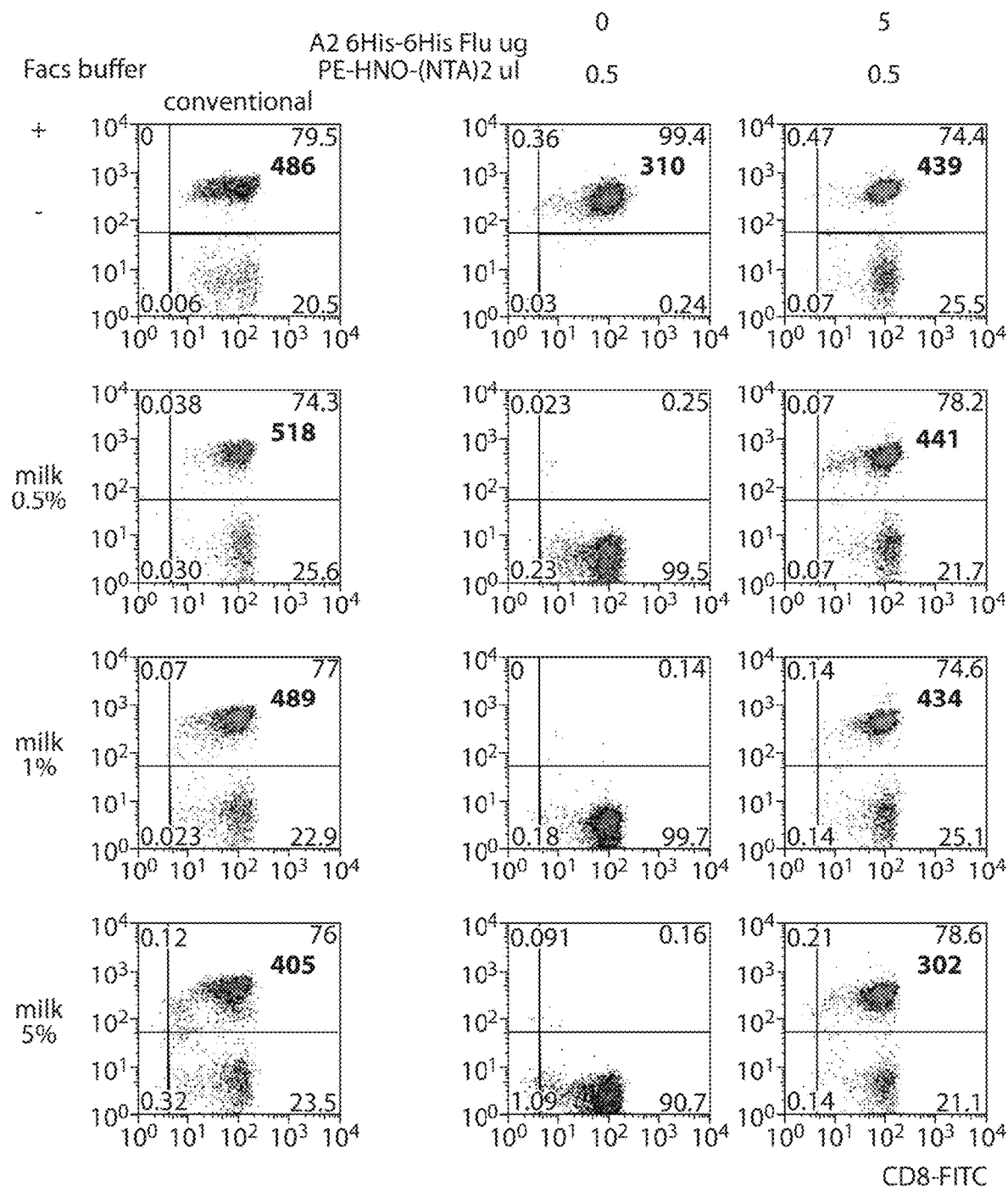
FIG. 34. Reduction of background staining by milk supplements. The sequence corresponds to a 2×His$_6$ (SEQ ID NO: 312) tag.
Figures 2, 34:
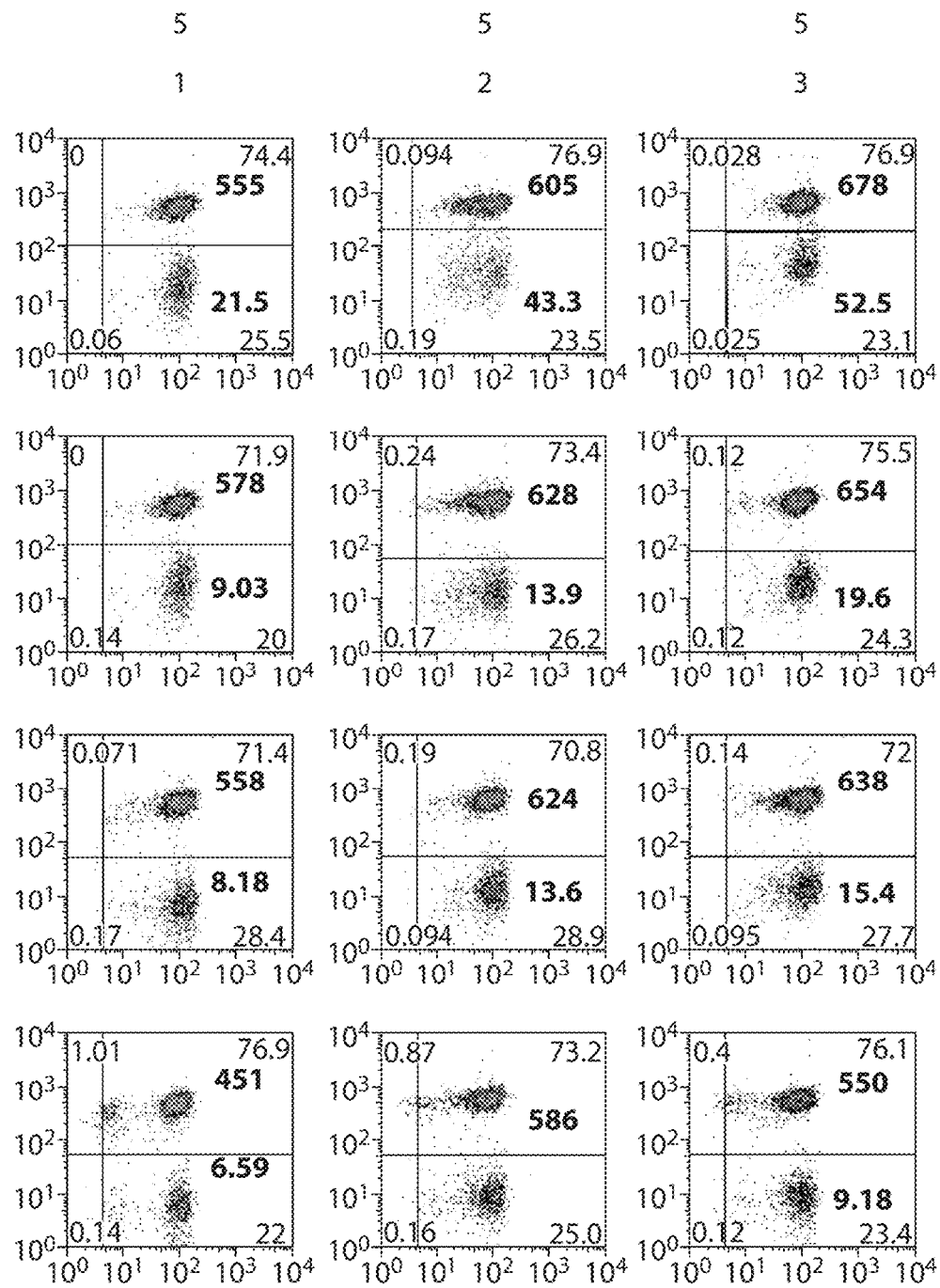

It was found that the background staining observed when using multimers generated via oxime chemistry can be reduced by using a protein supplement, for example, milk protein, during the staining procedure (FIG. 34). Cloned, A2/Flu matrix58-66 specific 81P1 cells were incubated with a A2/Melan-A-specific clone at 20° C. for 30 min with the indicated concentrations of conventional (column 1) or PE-HNO-NTA$_2$ containing multimers (columns 2, 3, 4, 5 and 6) in the absence (row 1) or presence of the indicated concentrations of dried milk powder (rows 2-4). Milk powder efficiently decreased the background staining of oxime-chemistry multimers.

Binding Titration of NTAmers to Determine Best Dilution for Ex Vivo Staining.

Figure 35A:
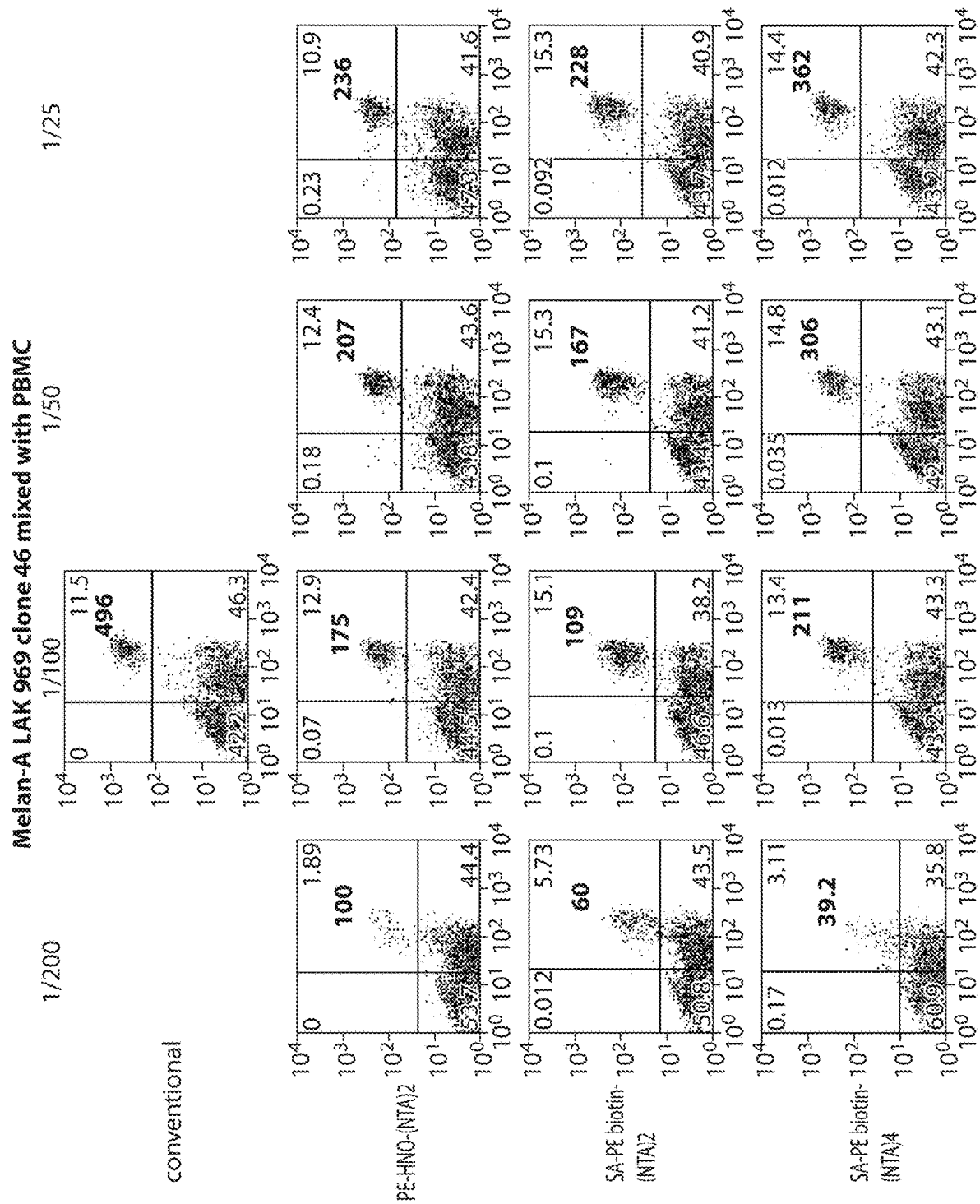
FIGS. 35A to 35B. Binding titration of NTAmers to determine best dilution for ex vivo staining.
Figure 35B:
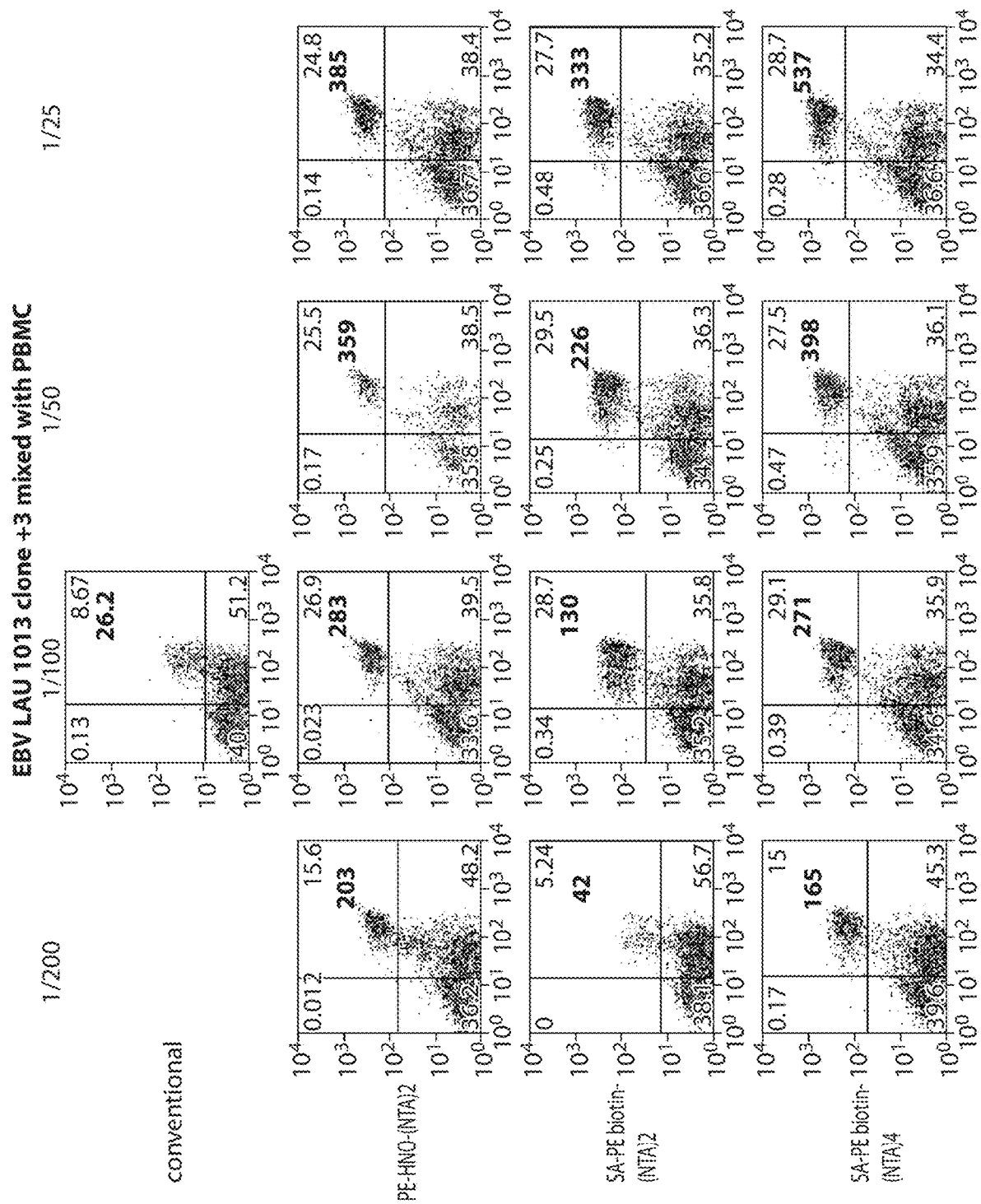

Cloned, Melan A LAU 959 46 (FIG. 35A) or EBV LAU 1013 specific cloned cells (FIG. 35B) were mixed with fresh PBMC and incubated at 20° C. for 30 min with graded dilution of PE-NTA$_2$ NTAmer (row 2), SA-PE multimers containing SA-PE biotin-NTA$_2$ (row 3) or SA-PE biotin-NTA$_4$ (row 4).

Figure 36:
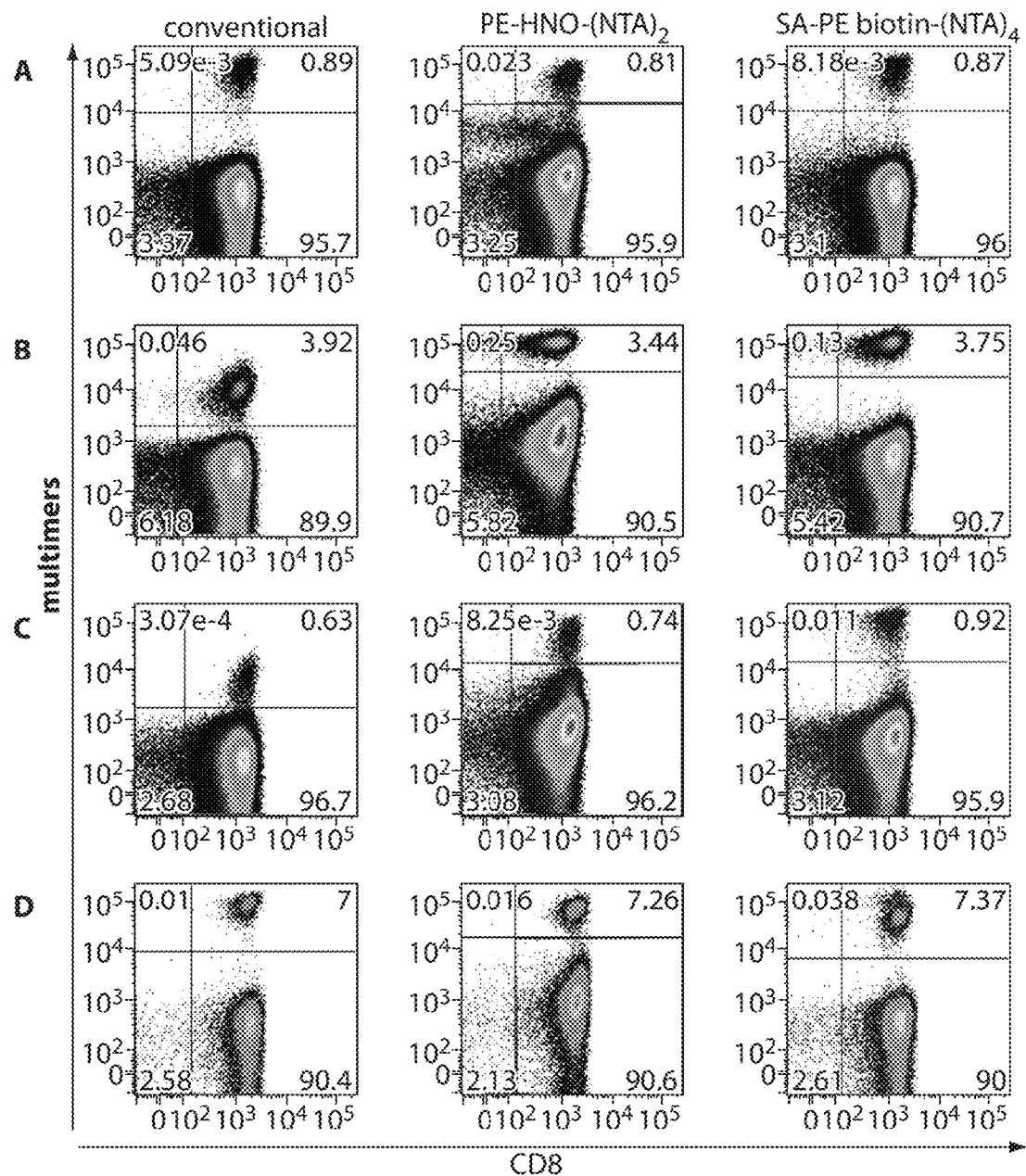
FIG. 36. Ex vivo staining with BSP and NTA multimers on fresh peripheral blood mononuclear cells (PBMCs).

Ex vivo staining with BSP and NTA multimers on fresh PBMC was also compared. FIG. 36 shows ex vivo flow cytometric analysis of PBMC stained with A2/peptide multimers containing BSP (conventional), PE-oxime NTA$_2$, or SA-PE biotin-NTA$_4$. PBMCs were obtained from EBV+ (BCL 7) individuals (FIG. 36A), CMV+(BCL 8) individuals (FIG. 36B), and from two melanoma patients: LAU 616 (FIG. 36C) and LAU 1164 (FIG. 36D).

Example 5

Use of Desthiobiotin for Purification of Correctly Peptide Loaded MHC H-Peptide Complexes In some embodiments, multimeric MHC II staining reagents described herein are generated by loading monomeric MHC molecules with a peptide of interest and purifying correctly peptide-loaded monomers for further processing and assembly to multimers. For example, in some embodiments, a hexahistidine (His6: SEQ ID NO: 310) tag is added N-terminally at the peptide and the complexes are purified on Ni$^{2+}$ NTA columns. In some embodiments, an N-terminal polyacidic tag is used, which allows purification of complexes by anion exchange chromatography. In some embodiments, a desthiobiotin (DTB) tag is N-terminally added to the peptide using conventional solid phase peptide synthesis (SPPS) and the target complexes are purified on streptactin columns using elution with free DTB. The column can be completely regenerated by washing with 2-(4'-hydroxyazobenzene) benzoic acid (HABA) and the Tris, pH 9.0. The recovery yields are close to 100%, and pMHC II complexes fully active.

Figure 37:
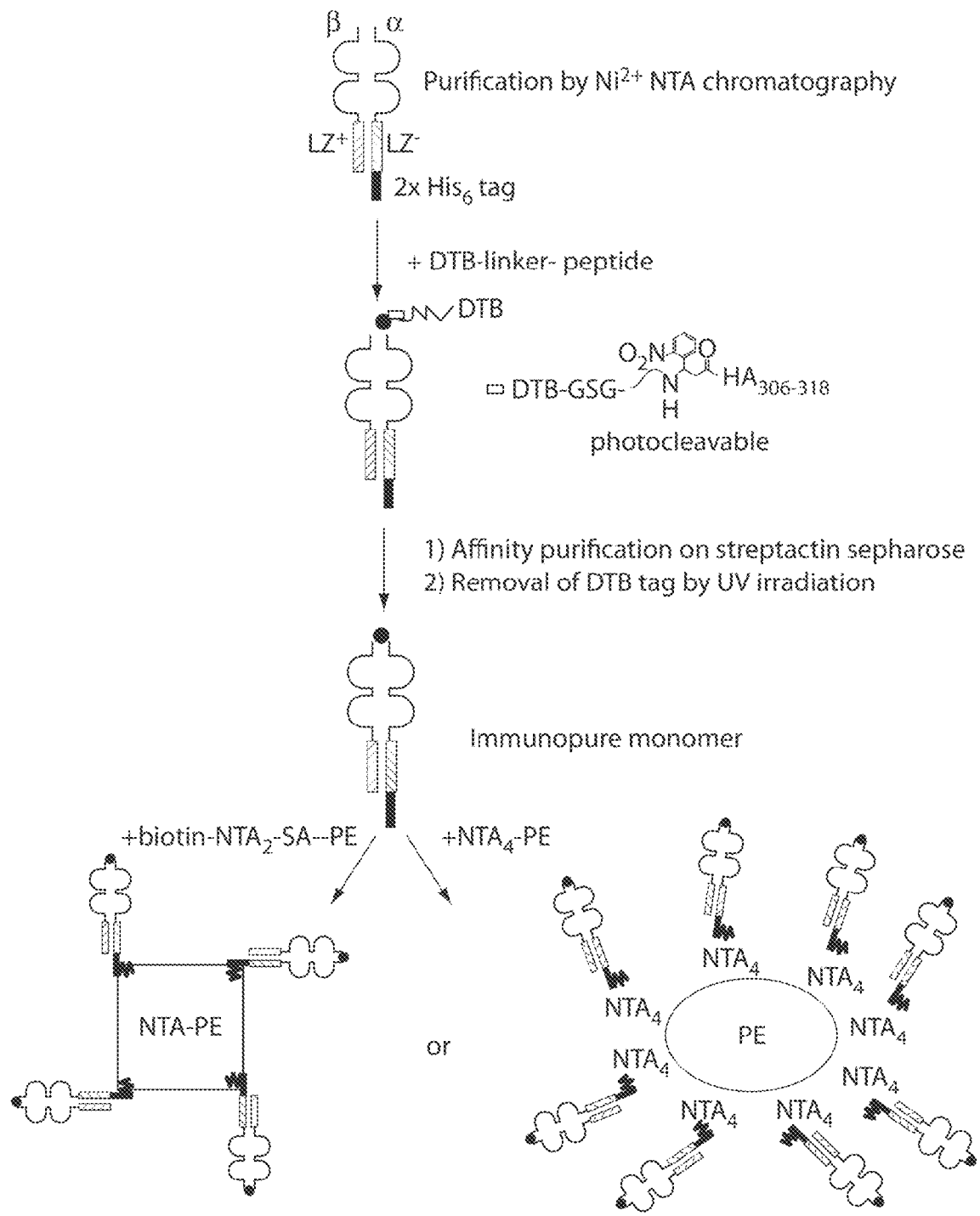
FIG. 37. Overview of an exemplary strategy for NTA-His tag multimer preparation using desthiobiotin (DTB). The sequence corresponds to a 2×His$_6$ (SEQ ID NO: 312) tag.

The use of DTB is less complex than using a poly-acidic tag and anion exchange chromatography, and has the advantage that a His tag can be used on the MHC II protein. In some embodiments, this allows i) gentle and universal purification of MHC II proteins from supernatants and ii) diverse conjugate formation based on the His tag-NTA chelate complex conjugation strategies described herein. An overview of an exemplary strategy for NTA-His tag multimer preparation using DTB is outlined in FIG. 37.

Protein Expression in Drosophila Cells

Serum-free adapted Drosophila melanogaster cell line (D.mel-2) were transfected concomitantly with two pMT-derived plasmids containing cloned extracellular parts of the a and beta chain of the MHC class II allele, followed by leucine zipper sequences and terminating with a Avi-Tag (beta chain) or a tandem His-tag (a chain). A pBS-derived plasmid containing the puromycin resistance gene is co-transfected to allow for antibiotic selection. After selection in 10 µg/ml puromycin (SIGMA-ALDRICH™), cells were cloned by limiting dilution and clones screened for high expression. Expression levels in supernatants of DR1, DR4 and DP4 proteins with C-terminal tandem His-tags range from 1 to 5 mg/ml as determined by ELISA.

Recombinant MHC Class II Protein Purification on IDA Columns

Clarified and 0.22 µm filtered supernatants from 3-5 day conditioned Sf900 II SFM media (INVITROGEN™) from insect cell culture were flowed through a column of 25-50 ml Chelating Sepharose FF (GE Healthcare Life Sciences) at 1.5-2 ml/min (previously equilibrated in PBS) and washed with 10 mM imidazole in PBS. Tandem His-tagged recombinant MHC class II proteins were eluted with 200 mM imidazole in PBS and the column regenerated with 20 mM EDTA in 50 mM Tris pH 8.0. The eluate was further concentrated in an Amicon cell concentrator (EMD MILLIPORE™) and buffer exchanged with a HILOAD® 26/10 gel filtration column (GE Healthcare Life Sciences) against the loading buffer (100 mM sodium citrate pH 6.0).

Peptide loading and purification of "immunopure" complexes

Loading of purified recombinant MHC class II protein with 100 µM desthiobiotin (DTB) or polyglutamate-tagged (pY-E8) HA308-318 or NY-ESO-1119-143 peptide at 100 M was performed at 37° C. for 24 h. To remove the excess peptide, the sample was passed through the HILOAD® 26/10 column twice in PBS (for DTB-tagged complexes) or 50 mM Tris pH 9.0 (for pY-E8-tagged complexes) and then applied to a StrepTrap HP 1 ml (for DTB-tagged complexes) or a MonoQ 4.6/100 (for pY-E8-tagged complexes). After a 5 CV wash, DTB-containing complexes were eluted with 50 mM desthiobiotin in PBS (pH corrected to 7.4) while the pY-E8 complexes were eluted with a NaCl gradient (0-1 M NaCl in 20 CV) at 400 mM NaCl. Flow rates were 1 ml/min for the StrepTrap column and 2 ml/min for the MonoQ column (both columns from GE Healthcare Life Sciences). The StrepTrap column is regenerated with 1 mM HABA (SIGMA-ALDRICH™) in PBS and equilibrated in 30 CV of PBS. The eluted proteins were diluted with an equal volume of PBS (DTB-tagged peptide) or 50 mM Tris pH 9.0 (pY-E8-tagged peptide) before being concentrated to 0.5-1 mg/ml in an Amicon-5 filter concentrator (EMD MILLIPORE™) Aliquots of 10-25 µg were snap frozen in liquid nitrogen and stored at −80° C. Optional tag removal by UV. In case the tag is linked to the peptide with a photocleavable amino-acid derivative (ONPA), it can be removed by irradiation with a 30 W UV lamp (365 nm) by irradiating for 10 min in V-bottom 96-well plates (1 µg MHC-peptide complex in 100 ul PBS).

Multimerization

Purified MHC class II-peptide complexes with C-terminal tandem His-tags are added to NTA-derivatized PE and SA-PE conjugates in a well of a V-bottom 96-well plate, vigorously mixed and incubated at least 2 hours at 4° C. before use in staining a cell sample.

Use of DTB to Isolate MHC-II Peptide Complexes

Figure 38:
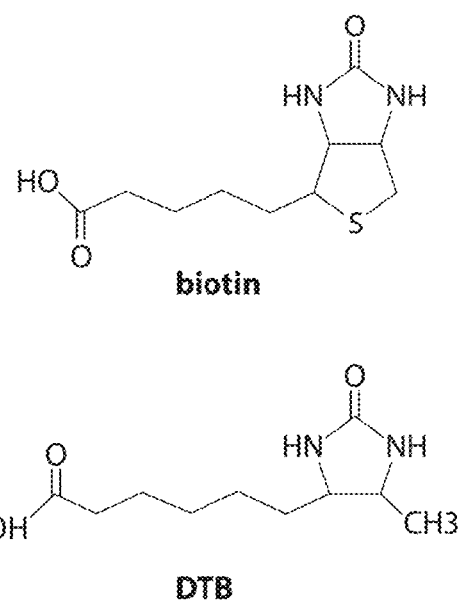
FIG. 38. Structures of biotin and DTB.

The structure of biotin and desthiobiotin are provided in FIG. 38. We found out that DTB binds to StreptActin with sufficient affinity to permit efficient retention and can be readily displaced by free DTB. Importantly, StreptActin columns could be completely regenerated by washing with HABA, which displaces DTB, and subsequently with Tris, pH 9.0, which removes HABA. Contrary to previous reports, the regeneration of streptavidin columns after elution with free DTB was incomplete (with HABA and/high or low pH). While streptactin columns are used for purifying Strep tag-containing molecules and monomer streptamer columns for purifying biotinylated molecules, we report here that StreptActin columns allow efficient purification of DTB tagged molecules and complete regeneration of the columns.

Evaluation of DTB Tag Peptide Purification Efficiency

Figure 39A:
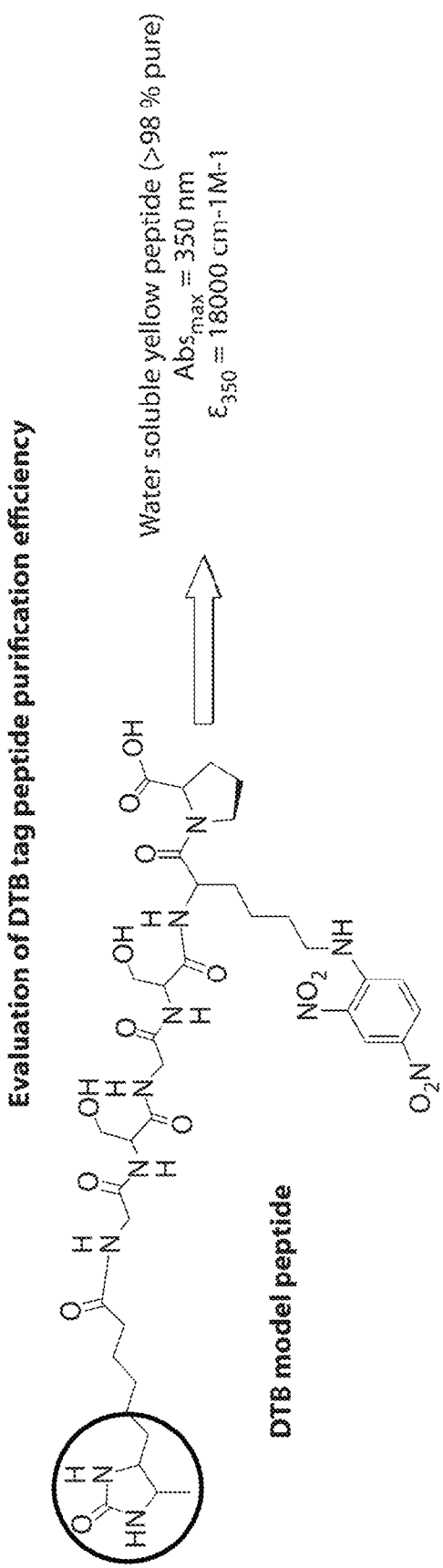
FIGS. 39A to 39C. Evaluation of DTB tag peptide purification efficiency.
Figures 39B, 39C:
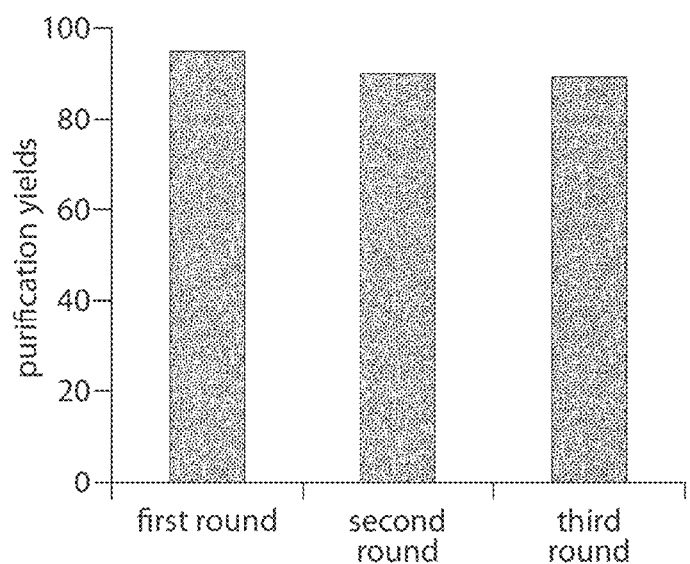

A DTB tagged model peptide was generated and purification performance was evaluated (FIG. 39). The structure of a low molecular weight colored peptide used for quantification of the purification efficiency is described in FIG. 39A. FIG. 39B shows a compilations of the efficiencies of retention, elution and regeneration for 3 different columns. FIG. 39C shows purification yields on StreptActin superflow high capacity column for three consecutive rounds of purification/regeneration. Regeneration buffer: HABA 0.1 M followed by Tris 0.2 M, pH 9.

Figure 40:
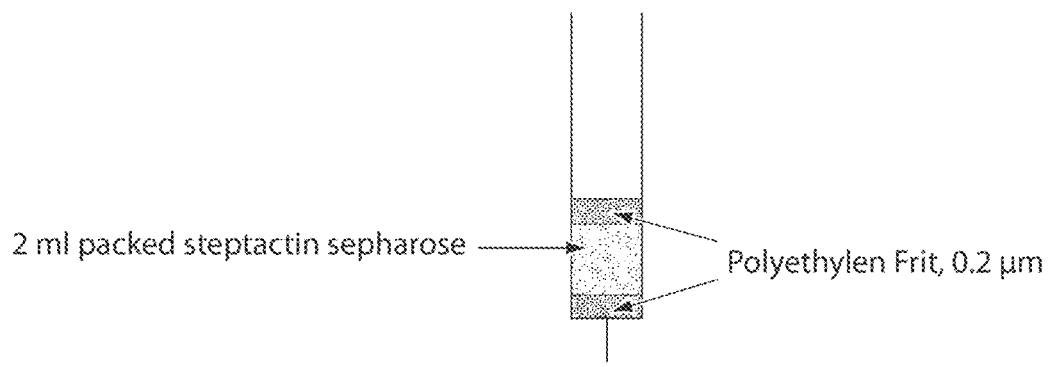
FIG. 40. Schematic of 2 ml of StreptActin High Capacity sepharose (IBA)
Figure 41:
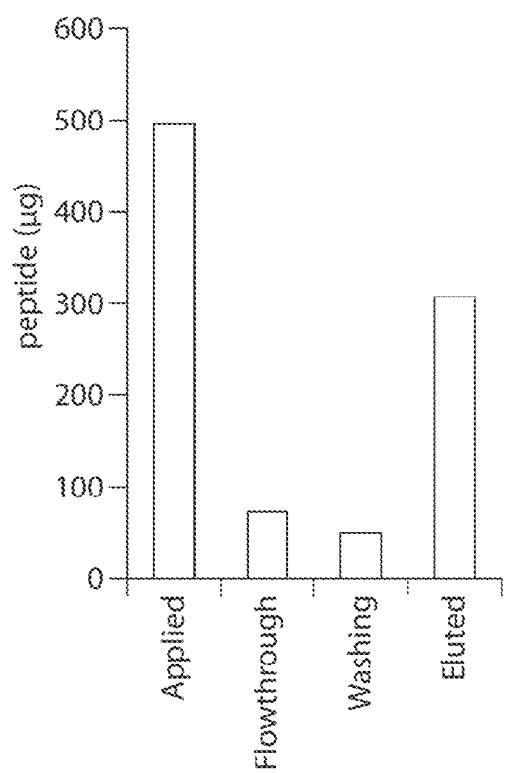
FIG. 41. Quantification of flowthrough, washing and elution of a DTB-tagged peptide.

DTB tag MHC I monomer purification efficiency was evaluated next (FIG. 40). Binding/Washing buffer: Tris 0.1 M, 150 mM NaCl, 1 mM EDTA, pH 8. Elution Buffer: Tris 0.1 M, 150 mM NaCl, 1 mM EDTA, pH 8, 50 mM DTB. Regeneration Buffer: Tris 0.1 M, 150 mM NaCl, 1 mM EDTA, pH 8, 1 mM 2-(4'-hydroxyazobenzene) benzoic acid (HABA). For purification evaluation, 499 µg of pMHC I monomers carrying a DTB C terminal on the heavy chain were applied onto 2 ml of StreptActin High Capacity sepharose (IBA). Flowthrough, washing and elution were quantified by at OD 350 nm measurements (FIG. 41). Elution was with 50 mM DTB with a recovery of 307 µg (85% yield).

Figures 42A, 42B:
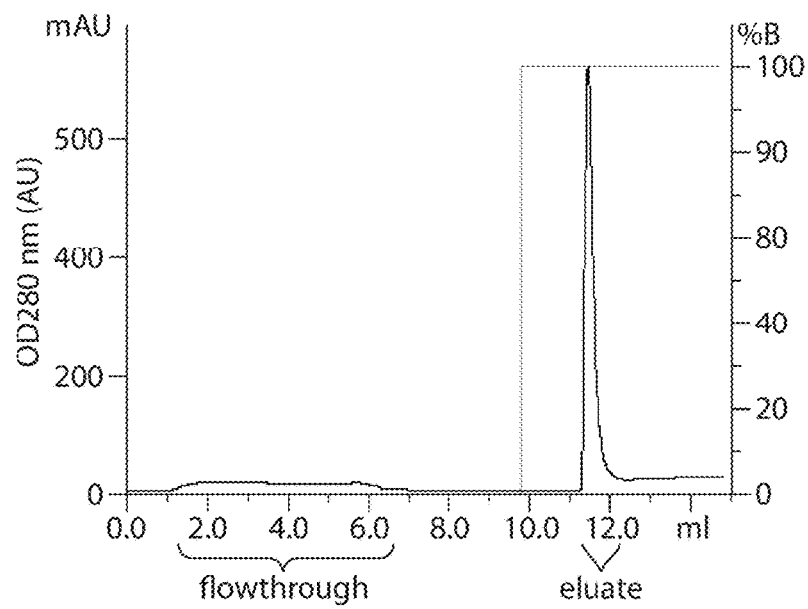
FIGS. 42A to 42B. Purification of MHC I-DTB peptide complexes on StreptActin sepharose.

Purification of pMHC I DTB complexes on StreptActin sepharose was also evaluated. FIG. 42A shows a chromatogram of a DTB-tagged protein purified on a StreptActin sepharose column. FIG. 42B shows the purification parameters for DTB tagged MHC class I-peptide complexes.

Figure 43A:
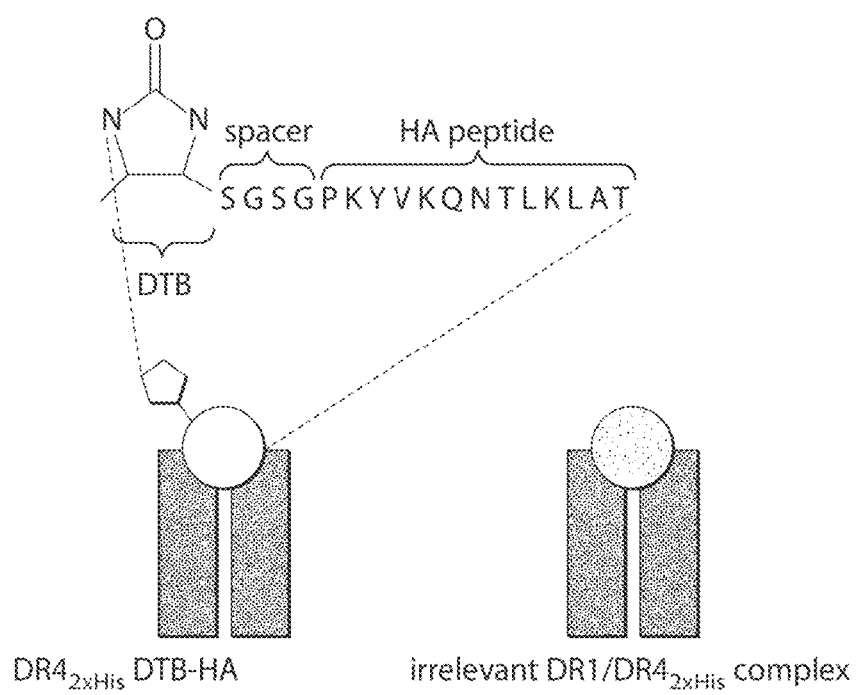
FIGS. 43A to 43B. Exemplary scheme of DTB-HA peptide loading and purification. The sequence of the DTB-SGSGPKYVKQNTLKLAT peptide corresponds to SEQ ID NO: 316.
Figure 43B:
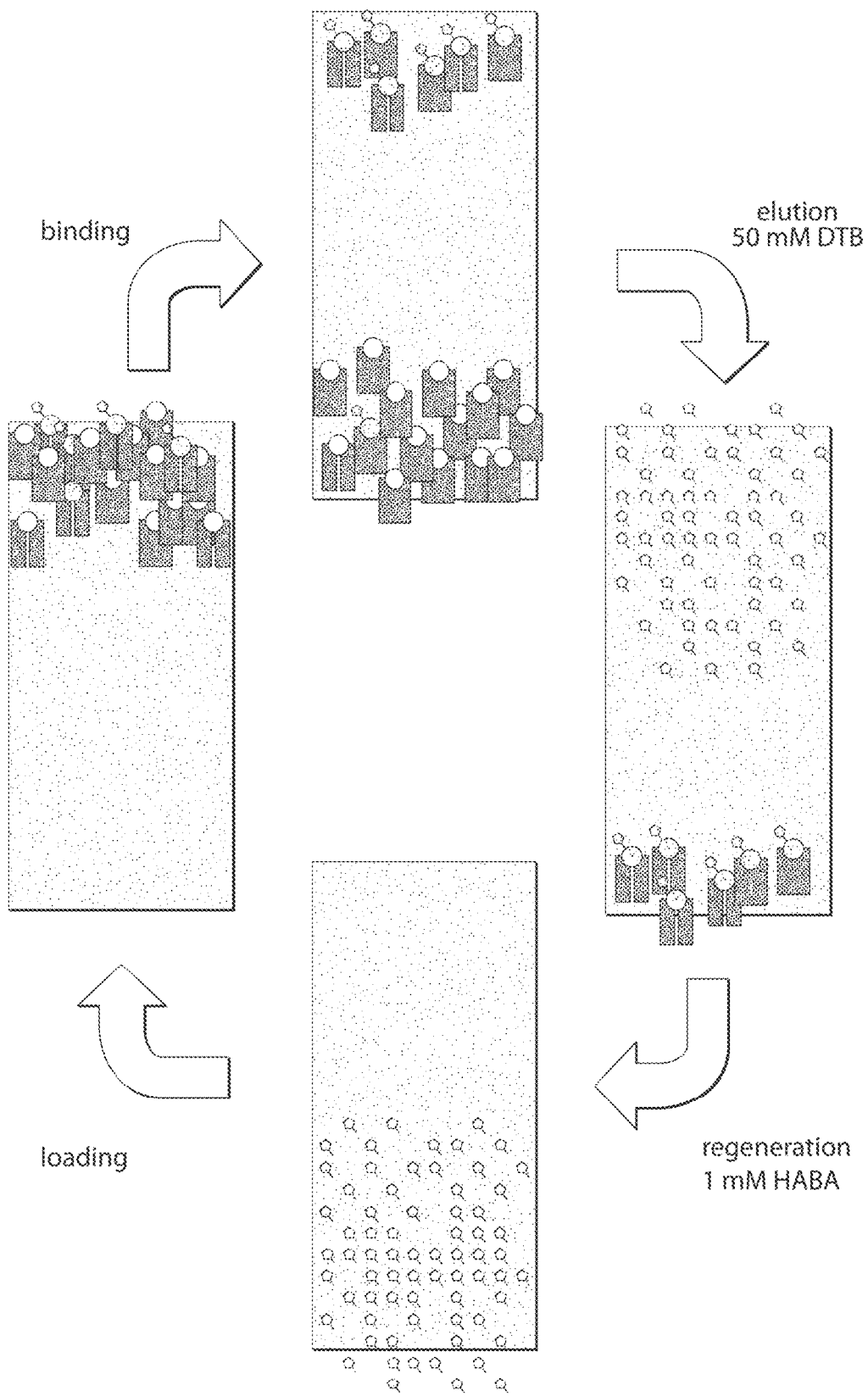

An exemplary scheme of DTB-HA peptide loading and purification is described in FIG. 43. An exemplary structure of DTB-HA and the corresponding DR42xHis DTB-HA complexes are depicted in FIG. 43A. A schematic of the purification and regeneration cycle of DR42xHis DTB-HA on a StreptActin sepharose column is illustrated in FIG. 43B.

Figure 44A:
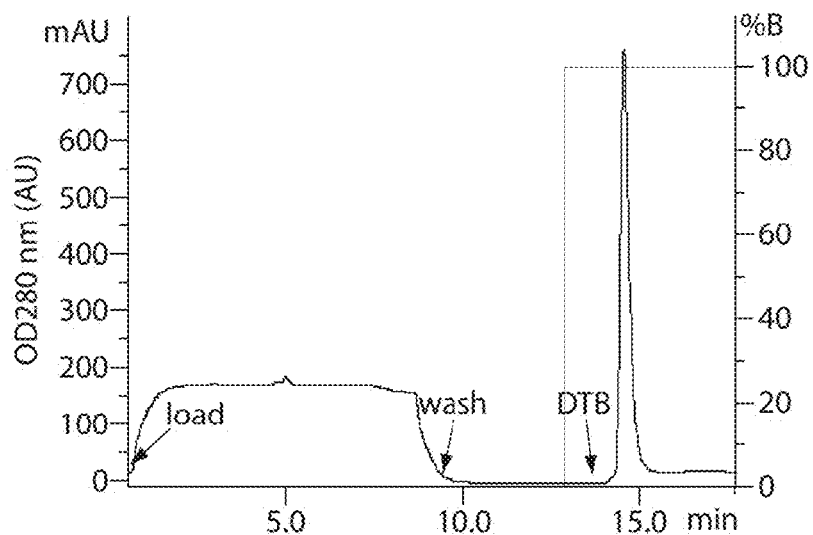
FIGS. 44A to 44B. Generation and purification of DR4-DTB-HA peptide complexes.
Figure 44B:
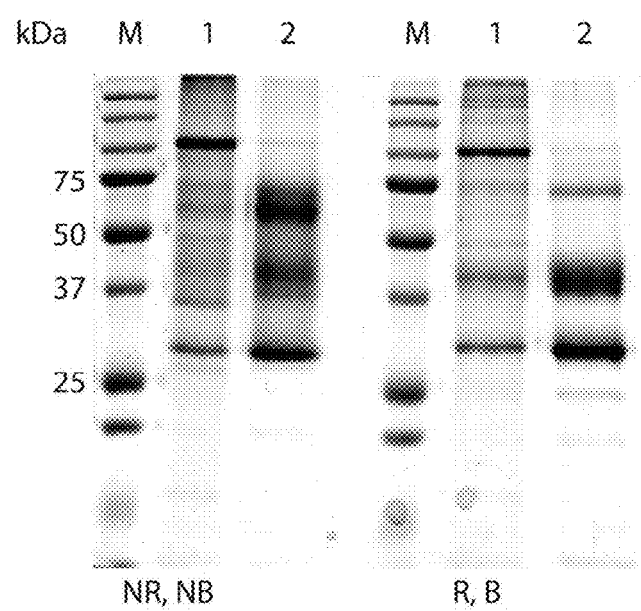

DR4-DTB-HA peptide complexes were generated and purified on a streptactin column. After peptide-loading, DR4-2xHis DTB-HA306-318 complexes were passed over a StreptActin column, washed and eluted with 50 nM DTB as indicated by arrows (FIG. 44A), and the OD of the effluent at 280 nm was monitored. Pure DR4-HA complexes eluted in a sharp peak (indicated by a box in FIG. 44A). DR4 2xHis DTB-HA306-318 complexes were analyzed by SDS-PAGE (12%) before (lane 1) and after (lane 2) purification on StreptActin sepharose (FIG. 44B). SDS-PAGE was performed under non-reducing, non-boiling (NR, NB, left gel image) or reducing and boiling conditions (R, B, right gel image). Each lane was loaded with 10 µg protein and the gel was stained with Coomassie blue. DTB-tag based purification resulted in highly pure peptide-loaded MHC preparations. Surprisingly, the purity of DTB-tagged peptide-loaded MHC molecules obtained by StreptActin column purification was observed to be superior to that of purification of polyanionic peptide tagged MHC molecules, which yield highly pure peptide-loaded MHC molecules.

Staining of CD4+ DR4-Restricted Flu-Specific T Cells with DTB Immunopure Multimers.

Figures 1, 45:
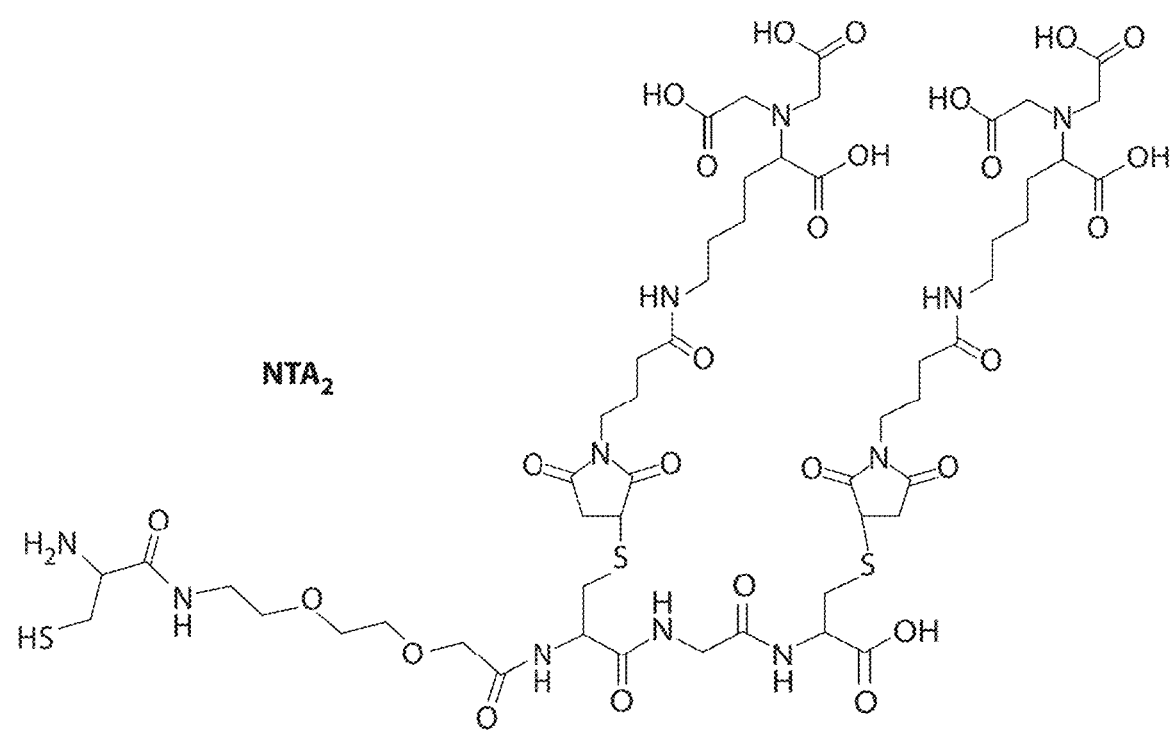
FIG. 45. NTA moieties used in PE-NTA$_2$ and biotin-NTA$_4$-SA-PE multimers.
Figures 2, 45:
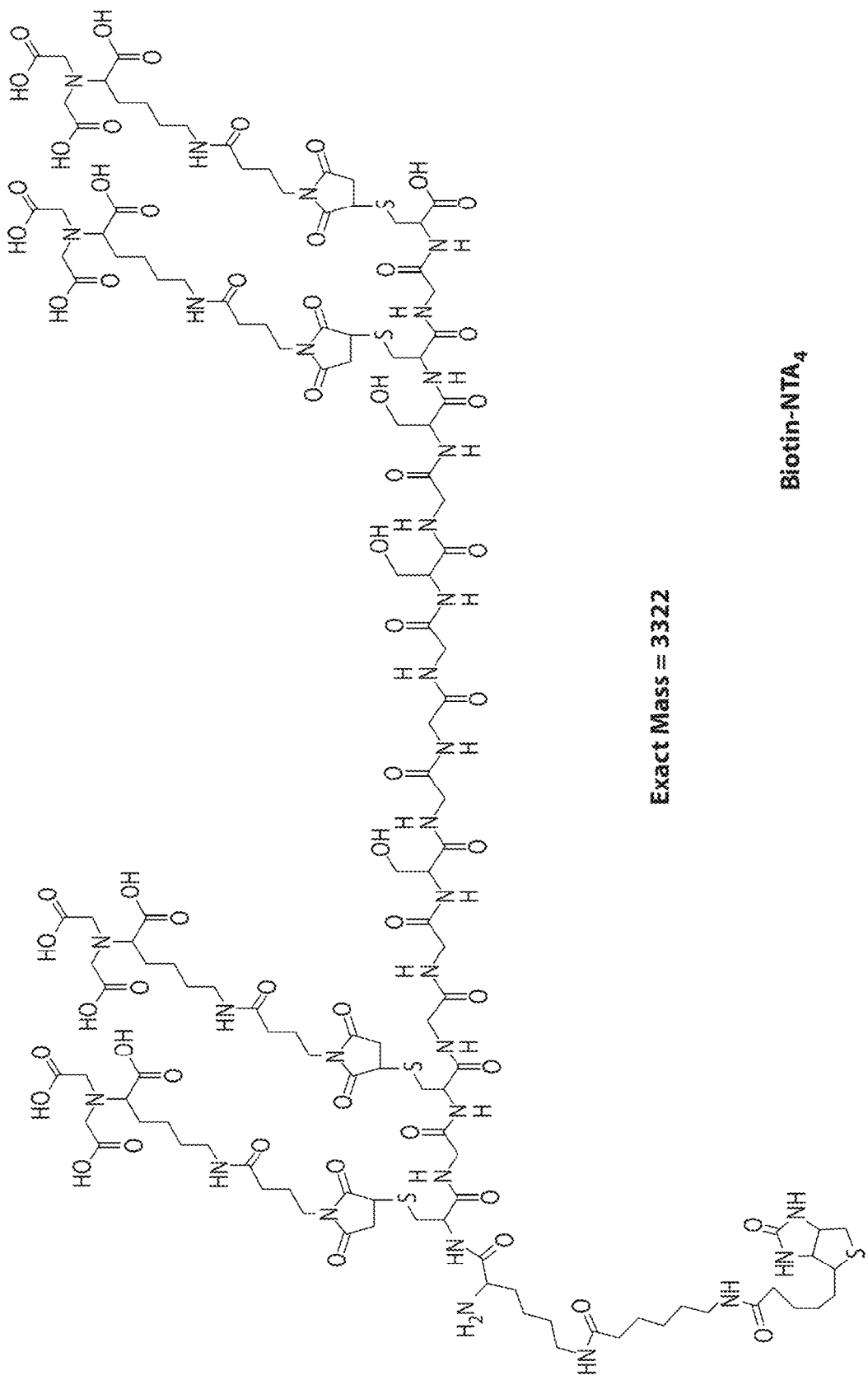

Staining performance of PE-NTA$_2$, biotin-NTA$_4$-SA-PE, and conventional BSP multimers was compared. As described in more detail elsewhere herein, PE-NTA$_2$ and biotin-NTA$_4$-SA-PE multimers contain the NTA moieties shown in FIG. 45.

MHC-peptide NTAmer preparation

5 µg DR4 2xHis DTB-HA complexes were incubated at 4° C. for 2-16 h with 1.4 µg PE NTA$_2$, or 2.8 µg SA-PE NTA$_4$ in wells of a V-bottom 96 well plate; then each incubation was diluted with EDTA-free FACS buffer (0.5% BSA in PBS with 0.05% sodium azide). Staining of cells was performed in 50 µl volume at room temperature (RT) or 37° C. for 1-2 h or as indicated. The PE-NTA$_2$ generated contained an estimated 7-10 monomers per conjugate. The BSP and biotin-NTA$_4$ multimers were prepared with the same SA-PE (from Caltag).

Figure 46A:
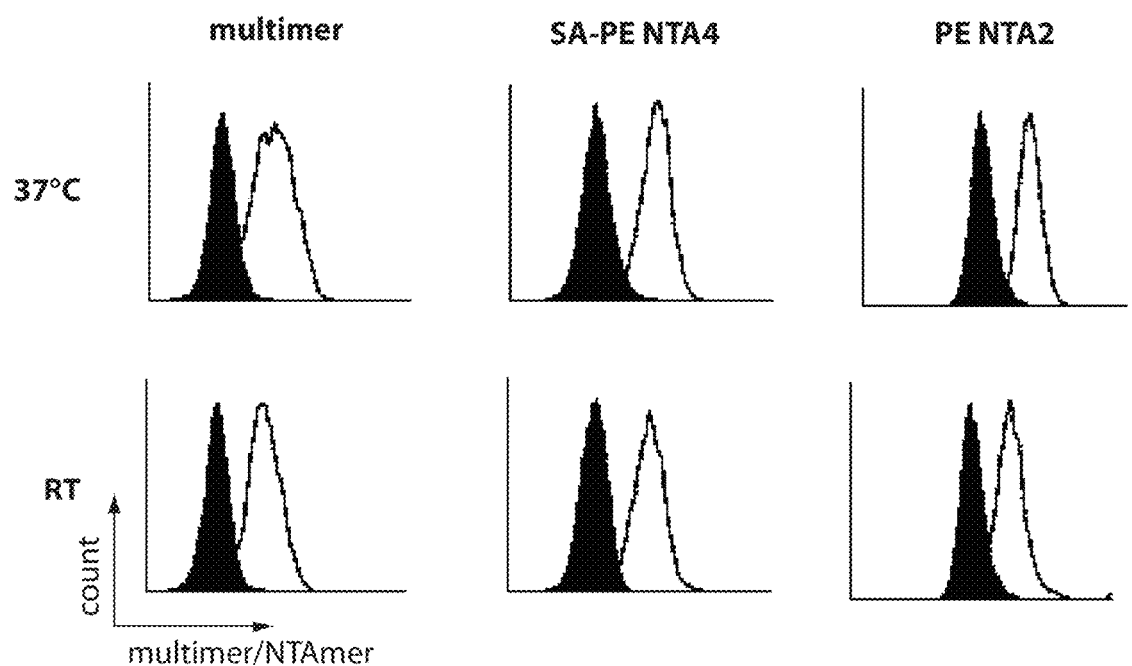
FIGS. 46A to 46B. Staining of Flu HA$_{306-318}$-specific CD4$^+$ T cells with DR4/HA$_{306-318}$ BSP, biotin-NTA$_4$-SA-PA, or PE-NTA$_2$ multimers made with DTB-streptactin purified monomers.
Figure 46B:
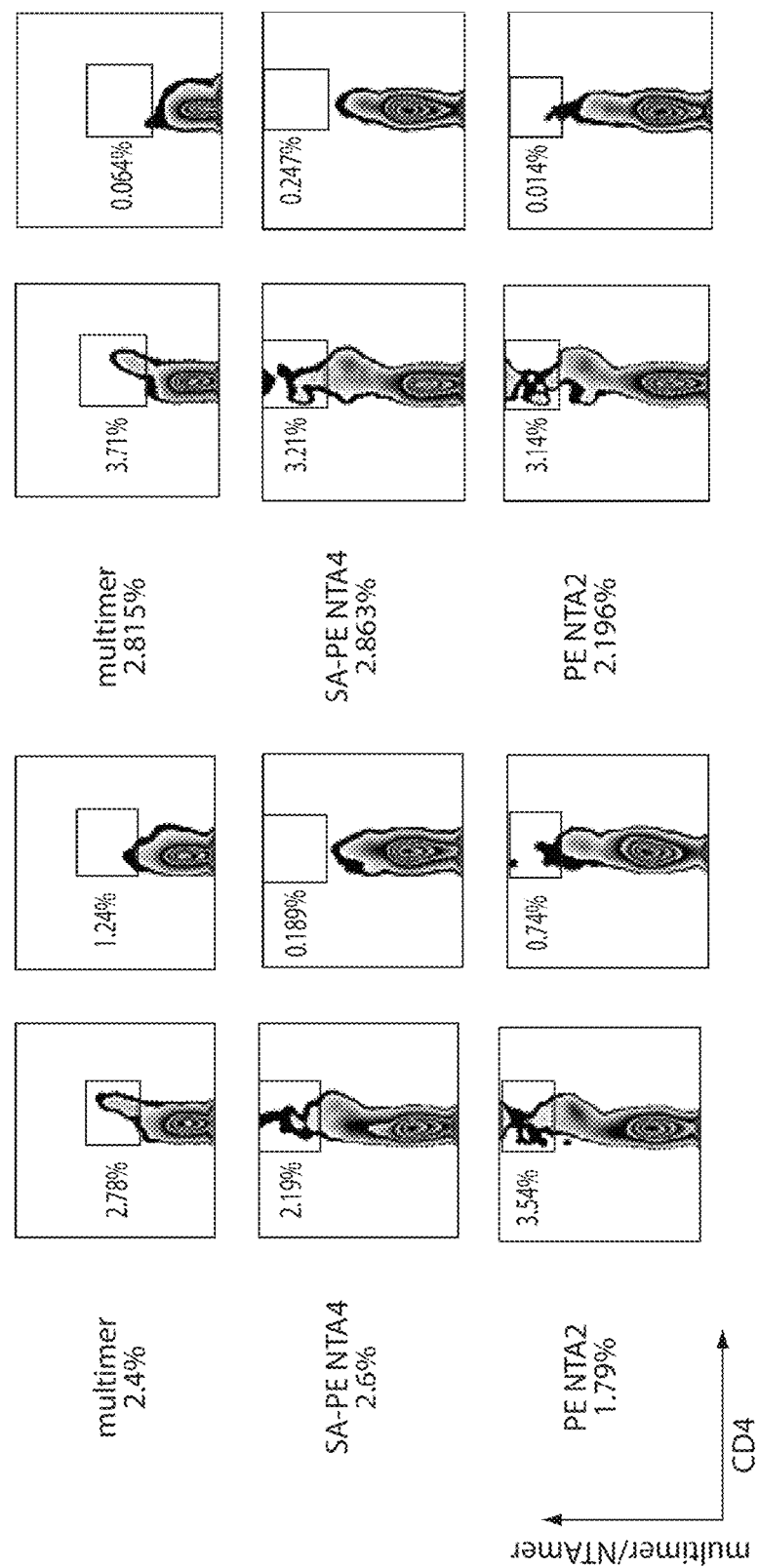

Cloned Flu HA$_{306-318}$-specific CD4$^+$ T cells (clone 23-1) were incubated at room temperature (RT) or 37° C. DR4/HA$_{306-318}$ BSP, biotin-NTA$_4$-SA-PA, or PE-NTA$_2$ multimers made with DTB-streptactin purified monomers and after washing were analyzed by flow cytometry (FIG. 46A, "multimer" refers to conventional BSP multimers). The background staining (black histograms) was assessed by parallel staining on a DR4-restricted/Flu matrix 61-72-specific clone. Five percent of cloned 23-1 clone cells were added to fresh PBMC and analyzed in the same manner (FIG. 46B).

Figure 47A:
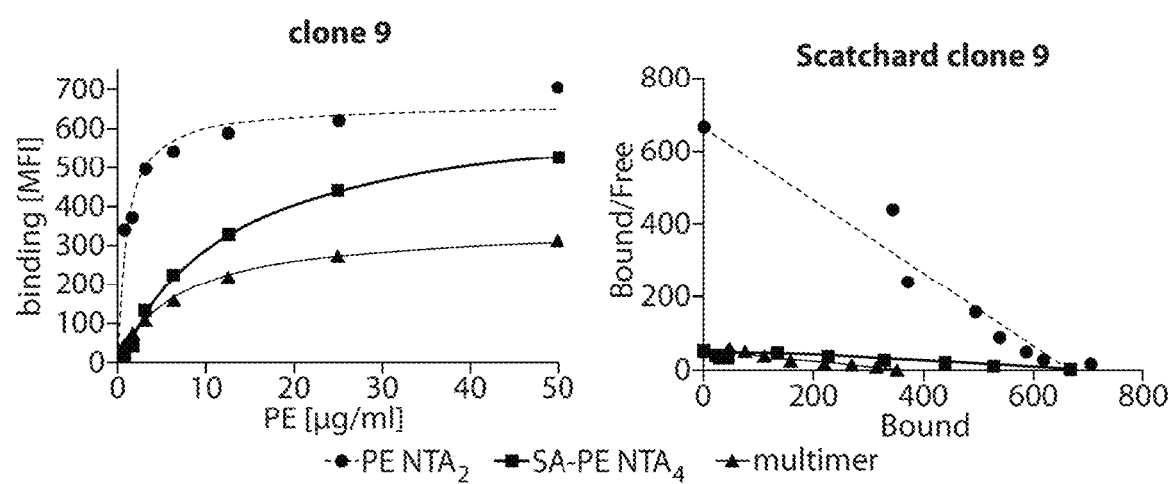
FIGS. 47A to 47B. Staining of HA-specific CD4+ T cell clones 9 (FIG. 47A) or 8 (FIG. 47B) with different concentrations of DR4/HA$_{306-318}$ BSP, biotin-NTA$_4$-SA-PA, or PE-NTA$_2$ multimers. Scatchard analysis was performed and the K$_D$ (dissociation constant) and B$_{max}$ (maximal binding) values are described in the tables on the right.
Figure 47B:
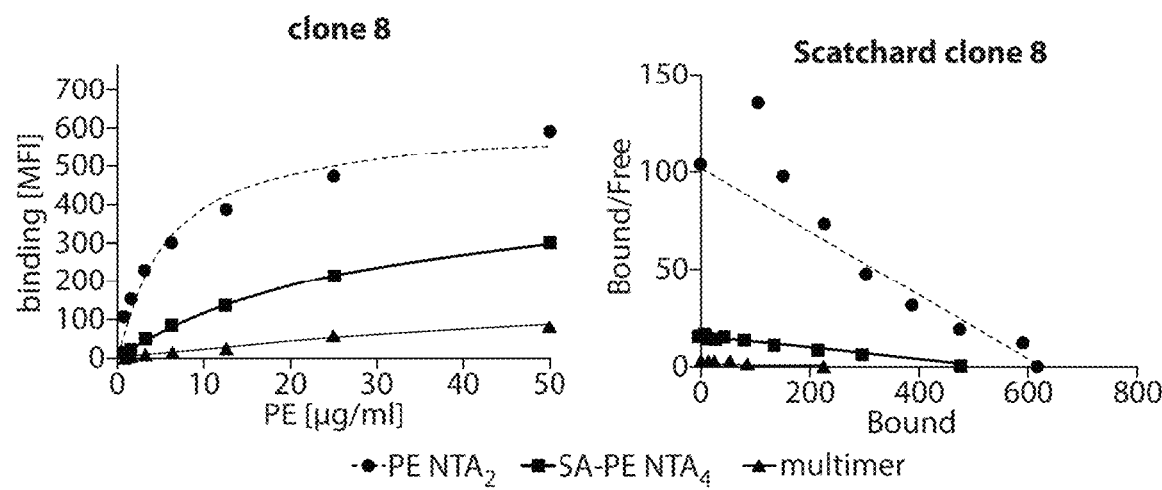

HA-specific CD4$^+$ T cell clones 9(A) or 8(B) were incubated for 1 hour at 37° C. with graded concentrations of DR4/HA$_{306-318}$ multimer (as in previous experiments), washed and analyzed by flow cytometry (FIG. 47). A DR4-restricted Flu matrix specific clone was used to evaluate nonspecific binding, which was subtracted. Scatchard analysis was performed and the K$_D$ (dissociation constant) and Bmax (maximal binding) values are described in the tables on the right.

The PE-NTA$_2$ multimers exhibited efficient binding/staining, particularly on clones that exhibited poor BSP multimer staining. Similarly, the biotin-NTA$_4$-SA-PE multimers stained with higher efficiency than BSP multimers. It is important to note, however, that significant clonal variations were observed.

Figure 48A:
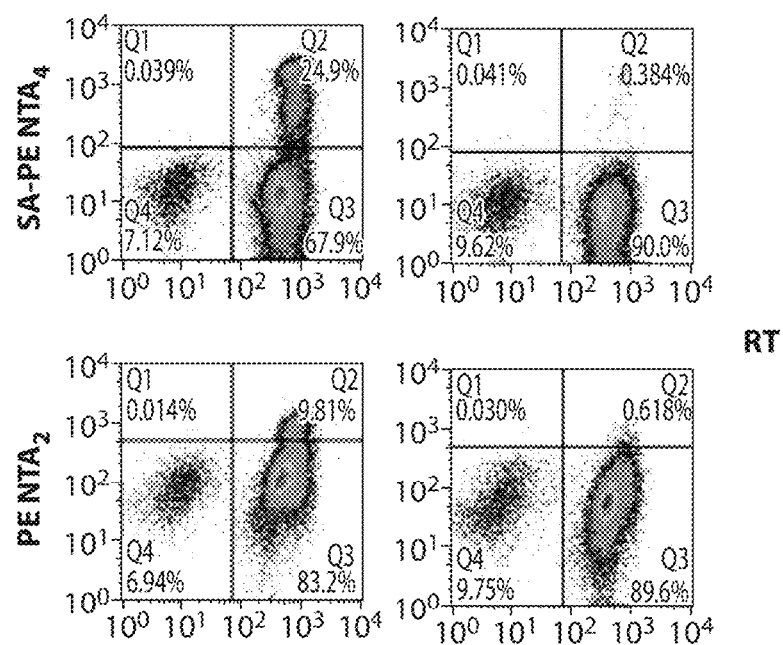
FIGS. 48A to 48C. Background staining of DR4/HA$_{306-318}$ SA-PE NTA$_4$ and PE NTA multimers. Background staining was efficiently suppressed by addition of 0.5% milk powder (see FIG. 34).
Figure 48B:
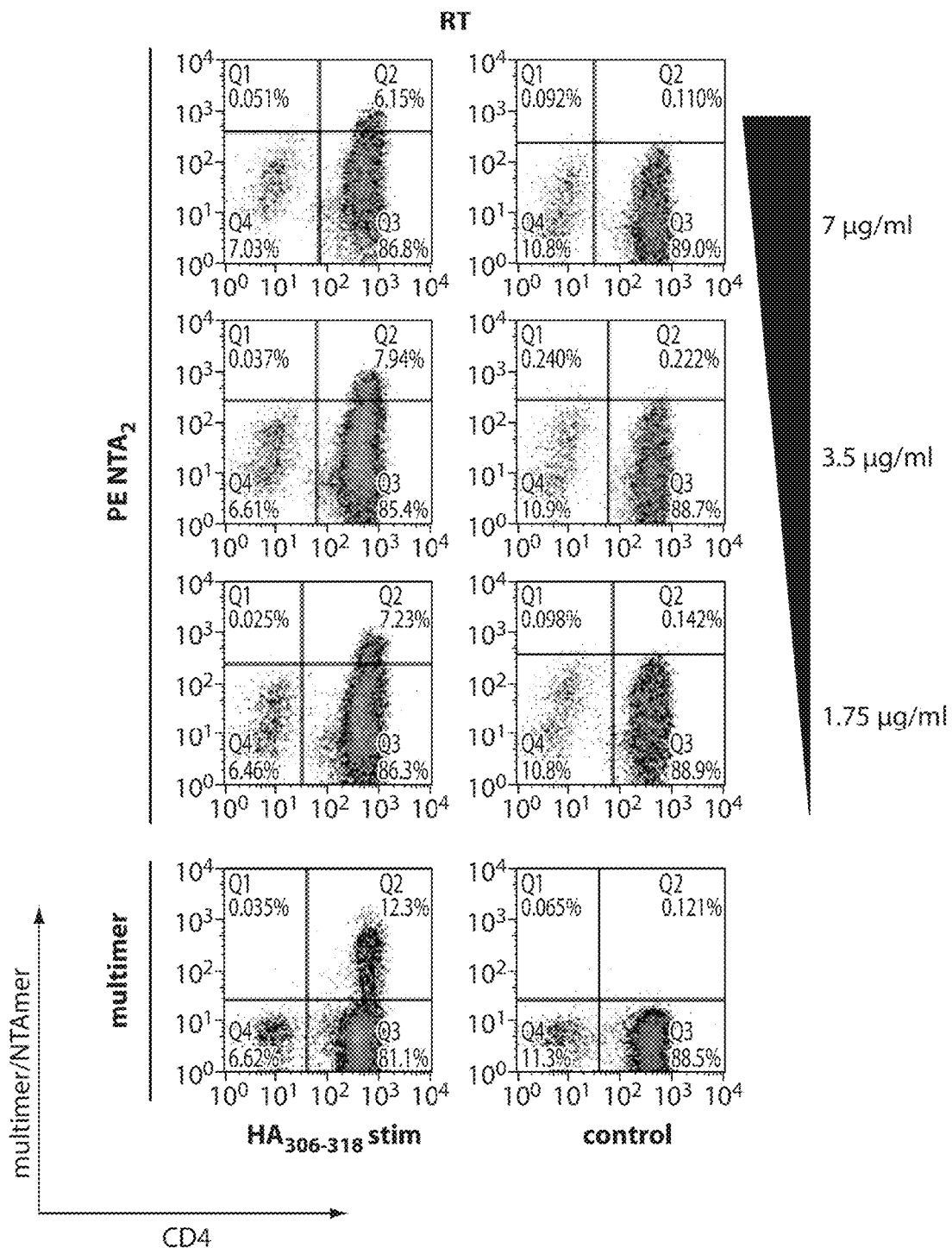
Figure 48C:
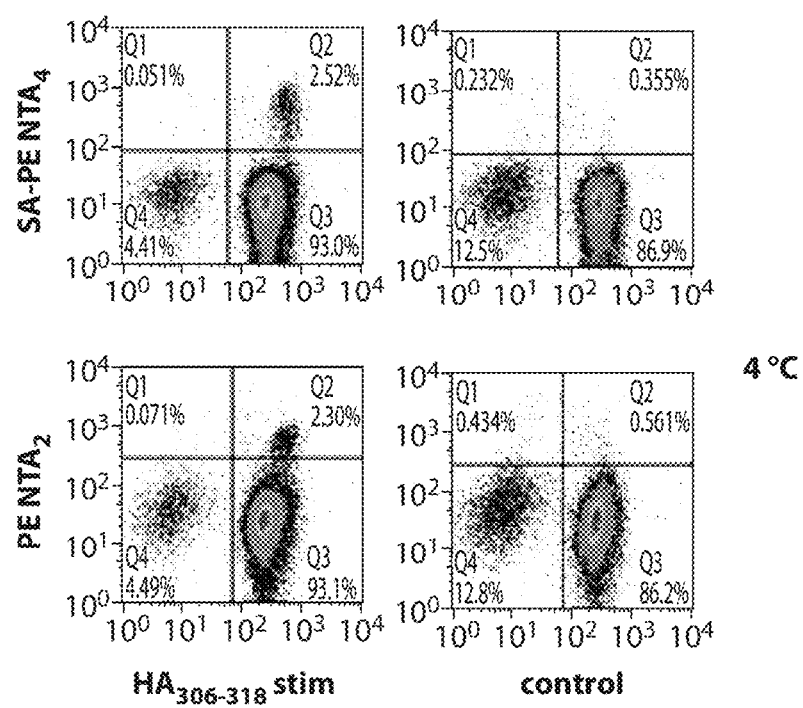
Figure 49A:
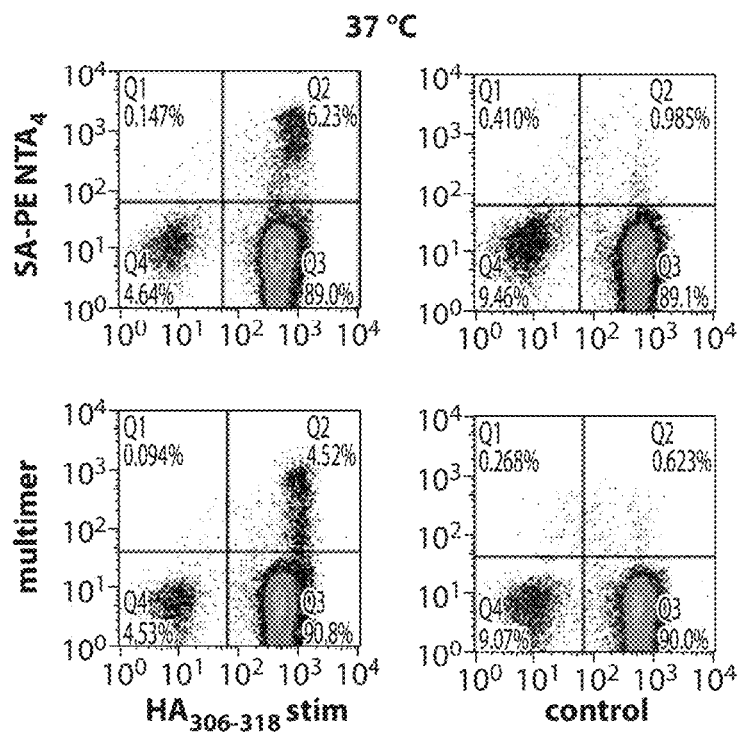
FIGS. 49A to 49D. SA-PE NTA4 DR4/HA$_{306-318}$ multimers were able to detect more antigen-specific cells than BSP multimers over a wide range of concentrations. Stimulated PBMCs were incubated for 1 h at 37° C.
Figure 49B:
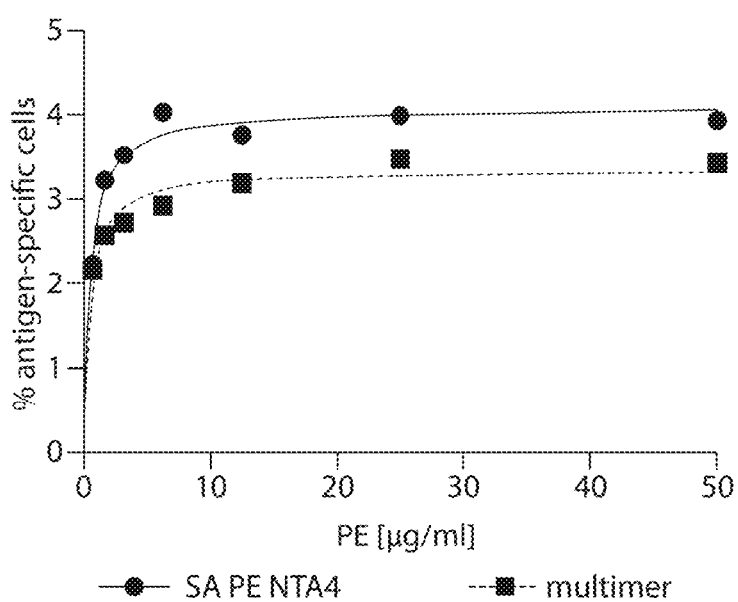
Figure 49C:
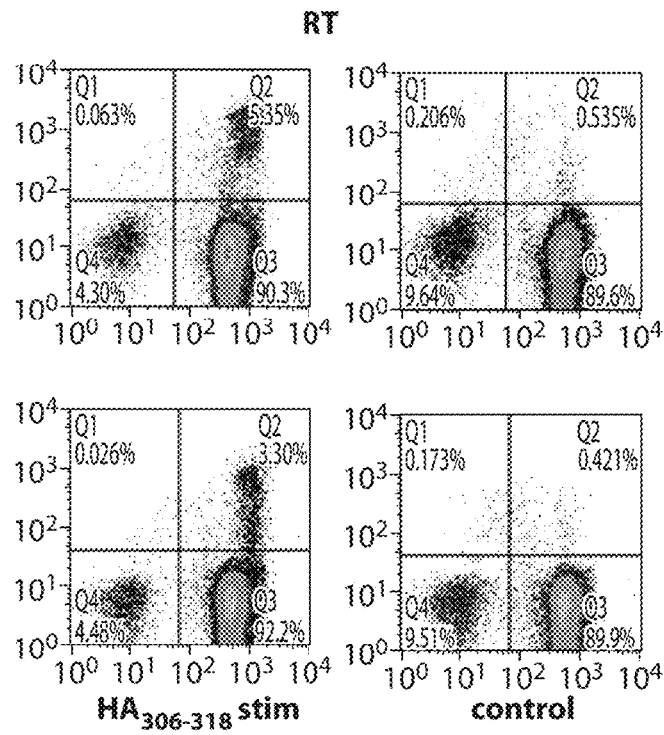
Figure 49D:
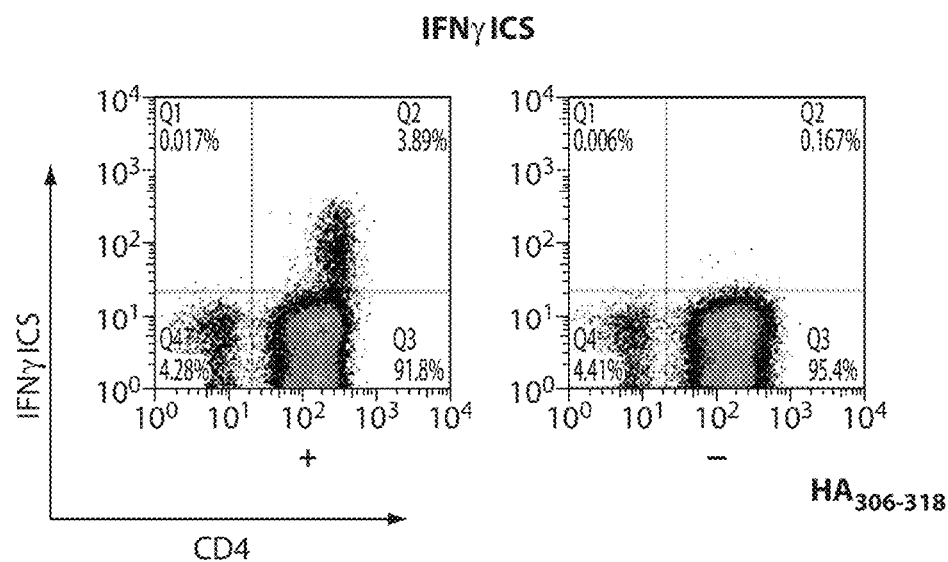

DR4/HA$_{306-318}$ SA-PE NTA$_4$ multimers exhibited less background staining than PE NTA$_2$ multimers (FIG. 48). HA peptide-stimulated PBMC were incubated at room Temperature (FIGS. 48A, 48B) or 4° C., (FIG. 48C). Optimal multimer concentrations (14 µg/ml for PE NTA$_2$, 28 µg/ml for SA-PE NTA$_4$) were used in (FIG. 48C A) and (FIG. 48C B). In (FIG. 48C C), three different concentrations of the PE NTA$_2$ reagent were compared. Non-stimulated PBMCs were used as a control.

The PE-NTA$_2$ multimers tended to exhibit increased background staining on control PBMCs. Background staining was efficiently suppressed by addition of 0.5% milk powder (as used, e.g., in Western blotting).

SA-PE NTA$_4$ DR4/HA$_{306-318}$ multimers were able to detect more antigen-specific cells than BSP multimers over a wide range of concentrations (FIG. 49). Stimulated PBMCs were incubated for 1 h at 37° C. (FIG. 49A) or room temperature (FIG. 49C) with 10 g/ml of the indicated HA peptide-loaded multimers and analyzed after washing by flow cytometry. Nonspecific background (control) was determined on TT$_{634-653}$ peptide stimulated PBMCs. Specific multimer staining was assessed in cells prepared and stained as in (A) over at different concentrations of multimers (FIG. 49B). For comparison the frequencies of IFNγ$^+$ T cells was assessed by ICS and flow cytometry with (+) or without (−) peptide stimulation.

Reversibility of Multimer Staining

Figure 50A:
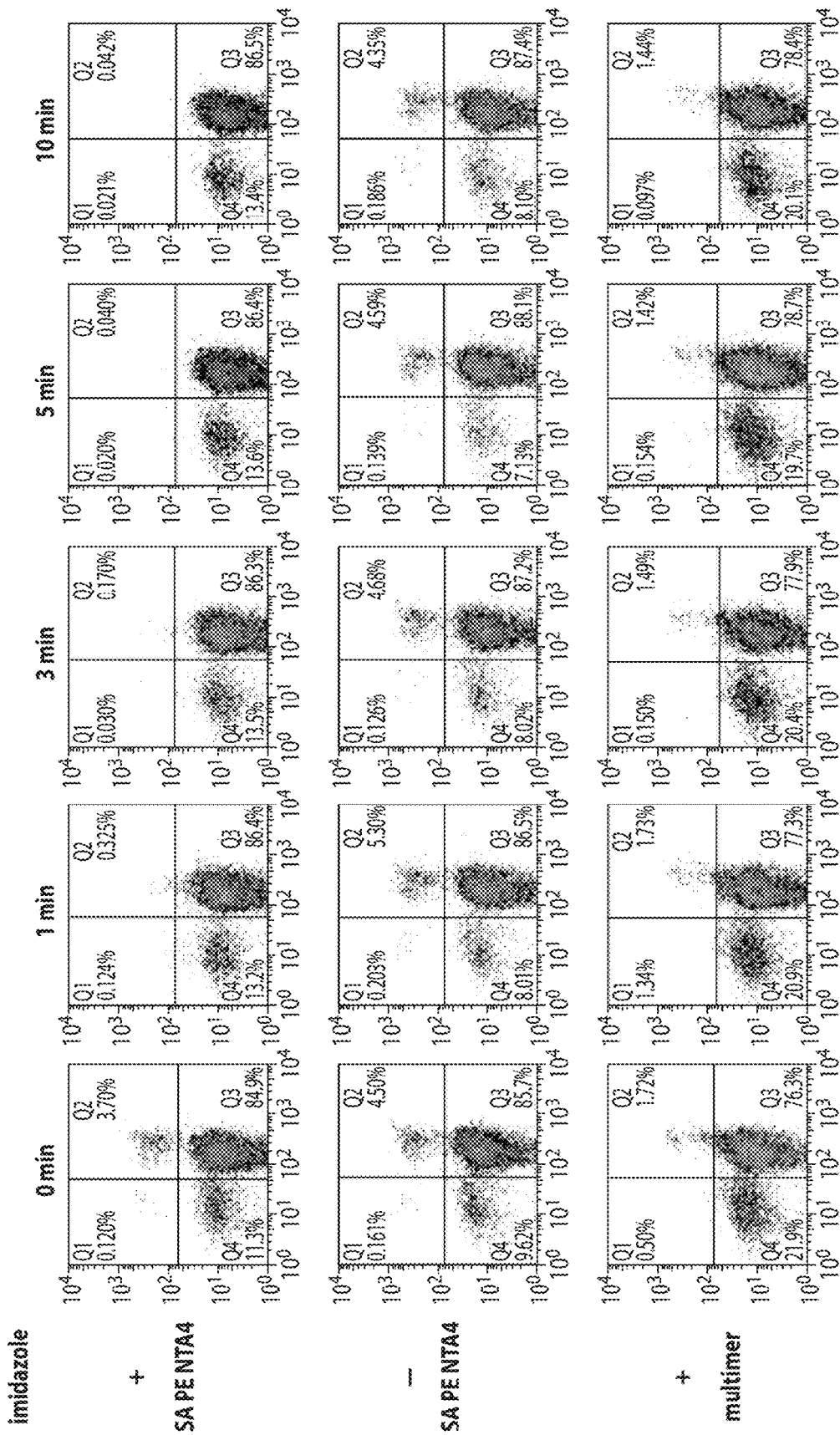
FIGS. 50A to 50B. Reversibility of multimer staining. Biotin-NTA$_4$, but not BSP multimers, can be rapidly removed from stained, antigen-specific cells.
Figure 50B:
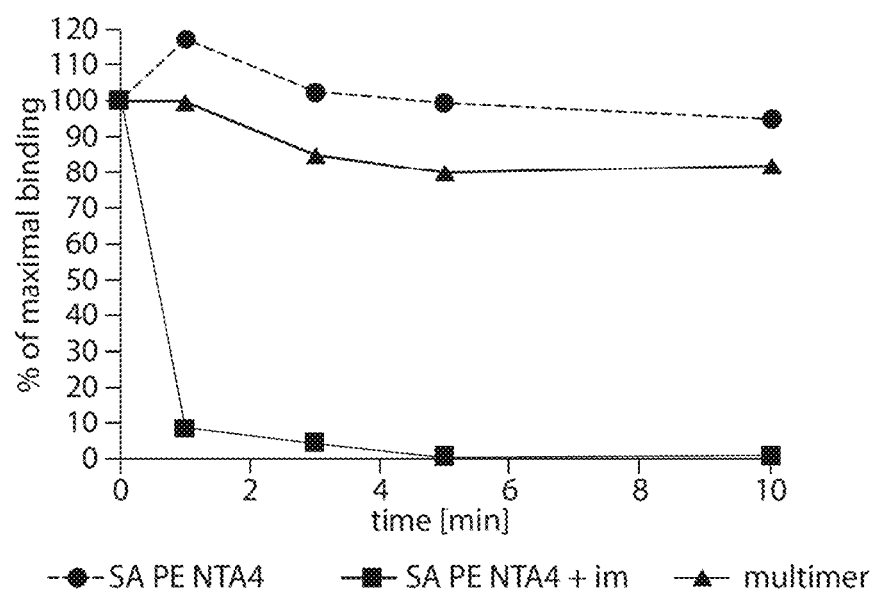

Biotin-NTA$_4$, but not BSP multimers, can be rapidly removed from stained, antigen-specific cells (FIG. 50). Peptide-stimulated PBMCs were stained with optimal concentrations (28 µg/ml for biotin-NTA$_4$-SA-PE and 16 µg/ml for BSP multimer) DR4-HA multimers at 4° C. for 1 h and washed with cold EDTA-free FACS buffer. After the initial acquisition (0 min), imidazole (100 mM final concentration) was added and data acquisitions (10,000 CD3+CD4+ events) was performed at 1, 3, 5 and 10 min by flow cytometry. Control cells stained with biotin-NTA$_4$-SA-PE multimer were not treated with imidazole (FIG. 50A). Specific binding observed in (FIG. 50A) was plotted versus the time elapsed (FIG. 50B). Biotin-NTA$_4$-SA-PE multimers were observed to be stable in the absence and rapidly reversible in the presence of imidazole. This prevents multimer staining-induced death of antigen-specific T-cells, for example, CD4+ T cells or CD8+ T cells. As described elsewhere herein.

Comparative Staining of a DR1/ESO$_{119-143}$ Cell Line by DR1/NY-ESO$_{119-143}$ BPS, PE-NTA$_2$ and Biotin-NTA$_4$-SA-PE Multimers.

Figure 51:
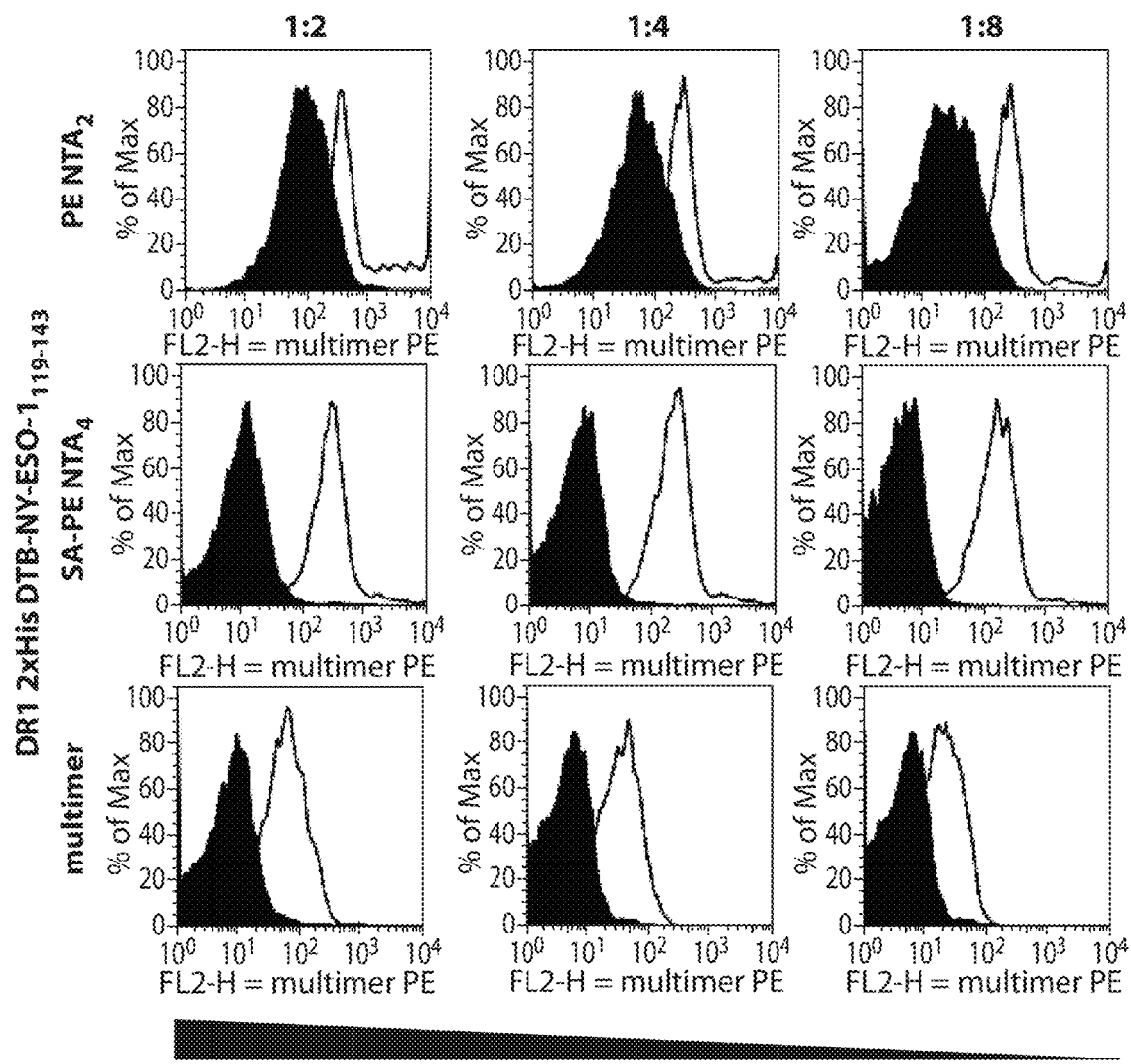
FIG. 51. Comparative staining of a DR1/ESO$_{119-143}$ cell line by DR1/NY-ESO$_{119-143}$ BPS, PE-NTA$_2$ and biotin-NTA$_4$-SA-PE multimers.

The staining reagents were prepared as described above from DTB/StreptActin purified DR1/NY-ESO$_{119}$-1$_{43}$ monomers. CD4+ cells were incubated with three different multimer dilutions (1:2, 1:4 and 1:8, corresponding to 14 µg/ml, 7 µg/ml, and 3.5 µg/ml for the SA-PE NTA$_4$ and the BSP multimers, and to 7 µg/ml, 3.5 µg/ml and 1.75 µg/ml for the PE NTA$_2$ multimers (FIG. 51 white histograms). Mouse splenocytes (C57BL/6J) were used as a negative control (black histograms). The DR1/ESO$_{119-143}$ cell line was derived from an HLA-DR1 transgenic mouse immunized with NY-ESO$_{119-143}$ peptide, and was maintained in IMDM-10, 50 µM beta-mercaptoethanol, pen/strep, with 50 U/ml of rmIL-2.

Example 6

Additional Tags

Figure 52A:
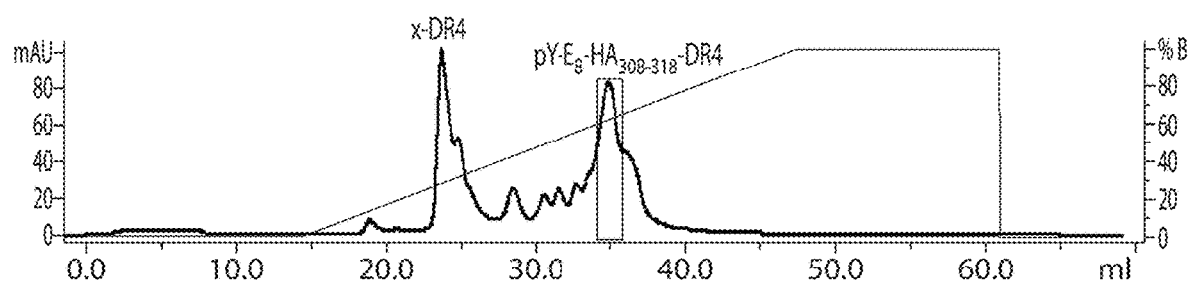
FIGS. 52A to 52B. Evaluation of additional tags for purification of peptide-loaded MHC monomers.
Figure 52B:
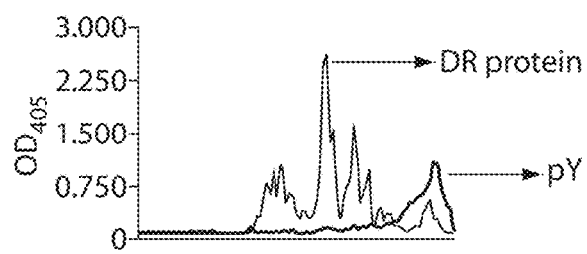

Additional tags for purification of peptide-loaded MHC monomers were evaluated (FIG. 52). Earlier elution on anion-exchange chromatography of pY-E8-HA peptide loaded than DR4-x (x=no/any peptide) from anion exchange chromatography column (MONO-Q™) upon elution with a linear gradient of NaCl is shown in FIG. 52. The gradient shown as a light line rises from 0 to 1 M NaCl. FIG. 52 B shows an ELISA of DR4 (light line) and pY (phosphotyrosine)(dark line).

Additional acidic tags that were successfully employed for the isolation of correctly peptide loaded MHC II monomers includes YP-D4-SGSG-*-HA, YS-D6-SGSG-*-HA, YP-E8-GSG-HA, YP-E8-GSG-HA, YP-DDGGDDGGDD-SGS-HA, P—PO$_4^{2-}$, —S—SO$^{3-}$.

Of the tags tested, the pY-E8 tag provided the best results. While anionic tags are suitable for the isolation of peptide-loaded MHC monomers, the disadvantages of using such tags include: i) difficulties in peptide synthesis, ii) the high NaCl concentration needed to elute the complexes may partially denature them; iii) an additional desalting step is need to remove the high NaCl concentrations.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

The invention claimed is:

1. A reversible protein multimer, comprising
(a) a multivalent carrier molecule, and
(b) a plurality of MHC class I molecules bound to the multivalent carrier molecule, wherein at least one MHC class I molecule of the plurality of MHC class I molecules is loaded with an antigenic peptide and is conjugated to the multivalent carrier molecule via a chelate complex bond, wherein the chelate complex bond comprises a first chelant conjugated to the at least one MHC class I molecule, and a second chelant comprising a nitrilotriacetic acid (NTA) moiety, wherein the NTA moiety is bound to a linker conjugated to the multivalent carrier molecule, wherein the reversible protein multimer is produced by a step that comprises providing MHC class I molecules which are loaded with an antigenic peptide.

2. The protein multimer of claim 1, wherein the chelate complex bond is a bond with a dissociation constant $5\ \mu M > K_D \geq 1\ fM$.

3. The protein multimer of claim 1, wherein the first chelant conjugated to the at least one MHC class I molecule is C-terminally conjugated to the MHC α chain.

4. The protein multimer of claim 1, wherein the first chelant conjugated to the at least one MHC class I molecule is a peptide comprising a chelant moiety.

5. The protein multimer of claim 4, wherein the peptide comprising the chelant moiety comprises a poly-Histidine sequence.

6. The protein multimer of claim 1, wherein the NTA moiety is bound to the multivalent carrier molecule in mono-NTA, di-NTA, tetra-NTA, or poly-NTA configuration.

7. The protein multimer of claim 1, wherein the linker is covalently conjugated to the multivalent carrier molecule.

8. The protein multimer of claim 1, wherein the linker is covalently conjugated to a ligand of a binding molecule, and wherein the binding molecule is covalently bound to the multivalent carrier molecule.

9. The protein multimer of claim 1, wherein the chelate complex bond further comprises a divalent cation, and wherein the divalent cation is an $Ni^{2+}$, $Cu^{2+}$, $Zn^{2+}$, $Co^{2+}$, $Cd^{2+}$, $Sr^{2+}$, $Mn^{2+}$, $Fe^{2+}$, $Mg^{2+}$, $Ca^{2+}$, or $Ba^{2+}$ ion.

10. The protein multimer of claim 1, wherein the multivalent carrier molecule is a fluorophore, a phycobilin, phycoerythrin, allophycocyanine, a quantum dot, a microsphere, a fluorescent microsphere, a magnetic particle, or a nanoparticle.

11. The protein multimer of claim 1, wherein the at least one MHC class I molecule loaded with the peptide is selected from the group consisting of HLA-A*0201, HLA-A*0101, HLA-A-0301, HLA-A*2301, HLA-A*2402, HLA-A*3101, HLA-A*6801, HLA-B*0702, HLA-B*1302, HLA-*1801, HLA-B3501, HLA-B3503, HLA-Cw*0304, HLA-Cw*0702, HLA-A*0201 α1 α2 H-2 Kb α3, H-2K$^d$, H-2D$^b$, H-2D$^k$, H-2D$^d$, H-2K$^b$, H-2L$^d$, H-2QAI, and TL T3B.

12. The protein multimer of claim 1, wherein the multimer is a tetramer.

13. The protein multimer of claim 1, wherein the second chelant conjugated to the multivalent carrier molecule is of a different structure than the first chelant conjugated to the at least one MHC class I molecule.

14. The protein multimer of claim 4, wherein the peptide comprising a chelant moiety is fused to a polypeptide chain comprised by the at least one MHC class I molecule.

15. The protein multimer of claim 5, wherein the poly-Histidine sequence comprises 3-24 His residues.

16. The protein multimer of claim 1, wherein the linker comprises a maleimide moiety, an oxime moiety, or derivatives thereof.

17. The protein multimer of claim 16, wherein the linker is between about 9 Å and about 23 Å long.

18. The protein multimer of claim 8, wherein the ligand is biotin and the binding molecule is streptavidin.

* * * * *